(12) United States Patent
Chan et al.

(10) Patent No.: US 10,927,104 B2
(45) Date of Patent: Feb. 23, 2021

(54) ETHER COMPOUNDS AND USES THEREOF

(71) Applicant: BioTheryX, Inc., Chappaqua, NY (US)

(72) Inventors: Kyle W. H. Chan, San Diego, CA (US); Frank Mercurio, Rancho Santa Fe, CA (US); Aparajita Hoskote Chourasia, San Diego, CA (US); Leah Fung, San Diego, CA (US); Robert Sullivan, Vista, CA (US)

(73) Assignee: BioTheryX, Inc., Chappaqua, NY (US)

( * ) Notice: Subject to any disclaimer, the term of this patent is extended or adjusted under 35 U.S.C. 154(b) by 0 days.

(21) Appl. No.: 16/719,805

(22) Filed: Dec. 18, 2019

(65) Prior Publication Data
US 2020/0231582 A1 Jul. 23, 2020

Related U.S. Application Data

(62) Division of application No. 16/056,163, filed on Aug. 6, 2018, now Pat. No. 10,513,515.

(60) Provisional application No. 62/550,489, filed on Aug. 25, 2017.

(51) Int. Cl.
| | | |
|---|---|---|
| *A61K 31/55* | (2006.01) | |
| *A61K 31/5355* | (2006.01) | |
| *C07D 413/14* | (2006.01) | |
| *A61P 43/00* | (2006.01) | |
| *C07D 401/14* | (2006.01) | |
| *C07D 403/04* | (2006.01) | |
| *C07D 403/14* | (2006.01) | |
| *C07D 413/12* | (2006.01) | |
| *C07D 495/14* | (2006.01) | |

(52) U.S. Cl.
CPC ............ *C07D 413/14* (2013.01); *A61P 43/00* (2018.01); *C07D 401/14* (2013.01); *C07D 403/04* (2013.01); *C07D 403/14* (2013.01); *C07D 413/12* (2013.01); *C07D 495/14* (2013.01)

(58) Field of Classification Search
CPC ......................... A61K 31/55; A61K 31/5355
See application file for complete search history.

(56) References Cited

U.S. PATENT DOCUMENTS

| | | |
|---|---|---|
| 3,331,835 A | 7/1967 | Bassiri et al. |
| 3,920,632 A | 11/1975 | Hohmann et al. |
| 4,339,600 A | 7/1982 | Ondetti et al. |
| 4,415,496 A | 11/1983 | Harris et al. |
| 4,644,069 A | 2/1987 | Baumann et al. |
| 5,015,650 A | 5/1991 | Stoltefuss et al. |
| 5,272,143 A | 12/1993 | Benson et al. |
| 5,272,158 A | 12/1993 | Hartman et al. |
| 5,376,522 A | 12/1994 | Takiguchi et al. |
| 5,463,063 A | 10/1995 | Muller |
| 5,504,080 A | 4/1996 | Karanewsky |
| 5,629,327 A | 5/1997 | D'Amato |
| 5,631,280 A | 5/1997 | Ciccarone et al. |
| 5,635,502 A | 6/1997 | Flynn |
| 5,845,025 A | 12/1998 | Garito et al. |
| 5,856,384 A | 1/1999 | Garito et al. |
| 5,932,582 A | 8/1999 | Young et al. |
| 5,977,134 A | 11/1999 | Ciccarone et al. |
| 6,207,697 B1 | 3/2001 | Han et al. |
| 6,248,740 B1 | 6/2001 | Kawano et al. |
| 6,284,755 B1 | 9/2001 | deSolms et al. |
| 6,388,090 B2 | 5/2002 | Huhtala et al. |
| 6,429,212 B1 | 8/2002 | Hashimoto |
| 6,476,052 B1 | 11/2002 | Muller et al. |
| 6,492,380 B1 | 12/2002 | Ross et al. |
| 6,569,858 B2 | 5/2003 | Prudhomme et al. |
| 6,686,477 B2 | 2/2004 | Boaz et al. |
| 6,719,925 B1 | 4/2004 | Breyne et al. |
| 7,071,181 B2 | 7/2006 | Davis et al. |
| 7,164,014 B2 | 1/2007 | Huang et al. |
| 7,189,738 B2 | 3/2007 | Straub et al. |
| 7,320,992 B2 | 1/2008 | Tegley et al. |
| 7,342,007 B2 | 3/2008 | Herzog et al. |
| 7,405,215 B2 | 7/2008 | Bennani et al. |
| 7,435,745 B2 | 10/2008 | D'Amato et al. |
| 7,569,580 B2 | 8/2009 | Thota et al. |
| 7,592,467 B2 | 9/2009 | Niestroj et al. |
| 7,700,641 B2 | 4/2010 | Chafeev et al. |
| 7,893,096 B2 | 2/2011 | Valiante, Jr. |
| 7,893,265 B2 | 2/2011 | Facchetti et al. |
| 8,063,225 B2 | 11/2011 | Gregor et al. |
| 8,143,284 B2 | 3/2012 | Gandhi et al. |

(Continued)

FOREIGN PATENT DOCUMENTS

| | | |
|---|---|---|
| CA | 793864 | 9/1968 |
| CN | 104004122 | 8/2014 |

(Continued)

OTHER PUBLICATIONS

Golub, 1999, Science, vol. 286, p. 531-537 (Year: 1999).*
Target Cancer Therapies Fact Sheet, retrieved from https://www.cancer.gov/about-cancer/treatment/types/targeted-therapies/targeted-therapies-fact-sheet on Dec. 8, 2015 (Year: 2015).*
Audit, 1994, Thalidomide-induced polyamine acylation: a new insight into the acylation mechanism, Biogenic Amines, 10(6):543-554.
Belyaev et al., 1992, A novel synthetic route to L-α-aminoadipic acid, Izsvestiya Akademi Nauk, Seriya Khimicheskaya, 7:1692-1693.

(Continued)

*Primary Examiner* — Karen Cheng
(74) *Attorney, Agent, or Firm* — Lin Yu, Esq.; Juniv LLP

(57) ABSTRACT

The present invention provides compounds that modulate protein function, to restore protein homeostasis and/or cell-cell adhesion. The invention provides methods of modulating protein-mediated diseases, such as cytokine-mediated diseases, disorders, conditions, or responses. Compositions of these compounds are also provided. Methods of treatment, amelioration, or prevention of protein-mediated diseases, disorders, and conditions are also provided.

26 Claims, 5 Drawing Sheets

(56) References Cited

U.S. PATENT DOCUMENTS

| | | |
|---|---|---|
| 8,222,248 B2 | 7/2012 | Sung et al. |
| 8,362,234 B2 | 1/2013 | Hatala et al. |
| 8,383,139 B2 | 2/2013 | Kunz et al. |
| 8,697,690 B2 | 4/2014 | Beshore et al. |
| 8,742,097 B2 | 6/2014 | Hernandez et al. |
| 8,815,906 B2 | 8/2014 | Gregor et al. |
| 8,822,500 B2 | 9/2014 | Gregor |
| 2003/0114448 A1 | 6/2003 | Zhang et al. |
| 2004/0110757 A1 | 6/2004 | Arrhenius et al. |
| 2004/0127482 A1 | 7/2004 | Robichaud et al. |
| 2006/0211724 A1 | 9/2006 | Verschueren et al. |
| 2008/0318998 A1 | 12/2008 | Prince et al. |
| 2009/0082368 A1 | 3/2009 | Vohra et al. |
| 2009/0286775 A1 | 11/2009 | Almansa Rosales et al. |
| 2010/0152240 A1 | 6/2010 | Zhang |
| 2010/0222363 A1 | 9/2010 | Almansa Rosales et al. |
| 2011/0196150 A1 | 8/2011 | Man et al. |
| 2011/0319411 A1 | 12/2011 | Vu et al. |
| 2012/0192297 A1 | 7/2012 | Handa et al. |
| 2012/0301398 A1 | 11/2012 | Heiser et al. |
| 2013/0310555 A1 | 11/2013 | Chong |
| 2013/0324518 A1 | 12/2013 | Man et al. |
| 2018/0037567 A1 | 2/2018 | Man et al. |

FOREIGN PATENT DOCUMENTS

| | | |
|---|---|---|
| DE | 292451 | 8/1991 |
| EP | 0 595 610 | 5/1997 |
| GB | 2450771 | 1/2009 |
| JP | 2000-159761 | 6/2000 |
| JP | 2009-0023986 | 2/2009 |
| JP | 2011-0153279 | 8/2011 |
| JP | 2012-0123292 | 6/2012 |
| KR | 2013131663 | 12/2013 |
| KR | 2014039383 | 4/2014 |
| KR | 2014103447 | 8/2014 |
| SU | 1708812 | 1/1992 |
| WO | WO 99/04390 | 1/1999 |
| WO | WO 00/064917 | 11/2000 |
| WO | WO 02/079147 | 10/2002 |
| WO | WO 04/092174 | 10/2004 |
| WO | WO 05/016326 | 2/2005 |
| WO | WO 07/000337 | 1/2007 |
| WO | WO 07/028789 | 3/2007 |
| WO | WO 07/117394 | 10/2007 |
| WO | WO 08/037266 | 4/2008 |
| WO | WO 08/073865 | 6/2008 |
| WO | WO 09/051417 | 4/2009 |
| WO | WO 09/070533 | 6/2009 |
| WO | WO 09/072581 | 6/2009 |
| WO | WO 09/083105 | 7/2009 |
| WO | WO 09/094668 | 7/2009 |
| WO | WO 09/112445 | 9/2009 |
| WO | WO 10/011924 | 1/2010 |
| WO | WO 11/136483 | 11/2011 |
| WO | WO 12/072019 | 6/2012 |
| WO | WO 12/129562 | 9/2012 |
| WO | WO 12/158475 | 11/2012 |
| WO | WO 13/010218 | 1/2013 |
| WO | WO 13/106409 | 7/2013 |
| WO | WO 14/055548 | 4/2014 |
| WO | WO 14/055634 | 4/2014 |
| WO | WO 14/106019 | 7/2014 |
| WO | WO 14/113485 | 7/2014 |
| WO | WO 16/065980 | 5/2016 |
| WO | WO 16/191178 | 12/2016 |
| WO | WO 17/024318 | 2/2017 |
| WO | WO 17/185023 | 10/2017 |

OTHER PUBLICATIONS

Belyaev et al., May 1991, A novel synthetic route to $N^6$-methyl-L-lysine and $N^5$-methyl-L-ornithine via $N^3$-protected (S)-3-aminolactams, Synthesis, 417-420.

Belyaev, Jan. 16, 1995, A novel synthetic route to enantiomers of epsilon-hydroxynorleucine and epsilon-chloronorleucine from L- and D,L-lysine, Tetrahedron Letters, 36(3):439-440.

CAS Registry 1212527-87-1, entered STN: Mar. 21, 2010.

David et al., 2004, Electrooxidation based strategy towards the core 3-amino-6-hydroxy-azepan-2-one, Synlett, 6:1029-1033.

Eger et al., 1990, Synthesis, central nervous system activity and teratogenicity of a homothalidomide, Arzneimittel-Forschung, 40(10):1073-1075.

Eger et al., Sep. 1988, Alpha-phthalimidoadipinimide—synthesis, teratogenic properties and effect on the central nervous-system of a homo-thalidomide, Archiv Der Pharmazie, 321(9):577.

Gutschow et al., Apr. 2001, Aza analogues of thalidomide: synthesis and evaluation as inhibitors of tumor necrosis factor-alpha production in vitro, Bioorganic & Medicinal Chemistry, 9(4):1059-1065.

Kralj et al., 1975, Mass spectrometric identification of some non-volatile organic compounds, Biomedical Mass Spectrometry, 2(4):215-218.

Lee et al., Jun. 2011, Assessing chiral self-recognition using chiral stationary phases, Tetrahedron, 67:7143-7147.

Olson et al., Dec. 18, 2017, Pharmacological perturbation of CDK9 using selective CDK9 inhibition or degradation, Nature Chemical Biology, 14 pp.

International Search Report and Written Opinion dated Oct. 17, 2018 in PCT/US2018/045626.

* cited by examiner

ETHER COMPOUNDS AND USES THEREOF

INCORPORATION BY REFERENCE TO ANY PRIORITY APPLICATIONS

This application is a division of U.S. application Ser. No. 16/056,163, filed Aug. 6, 2018, which claims the benefit of priority to U.S. Provisional Application No. 62/550,489, filed Aug. 25, 2017. Any and all applications for which a foreign or domestic priority claim is identified in the Application Data Sheet as filed with the present application are hereby incorporated by reference under 37 CFR 1.57.

BACKGROUND

Field

Compounds, methods of making such compounds, pharmaceutical compositions and medicaments comprising such compounds, and methods of using such compounds to treat, prevent or diagnose diseases, disorders, or conditions associated with protein malfunction are provided.

Description of the Related Technology

Protein levels are highly regulated in response to physiological cues. In cells, much of protein degradation is carried out by the ubiquitin-proteasome system (UPS). Aberrant protein function, and/or protein imbalance is a hallmark of many disease states. For example, dynamic modulation of key intracellular signaling proteins within the immune system is required to maintain proper balance of pro-inflammatory and anti-inflammatory mediators or cytokines. Some cytokines promote inflammation (pro-inflammatory cytokines), whereas other cytokines suppress the activity of the pro-inflammatory cytokines (anti-inflammatory cytokines). For example, IL-4, IL-10, and IL-13 are potent activators of B lymphocytes, and also act as anti-inflammatory agents. They are anti-inflammatory cytokines by virtue of their ability to suppress genes for pro-inflammatory cytokines such as interleukin 1 (IL-1), interleukin 6 (IL-6), tumor necrosis factor alpha (TNFα), and chemokines.

Unregulated activities of these mediators can lead to the development of serious inflammatory conditions. For example, autoimmune diseases arise when immune system cells (lymphocytes, macrophages) become sensitized against the "self." Lymphocytes, as well as macrophages, are usually under control in this system. However, a misdirection of the system toward the body's own tissues may happen in response to still unexplained triggers. One hypothesis is that lymphocytes recognize an antigen which mimics the "self" and a cascade of activation of different components of the immune system takes place, ultimately leading to tissue destruction. Genetic predisposition has also been postulated to be responsible for autoimmune disorders.

TNFα, IL-6, and IL-1 are pro-inflammatory cytokines that mediate inflammatory responses associated with infectious agents and other cellular stresses. Overproduction of these cytokines is believed to underlie the progression of many inflammatory diseases including rheumatoid arthritis (RA), Crohn's disease, inflammatory bowel disease, multiple sclerosis, endotoxin shock, osteoporosis, Alzheimer's disease, congestive heart failure, and psoriasis among others.

Recent data from clinical trials support the use of protein antagonists of cytokines, for example soluble TNFα receptor fusion protein (etanercept) or the monoclonal TNFα antibody (infliximab), for the treatment of rheumatoid arthritis, Crohn's disease, juvenile chronic arthritis and psoriatic arthritis. Thus, the reduction of pro-inflammatory cytokines such as TNFα, IL-6, and IL-I has become an accepted therapeutic approach for potential drug intervention in these conditions.

Moreover, IL-2 is now FDA approved for the treatment of renal cancer and melanoma patients, with durable, complete remissions achieved with IL-2 up to 148 months. However, the short half-life of IL-2 in serum requires that large amounts of IL-2 be injected to achieve therapeutic levels. Many attempts have been made to minimize side effects of systemic IL-2 treatment, for example, introducing IL-2 directly into the tumor, though this complicates treatment, and has largely been unsuccessful.

Local delivery of cytokines is appealing compared to systemic delivery for a variety of reasons. It takes advantage of the natural biology of cytokines that have evolved to act locally in a paracrine or autocrine fashion. Local expression also dramatically minimizes many of the side effects of systemic delivery of cytokines. Thus, compounds and methods to increase local expression of IL-2 would be better tolerated than high dose IL-2 treatment, which would expand therapeutic utility of strategies that increase IL-2.

Additional targets include several candidate genes involved in apoptosis and cell survival, including casein kinase 1α (CK1α) and the zinc-finger transcription factors aiolos, helios, and ikaros. Aiolos, helios, and ikaros are transcription factors whose expression is restricted to lymphoid lineages. For example, aiolos binds to the Bcl-2 promoter, and also interacts with the Bcl-2 and Bcl-XL proteins to promote cell survival. Upregulation of aiolos expression, for example, can reduce apoptosis of HIV-1 infected cells.

Likewise, expression of aiolos in lung and breast cancers predicts significantly reduced patient survival. Aiolos decreases expression of a large set of adhesion-related genes, disrupting cell-cell and cell-matrix interactions, facilitating metastasis. Aiolos may also function as an epigenetic driver of lymphocyte mimicry in certain metastatic epithelial cancers. Similarly, aberrant ikaros and helios expression may promote Bcl-XL expression, driving the development of hematopoietic malignancies. Thus, downregulation of aiolos, ikaros, and/or helios may reduce or eliminate metastasis.

Casein kinase 1α (CK1α) is a component of the β-catenin-degradation complex and a critical regulator of the Wnt signaling pathway, and its ablation induces both Wnt and p53 activation. Schittek and Sinnberg, *Mol. Cancer.* 2014, 13, 231; Cheong and Virshup, *J. Biochem.* Cell Biol. 2011, 43, 465-469; Elyada et al., *Nature* 2011, 470, 409-413. CK1α phosphorylates β-catenin, which is subsequently further phosphorylated by GSK-3β. This destabilizes β-catenin and marks the protein for ubiquitination and proteosomal degradation. Thus, CK1α functions as a molecular switch for the Wnt pathway. Amit et al., *Genes Dev.* 2002, 16, 1066-1076. CK1α is critical for embryogenesis and plays an important role in tissue development and response to DNA damage, at least partly coordinated with p53. Elyada et al., *Nature* 2011, 470, 409-413; Schneider et al., *Cancer Cell* 2014, 26, 509-520. Levine and Oren, *Nat. Rev. Cancer* 2009, 9, 749-758.

Indeed, CK1α also phosphorylates p53, which inhibits binding to MDM2 (a p53 inhibitor) and stabilizes p53's binding interactions with the transcriptional machinery.

Huart, et al., *J. Biol. Chem.* 2009, 284, 32384-32394. Thus, inhibiting CK1α activity increases cellular levels of p53.

One mechanism to disrupt protein drivers of disease is to decrease the cellular concentration of these proteins. For example, regulated proteolytic degradation of cellular proteins is essential to normal cell function. Hijacking this process, by targeting specific disease-related proteins, presents a novel mechanism for the treatment of disease. The irreversible nature of proteolysis makes it well-suited to serve as a regulatory switch for controlling unidirectional processes. For example, Ikaros is a transcriptional repressor of IL-2 expression. Accordingly, a reduction in Ikaros protein levels leads to enhanced IL-2 expression in activated T cells. IL-2 therapy is currently being evaluated for a wide array of clinical indications, including for treatment of systemic lupus erythematousus (SLE), wound healing, and immune-oncology.

SUMMARY OF THE INVENTION

Some embodiments provide a compound of Formula (I), or a pharmaceutically acceptable salt thereof:

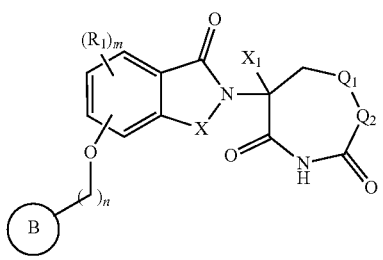

(I)

In some embodiments, $Q_1$ can be $CH_2$, O, $NR_2$, S, or a bond.

In some embodiments, $Q_2$ can be $CH_2$ or a bond.

In some embodiments, X can be $CH_2$ or C=O.

In some embodiments, $X_1$ can be hydrogen, deuterium, methyl, or fluoro.

In some embodiments, Ring B can be

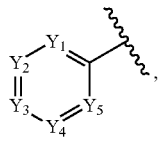

wherein $Y_1$ is N or $CR_{3A}$, $Y_2$ is N or $CR_{3B}$, $Y_3$ is N or $CR_{3C}$, $Y_4$ is N or $CR_{3D}$, and $Y_5$ is N or $CR_{3E}$.

In some embodiments, each $R_1$ can be independently deuterium, hydroxyl, halogen, nitro, a substituted or unsubstituted amino, a substituted or unsubstituted $C_1$-$C_6$ alkoxy, a substituted or unsubstituted $C_1$-$C_6$ alkyl, a substituted or unsubstituted $C_2$-$C_6$ alkenyl, a substituted or unsubstituted $C_3$-$C_8$ cycloalkyl, a substituted or unsubstituted 3 to 10 membered heterocyclyl, a substituted or unsubstituted $C_6$-$C_{10}$ aryl, a substituted or unsubstituted 5 to 10 membered heteroaryl, or L-Y.

In some embodiments, $R_2$ can be hydrogen, deuterium, a substituted or unsubstituted $C_1$-$C_6$ alkyl, a substituted or unsubstituted $C_2$-$C_6$ alkenyl, acyl, or —(SO_2)—$C_1$-$C_6$ alkyl.

In some embodiments, each of $R_{3A}$, $R_{3B}$, $R_{3C}$, $R_{3D}$, and $R_{3E}$ can be independently hydrogen, deuterium, hydroxyl, halogen, nitro, a substituted or unsubstituted amino, a substituted or unsubstituted $C_1$-$C_6$ alkoxy, a substituted or unsubstituted $C_1$-$C_6$ alkyl, a substituted or unsubstituted $C_2$-$C_6$ alkenyl, a substituted or unsubstituted $C_3$-$C_8$ cycloalkyl, a substituted or unsubstituted 3 to 10 membered heterocyclyl, a substituted or unsubstituted alkoxyalkyl, a substituted or unsubstituted cycloalkylalkyl, a substituted or unsubstituted heterocyclylalkyl, a substituted or unsubstituted aralkyl, a substituted or unsubstituted heteroaralkyl, or L-Y.

In some embodiments, m can be 0, 1, 2, or 3.

In some embodiments, n can be 1, 2, 3, or 4. In some embodiments, n can be 1 or 2.

In some embodiments, L can be —$Z_1$—$(R_4)_t$—$Z_2$—; —$Z_1$—$(R_4$—O—$R_4)_t$—$Z_2$—; —$Z_1$($R_4$—NH—$R_4)_t$—$Z_2$—; —$Z_1$—$(R_4$—(NHCO)—$R_4)_t$—$Z_2$—; —$Z_1$—$(R_4$—(NHC(O)NH)—$R_4)_t$—$Z_2$—; or —$Z_1$—$(R_4$—(CONH)—$R_4)_t$—$Z_2$—.

In some embodiments, $Z_1$ can be —$CH_2NH(CO)$—; —NH—; —O—; —$CH_2$—; —NH(CO)—; —(CO)NH—; —$CH_2NH$—; —(CO)NHCH$_2$—; —$CH_2CH_2NH$—; —$NHCH_2$—; or —$NHCH_2CH_2$—.

In some embodiments, $Z_2$ can be —NH—; —O—; —$CH_2$—; —NH(CO)—; —(CO)NH—; —$CH_2NH$—; —$NHCH_2$—; —(CO)NHCH$_2$—; —$CH_2CH_2NH$—; —$CH_2NH(CO)$—.

In some embodiments, each $R_4$ can be independently an unsubstituted $C_1$-$C_6$ alkylene.

In some embodiments, t can be 1, 2, 3, 4, 5, or 6.

In some embodiments, Y can be

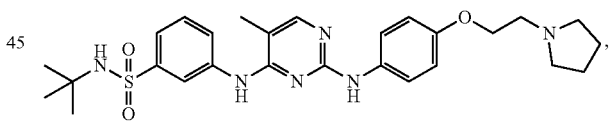

wherein Y can be derivatized to attach to L.

In some embodiments, at least one of $Y_1$, $Y_2$, $Y_3$, $Y_4$, and $Y_5$ can be carbon (bonded to one of $R_{3A}$, $R_{3B}$, $R_{3C}$, $R_{3D}$, and $R_{3E}$, respectively, e.g., $CR_{3A}$, $CR_{3B}$, $CR_{3C}$, $CR_{3D}$, and/or $CR_{3E}$).

In some embodiments, when $Q_1$ can be $CH_2$ or a bond, then one or more of $R_{3A}$, $R_{3B}$, $R_{3C}$, $R_{3D}$, and $R_{3E}$ cannot be hydrogen. In other embodiments, when $R_1$ can be L-Y, none of $R_{3A}$, $R_{3B}$, $R_{3C}$, $R_{3D}$, and $R_{3E}$ can be L-Y. In still other embodiments, when $Q_1$ is a bond, then m is not 0. In some embodiments, when $Q_1$ is a bond, $R_1$ is L-Y. In some embodiments, when $Q_1$ can be a bond, $X_1$ is hydrogen or methyl, and $Q_2$ is $CH_2$; then m is not 0. In other embodiments, when $Q_1$ can be a bond, $X_1$ can be hydrogen or methyl, and $Q_2$ can be $CH_2$; then one of $R_1$, $R_{3A}$, $R_{3B}$, $R_{3C}$, $R_{3D}$, and $R_{3E}$ is L-Y. In some embodiments, when $Q_2$ can be a bond, $Q_1$ can be a bond or $CH_2$.

Some embodiments provide a compound of Formula (I):

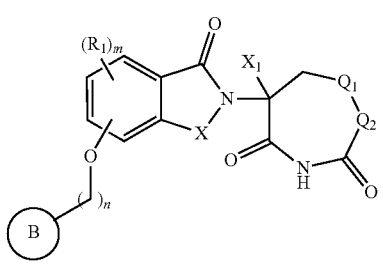

or a pharmaceutically acceptable salt thereof, wherein: $Q_1$ is $CH_2$, O, $NR_2$, S, or a bond; $Q_2$ is $CH_2$ or a bond; X is $CH_2$ or C=O; $X_1$ is hydrogen, deuterium, or fluoro; Ring B is

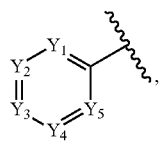

wherein $Y_1$ is N or $CR_{3A}$; $Y_2$ is N or $CR_{3B}$; $Y_3$ is N or $CR_{3C}$; $Y_4$ is N or $CR_{3D}$; $Y_5$ is N or $CR_{3E}$; each $R_1$ is independently deuterium, hydroxyl, halogen, nitro, a substituted or unsubstituted amino, a substituted or unsubstituted $C_1$ to $C_6$ haloalkyl, a substituted or unsubstituted $C_1$-$C_6$ alkoxy, a substituted or unsubstituted $C_1$-$C_6$ alkyl, a substituted or unsubstituted $C_2$-$C_6$ alkenyl, a substituted or unsubstituted $C_3$-$C_8$ cycloalkyl, a substituted or unsubstituted 3 to 10 membered heterocyclyl, a substituted or unsubstituted $C_6$-$C_{10}$ aryl, a substituted or unsubstituted 5 to 10 membered heteroaryl, or L-Y; $R_2$ is Hydrogen, deuterium, a substituted or unsubstituted $C_1$-$C_6$ alkyl, a substituted or unsubstituted $C_2$-$C_6$ alkenyl, acyl, or —($SO_2$)—$C_1$-$C_6$ alkyl; each $R_{3A}$, $R_{3B}$, $R_{3C}$, $R_{3D}$, and $R_{3E}$ is independently hydrogen, deuterium, hydroxyl, halogen, nitro, a substituted or unsubstituted amino, a substituted or unsubstituted $C_1$ to $C_6$ haloalkyl, a substituted or unsubstituted $C_1$-$C_6$ alkoxy, a substituted or unsubstituted $C_1$-$C_6$ alkyl, a substituted or unsubstituted $C_2$-$C_6$ alkenyl, a substituted or unsubstituted $C_3$-$C_8$ cycloalkyl, a substituted or unsubstituted 3 to 10 membered heterocyclyl, a substituted or unsubstituted alkoxyalkyl, a substituted or unsubstituted cycloalkylalkyl, a substituted or unsubstituted heterocyclylalkyl, a substituted or unsubstituted aralkyl, a substituted or unsubstituted heteroaralkyl, or L-Y; m is 0, 1, 2, or 3; n is 1, 2, or 3; L is —$Z_1$—($R_4$—O—$R_4$)$_t$—$Z_2$—; —$Z_1$($R_4$—NH—$R_4$)$_t$—$Z_2$—; —$Z_1$—($R_4$—(NHCO)—$R_4$)$_t$—$Z_2$—; —$Z_1$—($R_4$—(NHC(O)NH)—$R_4$)$_t$—$Z_2$—; or —$Z_1$—($R_4$—(CONH)—$R_4$)$_t$—$Z_2$—; $Z_1$ is —NH—; —O—; —$CH_2$—; —NH(CO)—; —(CO)NH—; —$CH_2$NH—; —$NHCH_2$—; —$CH_2$NH(CO)—; —$NHCH_2CH_2$—; $Z_2$ is —NH—; —O—; —$CH_2$—; —NH(CO)—; or —(CO)NH—; —$CH_2$NH—; —$NHCH_2$—; or —$NHCH_2CH_2$—; each $R_4$ is independently an unsubstituted $C_1$-$C_6$ alkylene; t is 1, 2, 3, 4, 5, or 6; and Y is

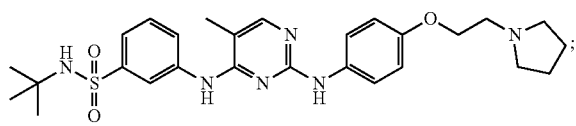

wherein Y is derivatized to attach to L; and wherein at least one of $Y_1$, $Y_2$, $Y_3$, $Y_4$, and $Y_5$ is respectively $R_{3A}$, $R_{3B}$, $R_{3C}$, $R_{3D}$, or $R_{3E}$; when $Q_1$ is $CH_2$ or a bond, then one or more of $R_{3A}$, $R_{3B}$, $R_{3C}$, $R_{3D}$, or $R_{3E}$ is not hydrogen; when $R_1$ is L-Y, none of $R_{3A}$, $R_{3B}$, $R_{3C}$, $R_{3D}$, and $R_{3E}$ is L-Y; and when $Q_1$ is a bond, then m is not 0.

In some embodiments, X can be $CH_2$. In some embodiments, X can be C=O.

In some embodiments, $X_1$ can be hydrogen. In other embodiments, $X_1$ can be deuterium. In still other embodiments, $X_1$ can be methyl. In some embodiments, $X_1$ can be fluoro.

In some embodiments, $Q_1$ can be $NR_2$. In some embodiments, $R_2$ can be hydrogen. In some embodiments, $R_2$ can be a substituted or unsubstituted $C_1$-$C_6$ alkyl. In some embodiments, $R_2$ can be an unsubstituted $C_1$-$C_6$ alkyl. In some embodiments, $R_2$ can be acyl. In some embodiments, $R_2$ can be —($SO_2$)—$C_1$-$C_6$ alkyl. In some embodiments, $R_2$ can be methyl.

In some embodiments, $Q_1$ can be $CH_2$. In some embodiments, $Q_1$ can be O. In some embodiments, $Q_1$ can be S. In some embodiments, $Q_1$ can be a bond. In some embodiments, when $Q_1$ is a bond, then m is not 0. In some embodiments, $Q_2$ can be $CH_2$. In some embodiments, $Q_2$ can be a bond. In some embodiments, when $Q_2$ can be a bond, $Q_1$ can be a bond or $CH_2$.

In some embodiments, n can be 1. In some embodiments, n can be 2. In some embodiments, n can be 3. In some embodiments, m can be 1. In some embodiments, m can be 2. In some embodiments, m can be 3. In some embodiments, m can be 0.

In some embodiments, each $R_1$ can be independently halogen, a substituted or unsubstituted amino, a substituted or unsubstituted $C_1$-$C_6$ alkoxy or a substituted or unsubstituted $C_1$-$C_6$ alkyl. In some embodiments, each $R_1$ can be independently halogen, an unsubstituted amino, an unsubstituted $C_1$-$C_6$ haloalkyl, an unsubstituted $C_1$-$C_6$ alkoxy or unsubstituted $C_1$-$C_6$ alkyl.

In some embodiments, each $R_1$ can be independently fluoro, chloro, —$NH_2$, —$NH(CH_3)$, —$N(CH_3)_2$, —$CF_3$, —$OCH_3$, —$OCH_2CH_3$, —$OCH(CH_3)_2$, —$CH_3$, —$CH_2CH_3$ or —$CH(CH_3)_2$.

In some embodiments, Ring B can be selected from:

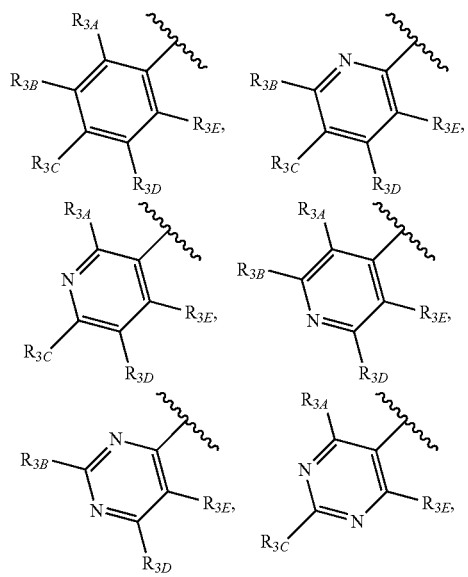

-continued

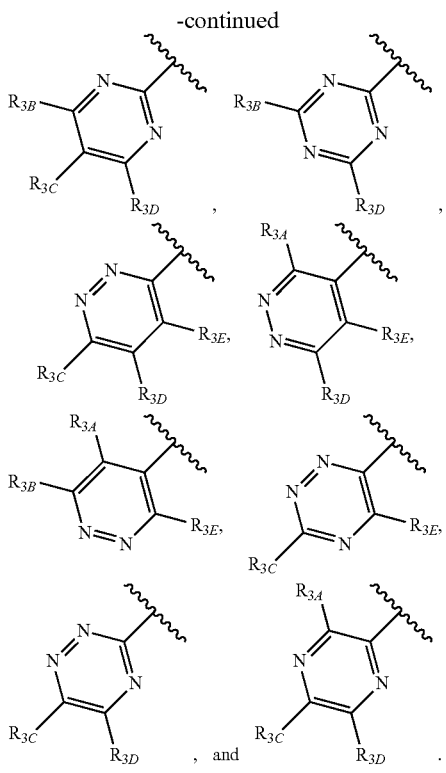

In some embodiments, each of $R_{3A}$, $R_{3B}$, $R_{3C}$, $R_{3D}$, and $R_{3E}$ can be independently hydrogen, deuterium, hydroxyl, halogen, nitro, a substituted or unsubstituted amino, a substituted or unsubstituted $C_1$-$C_6$ alkoxy, a substituted or unsubstituted $C_1$-$C_6$ alkyl, a substituted or unsubstituted $C_2$-$C_6$ alkenyl, a substituted or unsubstituted $C_3$-$C_8$ cycloalkyl, a substituted or unsubstituted 3 to 10 membered heterocyclyl, a substituted or unsubstituted alkoxyalkyl, a substituted or unsubstituted cycloalkylalkyl, a substituted or unsubstituted heterocyclylalkyl, a substituted or unsubstituted aralkyl or a substituted or unsubstituted heteroaralkyl.

In some embodiments, each of $R_{3A}$, $R_{3B}$, $R_{3C}$, $R_{3D}$, and $R_{3E}$ can be independently hydrogen, hydroxyl, halogen, nitro, an unsubstituted amino, an unsubstituted $C_1$-$C_6$ haloalkyl, an unsubstituted $C_1$-$C_6$ alkoxy, an unsubstituted $C_1$-$C_6$ alkyl, a substituted or unsubstituted $C_3$-$C_8$ cycloalkyl, a substituted or unsubstituted 3 to 10 membered heterocyclyl, a substituted or unsubstituted alkoxyalkyl, a substituted or unsubstituted cycloalkylalkyl, a substituted or unsubstituted heterocyclylalkyl, a substituted or unsubstituted aralkyl or a substituted or unsubstituted heteroaralkyl.

In some embodiments, each of $R_{3A}$, $R_{3B}$, $R_{3C}$, $R_{3D}$, and $R_{3E}$ can be independently hydrogen, hydroxyl, halogen, nitro, an unsubstituted amino, an unsubstituted $C_1$-$C_6$ haloalkyl, an unsubstituted $C_1$-$C_6$ alkoxy, an unsubstituted $C_1$-$C_6$ alkyl, an unsubstituted $C_3$-$C_8$ cycloalkyl, an unsubstituted 3 to 10 membered heterocyclyl, an unsubstituted cycloalkylalkyl, unsubstituted 3 to 10 membered heterocyclylalkyl, unsubstituted aralkyl or unsubstituted 5 to 10 membered heteroaralkyl.

In some embodiments, each of $R_{3A}$, $R_{3B}$, $R_{3C}$, $R_{3D}$, and $R_{3E}$ can be independently hydrogen, halogen, an unsubstituted $C_1$-$C_6$ haloalkyl, an unsubstituted $C_1$-$C_6$ alkoxy, an unsubstituted $C_1$-$C_6$ alkyl, an unsubstituted 3 to 10 membered heterocyclyl, or an unsubstituted 3 to 10 membered heterocyclylalkyl.

In some embodiments, one of $R_{3A}$, $R_{3B}$, $R_{3C}$, $R_{3D}$, and $R_{3E}$ can be halogen, an unsubstituted $C_1$-$C_6$ haloalkyl, an unsubstituted $C_1$-$C_6$ alkoxy, an unsubstituted $C_1$-$C_6$ alkyl, an unsubstituted 3 to 10 membered heterocyclyl, or an unsubstituted 3 to 10 membered heterocyclylalkyl and the other of $R_{3A}$, $R_{3B}$, $R_{3C}$, $R_{3D}$, and $R_{3E}$ are hydrogen.

In some embodiments, one of $R_{3A}$, $R_{3B}$, $R_{3C}$, $R_{3D}$, and $R_{3E}$ can be fluoro, chloro, —$CF_3$, —$OCH_3$, an unsubstituted $C_1$-$C_6$ alkyl, an unsubstituted 3 to 10 membered heterocyclyl, an unsubstituted 3 to 10 membered heterocyclylalkyl and the other of $R_{3A}$, $R_{3B}$, $R_{3C}$, $R_{3D}$, and $R_{3E}$ are hydrogen.

In some embodiments, one of $R_{3A}$, $R_{3B}$, $R_{3C}$, $R_{3D}$, and $R_{3E}$ can be

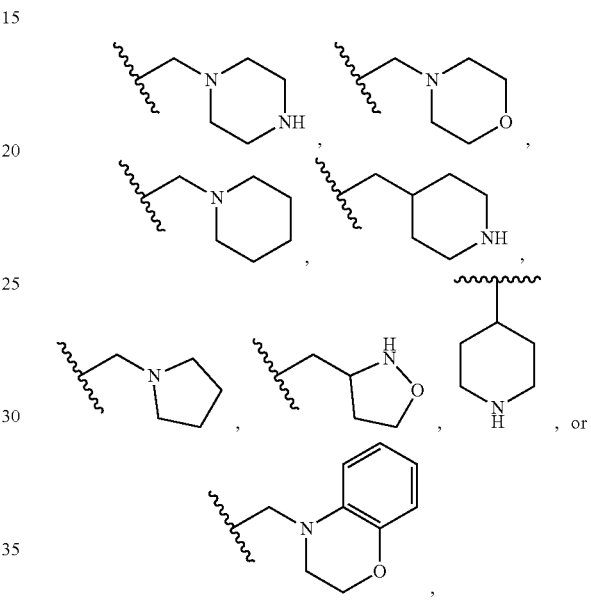

and the other of $R_{3A}$, $R_{3B}$, $R_{3C}$, $R_{3D}$, and $R_{3E}$ are hydrogen.

In some embodiments, one $R_1$ can be L-Y. In some embodiments, one of $R_{3A}$, $R_{3B}$, $R_{3C}$, $R_{3D}$, and $R_{3E}$ can be L-Y. In some embodiments, $Y_3$ can be C-L-Y.

In some embodiments, L can be —$Z_1$—$(R_4)_t$—$Z_2$—. In other embodiments, L can be —$Z_1$—$(R_4$—O—$R_4)_t$—$Z_2$—. In still other embodiments, L can be —$Z_1(R_4$—NH—$R_4)_t$—$Z_2$—. In some embodiments, L can be —$Z_1$—$(R_4$—(NHCO)—$R_4)_t$—$Z_2$—. In some embodiments, L can be —$Z_1$—$(R_4$—(CONH)—$R_4)_t$—$Z_2$—. In other embodiments, L can be —$Z_1$—$(R_4$—(NHC(O)NH)—$R_4)_t$—$Z_2$—.

In some embodiments, $Z_1$ can be —$CH_2NH(CO)$—. In other embodiments, $Z_1$ can be —NH—. In still other embodiments, $Z_1$ can be —O—. In some embodiments, $Z_1$ can be —$CH_2$—. In other embodiments, $Z_1$ can be —NH(CO)—. In still other embodiments, $Z_1$ can be —$CH_2NH$—. In some embodiments, $Z_1$ can be —$NHCH_2$—. In other embodiments, $Z_1$ can be —(CO)NH—. In still other embodiments, $Z_1$ can be —$NHCH_2CH_2$—. In some embodiments, $Z_1$ can be —(CO)$NHCH_2$—. In still other embodiments, $Z_1$ can be —$CH_2CH_2NH$—.

In some embodiments, $Z_2$ can be —NH—. In other embodiments, $Z_2$ can be —O—. In still other embodiments, $Z_2$ can be —$CH_2$—. In some embodiments, $Z_2$ can be —NH(CO)—. In other embodiments, $Z_2$ can be —(CO)NH—. In still other embodiments, $Z_2$ can be —$CH_2NH$—. In some embodiments, $Z_2$ can be —$NHCH_2$—. In other embodiments, $Z_2$ can be —(CO)NH—. In still other embodiments, $Z_2$ can be —$NHCH_2CH_2$—. In some embodiments, $Z_2$ can be —(CO)NHCH$_2$—. In other embodiments, $Z_2$ can be —CH$_2$CH$_2$NH—. In still other embodiments, $Z_2$ can be —CH$_2$NH(CO)—.

In some embodiments, each $R_4$ can be independently an unsubstituted $C_1$-$C_4$ alkylene. In some embodiments, each $R_4$ can be independently an unsubstituted $C_1$-$C_2$ alkylene.

In some embodiments, t can be 1. In some embodiments, t can be 2. In some embodiments, t can be 3. In some embodiments, t can be 4. In some embodiments, t can be 5. In some embodiments, t can be 6.

In some embodiments, the compound of Formula (I) is selected from:

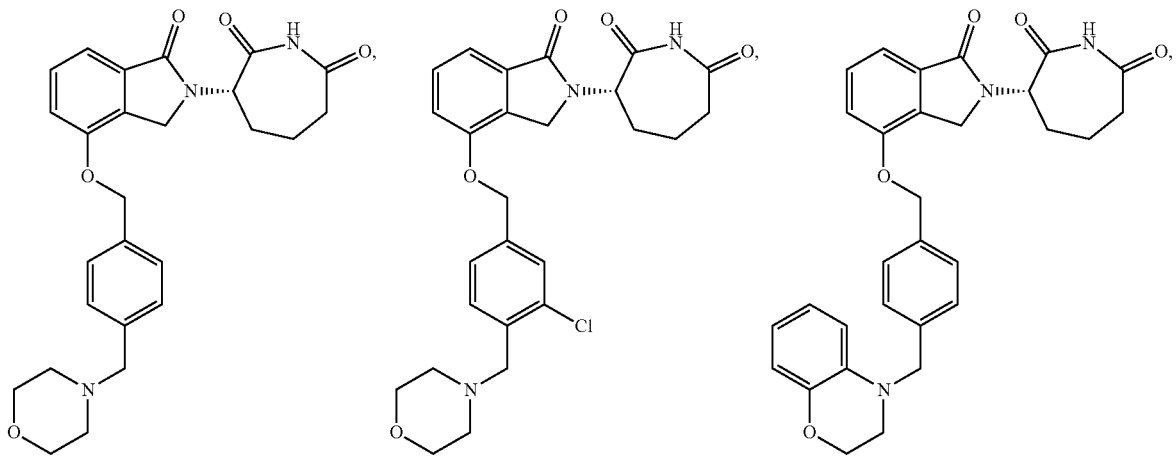

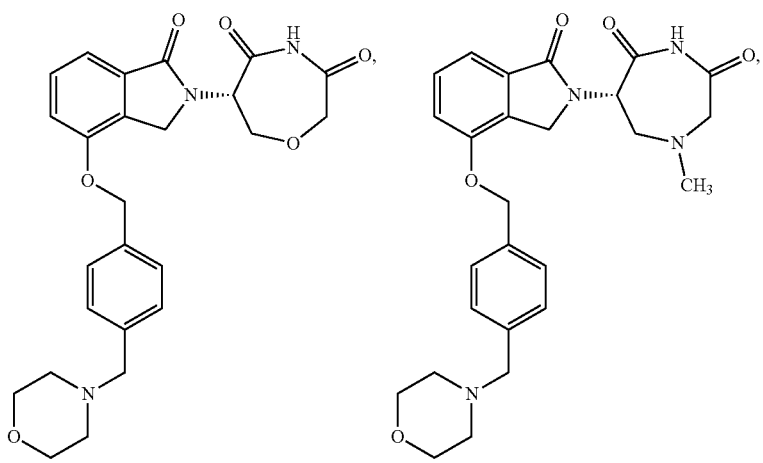

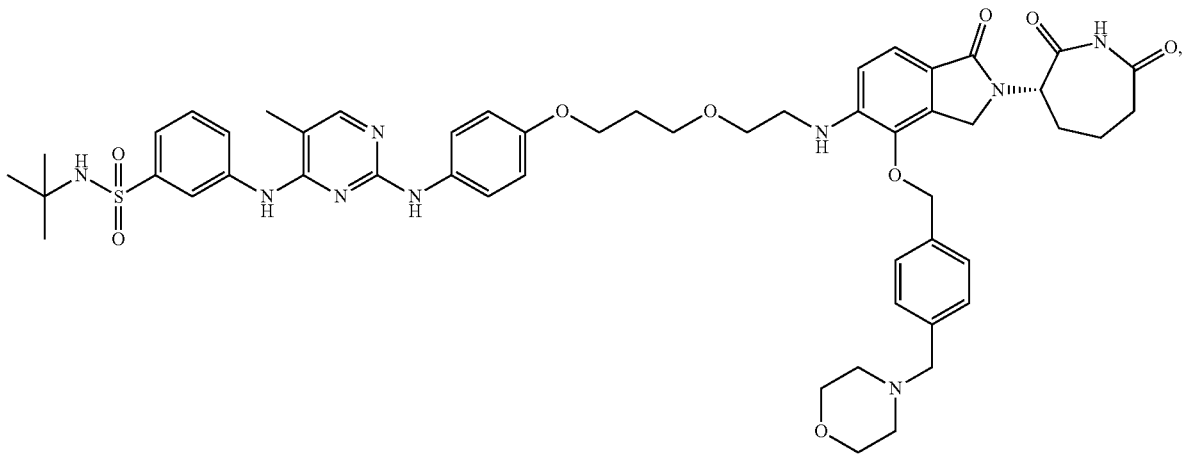

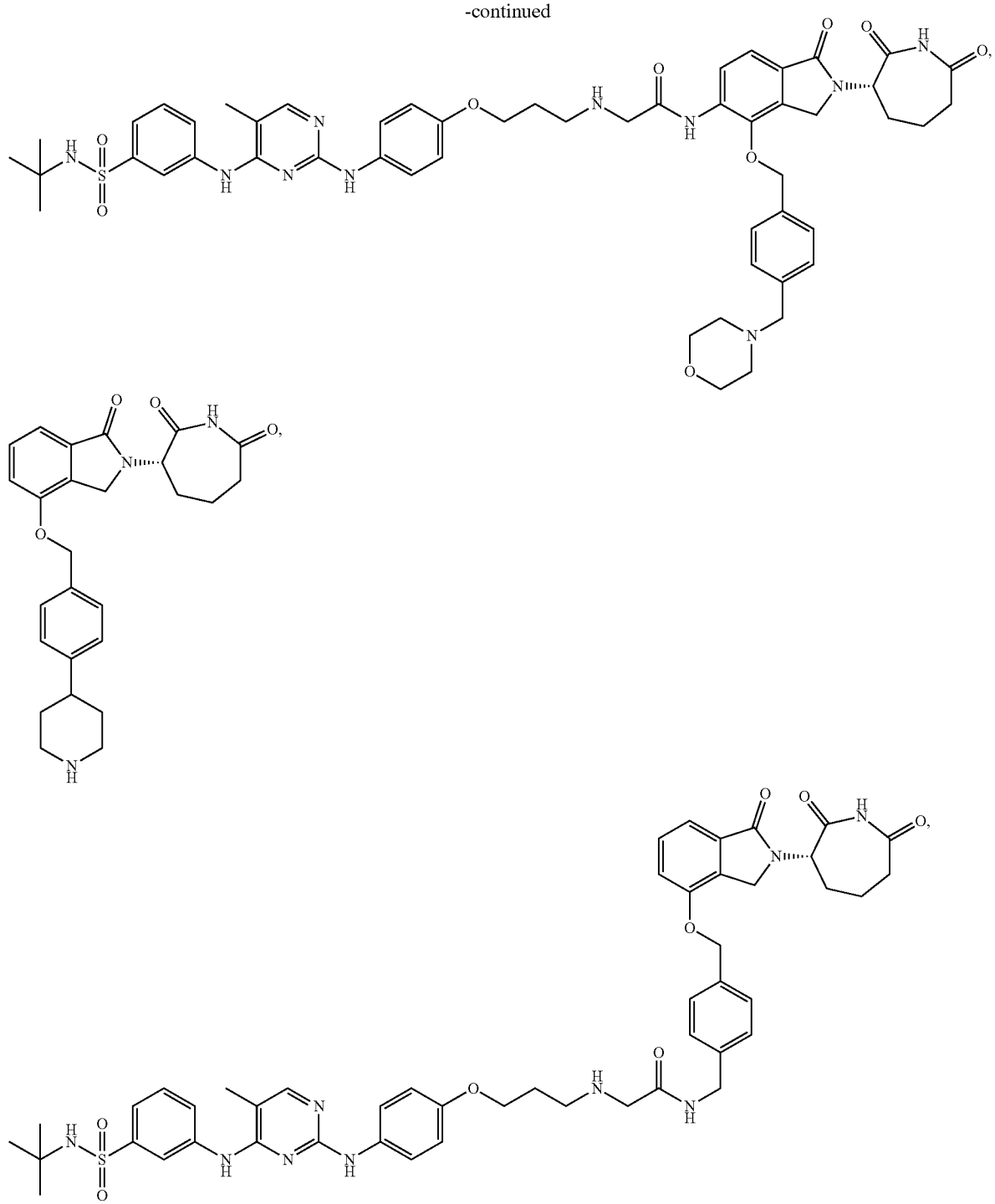

or a pharmaceutically acceptable salt of any of the foregoing.

Some embodiments provide a pharmaceutical composition comprising a compound of Formula (I), or a pharmaceutically acceptable salt thereof; and a pharmaceutically acceptable excipient.

Some embodiments provide a method of inhibiting the activity of a cytokine, comprising contacting a cell with an effective amount of a compound of Formula (I), or a pharmaceutically acceptable salt thereof. Other embodiments provide the use of a compound of Formula (I), or a pharmaceutically acceptable salt of any of the foregoing, for inhibiting the activity of a cytokine, comprising contacting a cell with an effective amount of a compound of Formula (I), or a pharmaceutically acceptable salt of any of the foregoing. Still other embodiments provide the use of a compound of Formula (I), or a pharmaceutically acceptable salt of any of the foregoing, for the manufacture a medicament for inhibiting the activity of a cytokine, comprising contacting a cell with an effective amount of a compound of Formula (I), or a pharmaceutically acceptable salt of any of the foregoing. In some embodiments, the cytokine is selected from: IL-1β, IL-2, IL-6, and TNFα. In some embodiments, the cytokine is TNFα. In some embodiments, the cell is a cancer cell.

Some embodiments provide a method of inhibiting the activity of aiolos, comprising contacting a cell with an effective amount of a compound of Formula (I), or a pharmaceutically acceptable salt thereof. Other embodiments provide the use of a compound of Formula (I), or a pharmaceutically acceptable salt of any of the foregoing, for inhibiting the activity of aiolos, comprising contacting a cell with an effective amount of a compound of Formula (I), or a pharmaceutically acceptable salt of any of the foregoing. Still other embodiments provide the use of a compound of Formula (I), or a pharmaceutically acceptable salt of any of the foregoing, for the manufacture a medicament for inhibiting the activity of aiolos, comprising contacting a cell with an effective amount of a compound of Formula (I), or a pharmaceutically acceptable salt of any of the foregoing. In some embodiments, the cell is a cancer cell.

Some embodiments provide a method of inhibiting the activity of ikaros, comprising contacting a cell with an effective amount of a compound of Formula (I), or a pharmaceutically acceptable salt thereof. Other embodiments provide the use of a compound of Formula (I), or a pharmaceutically acceptable salt of any of the foregoing, for inhibiting the activity of ikaros, comprising contacting a cell with an effective amount of a compound of Formula (I), or a pharmaceutically acceptable salt of any of the foregoing. Still other embodiments provide the use of a compound of Formula (I), or a pharmaceutically acceptable salt of any of the foregoing, for the manufacture a medicament for inhibiting the activity of ikaros, comprising contacting a cell with an effective amount of a compound of Formula (I), or a pharmaceutically acceptable salt of any of the foregoing. In some embodiments, the cell is a cancer cell.

Some embodiments provide a method of inhibiting the activity of helios, comprising contacting a cell with an effective amount of a compound of Formula (I), or a pharmaceutically acceptable salt thereof. Other embodiments provide the use of a compound of Formula (I), or a pharmaceutically acceptable salt of any of the foregoing, for inhibiting the activity of helios, comprising contacting a cell with an effective amount of a compound of Formula (I), or a pharmaceutically acceptable salt of any of the foregoing. Still other embodiments provide the use of a compound of Formula (I), or a pharmaceutically acceptable salt of any of the foregoing, for the manufacture a medicament for inhibiting the activity of helios, comprising contacting a cell with an effective amount of a compound of Formula (I), or a pharmaceutically acceptable salt of any of the foregoing. In some embodiments, the cell is a cancer cell.

Some embodiments provide a method of inhibiting the activity of CK-1α, comprising contacting a cell with an effective amount of a compound of Formula (I), or a pharmaceutically acceptable salt thereof. Other embodiments provide the use of a compound of Formula (I), or a pharmaceutically acceptable salt of any of the foregoing, for inhibiting the activity of CK-1α, comprising contacting a cell with an effective amount of a compound of Formula (I), or a pharmaceutically acceptable salt of any of the foregoing. Still other embodiments provide the use of a compound of Formula (I), or a pharmaceutically acceptable salt of any of the foregoing, for the manufacture a medicament for inhibiting the activity of CK-1α, comprising contacting a cell with an effective amount of a compound of Formula (I), or a pharmaceutically acceptable salt of any of the foregoing. In some embodiments, the cell is a cancer cell.

In some embodiments, the cell is a small cell lung cancer cell, a non-small cell lung cancer cell, a breast cancer cell, a prostate cancer cell, a head and neck cancer cell, a pancreatic cancer cell, a colon cancer cell, a rectal cancer cell, a teratoma cell, an ovarian cancer cell, an endometrial cancer cell, a brain cancer cell, a retinoblastoma cell, a leukemia cell, a skin cancer cell, a melanoma cell, a squamous cell carcinoma cell, a liposarcoma cell, a lymphoma cell, a multiple myeloma cell, a testicular cancer cell, a liver cancer cell, an esophageal cancer cell, a kidney carcinoma cell, an astrogliosis cell, a relapsed/refractory multiple myeloma cell, or a neuroblastoma cell.

Some embodiments provide a method of treating, ameliorating, or preventing a disease, disorder, or condition associated with a protein in a subject, the protein selected from a cytokine, aiolos, ikaros, helios, CK1α, and combinations of any of the foregoing; the method comprising administering a therapeutically effective amount of a compound of Formula (I), or a pharmaceutically acceptable salt thereof, or a pharmaceutical composition comprising a compound of Formula (I), or a pharmaceutically acceptable salt thereof, to the subject. Other embodiments provide the use of a compound of Formula (I), or a pharmaceutically acceptable salt of any of the foregoing, for treating, ameliorating, or preventing a disease, disorder, or condition associated with a protein selected from a cytokine, aiolos, ikaros, helios, CK1α, and combinations of any of the foregoing. Still other embodiments provide the use of a compound of Formula (I), or a pharmaceutically acceptable salt of any of the foregoing, for the manufacture a medicament for treating, ameliorating, or preventing a disease, disorder, or condition associated with a protein selected from a cytokine, aiolos, ikaros, helios, CK1α, and combinations of any of the foregoing.

In some embodiments, the disease, disorder, or condition is a cancer selected from a hematological malignancy and a solid tumor In some embodiments, the disease, disorder, or condition is a cancer selected from small cell lung cancer, non-small cell lung cancer, breast cancer, prostate cancer, head and neck cancer, pancreatic cancer, colon cancer, rectal cancer, teratoma, ovarian cancer, endometrial cancer, brain cancer, retinoblastoma, leukemia, skin cancer, melanoma, squamous cell carcinoma, liposarcoma, lymphoma, multiple myeloma, testicular cancer, liver cancer, esophageal cancer, kidney carcinoma, astrogliosis, relapsed/refractory multiple myeloma, and neuroblastoma.

In some embodiments, the disease, disorder, or condition is selected from inflammation, fibromyalgia, rheumatoid arthritis, osteoarthritis, ankylosing spondylitis, psoriasis, psoriatic arthritis, inflammatory bowel diseases, Crohn's disease, ulcerative colitis, uveitis, inflammatory lung diseases, chronic obstructive pulmonary disease, and Alzheimer's disease. In some embodiments, the disease, disorder, or condition is selected from fibromyalgia, rheumatoid arthritis, osteoarthritis, ankylosing spondylitis, psoriasis, psoriatic arthritis, Crohn's disease, and ulcerative colitis.

In some embodiments, the protein is a cytokine. In some embodiments, the cytokine is selected from: IL-1β, IL-2, IL-6, and TNFα. In some embodiments, the cytokine is TNFα. In some embodiments, the protein is aiolos. In some embodiments, the protein is ikaros. In some embodiments, the protein is helios. In some embodiments, the protein is CK1α.

Any of the features of an embodiment is applicable to all embodiments identified herein. Moreover, any of the features of an embodiment is independently combinable, partly or wholly with other embodiments described herein in any way, e.g., one, two, or three or more embodiments may be combinable in whole or in part. Further, any of the features of an embodiment may be made optional to other embodiments. Any embodiment of a method can comprise another embodiment of a compound, and any embodiment of a compound can be configured to perform a method of another embodiment.

DETAILED DESCRIPTION

Figure 1:
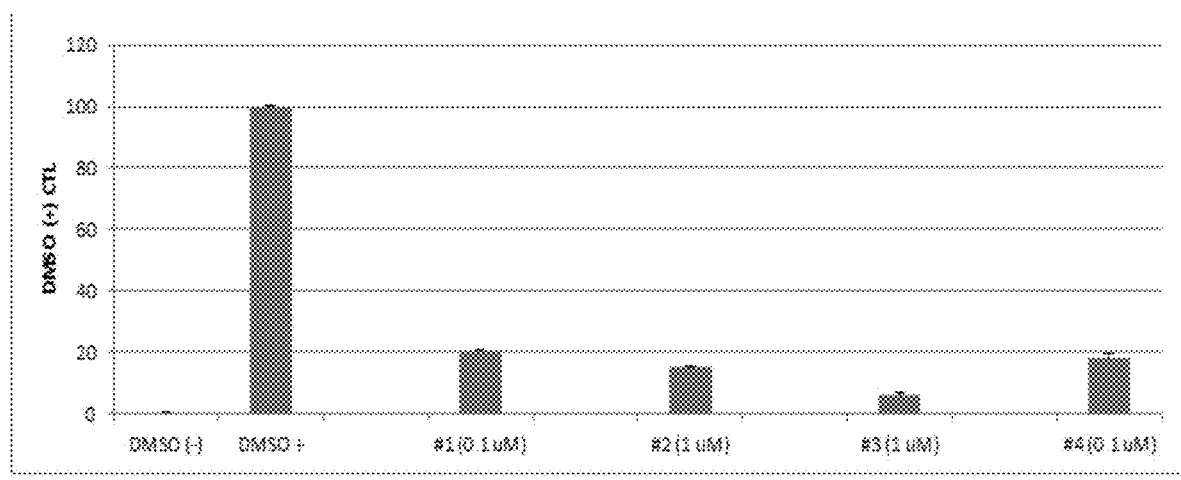
FIG. 1 represents the activity against IL-1-beta in peripheral blood mononuclear cells (PBMCs), plated in 96 well plates and pretreated with compound for 1 hour and then induced with 100 ng/mL LPS for 18-24 hrs. Cytokines in the media were measured according to MesoScale protocol. Negative control wells were treated with DMSO. Compound activity is measured as a percentage of LPS-induced activity.

Some embodiments provide a compound of Formula (I), or a pharmaceutically acceptable salt thereof:

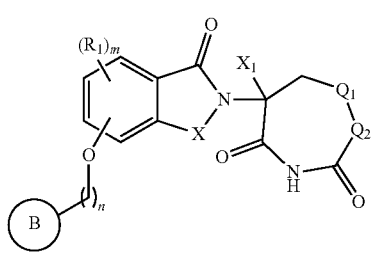

(I)

In some embodiments, $Q_1$ can be $CH_2$, O, $NR_2$, S, or a bond. In some embodiments, when $Q_1$ is a bond, then m is not 0. In some embodiments, $Q_2$ can be $CH_2$ or a bond. In some embodiments, when $Q_2$ can be a bond, $Q_1$ can be a bond or $CH_2$.

In some embodiments, X can be $CH_2$ or C=O. In some embodiments, X can be $CH_2$. In some embodiments, X can be C=O.

In some embodiments, $X_1$ can be hydrogen, deuterium, methyl, or fluoro. In some embodiments, $X_1$ can be hydrogen. In other embodiments, $X_1$ can be fluoro. In still other embodiments, $X_1$ can be methyl. In some embodiments, $X_1$ can be deuterium.

In some embodiments, Ring B can be

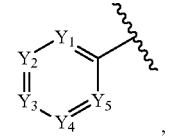

wherein $Y_1$ is N or $CR_{3A}$; $Y_2$ is N or $CR_{3B}$; $Y_3$ is N or $CR_{3C}$; $Y_4$ is N or $CR_{3D}$; $Y_5$ is N or $CR_{3E}$. In some embodiments, Ring B can be selected from:

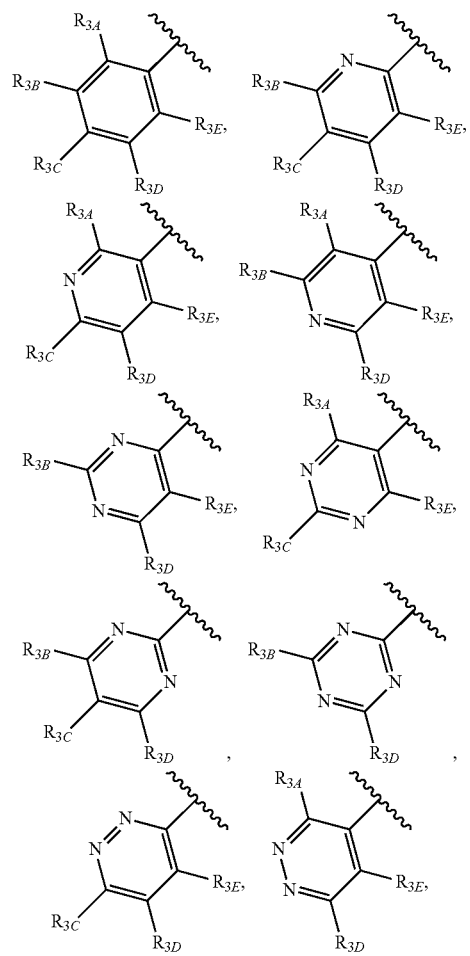

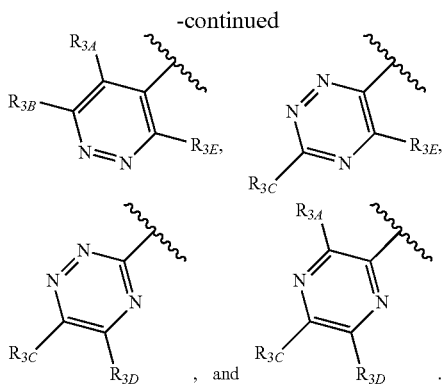

In some embodiments, Ring B is a phenyl group. In other embodiments, Ring B is a pyridyl group, such as a 2-pyridyl, 3-pyridyl, or 4-pyridyl group.

In some embodiments, m can be 0, 1, 2, or 3. In some embodiments, m is 1. In some embodiments, m is 2. In some embodiments, m is 3.

In some embodiments, each $R_1$ can independently be deuterium, hydroxyl, halogen, nitro, a substituted or unsubstituted amino, a substituted or unsubstituted $C_1$-$C_6$ alkoxy, a substituted or unsubstituted $C_1$-$C_6$ alkyl, a substituted or unsubstituted $C_2$-$C_6$ alkenyl, a substituted or unsubstituted $C_3$-$C_8$ cycloalkyl, a substituted or unsubstituted 3 to 10 membered heterocyclyl, a substituted or unsubstituted $C_6$-$C_{10}$ aryl, a substituted or unsubstituted 5 to 10 membered heteroaryl, or L-Y. In some embodiments, $R_1$ can be deuterium. In some embodiments, $R_1$ can be hydroxyl. In some embodiments, $R_1$ can be halogen, for example, fluoro, chloro, or bromo. In some embodiments, $R_1$ can be nitro. In some embodiments, $R_1$ can be a substituted amino, for example, a ($C_1$-$C_6$ alkyl)amino, a (3 to 10 membered heterocyclyl)amino or a ($C_6$-$C_{10}$ aryl)amino. In some embodiments, $R_1$ can be an unsubstituted amino. In some embodiments, $R_1$ can be a substituted $C_1$-$C_6$ alkyl which is an unsubstituted $C_1$-$C_6$ haloalkyl, for example, halomethyl, haloethyl, halo-n-propyl, haloisopropyl, halo-n-butyl, haloisobutyl, halo-sec-butyl, halo-t-butyl, halopentyl (straight-chained or branched), or halohexyl (straight-chained or branched). In some embodiments, $R_1$ can be an unsubstituted $C_1$-$C_6$ fluoroalkyl. In some embodiments, $R_1$ can be an unsubstituted $C_1$-$C_6$ chloroalkyl. In some embodiments, $R_1$ can be an unsubstituted $C_1$-$C_6$ haloalkyl including both fluorine and chlorine. In some embodiments, $R_1$ can be a substituted or unsubstituted $C_1$-$C_6$ alkoxy, for example, methoxy, ethoxy, n-propoxy, isopropoxy, n-butoxy, isobutoxy, sec-butoxy, t-butoxy, pentoxy (straight-chained or branched), or hexoxy (straight-chained or branched). In some embodiments, $R_1$ can be an unsubstituted $C_1$-$C_6$ alkoxy, for example, methoxy, ethoxy, n-propoxy, isopropoxy, n-butoxy, isobutoxy, sec-butoxy, t-butoxy, pentoxy (straight-chained or branched), or hexoxy (straight-chained or branched). In some embodiments, $R_1$ can be a substituted or unsubstituted $C_1$-$C_6$ alkyl, for example, methyl, ethyl, n-propyl, isopropyl, n-butyl, isobutyl, sec-butyl, t-butyl, pentyl (straight-chained or branched), or hexyl (straight-chained or branched). In some embodiments, $R_1$ can be an unsubstituted $C_1$-$C_6$ alkyl, for example, methyl, ethyl, n-propyl, isopropyl, n-butyl, isobutyl, sec-butyl, t-butyl, pentyl (straight-chained or branched), or hexyl (straight-chained or branched). In some embodiments, $R_1$ can be a substituted or unsubstituted $C_2$-$C_6$ alkenyl, for example, methylene, ethylene, n-propylene, isopropylene, n-butylene, isobutylene, sec-butylene, t-butylene, pentylene (straight-chained or branched), or hexylene (straight-chained or branched). In some embodiments, $R_1$ can be an unsubstituted $C_2$-$C_6$ alkenyl, for example, methylene, ethylene, n-propylene, isopropylene, n-butylene, isobutylene, sec-butylene, t-butylene, pentylene (straight-chained or branched), or hexylene (straight-chained or branched). In some embodiments, $R_1$ can be a substituted or unsubstituted $C_3$-$C_8$ cycloalkyl, for example, a $C_3$-$C_8$ monocyclic cycloalkyl or a $C_6$-$C_8$ bridged, fused, or spiro bicyclic cycloalkyl. In some embodiments, $R_1$ can be an unsubstituted $C_3$-$C_8$ $C_8$ cycloalkyl, for example, a $C_3$-$C_8$ monocyclic cycloalkyl or a $C_6$-$C_8$ bridged, fused, or spiro bicyclic cycloalkyl, such as cyclopropyl, cyclobutyl, cyclopentyl, cyclohexyl, cycloheptyl, cyclooctyl, octahydropentalene, decahydronaphthalene, bicyclo[4.2.0]octane, and bicyclo[3.1.1]heptane. In some embodiments, $R_1$ can be a substituted or unsubstituted 3 to 10 membered heterocyclyl, for example, a 3 to 8 membered monocyclic heterocyclyl, a 6 to 8 membered bridged, fused, or spiro bicyclic heterocyclyl, or a 3 to 8 membered nitrogen-containing heterocyclyl. In some embodiments, $R_1$ can be an unsubstituted 3 to 10 membered heterocyclyl, for example, a 3 to 8 membered monocyclic heterocyclyl, a 6 to 8 membered bridged, fused, or spiro bicyclic heterocyclyl, or a 3 to 8 membered nitrogen-containing heterocyclyl. In some embodiments, $R_1$ can be a substituted or unsubstituted $C_6$-$C_{10}$ aryl, for example, a phenyl or naphthyl. In some embodiments, $R_1$ can be an unsubstituted $C_6$-$C_{10}$ aryl such as phenyl or naphthyl. In some embodiments, $R_1$ can be a substituted or unsubstituted 5 to 10 membered heteroaryl, for example, a 5 membered heteroaryl, a 6 membered heteroaryl, a 10 membered heteroaryl, or a 5 to 10 membered heteroaryl with one or two nitrogen atoms. In some embodiments, $R_1$ can be an unsubstituted 5 to 10 membered heteroaryl, for example, a 5 membered heteroaryl, a 6 membered heteroaryl, a 10 membered heteroaryl, or a 5 to 10 membered heteroaryl with one or two nitrogen atoms. In some embodiments, $R_1$ can be L-Y, for example:

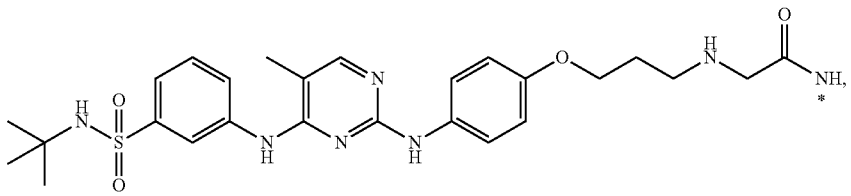

-continued
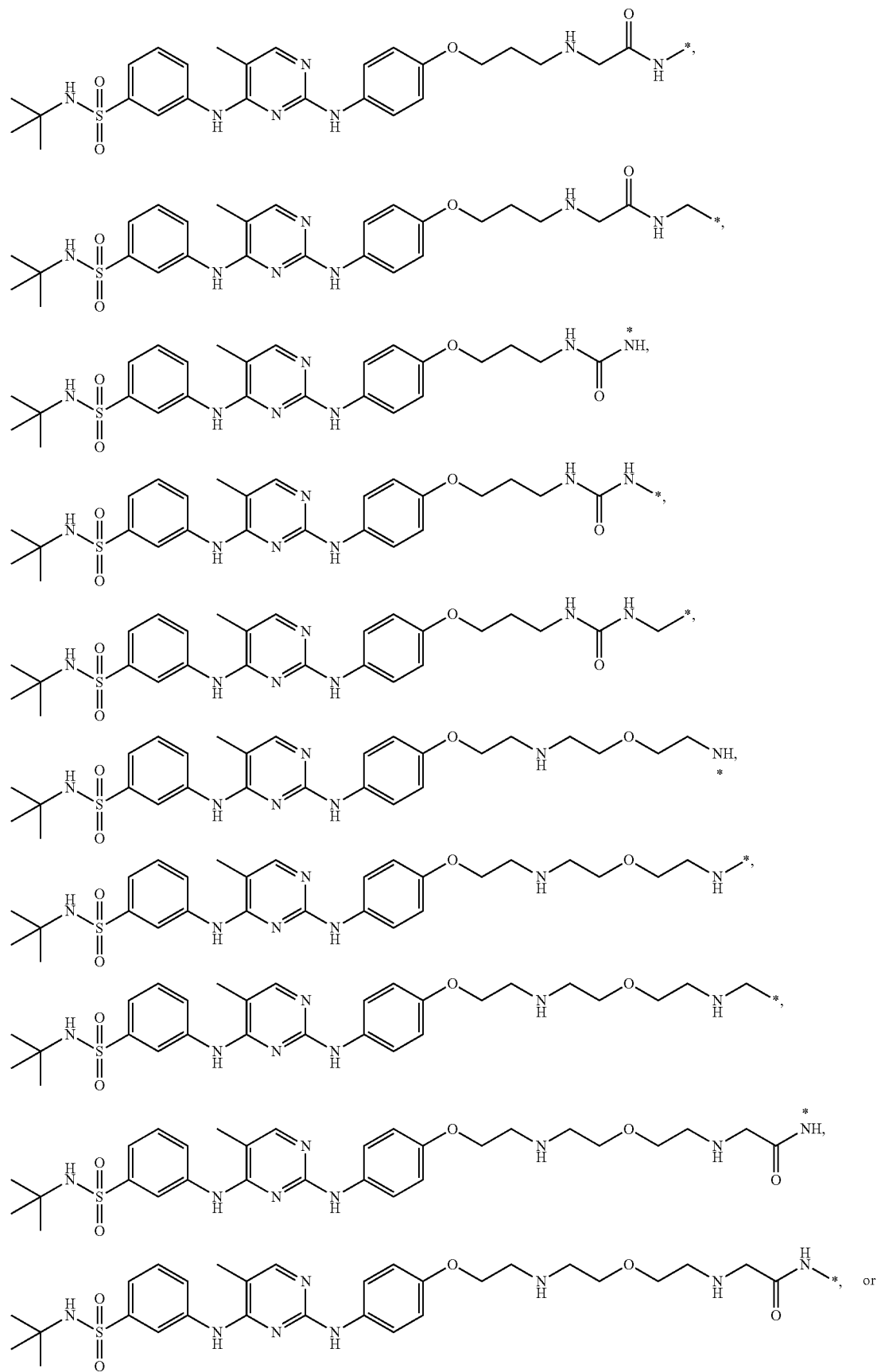

-continued

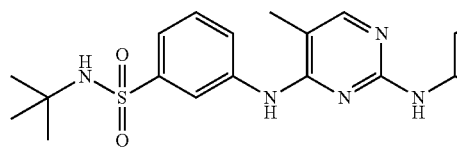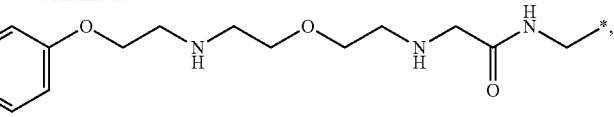

where "*" represents the point of connection of the L-Y moiety to the rest of the molecule. In some embodiments, when $R_1$ can be L-Y, none of $R_{3A}$, $R_{3B}$, $R_{3C}$, $R_{3D}$, and $R_{3E}$ can be L-Y.

In some embodiments, $R_2$ can be Hydrogen, deuterium, a substituted or unsubstituted $C_1$-$C_6$ alkyl, a substituted or unsubstituted $C_2$-$C_6$ alkenyl, acyl, or —($SO_2$)—$C_1$-$C_6$ alkyl. In some embodiments, $R_2$ can be hydrogen. In some embodiments, $R_2$ can be deuterium. In some embodiments, $R_2$ can be a substituted or unsubstituted $C_1$-$C_6$, for example, methyl, ethyl, n-propyl, isopropyl, n-butyl, isobutyl, sec-butyl, t-butyl, pentyl (straight-chained or branched), or hexyl (straight-chained or branched). In some embodiments, $R_2$ can be an unsubstituted $C_1$-$C_6$, for example, methyl, ethyl, n-propyl, isopropyl, n-butyl, isobutyl, sec-butyl, t-butyl, pentyl (straight-chained or branched), or hexyl (straight-chained or branched). In some embodiments, $R_2$ can be a substituted or unsubstituted $C_2$-$C_6$ alkenyl, for example, methylene, ethylene, n-propylene, isopropylene, n-butylene, isobutylene, sec-butylene, t-butylene, pentylene (straight-chained or branched), or hexylene (straight-chained or branched). In some embodiments, $R_2$ can be an unsubstituted $C_2$-$C_6$ alkenyl, for example, methylene, ethylene, n-propylene, isopropylene, n-butylene, isobutylene, sec-butylene, t-butylene, pentylene (straight-chained or branched), or hexylene (straight-chained or branched). In some embodiments, $R_2$ can be acyl, for example, a $C_1$-$C_6$ alkyl carbonyl such as acetyl (ethan-1-one), propan-1-one, or 3-methylbutan-1-one. In some embodiments, $R_2$ can be —($SO_2$)—$C_1$-$C_6$ alkyl, for example, —($SO_2$)-methyl, —($SO_2$)-ethyl, —($SO_2$)-n-propyl, —($SO_2$)-isopropyl, —($SO_2$)-n-butyl, —($SO_2$)-isobutyl, —($SO_2$)-sec-butyl, —($SO_2$)-t-butyl, —($SO_2$)-pentyl (straight-chained or branched), or —($SO_2$)-hexyl (straight-chained or branched).

In some embodiments, n can be 1, 2, or 3. In some embodiments, n can be 1 or 2. In some embodiments, n can be 1. In some embodiments, n can be 2.

In some embodiments, each of $R_{3A}$, $R_{3B}$, $R_{3C}$, $R_{3D}$, and $R_{3E}$ can be independently Hydrogen, deuterium, hydroxyl, halogen, nitro, a substituted or unsubstituted amino, a substituted or unsubstituted $C_1$-$C_6$ alkoxy, a substituted or unsubstituted $C_1$-$C_6$ alkyl, a substituted or unsubstituted $C_2$-$C_6$ alkenyl, a substituted or unsubstituted $C_3$-$C_8$ cycloalkyl, a substituted or unsubstituted 3 to 10 membered heterocyclyl, a substituted or unsubstituted alkoxyalkyl, a substituted or unsubstituted cycloalkylalkyl, a substituted or unsubstituted heterocyclylalkyl, a substituted or unsubstituted aralkyl, a substituted or unsubstituted heteroaralkyl, or L-Y. In some embodiments, one or more of $R_{3A}$, $R_{3B}$, $R_{3C}$, $R_{3D}$, and $R_{3E}$ can be hydrogen. In some embodiments, one or more of $R_{3A}$, $R_{3B}$, $R_{3C}$, $R_{3D}$, and $R_{3E}$ can be deuterium. In some embodiments, one or more of $R_{3A}$, $R_{3B}$, $R_{3C}$, $R_{3D}$, and $R_{3E}$ can be hydroxyl. In some embodiments, one or more of $R_{3A}$, $R_{3B}$, $R_{3C}$, $R_{3D}$, and $R_{3E}$ can be halogen, for example, fluoro, chloro, or bromo. In some embodiments, one or more of $R_{3A}$, $R_{3B}$, $R_{3C}$, $R_{3D}$, and $R_{3E}$ can be nitro. In some embodiments, one or more of $R_{3A}$, $R_{3B}$, $R_{3C}$, $R_{3D}$, and $R_{3E}$ can be a substituted amino, for example, a ($C_1$-$C_6$ alkyl)amino, a (3 to 10 membered heterocyclyl)amino or a ($C_6$-$C_{10}$ aryl)amino. In some embodiments, one or more of $R_{3A}$, $R_{3B}$, $R_{3C}$, $R_{3D}$, and $R_{3E}$ can be an unsubstituted amino. In some embodiments, one or more of $R_{3A}$, $R_{3B}$, $R_{3C}$, $R_{3D}$, and $R_{3E}$ can be a substituted $C_1$-$C_6$ alkyl which is an unsubstituted $C_1$-$C_6$ haloalkyl, for example, halomethyl, haloethyl, halo-n-propyl, haloisopropyl, halo-n-butyl, haloisobutyl, halo-sec-butyl, halo-t-butyl, halopentyl (straight-chained or branched), or halohexyl (straight-chained or branched). In some embodiments, one or more of $R_{3A}$, $R_{3B}$, $R_{3C}$, $R_{3D}$, and $R_{3E}$ can be an unsubstituted $C_1$-$C_6$ fluoroalkyl. In some embodiments, one or more of $R_{3A}$, $R_{3B}$, $R_{3C}$, $R_{3D}$, and $R_{3E}$ can be an unsubstituted $C_1$-$C_6$ chloroalkyl. In some embodiments, one or more of $R_{3A}$, $R_{3B}$, $R_{3C}$, $R_{3D}$, and $R_{3E}$ can be an unsubstituted $C_1$-$C_6$ haloalkyl including both fluorine and chlorine. In some embodiments, one or more of $R_{3A}$, $R_{3B}$, $R_{3C}$, $R_{3D}$, and $R_{3E}$ can be a substituted or unsubstituted $C_1$-$C_6$ alkoxy, for example, methoxy, ethoxy, n-propoxy, isopropoxy, n-butoxy, isobutoxy, sec-butoxy, t-butoxy, pentoxy (straight-chained or branched), or hexoxy (straight-chained or branched). In some embodiments, one or more of $R_{3A}$, $R_{3B}$, $R_{3C}$, $R_{3D}$, and $R_{3E}$ can be an unsubstituted $C_1$-$C_6$ alkoxy, for example, methoxy, ethoxy, n-propoxy, isopropoxy, n-butoxy, isobutoxy, sec-butoxy, t-butoxy, pentoxy (straight-chained or branched), or hexoxy (straight-chained or branched). In some embodiments, one or more of $R_{3A}$, $R_{3B}$, $R_{3C}$, $R_{3D}$, and $R_{3E}$ can be a substituted or unsubstituted $C_1$-$C_6$ alkyl, for example, methyl, ethyl, n-propyl, isopropyl, n-butyl, isobutyl, sec-butyl, t-butyl, pentyl (straight-chained or branched), or hexyl (straight-chained or branched). In some embodiments, one or more of $R_{3A}$, $R_{3B}$, $R_{3C}$, $R_{3D}$, and $R_{3E}$ can be an unsubstituted $C_1$-$C_6$ alkyl, for example, methyl, ethyl, n-propyl, isopropyl, n-butyl, isobutyl, sec-butyl, t-butyl, pentyl (straight-chained or branched), or hexyl (straight-chained or branched). In some embodiments, one or more of $R_{3A}$, $R_{3B}$, $R_{3C}$, $R_{3D}$, and $R_{3E}$ can be a substituted or unsubstituted $C_2$-$C_6$ alkenyl, for example, methylene, ethylene, n-propylene, isopropylene, n-butylene, isobutylene, sec-butylene, t-butylene, pentylene (straight-chained or branched), or hexylene (straight-chained or branched). In some embodiments, one or more of $R_{3A}$, $R_{3B}$, $R_{3C}$, $R_{3D}$, and $R_{3E}$ can be an unsubstituted $C_2$-$C_6$ alkenyl, for example, methylene, ethylene, n-propylene, isopropylene, n-butylene, isobutylene, sec-butylene, t-butylene, pentylene (straight-chained or branched), or hexylene (straight-chained or branched). In some embodiments, one or more of $R_{3A}$, $R_{3B}$, $R_{3C}$, $R_{3D}$, and $R_{3E}$ can be a substituted or unsubstituted $C_3$-$C_8$ cycloalkyl, for example, a $C_3$-$C_8$ monocyclic cycloalkyl or a $C_6$-$C_8$ bridged, fused, or spiro bicyclic cycloalkyl. In some embodiments, one or more of $R_{3A}$, $R_{3B}$, $R_{3C}$, $R_{3D}$, and $R_{3E}$ can be an unsubstituted $C_3$-$C_8$ cycloalkyl, for example, a $C_3$-$C_8$ monocyclic cycloalkyl or a $C_6$-$C_8$ bridged, fused, or spiro bicyclic cycloalkyl, such as cyclopropyl, cyclobutyl, cyclopentyl, cyclohexyl, cycloheptyl, cyclooctyl, octahydropentalene, decahydronaphthalene, bicyclo

[4.2.0]octane, and bicyclo[3.1.1]heptane. In some embodiments, one or more of $R_{3A}$, $R_{3B}$, $R_{3C}$, $R_{3D}$, and $R_{3E}$ can be a substituted or unsubstituted 3 to 10 membered heterocyclyl, for example, a 3 to 8 membered monocyclic heterocyclyl, a 6 to 8 membered bridged, fused, or spiro bicyclic heterocyclyl, or a 3 to 8 membered nitrogen-containing heterocyclyl. In some embodiments, one or more of $R_{3A}$, $R_{3B}$, $R_{3C}$, $R_{3D}$, and $R_{3E}$ can be an unsubstituted 3 to 10 membered heterocyclyl, for example, a 3 to 8 membered monocyclic heterocyclyl, a 6 to 8 membered bridged, fused, or spiro bicyclic heterocyclyl, or a 3 to 8 membered nitrogen-containing heterocyclyl. In some embodiments, one or more of $R_{3A}$, $R_{3B}$, $R_{3C}$, $R_{3D}$, and $R_{3E}$ can be a substituted or unsubstituted alkoxyalkyl, for example, a $C_1$-$C_4$ alkoxy, as described herein and a $C_1$-$C_4$ alkyl, as described herein. In some embodiments, one or more of $R_{3A}$, $R_{3B}$, $R_{3C}$, $R_{3D}$, and $R_{3E}$ can be an unsubstituted alkoxyalkyl, for example, a $C_1$-$C_4$ alkoxy, as described herein and a $C_1$-$C_4$ alkyl, as described herein, such as methoxymethyl, ethoxymethyl, or ethoxypropyl. In some embodiments, one or more of $R_{3A}$, $R_{3B}$, $R_{3C}$, $R_{3D}$, and $R_{3E}$ can be a substituted or unsubstituted cycloalkylalkyl, for example, a $C_3$-$C_8$ monocyclic cycloalkyl or a $C_6$-$C_8$ bridged, fused, or spiro bicyclic cycloalkyl and a $C_1$-$C_6$ alkyl, as described herein. In some embodiments, one or more of $R_{3A}$, $R_{3B}$, $R_{3C}$, $R_{3D}$, and $R_{3E}$ can be an unsubstituted cycloalkylalkyl, for example, a $C_3$-$C_8$ monocyclic cycloalkyl or a $C_6$-$C_8$ bridged, fused, or spiro bicyclic cycloalkyl and a $C_1$-$C_6$ alkyl, as described herein, such as cyclopropylmethyl, cyclobutylmethyl, cyclopentylethyl, or cyclohexylethyl. In some embodiments, one or more of $R_{3A}$, $R_{3B}$, $R_{3C}$, $R_{3D}$, and $R_{3E}$ can be a substituted or unsubstituted heterocyclylalkyl, for example, a 3 to 8 membered monocyclic heterocyclyl, a 6 to 8 membered bridged, fused, or spiro bicyclic heterocyclyl, or a 3 to 8 membered nitrogen-containing heterocyclyl, and a $C_1$-$C_6$ alkyl, as described herein. In some embodiments, one or more of $R_{3A}$, $R_{3B}$, $R_{3C}$, $R_{3D}$, and $R_{3E}$ can be an unsubstituted heterocyclylalkyl, for example, a 3 to 8 membered monocyclic heterocyclyl, a 6 to 8 membered bridged, fused, or spiro bicyclic heterocyclyl, or a 3 to 8 membered nitrogen-containing heterocyclyl, and a $C_1$-$C_6$ alkyl, as described herein, such as pyrrolidinylmethyl, piperidinylmethyl, piperazinylmethyl, or morpholinomethyl. In some embodiments, one or more of $R_{3A}$, $R_{3B}$, $R_{3C}$, $R_{3D}$, and $R_{3E}$ can be a substituted or unsubstituted aralkyl, for example, a $C_6$-$C_{10}$ aryl such as phenyl or naphthyl and a $C_1$-$C_6$ alkyl, as described herein. In some embodiments, one or more of $R_{3A}$, $R_{3B}$, $R_{3C}$, $R_{3D}$, and $R_{3E}$ can be an unsubstituted aralkyl, for example, a $C_6$-$C_{10}$ aryl such as phenyl or naphthyl and a $C_1$-$C_6$ alkyl, as described herein, such as benzyl or phenethyl. In some embodiments, one or more of $R_{3A}$, $R_{3B}$, $R_{3C}$, $R_{3D}$, and $R_{3E}$ can be a substituted or unsubstituted heteroaralkyl, for example, a 5 membered heteroaryl, a 6 membered heteroaryl, a 10 membered heteroaryl, or a 5 to 10 membered heteroaryl with one or two nitrogen atoms, and a $C_1$-$C_6$ alkyl, as described herein. In some embodiments, one or more of $R_{3A}$, $R_{3B}$, $R_{3C}$, $R_{3D}$, and $R_{3E}$ can be an unsubstituted heteroaralkyl, for example, a 5 membered heteroaryl, a 6 membered heteroaryl, a 10 membered heteroaryl, or a 5 to 10 membered heteroaryl with one or two nitrogen atoms, and a $C_1$-$C_6$ alkyl, as described herein, such as pyridinylmethyl, pyrimidinylmethyl, or imidazolomethyl. In some embodiments, one of $R_{3A}$, $R_{3B}$, $R_{3C}$, $R_{3D}$, and $R_{3E}$ can be L-Y, for example:

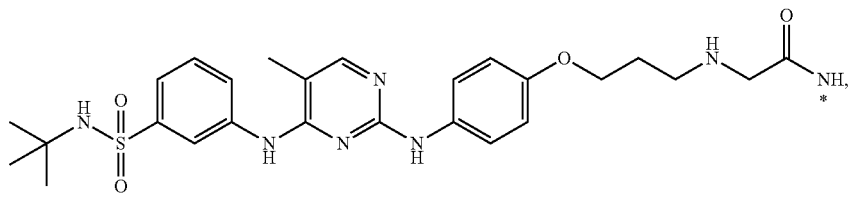

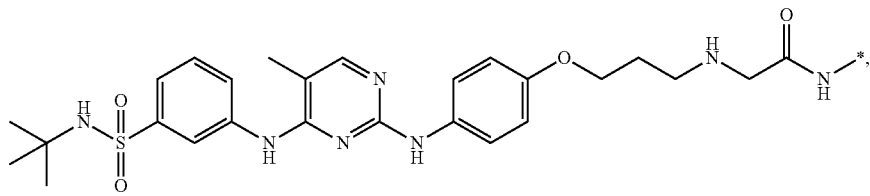

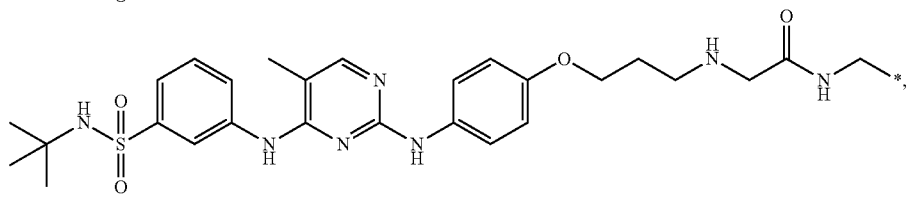

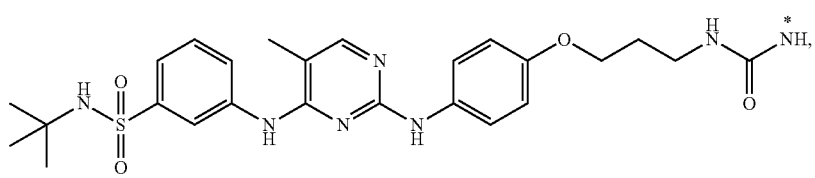

-continued

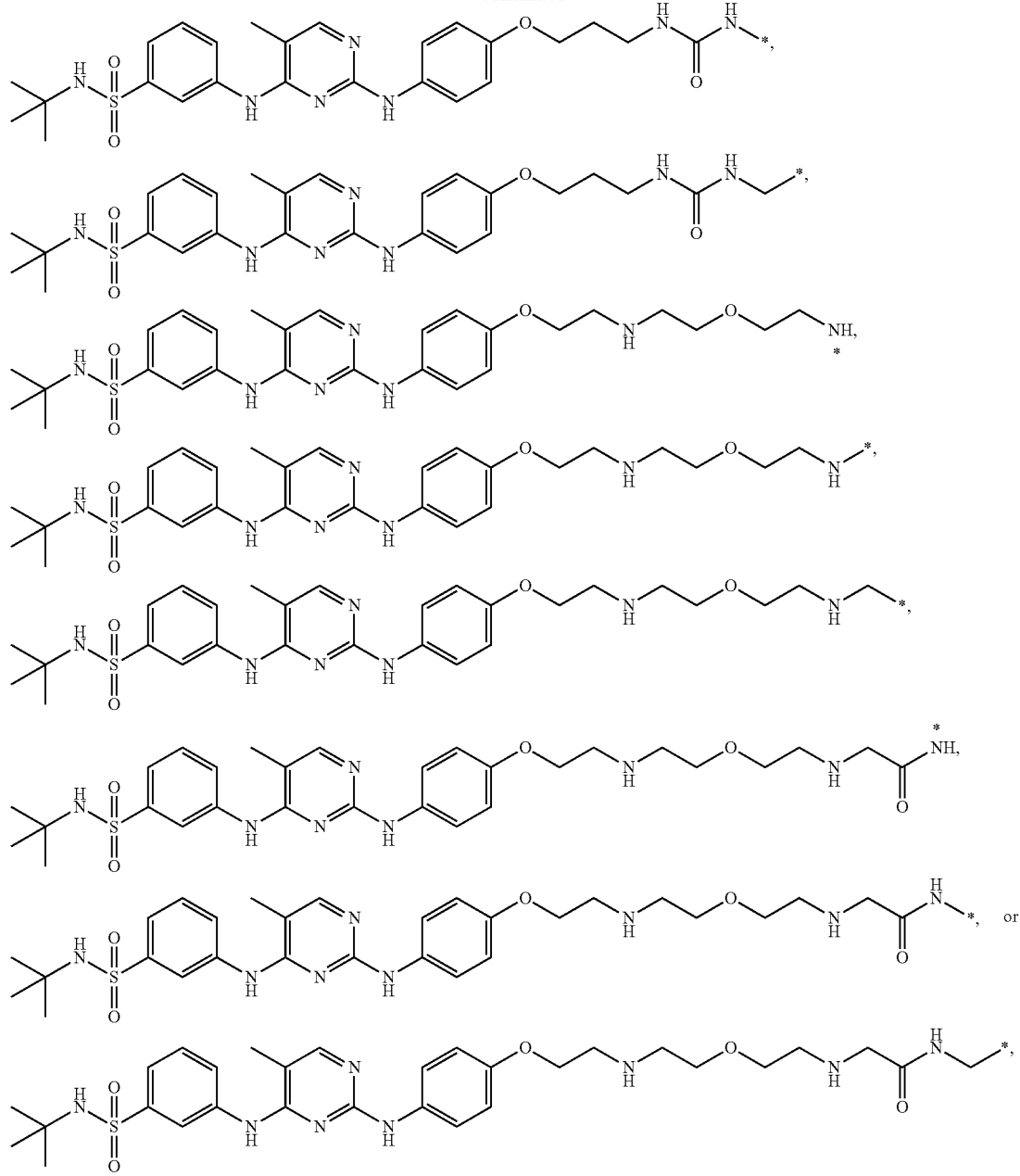

where "*" represents the point of connection of the L-Y moiety to the rest of the molecule.

In some embodiments, when any one of $R_{3A}$, $R_{3B}$, $R_{3C}$, $R_{3D}$, and $R_{3E}$ can be L-Y, $R_1$ cannot be L-Y. In some embodiments, $R_{3A}$ cannot be hydrogen. In some embodiments, $R_{3B}$ cannot be hydrogen. In some embodiments, $R_{3C}$ cannot be hydrogen. In some embodiments, $R_{3D}$ cannot be hydrogen. In some embodiments, $R_{3E}$ cannot be hydrogen.

In some embodiments, L can be —$Z_1$—($R_4$)$_t$—$Z_2$—; —$Z_1$—($R_4$—O—$R_4$)$_t$—$Z_2$—; —$Z_1$($R_4$—NH—$R_4$)$_t$—$Z_2$—; —$Z_1$—($R_4$—(NHCO)—$R_4$)$_t$—$Z_2$—; or —$Z_1$—($R_4$—(CONH)—$R_4$)$_t$—$Z_2$—. In some embodiments, L can be —$Z_1$—($R_4$—O—$R_4$)$_t$—$Z_2$—. In other embodiments, L can be —$Z_1$($R_4$—NH—$R_4$)$_t$—$Z_2$—. In still other embodiments, L can be —$Z_1$—($R_4$—(NHCO)—$R_4$)$_t$—$Z_2$—. In some embodiments, L can be $Z_1$—($R_4$—(CONH)—$R_4$)$_t$—$Z_2$—.

In other embodiments, L can be —$Z_1$—($R_4$)$_t$—$Z_2$—. In still other embodiments, L can be —$Z_1$—($R_4$—(NHC(O)NH)—$R_4$)$_t$—$Z_2$—.

In some embodiments, each $R_4$ can be independently an unsubstituted $C_1$-$C_6$ alkylene, for example, methylene, ethylene, n-propylene, isopropylene, n-butylene, isobutylene, sec-butylene, t-butylene, pentylene (straight-chained or branched), or hexylene (straight-chained or branched). In some embodiments, each $R_4$ group is the same. In some embodiments, each $R_4$ group is different.

In some embodiments, t can be 1, 2, 3, 4, 5, or 6. In some embodiments, t can be 1. In some embodiments, t can be 2. In some embodiments, t can be 3. In some embodiments, t can be 4. In some embodiments, t can be 5. In some embodiments, t can be 6.

Some embodiments of L are shown in Table A, below.

TABLE A

| L | $Z_1$ | $Z_2$ | t |
|---|---|---|---|
| $-Z_1-(R_4-O-R_4)_r-Z_2-$ | $-CH_2NH(CO)-$ | $-NH-$ | 1 |
| $-Z_1-(R_4-O-R_4)_r-Z_2-$ | $-NH-$ | $-NH-$ | 1 |
| $-Z_1-(R_4-O-R_4)_r-Z_2-$ | $-O-$ | $-NH-$ | 1 |
| $-Z_1-(R_4-O-R_4)_r-Z_2-$ | $-CH_2-$ | $-NH-$ | 1 |
| $-Z_1-(R_4-O-R_4)_r-Z_2-$ | $-NH(CO)-$ | $-NH-$ | 1 |
| $-Z_1-(R_4-O-R_4)_r-Z_2-$ | $-CH_2NH-$ | $-NH-$ | 1 |
| $-Z_1-(R_4-O-R_4)_r-Z_2-$ | $-NHCH_2-$ | $-NH-$ | 1 |
| $-Z_1-(R_4-O-R_4)_r-Z_2-$ | $-CH_2NH(CO)-$ | $-O-$ | 1 |
| $-Z_1-(R_4-O-R_4)_r-Z_2-$ | $-NH-$ | $-O-$ | 1 |
| $-Z_1-(R_4-O-R_4)_r-Z_2-$ | $-O-$ | $-O-$ | 1 |
| $-Z_1-(R_4-O-R_4)_r-Z_2-$ | $-CH_2-$ | $-O-$ | 1 |
| $-Z_1-(R_4-O-R_4)_r-Z_2-$ | $-NH(CO)-$ | $-O-$ | 1 |
| $-Z_1-(R_4-O-R_4)_r-Z_2-$ | $-CH_2NH-$ | $-O-$ | 1 |
| $-Z_1-(R_4-O-R_4)_r-Z_2-$ | $-NHCH_2-$ | $-O-$ | 1 |
| $-Z_1-(R_4-O-R_4)_r-Z_2-$ | $-CH_2NH(CO)-$ | $-CH_2-$ | 1 |
| $-Z_1-(R_4-O-R_4)_r-Z_2-$ | $-NH-$ | $-CH_2-$ | 1 |
| $-Z_1-(R_4-O-R_4)_r-Z_2-$ | $-O-$ | $-CH_2-$ | 1 |
| $-Z_1-(R_4-O-R_4)_r-Z_2-$ | $-CH_2-$ | $-CH_2-$ | 1 |
| $-Z_1-(R_4-O-R_4)_r-Z_2-$ | $-NH(CO)-$ | $-CH_2-$ | 1 |
| $-Z_1-(R_4-O-R_4)_r-Z_2-$ | $-CH_2NH-$ | $-CH_2-$ | 1 |
| $-Z_1-(R_4-O-R_4)_r-Z_2-$ | $-NHCH_2-$ | $-CH_2-$ | 1 |
| $-Z_1-(R_4-O-R_4)_r-Z_2-$ | $-CH_2NH(CO)-$ | $-NH(CO)-$ | 1 |
| $-Z_1-(R_4-O-R_4)_r-Z_2-$ | $-NH-$ | $-NH(CO)-$ | 1 |
| $-Z_1-(R_4-O-R_4)_r-Z_2-$ | $-O-$ | $-NH(CO)-$ | 1 |
| $-Z_1-(R_4-O-R_4)_r-Z_2-$ | $-CH_2-$ | $-NH(CO)-$ | 1 |
| $-Z_1-(R_4-O-R_4)_r-Z_2-$ | $-NH(CO)-$ | $-NH(CO)-$ | 1 |
| $-Z_1-(R_4-O-R_4)_r-Z_2-$ | $-CH_2NH-$ | $-NH(CO)-$ | 1 |
| $-Z_1-(R_4-O-R_4)_r-Z_2-$ | $-NHCH_2-$ | $-NH(CO)-$ | 1 |
| $-Z_1-(R_4-O-R_4)_r-Z_2-$ | $-CH_2NH(CO)-$ | $-(CO)NH-$ | 1 |
| $-Z_1-(R_4-O-R_4)_r-Z_2-$ | $-NH-$ | $-(CO)NH-$ | 1 |
| $-Z_1-(R_4-O-R_4)_r-Z_2-$ | $-O-$ | $-(CO)NH-$ | 1 |
| $-Z_1-(R_4-O-R_4)_r-Z_2-$ | $-CH_2-$ | $-(CO)NH-$ | 1 |
| $-Z_1-(R_4-O-R_4)_r-Z_2-$ | $-NH(CO)-$ | $-(CO)NH-$ | 1 |
| $-Z_1-(R_4-O-R_4)_r-Z_2-$ | $-CH_2NH-$ | $-(CO)NH-$ | 1 |
| $-Z_1-(R_4-O-R_4)_r-Z_2-$ | $-NHCH_2-$ | $-(CO)NH-$ | 1 |
| $-Z_1-(R_4-O-R_4)_r-Z_2-$ | $-CH_2NH(CO)-$ | $-CH_2NH-$ | 1 |
| $-Z_1-(R_4-O-R_4)_r-Z_2-$ | $-NH-$ | $-CH_2NH-$ | 1 |
| $-Z_1-(R_4-O-R_4)_r-Z_2-$ | $-O-$ | $-CH_2NH-$ | 1 |
| $-Z_1-(R_4-O-R_4)_r-Z_2-$ | $-CH_2-$ | $-CH_2NH-$ | 1 |
| $-Z_1-(R_4-O-R_4)_r-Z_2-$ | $-NH(CO)-$ | $-CH_2NH-$ | 1 |
| $-Z_1-(R_4-O-R_4)_r-Z_2-$ | $-CH_2NH-$ | $-CH_2NH-$ | 1 |
| $-Z_1-(R_4-O-R_4)_r-Z_2-$ | $-NHCH_2-$ | $-CH_2NH-$ | 1 |
| $-Z_1-(R_4-O-R_4)_r-Z_2-$ | $-CH_2NH(CO)-$ | $-NHCH_2-$ | 1 |
| $-Z_1-(R_4-O-R_4)_r-Z_2-$ | $-NH-$ | $-NHCH_2-$ | 1 |
| $-Z_1-(R_4-O-R_4)_r-Z_2-$ | $-O-$ | $-NHCH_2-$ | 1 |
| $-Z_1-(R_4-O-R_4)_r-Z_2-$ | $-CH_2-$ | $-NHCH_2-$ | 1 |
| $-Z_1-(R_4-O-R_4)_r-Z_2-$ | $-NH(CO)-$ | $-NHCH_2-$ | 1 |
| $-Z_1-(R_4-O-R_4)_r-Z_2-$ | $-CH_2NH-$ | $-NHCH_2-$ | 1 |
| $-Z_1-(R_4-O-R_4)_r-Z_2-$ | $-NHCH_2-$ | $-NHCH_2-$ | 1 |
| $-Z_1(R_4-NH-R_4)_r-Z_2-$ | $-CH_2NH(CO)-$ | $-NH-$ | 1 |
| $-Z_1(R_4-NH-R_4)_r-Z_2-$ | $-NH-$ | $-NH-$ | 1 |
| $-Z_1(R_4-NH-R_4)_r-Z_2-$ | $-O-$ | $-NH-$ | 1 |
| $-Z_1(R_4-NH-R_4)_r-Z_2-$ | $-CH_2-$ | $-NH-$ | 1 |
| $-Z_1(R_4-NH-R_4)_r-Z_2-$ | $-NH(CO)-$ | $-NH-$ | 1 |
| $-Z_1(R_4-NH-R_4)_r-Z_2-$ | $-CH_2NH-$ | $-NH-$ | 1 |
| $-Z_1(R_4-NH-R_4)_r-Z_2-$ | $-NHCH_2-$ | $-NH-$ | 1 |
| $-Z_1(R_4-NH-R_4)_r-Z_2-$ | $-CH_2NH(CO)-$ | $-O-$ | 1 |
| $-Z_1(R_4-NH-R_4)_r-Z_2-$ | $-NH-$ | $-O-$ | 1 |
| $-Z_1(R_4-NH-R_4)_r-Z_2-$ | $-O-$ | $-O-$ | 1 |
| $-Z_1(R_4-NH-R_4)_r-Z_2-$ | $-CH_2-$ | $-O-$ | 1 |
| $-Z_1(R_4-NH-R_4)_r-Z_2-$ | $-NH(CO)-$ | $-O-$ | 1 |
| $-Z_1(R_4-NH-R_4)_r-Z_2-$ | $-CH_2NH-$ | $-O-$ | 1 |
| $-Z_1(R_4-NH-R_4)_r-Z_2-$ | $-NHCH_2-$ | $-O-$ | 1 |
| $-Z_1(R_4-NH-R_4)_r-Z_2-$ | $-CH_2NH(CO)-$ | $-CH_2-$ | 1 |
| $-Z_1(R_4-NH-R_4)_r-Z_2-$ | $-NH-$ | $-CH_2-$ | 1 |
| $-Z_1(R_4-NH-R_4)_r-Z_2-$ | $-O-$ | $-CH_2-$ | 1 |
| $-Z_1(R_4-NH-R_4)_r-Z_2-$ | $-CH_2-$ | $-CH_2-$ | 1 |
| $-Z_1(R_4-NH-R_4)_r-Z_2-$ | $-NH(CO)-$ | $-CH_2-$ | 1 |
| $-Z_1(R_4-NH-R_4)_r-Z_2-$ | $-CH_2NH-$ | $-CH_2-$ | 1 |
| $-Z_1(R_4-NH-R_4)_r-Z_2-$ | $-NHCH_2-$ | $-CH_2-$ | 1 |
| $-Z_1(R_4-NH-R_4)_r-Z_2-$ | $-CH_2NH(CO)-$ | $-NH(CO)-$ | 1 |
| $-Z_1(R_4-NH-R_4)_r-Z_2-$ | $-NH-$ | $-NH(CO)-$ | 1 |
| $-Z_1(R_4-NH-R_4)_r-Z_2-$ | $-O-$ | $-NH(CO)-$ | 1 |
| $-Z_1(R_4-NH-R_4)_r-Z_2-$ | $-CH_2-$ | $-NH(CO)-$ | 1 |
| $-Z_1(R_4-NH-R_4)_r-Z_2-$ | $-NH(CO)-$ | $-NH(CO)-$ | 1 |
| $-Z_1(R_4-NH-R_4)_r-Z_2-$ | $-CH_2NH-$ | $-NH(CO)-$ | 1 |

TABLE A-continued

| L | $Z_1$ | $Z_2$ | t |
|---|---|---|---|
| $-Z_1(R_4-NH-R_4)_t-Z_2-$ | $-NHCH_2-$ | $-NH(CO)-$ | 1 |
| $-Z_1(R_4-NH-R_4)_t-Z_2-$ | $-CH_2NH(CO)-$ | $-(CO)NH-$ | 1 |
| $-Z_1(R_4-NH-R_4)_t-Z_2-$ | $-NH-$ | $-(CO)NH-$ | 1 |
| $-Z_1(R_4-NH-R_4)_t-Z_2-$ | $-O-$ | $-(CO)NH-$ | 1 |
| $-Z_1(R_4-NH-R_4)_t-Z_2-$ | $-CH_2-$ | $-(CO)NH-$ | 1 |
| $-Z_1(R_4-NH-R_4)_t-Z_2-$ | $-NH(CO)-$ | $-(CO)NH-$ | 1 |
| $-Z_1(R_4-NH-R_4)_t-Z_2-$ | $-CH_2NH-$ | $-(CO)NH-$ | 1 |
| $-Z_1(R_4-NH-R_4)_t-Z_2-$ | $-NHCH_2-$ | $-(CO)NH-$ | 1 |
| $-Z_1(R_4-NH-R_4)_t-Z_2-$ | $-CH_2NH(CO)-$ | $-CH_2NH-$ | 1 |
| $-Z_1(R_4-NH-R_4)_t-Z_2-$ | $-NH-$ | $-CH_2NH-$ | 1 |
| $-Z_1(R_4-NH-R_4)_t-Z_2-$ | $-O-$ | $-CH_2NH-$ | 1 |
| $-Z_1(R_4-NH-R_4)_t-Z_2-$ | $-CH_2-$ | $-CH_2NH-$ | 1 |
| $-Z_1(R_4-NH-R_4)_t-Z_2-$ | $-NH(CO)-$ | $-CH_2NH-$ | 1 |
| $-Z_1(R_4-NH-R_4)_t-Z_2-$ | $-CH_2NH-$ | $-CH_2NH-$ | 1 |
| $-Z_1(R_4-NH-R_4)_t-Z_2-$ | $-NHCH_2-$ | $-CH_2NH-$ | 1 |
| $-Z_1(R_4-NH-R_4)_t-Z_2-$ | $-CH_2NH(CO)-$ | $-NHCH_2-$ | 1 |
| $-Z_1(R_4-NH-R_4)_t-Z_2-$ | $-NH-$ | $-NHCH_2-$ | 1 |
| $-Z_1(R_4-NH-R_4)_t-Z_2-$ | $-O-$ | $-NHCH_2-$ | 1 |
| $-Z_1(R_4-NH-R_4)_t-Z_2-$ | $-CH_2-$ | $-NHCH_2-$ | 1 |
| $-Z_1(R_4-NH-R_4)_t-Z_2-$ | $-NH(CO)-$ | $-NHCH_2-$ | 1 |
| $-Z_1(R_4-NH-R_4)_t-Z_2-$ | $-CH_2NH-$ | $-NHCH_2-$ | 1 |
| $-Z_1(R_4-NH-R_4)_t-Z_2-$ | $-NHCH_2-$ | $-NHCH_2-$ | 1 |
| $-Z_1-(R_4-(NHCO)-R_4)_t-Z_2-$ | $-CH_2NH(CO)-$ | $-NH-$ | 1 |
| $-Z_1-(R_4-(NHCO)-R_4)_t-Z_2-$ | $-NH-$ | $-NH-$ | 1 |
| $-Z_1-(R_4-(NHCO)-R_4)_t-Z_2-$ | $-O-$ | $-NH-$ | 1 |
| $-Z_1-(R_4-(NHCO)-R_4)_t-Z_2-$ | $-CH_2-$ | $-NH-$ | 1 |
| $-Z_1-(R_4-(NHCO)-R_4)_t-Z_2-$ | $-NH(CO)-$ | $-NH-$ | 1 |
| $-Z_1-(R_4-(NHCO)-R_4)_t-Z_2-$ | $-CH_2NH-$ | $-NH-$ | 1 |
| $-Z_1-(R_4-(NHCO)-R_4)_t-Z_2-$ | $-NHCH_2-$ | $-NH-$ | 1 |
| $-Z_1-(R_4-(NHCO)-R_4)_t-Z_2-$ | $-CH_2NH(CO)-$ | $-O-$ | 1 |
| $-Z_1-(R_4-(NHCO)-R_4)_t-Z_2-$ | $-NH-$ | $-O-$ | 1 |
| $-Z_1-(R_4-(NHCO)-R_4)_t-Z_2-$ | $-O-$ | $-O-$ | 1 |
| $-Z_1-(R_4-(NHCO)-R_4)_t-Z_2-$ | $-CH_2-$ | $-O-$ | 1 |
| $-Z_1-(R_4-(NHCO)-R_4)_t-Z_2-$ | $-NH(CO)-$ | $-O-$ | 1 |
| $-Z_1-(R_4-(NHCO)-R_4)_t-Z_2-$ | $-CH_2NH-$ | $-O-$ | 1 |
| $-Z_1-(R_4-(NHCO)-R_4)_t-Z_2-$ | $-NHCH_2-$ | $-O-$ | 1 |
| $-Z_1-(R_4-(NHCO)-R_4)_t-Z_2-$ | $-CH_2NH(CO)-$ | $-CH_2-$ | 1 |
| $-Z_1-(R_4-(NHCO)-R_4)_t-Z_2-$ | $-NH-$ | $-CH_2-$ | 1 |
| $-Z_1-(R_4-(NHCO)-R_4)_t-Z_2-$ | $-O-$ | $-CH_2-$ | 1 |
| $-Z_1-(R_4-(NHCO)-R_4)_t-Z_2-$ | $-CH_2-$ | $-CH_2-$ | 1 |
| $-Z_1-(R_4-(NHCO)-R_4)_t-Z_2-$ | $-NH(CO)-$ | $-CH_2-$ | 1 |
| $-Z_1-(R_4-(NHCO)-R_4)_t-Z_2-$ | $-CH_2NH-$ | $-CH_2-$ | 1 |
| $-Z_1-(R_4-(NHCO)-R_4)_t-Z_2-$ | $-NHCH_2-$ | $-CH_2-$ | 1 |
| $-Z_1-(R_4-(NHCO)-R_4)_t-Z_2-$ | $-CH_2NH(CO)-$ | $-NH(CO)-$ | 1 |
| $-Z_1-(R_4-(NHCO)-R_4)_t-Z_2-$ | $-NH-$ | $-NH(CO)-$ | 1 |
| $-Z_1-(R_4-(NHCO)-R_4)_t-Z_2-$ | $-O-$ | $-NH(CO)-$ | 1 |
| $-Z_1-(R_4-(NHCO)-R_4)_t-Z_2-$ | $-CH_2-$ | $-NH(CO)-$ | 1 |
| $-Z_1-(R_4-(NHCO)-R_4)_t-Z_2-$ | $-NH(CO)-$ | $-NH(CO)-$ | 1 |
| $-Z_1-(R_4-(NHCO)-R_4)_t-Z_2-$ | $-CH_2NH-$ | $-NH(CO)-$ | 1 |
| $-Z_1-(R_4-(NHCO)-R_4)_t-Z_2-$ | $-NHCH_2-$ | $-NH(CO)-$ | 1 |
| $-Z_1-(R_4-(NHCO)-R_4)_t-Z_2-$ | $-CH_2NH(CO)-$ | $-(CO)NH-$ | 1 |
| $-Z_1-(R_4-(NHCO)-R_4)_t-Z_2-$ | $-NH-$ | $-(CO)NH-$ | 1 |
| $-Z_1-(R_4-(NHCO)-R_4)_t-Z_2-$ | $-O-$ | $-(CO)NH-$ | 1 |
| $-Z_1-(R_4-(NHCO)-R_4)_t-Z_2-$ | $-CH_2-$ | $-(CO)NH-$ | 1 |
| $-Z_1-(R_4-(NHCO)-R_4)_t-Z_2-$ | $-NH(CO)-$ | $-(CO)NH-$ | 1 |
| $-Z_1-(R_4-(NHCO)-R_4)_t-Z_2-$ | $-CH_2NH-$ | $-(CO)NH-$ | 1 |
| $-Z_1-(R_4-(NHCO)-R_4)_t-Z_2-$ | $-NHCH_2-$ | $-(CO)NH-$ | 1 |
| $-Z_1-(R_4-(NHCO)-R_4)_t-Z_2-$ | $-CH_2NH(CO)-$ | $-CH_2NH-$ | 1 |
| $-Z_1-(R_4-(NHCO)-R_4)_t-Z_2-$ | $-NH-$ | $-CH_2NH-$ | 1 |
| $-Z_1-(R_4-(NHCO)-R_4)_t-Z_2-$ | $-O-$ | $-CH_2NH-$ | 1 |
| $-Z_1-(R_4-(NHCO)-R_4)_t-Z_2-$ | $-CH_2-$ | $-CH_2NH-$ | 1 |
| $-Z_1-(R_4-(NHCO)-R_4)_t-Z_2-$ | $-NH(CO)-$ | $-CH_2NH-$ | 1 |
| $-Z_1-(R_4-(NHCO)-R_4)_t-Z_2-$ | $-CH_2NH-$ | $-CH_2NH-$ | 1 |
| $-Z_1-(R_4-(NHCO)-R_4)_t-Z_2-$ | $-NHCH_2-$ | $-CH_2NH-$ | 1 |
| $-Z_1-(R_4-(NHCO)-R_4)_t-Z_2-$ | $-CH_2NH(CO)-$ | $-NHCH_2-$ | 1 |
| $-Z_1-(R_4-(NHCO)-R_4)_t-Z_2-$ | $-NH-$ | $-NHCH_2-$ | 1 |
| $-Z_1-(R_4-(NHCO)-R_4)_t-Z_2-$ | $-O-$ | $-NHCH_2-$ | 1 |
| $-Z_1-(R_4-(NHCO)-R_4)_t-Z_2-$ | $-CH_2-$ | $-NHCH_2-$ | 1 |
| $-Z_1-(R_4-(NHCO)-R_4)_t-Z_2-$ | $-NH(CO)-$ | $-NHCH_2-$ | 1 |
| $-Z_1-(R_4-(NHCO)-R_4)_t-Z_2-$ | $-CH_2NH-$ | $-NHCH_2-$ | 1 |
| $-Z_1-(R_4-(NHCO)-R_4)_t-Z_2-$ | $-NHCH_2-$ | $-NHCH_2-$ | 1 |
| $-Z_1-(R_4-(CONH)-R_4)_t-Z_2-$ | $-CH_2NH(CO)-$ | $-NH-$ | 1 |
| $-Z_1-(R_4-(CONH)-R_4)_t-Z_2-$ | $-NH-$ | $-NH-$ | 1 |
| $-Z_1-(R_4-(CONH)-R_4)_t-Z_2-$ | $-O-$ | $-NH-$ | 1 |
| $-Z_1-(R_4-(CONH)-R_4)_t-Z_2-$ | $-CH_2-$ | $-NH-$ | 1 |
| $-Z_1-(R_4-(CONH)-R_4)_t-Z_2-$ | $-NH(CO)-$ | $-NH-$ | 1 |
| $-Z_1-(R_4-(CONH)-R_4)_t-Z_2-$ | $-CH_2NH-$ | $-NH-$ | 1 |
| $-Z_1-(R_4-(CONH)-R_4)_t-Z_2-$ | $-NHCH_2-$ | $-NH-$ | 1 |

TABLE A-continued

| L | $Z_1$ | $Z_2$ | t |
|---|---|---|---|
| —$Z_1$—($R_4$—(CONH)—$R_4$)$_t$—$Z_2$— | —$CH_2$NH(CO)— | —O— | 1 |
| —$Z_1$—($R_4$—(CONH)—$R_4$)$_t$—$Z_2$— | —NH— | —O— | 1 |
| —$Z_1$—($R_4$—(CONH)—$R_4$)$_t$—$Z_2$— | —O— | —O— | 1 |
| —$Z_1$—($R_4$—(CONH)—$R_4$)$_t$—$Z_2$— | —$CH_2$— | —O— | 1 |
| —$Z_1$—($R_4$—(CONH)—$R_4$)$_t$—$Z_2$— | —NH(CO)— | —O— | 1 |
| —$Z_1$—($R_4$—(CONH)—$R_4$)$_t$—$Z_2$— | —$CH_2$NH— | —O— | 1 |
| —$Z_1$—($R_4$—(CONH)—$R_4$)$_t$—$Z_2$— | —NH$CH_2$— | —O— | 1 |
| —$Z_1$—($R_4$—(CONH)—$R_4$)$_t$—$Z_2$— | —$CH_2$NH(CO)— | —$CH_2$— | 1 |
| —$Z_1$—($R_4$—(CONH)—$R_4$)$_t$—$Z_2$— | —NH— | —$CH_2$— | 1 |
| —$Z_1$—($R_4$—(CONH)—$R_4$)$_t$—$Z_2$— | —O— | —$CH_2$— | 1 |
| —$Z_1$—($R_4$—(CONH)—$R_4$)$_t$—$Z_2$— | —$CH_2$— | —$CH_2$— | 1 |
| —$Z_1$—($R_4$—(CONH)—$R_4$)$_t$—$Z_2$— | —NH(CO)— | —$CH_2$— | 1 |
| —$Z_1$—($R_4$—(CONH)—$R_4$)$_t$—$Z_2$— | —$CH_2$NH— | —$CH_2$— | 1 |
| —$Z_1$—($R_4$—(CONH)—$R_4$)$_t$—$Z_2$— | —NH$CH_2$— | —$CH_2$— | 1 |
| —$Z_1$—($R_4$—(CONH)—$R_4$)$_t$—$Z_2$— | —$CH_2$NH(CO)— | —NH(CO)— | 1 |
| —$Z_1$—($R_4$—(CONH)—$R_4$)$_t$—$Z_2$— | —NH— | —NH(CO)— | 1 |
| —$Z_1$—($R_4$—(CONH)—$R_4$)$_t$—$Z_2$— | —O— | —NH(CO)— | 1 |
| —$Z_1$—($R_4$—(CONH)—$R_4$)$_t$—$Z_2$— | —$CH_2$— | —NH(CO)— | 1 |
| —$Z_1$—($R_4$—(CONH)—$R_4$)$_t$—$Z_2$— | —NH(CO)— | —NH(CO)— | 1 |
| —$Z_1$—($R_4$—(CONH)—$R_4$)$_t$—$Z_2$— | —$CH_2$NH— | —NH(CO)— | 1 |
| —$Z_1$—($R_4$—(CONH)—$R_4$)$_t$—$Z_2$— | —NH$CH_2$— | —NH(CO)— | 1 |
| —$Z_1$—($R_4$—(CONH)—$R_4$)$_t$—$Z_2$— | —$CH_2$NH(CO)— | —(CO)NH— | 1 |
| —$Z_1$—($R_4$—(CONH)—$R_4$)$_t$—$Z_2$— | —NH— | —(CO)NH— | 1 |
| —$Z_1$—($R_4$—(CONH)—$R_4$)$_t$—$Z_2$— | —O— | —(CO)NH— | 1 |
| —$Z_1$—($R_4$—(CONH)—$R_4$)$_t$—$Z_2$— | —$CH_2$— | —(CO)NH— | 1 |
| —$Z_1$—($R_4$—(CONH)—$R_4$)$_t$—$Z_2$— | —NH(CO)— | —(CO)NH— | 1 |
| —$Z_1$—($R_4$—(CONH)—$R_4$)$_t$—$Z_2$— | —$CH_2$NH— | —(CO)NH— | 1 |
| —$Z_1$—($R_4$—(CONH)—$R_4$)$_t$—$Z_2$— | —NH$CH_2$— | —(CO)NH— | 1 |
| —$Z_1$—($R_4$—(CONH)—$R_4$)$_t$—$Z_2$— | —$CH_2$NH(CO)— | —$CH_2$NH— | 1 |
| —$Z_1$—($R_4$—(CONH)—$R_4$)$_t$—$Z_2$— | —NH— | —$CH_2$NH— | 1 |
| —$Z_1$—($R_4$—(CONH)—$R_4$)$_t$—$Z_2$— | —O— | —$CH_2$NH— | 1 |
| —$Z_1$—($R_4$—(CONH)—$R_4$)$_t$—$Z_2$— | —$CH_2$— | —$CH_2$NH— | 1 |
| —$Z_1$—($R_4$—(CONH)—$R_4$)$_t$—$Z_2$— | —NH(CO)— | —$CH_2$NH— | 1 |
| —$Z_1$—($R_4$—(CONH)—$R_4$)$_t$—$Z_2$— | —$CH_2$NH— | —$CH_2$NH— | 1 |
| —$Z_1$—($R_4$—(CONH)—$R_4$)$_t$—$Z_2$— | —NH$CH_2$— | —$CH_2$NH— | 1 |
| —$Z_1$—($R_4$—(CONH)—$R_4$)$_t$—$Z_2$— | —$CH_2$NH(CO)— | —NH$CH_2$— | 1 |
| —$Z_1$—($R_4$—(CONH)—$R_4$)$_t$—$Z_2$— | —NH— | —NH$CH_2$— | 1 |
| —$Z_1$—($R_4$—(CONH)—$R_4$)$_t$—$Z_2$— | —O— | —NH$CH_2$— | 1 |
| —$Z_1$—($R_4$—(CONH)—$R_4$)$_t$—$Z_2$— | —$CH_2$— | —NH$CH_2$— | 1 |
| —$Z_1$—($R_4$—(CONH)—$R_4$)$_t$—$Z_2$— | —NH(CO)— | —NH$CH_2$— | 1 |
| —$Z_1$—($R_4$—(CONH)—$R_4$)$_t$—$Z_2$— | —$CH_2$NH— | —NH$CH_2$— | 1 |
| —$Z_1$—($R_4$—(CONH)—$R_4$)$_t$—$Z_2$— | —NH$CH_2$— | —NH$CH_2$— | 1 |
| —$Z_1$—($R_4$—(NHC(O)NH)—$R_4$)$_t$—$Z_2$— | —$CH_2$NH(CO)— | —NH— | 1 |
| —$Z_1$—($R_4$—(NHC(O)NH)—$R_4$)$_t$—$Z_2$— | —NH— | —NH— | 1 |
| —$Z_1$—($R_4$—(NHC(O)NH)—$R_4$)$_t$—$Z_2$— | —O— | —NH— | 1 |
| —$Z_1$—($R_4$—(NHC(O)NH)—$R_4$)$_t$—$Z_2$— | —$CH_2$— | —NH— | 1 |
| —$Z_1$—($R_4$—(NHC(O)NH)—$R_4$)$_t$—$Z_2$— | —NH(CO)— | —NH— | 1 |
| —$Z_1$—($R_4$—(NHC(O)NH)—$R_4$)$_t$—$Z_2$— | —$CH_2$NH— | —NH— | 1 |
| —$Z_1$—($R_4$—(NHC(O)NH)—$R_4$)$_t$—$Z_2$— | —NH$CH_2$— | —NH— | 1 |
| —$Z_1$—($R_4$—(NHC(O)NH)—$R_4$)$_t$—$Z_2$— | —$CH_2$NH(CO)— | —O— | 1 |
| —$Z_1$—($R_4$—(NHC(O)NH)—$R_4$)$_t$—$Z_2$— | —NH— | —O— | 1 |
| —$Z_1$—($R_4$—(NHC(O)NH)—$R_4$)$_t$—$Z_2$— | —O— | —O— | 1 |
| —$Z_1$—($R_4$—(NHC(O)NH)—$R_4$)$_t$—$Z_2$— | —$CH_2$— | —O— | 1 |
| —$Z_1$—($R_4$—(NHC(O)NH)—$R_4$)$_t$—$Z_2$— | —NH(CO)— | —O— | 1 |
| —$Z_1$—($R_4$—(NHC(O)NH)—$R_4$)$_t$—$Z_2$— | —$CH_2$NH— | —O— | 1 |
| —$Z_1$—($R_4$—(NHC(O)NH)—$R_4$)$_t$—$Z_2$— | —NH$CH_2$— | —O— | 1 |
| —$Z_1$—($R_4$—(NHC(O)NH)—$R_4$)$_t$—$Z_2$— | —$CH_2$NH(CO)— | —$CH_2$— | 1 |
| —$Z_1$—($R_4$—(NHC(O)NH)—$R_4$)$_t$—$Z_2$— | —NH— | —$CH_2$— | 1 |
| —$Z_1$—($R_4$—(NHC(O)NH)—$R_4$)$_t$—$Z_2$— | —O— | —$CH_2$— | 1 |
| —$Z_1$—($R_4$—(NHC(O)NH)—$R_4$)$_t$—$Z_2$— | —$CH_2$— | —$CH_2$— | 1 |
| —$Z_1$—($R_4$—(NHC(O)NH)—$R_4$)$_t$—$Z_2$— | —NH(CO)— | —$CH_2$— | 1 |
| —$Z_1$—($R_4$—(NHC(O)NH)—$R_4$)$_t$—$Z_2$— | —$CH_2$NH— | —$CH_2$— | 1 |
| —$Z_1$—($R_4$—(NHC(O)NH)—$R_4$)$_t$—$Z_2$— | —NH$CH_2$— | —$CH_2$— | 1 |
| —$Z_1$—($R_4$—(NHC(O)NH)—$R_4$)$_t$—$Z_2$— | —$CH_2$NH(CO)— | —NH(CO)— | 1 |
| —$Z_1$—($R_4$—(NHC(O)NH)—$R_4$)$_t$—$Z_2$— | —NH— | —NH(CO)— | 1 |
| —$Z_1$—($R_4$—(NHC(O)NH)—$R_4$)$_t$—$Z_2$— | —O— | —NH(CO)— | 1 |
| —$Z_1$—($R_4$—(NHC(O)NH)—$R_4$)$_t$—$Z_2$— | —$CH_2$— | —NH(CO)— | 1 |
| —$Z_1$—($R_4$—(NHC(O)NH)—$R_4$)$_t$—$Z_2$— | —NH(CO)— | —NH(CO)— | 1 |
| —$Z_1$—($R_4$—(NHC(O)NH)—$R_4$)$_t$—$Z_2$— | —$CH_2$NH— | —NH(CO)— | 1 |
| —$Z_1$—($R_4$—(NHC(O)NH)—$R_4$)$_t$—$Z_2$— | —NH$CH_2$— | —NH(CO)— | 1 |
| —$Z_1$—($R_4$—(NHC(O)NH)—$R_4$)$_t$—$Z_2$— | —$CH_2$NH(CO)— | —(CO)NH— | 1 |
| —$Z_1$—($R_4$—(NHC(O)NH)—$R_4$)$_t$—$Z_2$— | —NH— | —(CO)NH— | 1 |
| —$Z_1$—($R_4$—(NHC(O)NH)—$R_4$)$_t$—$Z_2$— | —O— | —(CO)NH— | 1 |
| —$Z_1$—($R_4$—(NHC(O)NH)—$R_4$)$_t$—$Z_2$— | —$CH_2$— | —(CO)NH— | 1 |
| —$Z_1$—($R_4$—(NHC(O)NH)—$R_4$)$_t$—$Z_2$— | —NH(CO)— | —(CO)NH— | 1 |
| —$Z_1$—($R_4$—(NHC(O)NH)—$R_4$)$_t$—$Z_2$— | —$CH_2$NH— | —(CO)NH— | 1 |
| —$Z_1$—($R_4$—(NHC(O)NH)—$R_4$)$_t$—$Z_2$— | —NH$CH_2$— | —(CO)NH— | 1 |
| —$Z_1$—($R_4$—(NHC(O)NH)—$R_4$)$_t$—$Z_2$— | —$CH_2$NH(CO)— | —$CH_2$NH— | 1 |

TABLE A-continued

| L | $Z_1$ | $Z_2$ | t |
|---|---|---|---|
| —$Z_1$—($R_4$—(NHC(O)NH)—$R_4$)$_t$—$Z_2$— | —NH— | —$CH_2NH$— | 1 |
| —$Z_1$—($R_4$—(NHC(O)NH)—$R_4$)$_t$—$Z_2$— | —O— | —$CH_2NH$— | 1 |
| —$Z_1$—($R_4$—(NHC(O)NH)—$R_4$)$_t$—$Z_2$— | —$CH_2$— | —$CH_2NH$— | 1 |
| —$Z_1$—($R_4$—(NHC(O)NH)—$R_4$)$_t$—$Z_2$— | —NH(CO)— | —$CH_2NH$— | 1 |
| —$Z_1$—($R_4$—(NHC(O)NH)—$R_4$)$_t$—$Z_2$— | —$CH_2NH$— | —$CH_2NH$— | 1 |
| —$Z_1$—($R_4$—(NHC(O)NH)—$R_4$)$_t$—$Z_2$— | —$NHCH_2$— | —$CH_2NH$— | 1 |
| —$Z_1$—($R_4$—(NHC(O)NH)—$R_4$)$_t$—$Z_2$— | —$CH_2NH(CO)$— | —$NHCH_2$— | 1 |
| —$Z_1$—($R_4$—(NHC(O)NH)—$R_4$)$_t$—$Z_2$— | —NH— | —$NHCH_2$— | 1 |
| —$Z_1$—($R_4$—(NHC(O)NH)—$R_4$)$_t$—$Z_2$— | —O— | —$NHCH_2$— | 1 |
| —$Z_1$—($R_4$—(NHC(O)NH)—$R_4$)$_t$—$Z_2$— | —$CH_2$— | —$NHCH_2$— | 1 |
| —$Z_1$—($R_4$—(NHC(O)NH)—$R_4$)$_t$—$Z_2$— | —NH(CO)— | —$NHCH_2$— | 1 |
| —$Z_1$—($R_4$—(NHC(O)NH)—$R_4$)$_t$—$Z_2$— | —$CH_2NH$— | —$NHCH_2$— | 1 |
| —$Z_1$—($R_4$—(NHC(O)NH)—$R_4$)$_t$—$Z_2$— | —$NHCH_2$— | —$NHCH_2$— | 1 |
| —$Z_1$—($R_4$—(NHC(O)NH)—$R_4$)$_t$—$Z_2$— | —$CH_2NH(CO)$— | —NH— | 1 |
| —$Z_1$—($R_4$—(NHC(O)NH)—$R_4$)$_t$—$Z_2$— | —NH— | —NH— | 1 |
| —$Z_1$—($R_4$—(NHC(O)NH)—$R_4$)$_t$—$Z_2$— | —O— | —NH— | 1 |
| —$Z_1$—($R_4$—(NHC(O)NH)—$R_4$)$_t$—$Z_2$— | —$CH_2$— | —NH— | 1 |
| —$Z_1$—($R_4$—(NHC(O)NH)—$R_4$)$_t$—$Z_2$— | —NH(CO)— | —NH— | 1 |
| —$Z_1$—($R_4$—(NHC(O)NH)—$R_4$)$_t$—$Z_2$— | —$CH_2NH$— | —NH— | 1 |
| —$Z_1$—($R_4$—(NHC(O)NH)—$R_4$)$_t$—$Z_2$— | —$NHCH_2$— | —NH— | 1 |
| —$Z_1$—($R_4$—(NHC(O)NH)—$R_4$)$_t$—$Z_2$— | —$CH_2NH(CO)$— | —O— | 1 |
| —$Z_1$—($R_4$—(NHC(O)NH)—$R_4$)$_t$—$Z_2$— | —NH— | —O— | 1 |
| —$Z_1$—($R_4$—(NHC(O)NH)—$R_4$)$_t$—$Z_2$— | —O— | —O— | 1 |
| —$Z_1$—($R_4$—(NHC(O)NH)—$R_4$)$_t$—$Z_2$— | —$CH_2$— | —O— | 1 |
| —$Z_1$—($R_4$—(NHC(O)NH)—$R_4$)$_t$—$Z_2$— | —NH(CO)— | —O— | 1 |
| —$Z_1$—($R_4$—(NHC(O)NH)—$R_4$)$_t$—$Z_2$— | —$CH_2NH$— | —O— | 1 |
| —$Z_1$—($R_4$—(NHC(O)NH)—$R_4$)$_t$—$Z_2$— | —$NHCH_2$— | —O— | 1 |
| —$Z_1$—($R_4$—(NHC(O)NH)—$R_4$)$_t$—$Z_2$— | —$CH_2NH(CO)$— | —$CH_2$— | 1 |
| —$Z_1$—($R_4$—(NHC(O)NH)—$R_4$)$_t$—$Z_2$— | —NH— | —$CH_2$— | 1 |
| —$Z_1$—($R_4$—(NHC(O)NH)—$R_4$)$_t$—$Z_2$— | —O— | —$CH_2$— | 1 |
| —$Z_1$—($R_4$—(NHC(O)NH)—$R_4$)$_t$—$Z_2$— | —$CH_2$— | —$CH_2$— | 1 |
| —$Z_1$—($R_4$—(NHC(O)NH)—$R_4$)$_t$—$Z_2$— | —NH(CO)— | —$CH_2$— | 1 |
| —$Z_1$—($R_4$—(NHC(O)NH)—$R_4$)$_t$—$Z_2$— | —$CH_2NH$— | —$CH_2$— | 1 |
| —$Z_1$—($R_4$—(NHC(O)NH)—$R_4$)$_t$—$Z_2$— | —$NHCH_2$— | —$CH_2$— | 1 |
| —$Z_1$—($R_4$—(NHC(O)NH)—$R_4$)$_t$—$Z_2$— | —$CH_2NH(CO)$— | —NH(CO)— | 1 |
| —$Z_1$—($R_4$—(NHC(O)NH)—$R_4$)$_t$—$Z_2$— | —NH— | —NH(CO)— | 1 |
| —$Z_1$—($R_4$—(NHC(O)NH)—$R_4$)$_t$—$Z_2$— | —O— | —NH(CO)— | 1 |
| —$Z_1$—($R_4$—(NHC(O)NH)—$R_4$)$_t$—$Z_2$— | —$CH_2$— | —NH(CO)— | 1 |
| —$Z_1$—($R_4$—(NHC(O)NH)—$R_4$)$_t$—$Z_2$— | —NH(CO)— | —NH(CO)— | 1 |
| —$Z_1$—($R_4$—(NHC(O)NH)—$R_4$)$_t$—$Z_2$— | —$CH_2NH$— | —NH(CO)— | 1 |
| —$Z_1$—($R_4$—(NHC(O)NH)—$R_4$)$_t$—$Z_2$— | —$NHCH_2$— | —NH(CO)— | 1 |
| —$Z_1$—($R_4$—(NHC(O)NH)—$R_4$)$_t$—$Z_2$— | —$CH_2NH(CO)$— | —(CO)NH— | 1 |
| —$Z_1$—($R_4$—(NHC(O)NH)—$R_4$)$_t$—$Z_2$— | —NH— | —(CO)NH— | 1 |
| —$Z_1$—($R_4$—(NHC(O)NH)—$R_4$)$_t$—$Z_2$— | —O— | —(CO)NH— | 1 |
| —$Z_1$—($R_4$—(NHC(O)NH)—$R_4$)$_t$—$Z_2$— | —$CH_2$— | —(CO)NH— | 1 |
| —$Z_1$—($R_4$—(NHC(O)NH)—$R_4$)$_t$—$Z_2$— | —NH(CO)— | —(CO)NH— | 1 |
| —$Z_1$—($R_4$—(NHC(O)NH)—$R_4$)$_t$—$Z_2$— | —$CH_2NH$— | —(CO)NH— | 1 |
| —$Z_1$—($R_4$—(NHC(O)NH)—$R_4$)$_t$—$Z_2$— | —$NHCH_2$— | —(CO)NH— | 1 |
| —$Z_1$—($R_4$—(NHC(O)NH)—$R_4$)$_t$—$Z_2$— | —$CH_2NH(CO)$— | —$CH_2NH$— | 1 |
| —$Z_1$—($R_4$—(NHC(O)NH)—$R_4$)$_t$—$Z_2$— | —NH— | —$CH_2NH$— | 1 |
| —$Z_1$—($R_4$—(NHC(O)NH)—$R_4$)$_t$—$Z_2$— | —O— | —$CH_2NH$— | 1 |
| —$Z_1$—($R_4$—(NHC(O)NH)—$R_4$)$_t$—$Z_2$— | —$CH_2$— | —$CH_2NH$— | 1 |
| —$Z_1$—($R_4$—(NHC(O)NH)—$R_4$)$_t$—$Z_2$— | —NH(CO)— | —$CH_2NH$— | 1 |
| —$Z_1$—($R_4$—(NHC(O)NH)—$R_4$)$_t$—$Z_2$— | —$CH_2NH$— | —$CH_2NH$— | 1 |
| —$Z_1$—($R_4$—(NHC(O)NH)—$R_4$)$_t$—$Z_2$— | —$NHCH_2$— | —$CH_2NH$— | 1 |
| —$Z_1$—($R_4$—(NHC(O)NH)—$R_4$)$_t$—$Z_2$— | —$CH_2NH(CO)$— | —$NHCH_2$— | 1 |
| —$Z_1$—($R_4$—(NHC(O)NH)—$R_4$)$_t$—$Z_2$— | —NH— | —$NHCH_2$— | 1 |
| —$Z_1$—($R_4$—(NHC(O)NH)—$R_4$)$_t$—$Z_2$— | —O— | —$NHCH_2$— | 1 |
| —$Z_1$—($R_4$—(NHC(O)NH)—$R_4$)$_t$—$Z_2$— | —$CH_2$— | —$NHCH_2$— | 1 |
| —$Z_1$—($R_4$—(NHC(O)NH)—$R_4$)$_t$—$Z_2$— | —NH(CO)— | —$NHCH_2$— | 1 |
| —$Z_1$—($R_4$—(NHC(O)NH)—$R_4$)$_t$—$Z_2$— | —$CH_2NH$— | —$NHCH_2$— | 1 |
| —$Z_1$—($R_4$—(NHC(O)NH)—$R_4$)$_t$—$Z_2$— | —$NHCH_2$— | —$NHCH_2$— | 1 |

In some embodiments of Table A, each $R_4$ can independently be a $C_1$-$C_4$ alkylene, for example, methylene, ethylene, n-propylene, isopropylene, n-butylene, isobutylene, or sec-butylene. In some embodiments of Table A, each $R_4$ is methylene. In some embodiments of Table A, each $R_4$ is ethylene. In some embodiments of Table A, each $R_4$ is n-propylene. In some embodiments of Table A, each $R_4$ is n-butylene. In some embodiments of Table A, each $R_4$ can be the same. In some embodiments of Table A, each $R_4$ can be different. For example, one $R_4$ can be methylene and the other $R_4$ can be ethylene; one $R_4$ can be methylene and the other $R_4$ can be n-propylene; one $R_4$ can be methylene and the other $R_4$ can be n-butylene; one $R_4$ can be ethylene and the other $R_4$ can be n-propylene; or one $R_4$ can be ethylene and the other $R_4$ can be n-butylene.

In some embodiments, Y can be

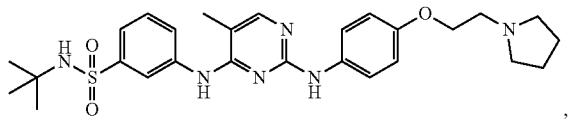 [SMILES: Cc1cnc(Nc2ccc(OCCN3CCCC3)cc2)nc1Nc1cccc(S(=O)(=O)NC(C)(C)C)c1]

wherein Y can be derivatized to attach to L. As used herein, the phrase "Y is derivatized to attach to L" is used as would be understood by one having ordinary skill in the art. For example, when Y is derivatized to attached to L, Y can be:

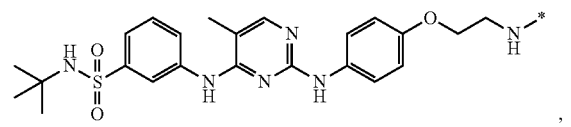

,

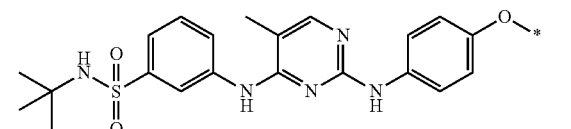

,

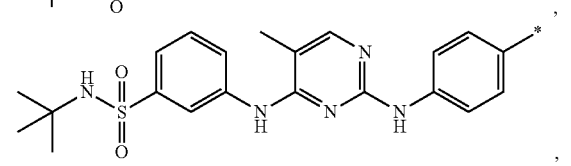

,

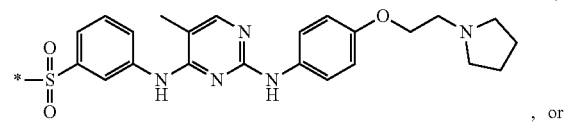

, or

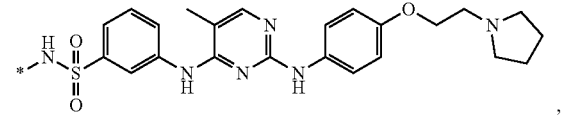

, wherein * represents the point of attachment to the L group.

In some embodiments, at least one of $Y_1$, $Y_2$, $Y_3$, $Y_4$, and $Y_5$ is carbon (e.g., $CR_{3A}$, $CR_{3B}$, $CR_{3C}$, $CR_{3D}$, and/or $CR_{3E}$). In some embodiments, one of $Y_1$, $Y_2$, $Y_3$, $Y_4$, and $Y_5$ is carbon. In some embodiments, two of $Y_1$, $Y_2$, $Y_3$, $Y_4$, and $Y_5$ are carbon. In some embodiments, three of $Y_1$, $Y_2$, $Y_3$, $Y_4$, and $Y_5$ are carbon. In some embodiments, four of $Y_1$, $Y_2$, $Y_3$, $Y_4$, and $Y_5$ are carbon. In some embodiments, all five of $Y_1$, $Y_2$, $Y_3$, $Y_4$, and $Y_5$ are carbon.

In some embodiments, when $Q_1$ is $CH_2$, then one or more of $R_{3A}$, $R_{3B}$, $R_{3C}$, $R_{3D}$, and $R_{3E}$ cannot be hydrogen. In some embodiments, when $Q_1$ is a bond, then one or more of $R_{3A}$, $R_{3B}$, $R_{3C}$, $R_{3D}$, and $R_{3E}$ cannot be hydrogen. In some embodiments, when $R_1$ is L-Y, none of $R_{3A}$, $R_{3B}$, $R_{3C}$, $R_{3D}$, and $R_{3E}$ can be L-Y. In some embodiments, when $Q_1$ is a bond, $X_1$ is hydrogen or methyl, and $Q_2$ is $CH_2$; then one of $R_1$, $R_{3A}$, $R_{3B}$, $R_{3C}$, $R_{3D}$, and $R_{3E}$ is L-Y. In some embodiments, when $Q_2$ can be a bond, $Q_1$ can be a bond or $CH_2$.

In some embodiments, each $R_1$ can be independently halogen (for example, fluoro, chloro, or bromo), a substituted or unsubstituted amino (for example, $-NH_2$, dimethylamino, diethylamino, isopropylethylamino, phenylamino, or benzylamino), an unsubstituted $C_1$-$C_6$ haloalkyl (for example, $-CF_3$, $-CHF_2$, $-CH_2F$, $-CH_2CF_3$, or $-CH_2CH_2CF_3$), a substituted or unsubstituted $C_1$-$C_6$ alkoxy (for example, (for example, methoxy, ethoxy, n-propoxy, isopropoxy, n-butoxy, isobutoxy, sec-butoxy, t-butoxy, pentoxy (straight-chained or branched), or hexoxy (straight-chained or branched)), or a substituted or unsubstituted $C_1$-$C_6$ alkyl (for example, methyl, ethyl, n-propyl, isopropyl, n-butyl, isobutyl, sec-butyl, t-butyl, pentyl (straight-chained or branched), or hexyl (straight-chained or branched)). In some embodiments, each $R_1$ can be independently halogen (for example, fluoro, chloro, or bromo), an unsubstituted amino, an unsubstituted $C_1$-$C_6$ haloalkyl, an unsubstituted $C_1$-$C_6$ alkoxy (for example, (for example, methoxy, ethoxy, n-propoxy, isopropoxy, n-butoxy, isobutoxy, sec-butoxy, t-butoxy, pentoxy (straight-chained or branched), or hexoxy (straight-chained or branched)), or unsubstituted $C_1$-$C_6$ alkyl (for example, methyl, ethyl, n-propyl, isopropyl, n-butyl, isobutyl, sec-butyl, t-butyl, pentyl (straight-chained or branched), or hexyl (straight-chained or branched)).

In some embodiments, each $R_1$ can be independently fluoro, chloro, $-NH_2$, $-NH(CH_3)$, $-N(CH_3)_2$, $-CF_3$, $-OCH_3$, $-OCH_2CH_3$, $-OCH(CH_3)_2$, $-CH_3$, $-CH_2CH_3$ or $-CH(CH_3)_2$.

In some embodiments, Ring B can be selected from:

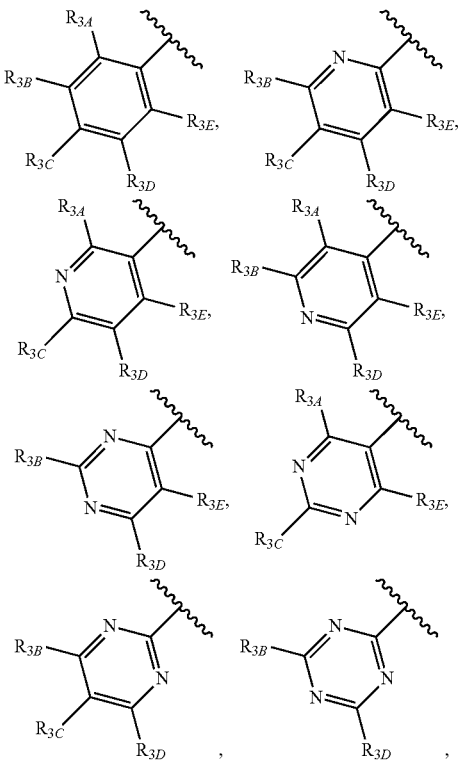

,

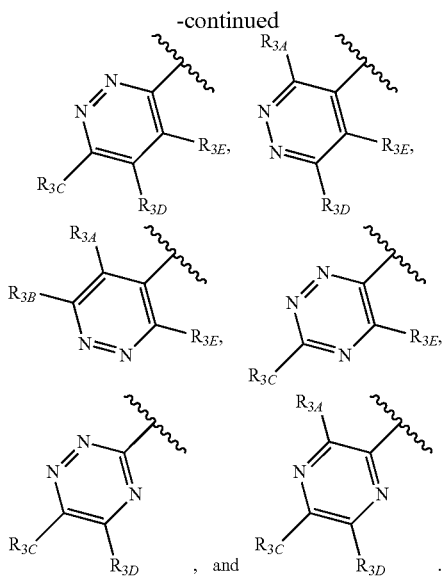

In some embodiments, each of $R_{3A}$, $R_{3B}$, $R_{3C}$, $R_{3D}$, and $R_{3E}$ can be independently hydrogen, deuterium, hydroxyl, halogen (for example, fluoro, chloro, or bromo), nitro, a substituted or unsubstituted amino (for example, —NH$_2$, dimethylamino, diethylamino, isopropylethylamino, phenylamino, or benzylamino), a substituted or unsubstituted $C_1$-$C_6$ alkoxy (for example, (for example, methoxy, ethoxy, n-propoxy, isopropoxy, n-butoxy, isobutoxy, sec-butoxy, t-butoxy, pentoxy (straight-chained or branched), or hexoxy (straight-chained or branched)), or a substituted or unsubstituted $C_1$-$C_6$ alkyl (for example, methyl, ethyl, n-propyl, isopropyl, n-butyl, isobutyl, sec-butyl, t-butyl, pentyl (straight-chained or branched), or hexyl (straight-chained or branched)), a substituted or unsubstituted $C_2$-$C_6$ alkenyl (for example, ethylene, n-propylene, isopropylene, n-butylene, isobutylene, sec-butylene, t-butylene, pentylene (straight-chained or branched), or hexylene (straight-chained or branched)), a substituted or unsubstituted $C_3$-$C_8$ cycloalkyl (for example, cyclopropyl, cyclobutyl, cyclopentyl, cyclohexyl, cycloheptyl, or cyclooctyl), a substituted or unsubstituted 3 to 8 membered monocyclic heterocyclyl containing one or two heteroatoms selected from oxygen and nitrogen, or a 6 to 8 membered bicyclic heterocyclyl containing one or two heteroatoms selected from oxygen and nitrogen), a substituted or unsubstituted alkoxyalkyl (for example, methoxymethyl, ethoxyethyl, or methoxy-t-butyl), a substituted or unsubstituted cycloalkylalkyl (for example, a $C_3$-$C_8$ cycloalkyl group such as cyclopropyl, cyclobutyl, cyclopentyl, cyclohexyl, cycloheptyl, or cyclooctyl, connected to the rest of the compound via a $C_1$-$C_3$ alkyl group such as methyl, ethyl, n-propyl, or isopropyl), a substituted or unsubstituted heterocyclylalkyl (for example, for example a 3 to 8 membered monocyclic heterocyclyl containing one or two heteroatoms selected from oxygen and nitrogen, connected to the rest of the compound via a $C_1$-$C_3$ alkyl group such as methyl, ethyl, n-propyl, or isopropyl), a substituted or unsubstituted aralkyl (for example, phenyl or naphthyl, connected to the rest of the compound via a $C_1$-$C_3$ alkyl group such as methyl, ethyl, n-propyl, or isopropyl), or a substituted or unsubstituted heteroaralkyl, for example, a five, six, or ten membered heteroaryl group containing either one oxygen, one nitrogen, one oxygen and one nitrogen, two nitrogens, or three nitrogens, connected to the rest of the compound via a $C_1$-$C_3$ alkyl group such as methyl, ethyl, n-propyl, or isopropyl).

In some embodiments, each of $R_{3A}$, $R_{3B}$, $R_{3C}$, $R_{3D}$, and $R_{3E}$ can be independently Hydrogen, deuterium, hydroxyl, halogen (for example, fluoro, chloro, or bromo), nitro, a substituted or unsubstituted amino (for example, —NH$_2$, dimethylamino, diethylamino, isopropylethylamino, phenylamino, or benzylamino), an unsubstituted $C_1$-$C_6$ haloalkyl (for example, —CF$_3$, —CHF$_2$, —CH$_2$F, —CH$_2$CF$_3$, or —CH$_2$CH$_2$CF$_3$), an unsubstituted $C_1$-$C_6$ alkoxy (for example, methoxy, ethoxy, n-propoxy, isopropoxy, n-butoxy, isobutoxy, sec-butoxy, t-butoxy, pentoxy (straight-chained or branched), or hexoxy (straight-chained or branched)), or unsubstituted $C_1$-$C_6$ alkyl (for example, methyl, ethyl, n-propyl, isopropyl, n-butyl, isobutyl, sec-butyl, t-butyl, pentyl (straight-chained or branched), or hexyl (straight-chained or branched)), an unsubstituted $C_2$-$C_6$ alkenyl (for example, ethylene, n-propylene, isopropylene, n-butylene, isobutylene, sec-butylene, t-butylene, pentylene (straight-chained or branched), or hexylene (straight-chained or branched)), an unsubstituted $C_3$-$C_8$ cycloalkyl (for example, cyclopropyl, cyclobutyl, cyclopentyl, cyclohexyl, cycloheptyl, or cyclooctyl), an unsubstituted 3 to 10 membered heterocyclyl (for example a 3 to 8 membered monocyclic heterocyclyl containing one or two heteroatoms selected from oxygen and nitrogen, or a 6 to 8 membered bicyclic heterocyclyl containing one or two heteroatoms selected from oxygen and nitrogen), an unsubstituted alkoxyalkyl (for example, methoxymethyl, ethoxyethyl, or methoxy-t-butyl), an unsubstituted cycloalkylalkyl (for example, a $C_3$-$C_8$ cycloalkyl group such as cyclopropyl, cyclobutyl, cyclopentyl, cyclohexyl, cycloheptyl, or cyclooctyl, connected to the rest of the compound via a $C_1$-$C_3$ alkyl group such as methyl, ethyl, n-propyl, or isopropyl), an unsubstituted heterocyclylalkyl (for example, for example a 3 to 8 membered monocyclic heterocyclyl containing one or two heteroatoms selected from oxygen and nitrogen, connected to the rest of the compound via a $C_1$-$C_3$ alkyl group such as methyl, ethyl, n-propyl, or isopropyl), an unsubstituted aralkyl (for example, phenyl or naphthyl, connected to the rest of the compound via a $C_1$-$C_3$ alkyl group such as methyl, ethyl, n-propyl, or isopropyl), or unsubstituted heteroaralkyl (for example, a five, six, or ten membered heteroaryl group containing either one oxygen, one nitrogen, one oxygen and one nitrogen, two nitrogens, or three nitrogens, connected to the rest of the compound via a $C_1$-$C_3$ alkyl group such as methyl, ethyl, n-propyl, or isopropyl).

In some embodiments, each of $R_{3A}$, $R_{3B}$, $R_{3C}$, $R_{3D}$, and $R_{3E}$ can be independently hydrogen, halogen (for example, fluoro, chloro, or bromo), an unsubstituted $C_1$-$C_6$ haloalkyl (for example, —CF$_3$, —CHF$_2$, —CH$_2$F, —CH$_2$CF$_3$, or —CH$_2$CH$_2$CF$_3$), an unsubstituted $C_1$-$C_6$ alkoxy (for example, methoxy, ethoxy, n-propoxy, isopropoxy, n-butoxy, isobutoxy, sec-butoxy, t-butoxy, pentoxy (straight-chained or branched), or hexoxy (straight-chained or branched)), an unsubstituted $C_1$-$C_6$ alkyl (for example, methyl, ethyl, n-propyl, isopropyl, n-butyl, isobutyl, sec-butyl, t-butyl, pentyl (straight-chained or branched), or hexyl (straight-chained or branched)), an unsubstituted 3 to 10 membered heterocyclyl (for example a 3 to 8 membered monocyclic heterocyclyl containing one or two heteroatoms selected from oxygen and nitrogen, or a 6 to 8 membered bicyclic heterocyclyl containing one or two heteroatoms selected from oxygen and nitrogen), or an unsubstituted 3 to 10 membered heterocyclylalkyl (for example a 3 to 8 membered monocyclic heterocyclyl containing one or two heteroatoms selected from oxygen and nitrogen, or a 6 to 8 membered bicyclic heterocyclyl containing one or two heteroatoms selected from oxygen and nitrogen, connected to the rest of the compound by a methyl, ethyl, n-propyl, isopropyl, n-butyl, isobutyl, sec-butyl, t-butyl, pentyl (straight-chained or branched), or hexyl (straight-chained or branched) group).

In some embodiments, one of $R_{3A}$, $R_{3B}$, $R_{3C}$, $R_{3D}$, and $R_{3E}$ can be halogen (for example, fluoro, chloro, or bromo), an unsubstituted $C_1$-$C_6$ haloalkyl, an unsubstituted $C_1$-$C_6$ alkoxy (for example, methoxy, ethoxy, n-propoxy, isopropoxy, n-butoxy, isobutoxy, sec-butoxy, t-butoxy, pentoxy (straight-chained or branched), or hexoxy (straight-chained or branched)), an unsubstituted $C_1$-$C_6$ alkyl (for example, methyl, ethyl, n-propyl, isopropyl, n-butyl, isobutyl, sec-butyl, t-butyl, pentyl (straight-chained or branched), or hexyl (straight-chained or branched)), an unsubstituted 3 to 10 membered heterocyclyl (for example a 3 to 8 membered monocyclic heterocyclyl containing one or two heteroatoms selected from oxygen and nitrogen, or a 6 to 8 membered bicyclic heterocyclyl containing one or two heteroatoms selected from oxygen and nitrogen), or an unsubstituted 3 to 10 membered heterocyclylalkyl (for example a 3 to 8 membered monocyclic heterocyclyl containing one or two heteroatoms selected from oxygen and nitrogen, or a 6 to 8 membered bicyclic heterocyclyl containing one or two heteroatoms selected from oxygen and nitrogen, connected to the rest of the compound by a methyl, ethyl, n-propyl, isopropyl, n-butyl, isobutyl, sec-butyl, t-butyl, pentyl (straight-chained or branched), or hexyl (straight-chained or branched) group) and the other of $R_{3A}$, $R_{3B}$, $R_{3C}$, $R_{3D}$, and $R_{3E}$ are hydrogen.

In some embodiments, one of $R_{3A}$, $R_{3B}$, $R_{3C}$, $R_{3D}$, and $R_{3E}$ can be fluoro, chloro, —$CF_3$, —$OCH_3$, an unsubstituted $C_1$-$C_6$ alkyl (for example, methyl, ethyl, n-propyl, isopropyl, n-butyl, isobutyl, sec-butyl, t-butyl, pentyl (straight-chained or branched), or hexyl (straight-chained or branched)), an unsubstituted 3 to 10 membered heterocyclyl (for example a 3 to 8 membered monocyclic heterocyclyl containing one or two heteroatoms selected from oxygen and nitrogen, or a 6 to 8 membered bicyclic heterocyclyl containing one or two heteroatoms selected from oxygen and nitrogen), or an unsubstituted 3 to 10 membered heterocyclylalkyl (for example a 3 to 8 membered monocyclic heterocyclyl containing one or two heteroatoms selected from oxygen and nitrogen, or a 6 to 8 membered bicyclic heterocyclyl containing one or two heteroatoms selected from oxygen and nitrogen, connected to the rest of the compound by a methyl, ethyl, n-propyl, isopropyl, n-butyl, isobutyl, sec-butyl, t-butyl, pentyl (straight-chained or branched), or hexyl (straight-chained or branched) group) and the other of $R_{3A}$, $R_{3B}$, $R_{3C}$, $R_{3D}$, and $R_{3E}$ are hydrogen.

In some embodiments, one of $R_{3A}$, $R_{3B}$, $R_{3C}$, $R_{3D}$, and $R_{3E}$ can be selected from:

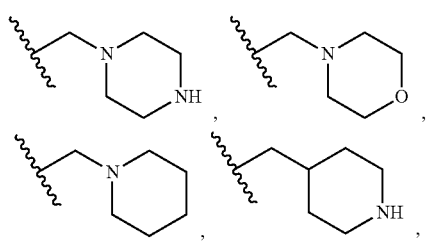

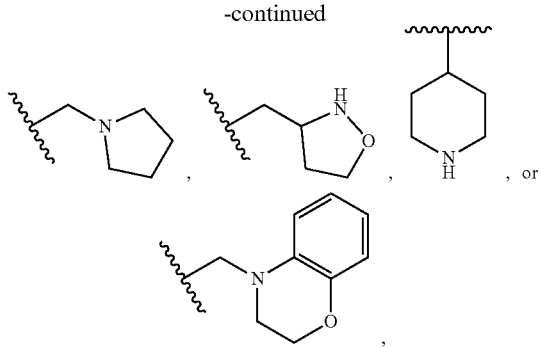

and the other of $R_{3A}$, $R_{3B}$, $R_{3C}$, $R_{3D}$, and $R_{3E}$ can be hydrogen.

In some embodiments, one $R_1$ can be L-Y. In some embodiments, one of $R_{3A}$, $R_{3B}$, $R_{3C}$, $R_{3D}$, and $R_{3E}$ can be L-Y. In some embodiments, $Y_3$ can be C-L-Y.

In some embodiments, L can be —$Z_1$—($R_4$—O—$R_4$)$_t$—$Z_2$—. In some embodiments, L can be —$Z_1$($R_4$—NH—$R_4$)$_t$—$Z_2$—. In some embodiments, L can be $Z_1$—($R_4$—(NHCO)—$R_4$)$_t$—$Z_2$—. In some embodiments, L can be —$Z_1$—($R_4$—(CONH)—$R_4$)$_t$—$Z_2$—. In other embodiments, L can be —$Z_1$—($R_4$—(NHC(O)NH)—$R_4$)$_t$—$Z_2$—. In some embodiments of this paragraph, t is 1. In some embodiments of this paragraph, t is 2.

In some embodiments, $Z_1$ can be —NH—. In some embodiments, $Z_1$ can be —O—. In some embodiments, $Z_1$ can be —$CH_2$—. In some embodiments, $Z_1$ can be —NH(CO)—. In some embodiments, $Z_1$ can be —$CH_2$NH—. In some embodiments, $Z_1$ can be —NHCH$_2$—. In some embodiments, $Z_2$ can be —NH—. In some embodiments, $Z_2$ can be —O—. In some embodiments, $Z_2$ can be —$CH_2$—. In some embodiments, $Z_2$ can be —NH(CO)—. In some embodiments, $Z_2$ can be —(CO)NH—. In some embodiments, $Z_2$ can be —$CH_2$NH—. In some embodiments, $Z_2$ can be —NHCH$_2$— In some embodiments of this paragraph, $Z_1$ and $Z_2$ are the same. In some embodiments of this paragraph, $Z_1$ and $Z_2$ are different. In some embodiments of this paragraph, when $Z_1$ can be —NH—, $Z_2$ can be —NH—. In some embodiments of this paragraph, when $Z_1$ can be —O—, $Z_2$ can be —O—. In some embodiments of this paragraph, when $Z_1$ can be —$CH_2$—, $Z_2$ can be —$CH_2$—. In some embodiments of this paragraph, when $Z_1$ can be —NH(CO)—, $Z_2$ can be —NH(CO)—. In some embodiments of this paragraph, when $Z_1$ can be —$CH_2$NH—, $Z_2$ can be —$CH_2$NH—. In some embodiments of this paragraph, when $Z_1$ can be —$CH_2$NH(CO)—, $Z_2$ can be —NH—. In some embodiments of this paragraph, when $Z_1$ can be —$CH_2$NH(CO)—, $Z_2$ can be —O—. In some embodiments of this paragraph, when $Z_1$ can be —$CH_2$NH(CO)—, $Z_2$ can be —$CH_2$—. In some embodiments of this paragraph, when $Z_1$ can be —$CH_2$NH(CO)—, $Z_2$ can be —NH(CO)—. In some embodiments of this paragraph, when $Z_1$ can be —$CH_2$NH(CO)—, $Z_2$ can be —$CH_2$NH—.

In some embodiments, each $R_4$ can be independently an unsubstituted $C_1$-$C_4$ alkylene, for example, methylene, ethylene, n-propylene, isopropylene, n-butylene, sec-butylene, or t-butylene. In some embodiments, each $R_4$ can be independently an unsubstituted $C_1$-$C_2$ alkylene, such as methylene or ethylene.

In some embodiments, t can be 1. In some embodiments, t can be 2. In some embodiments, t can be 3. In some embodiments, t can be 4. In some embodiments, t can be 5. In some embodiments, t can be 6.

In some embodiments, the compound of Formula (I) is selected from:
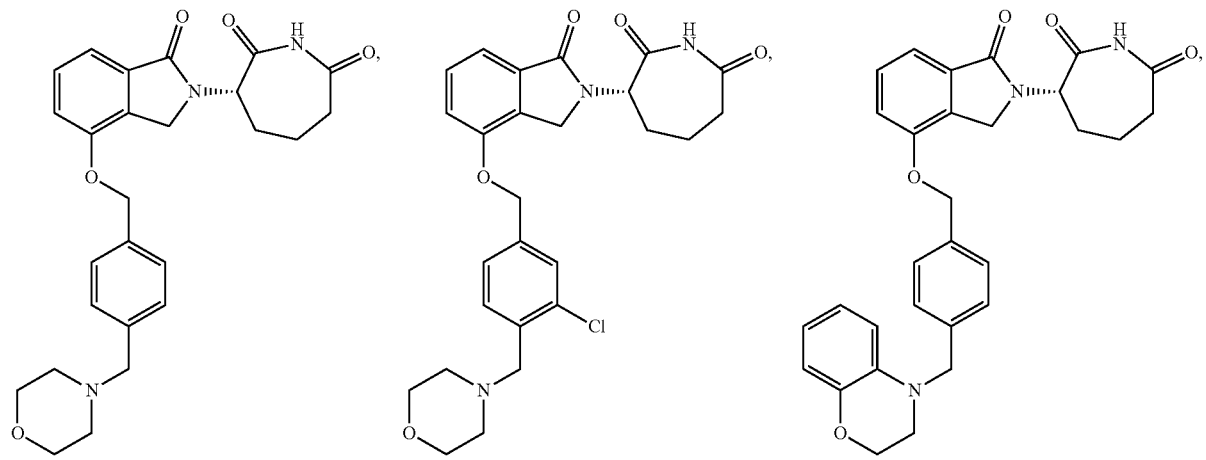
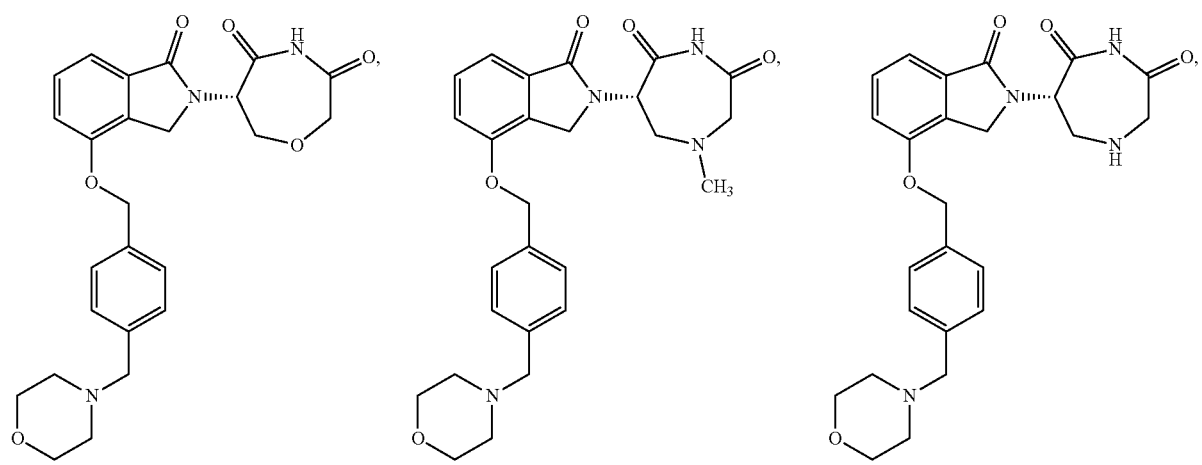
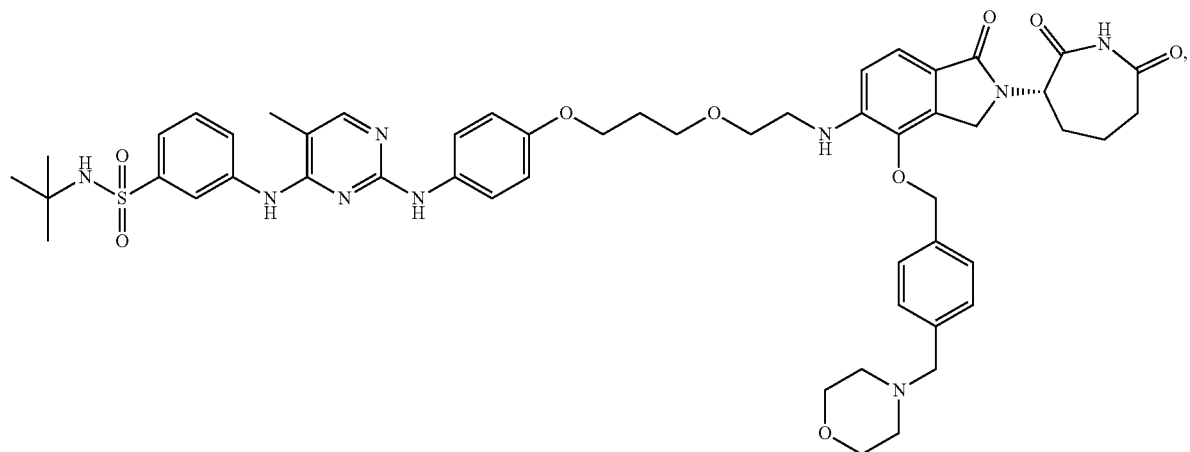

-continued
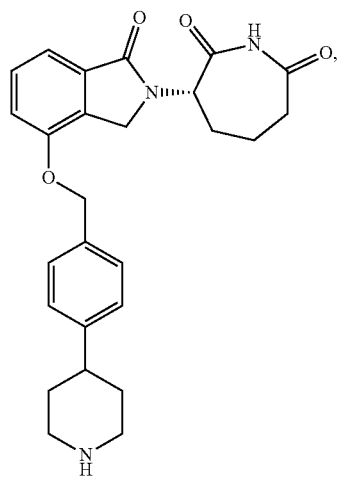
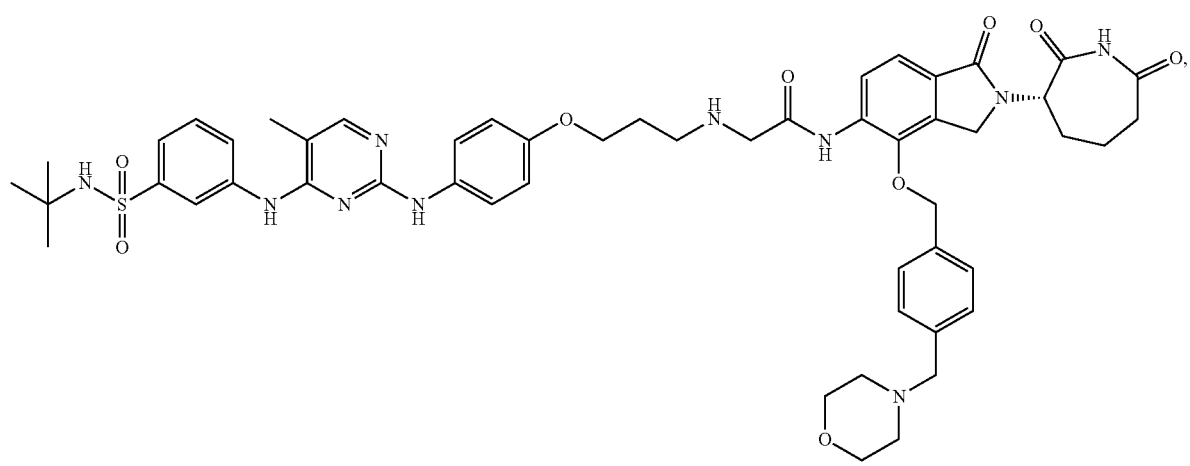
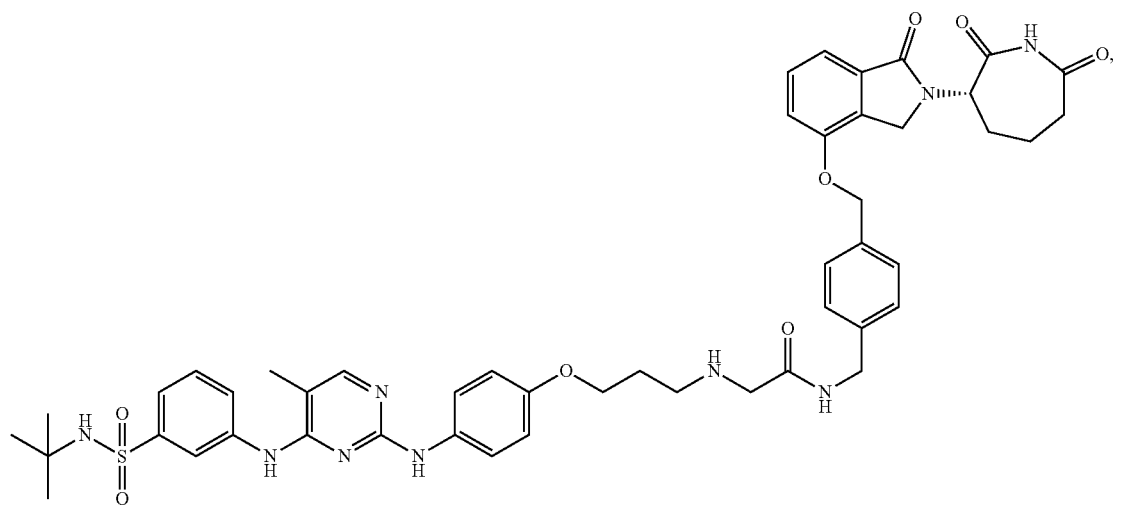

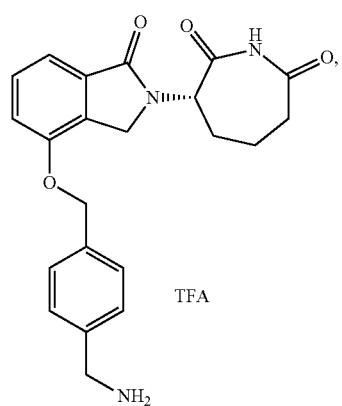
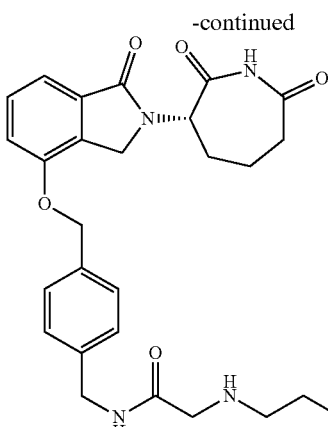
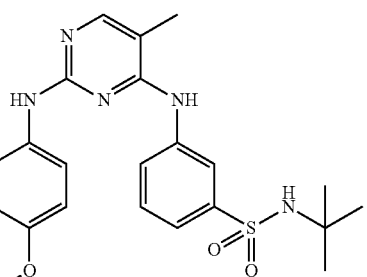
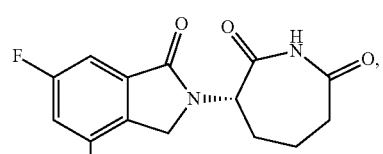
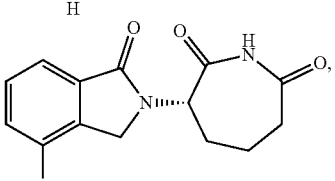
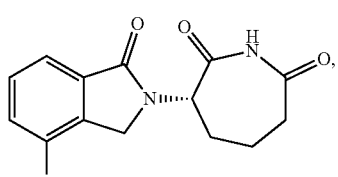
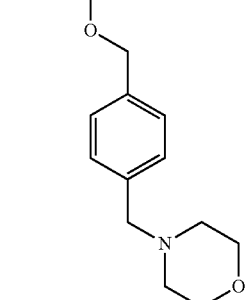
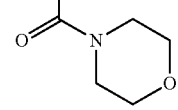
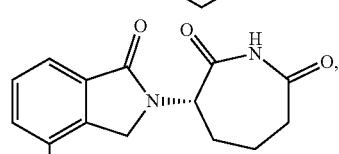
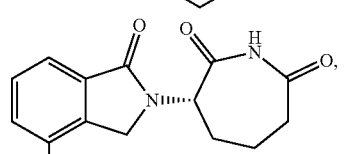
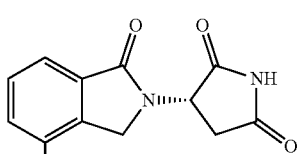
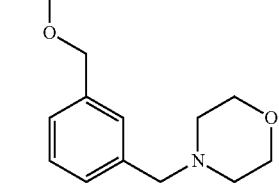
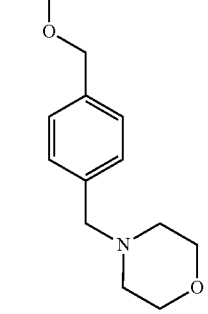
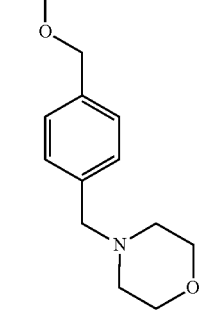
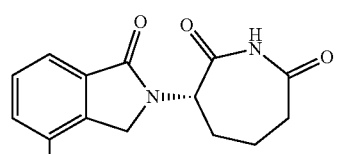
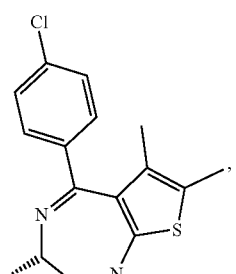
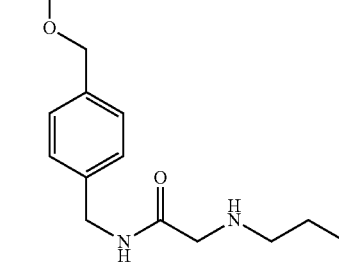
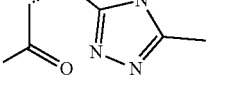

-continued
47
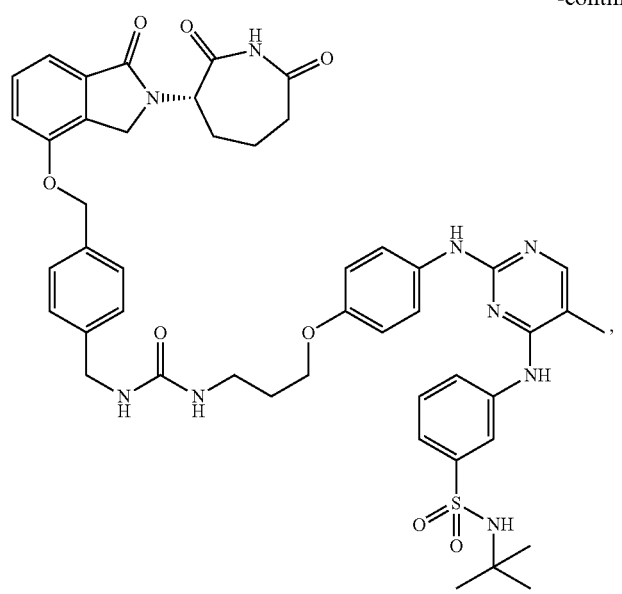
48
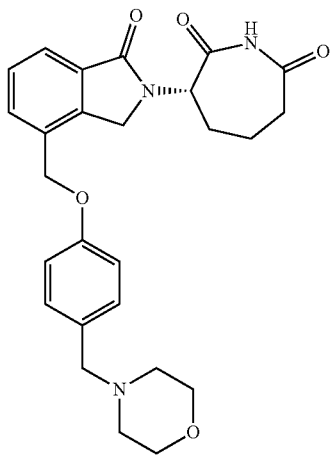
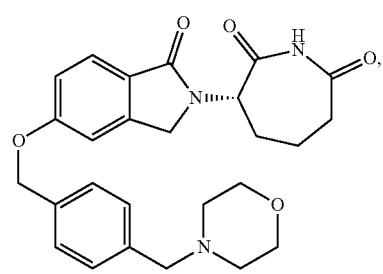
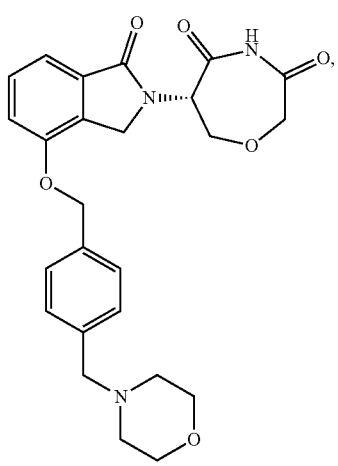
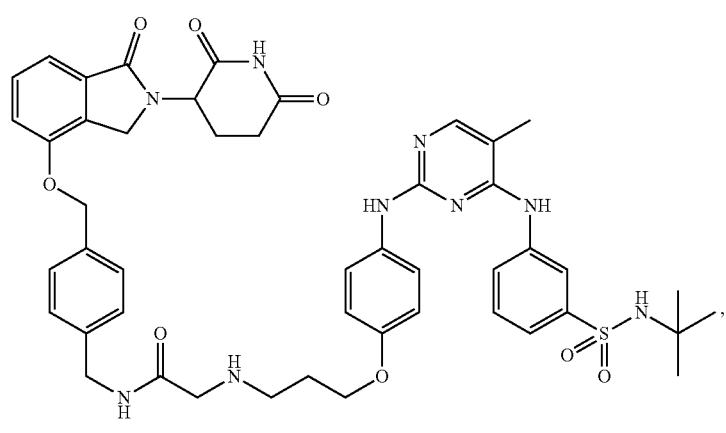
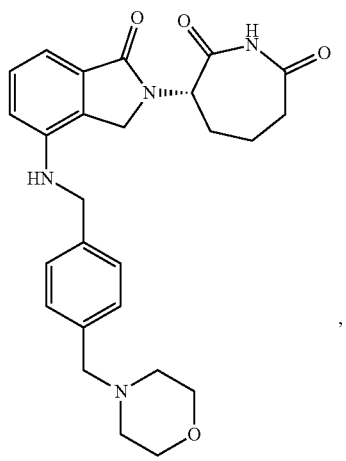

-continued
49
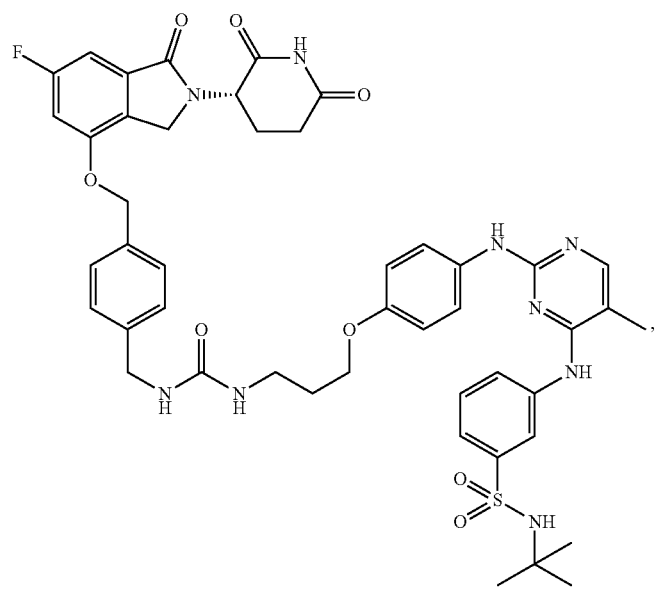
50
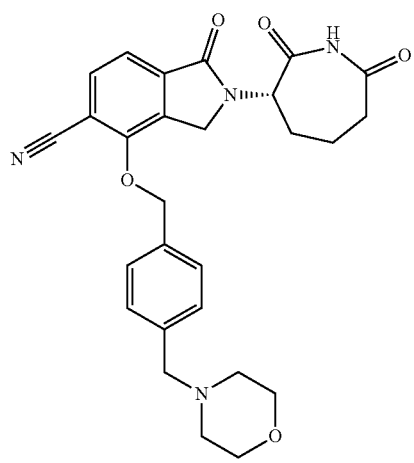
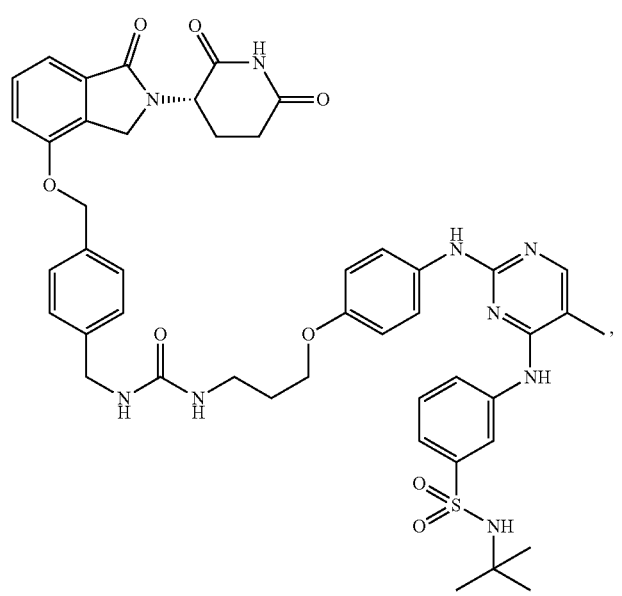
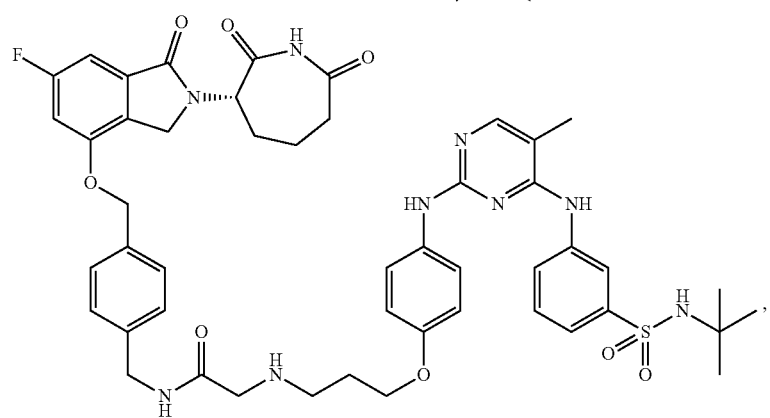

-continued
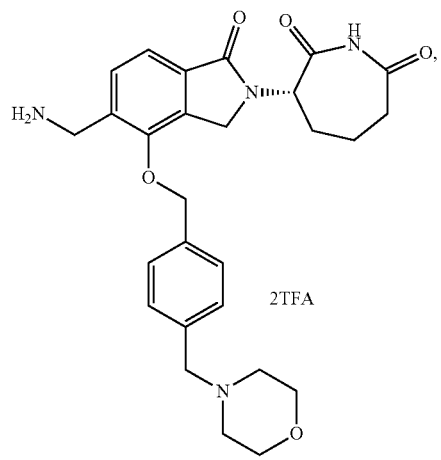
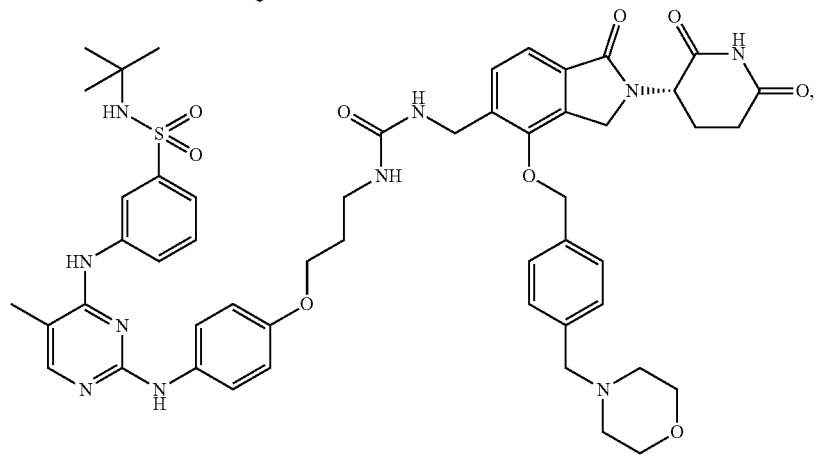
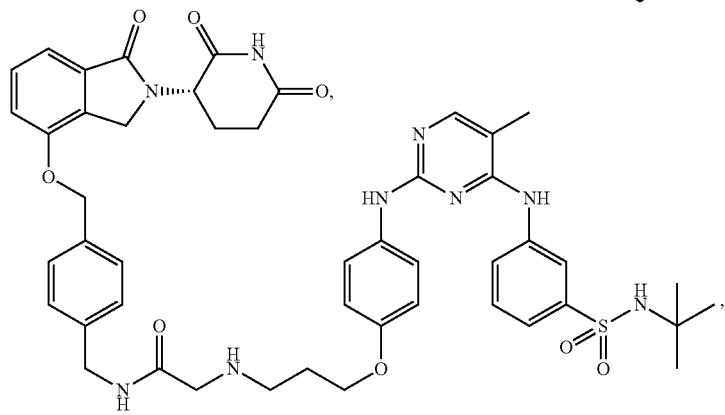
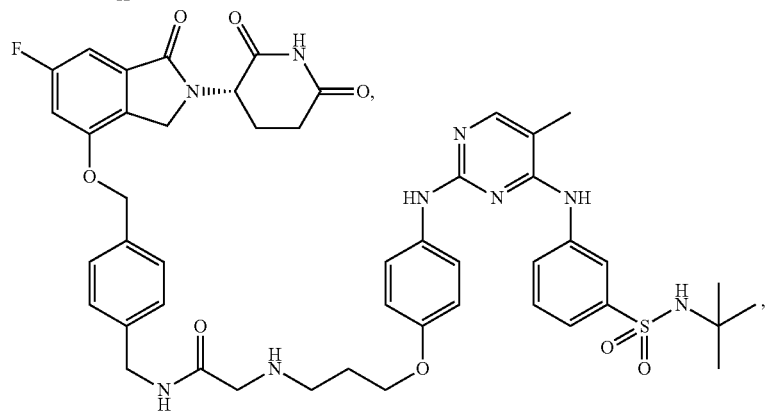
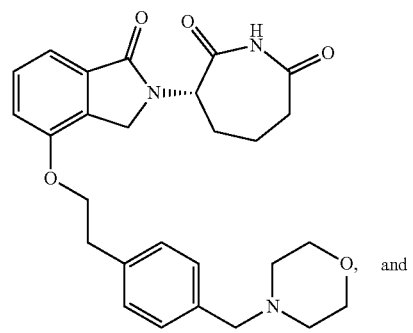

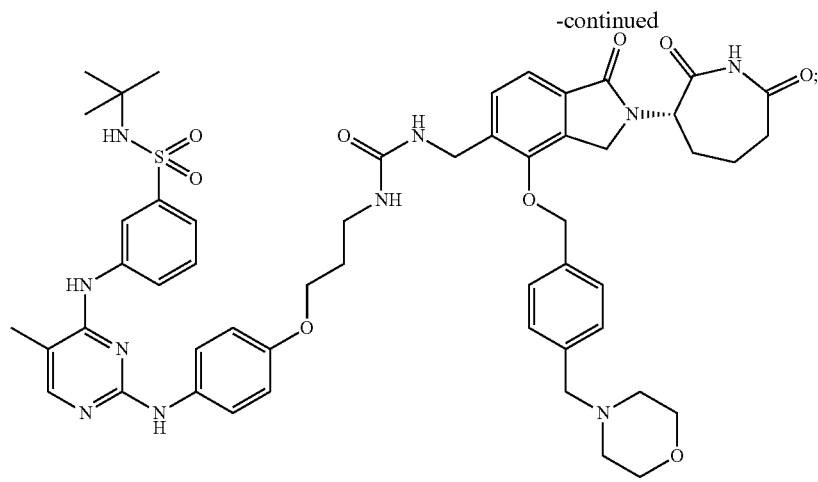

or a pharmaceutically acceptable salt of any of the foregoing.

Some embodiments of compounds of Formula (I) are shown in Table B, below.

TABLE B

| X | $X_1$ | $Q_1$ | $Q_2$ | $Y_1$ | $Y_2$ | $Y_3$ | $Y_4$ | $Y_5$ |
|---|---|---|---|---|---|---|---|---|
| C=O | H | $CH_2$ | $CH_2$ or bond | $CR_3$ | $CR_3$ | $CR_3$ | $CR_3$ | $CR_3$ |
| C=O | H | O | $CH_2$ or bond | $CR_3$ | $CR_3$ | $CR_3$ | $CR_3$ | $CR_3$ |
| C=O | H | $NR_2$ | $CH_2$ or bond | $CR_3$ | $CR_3$ | $CR_3$ | $CR_3$ | $CR_3$ |
| C=O | H | S | $CH_2$ or bond | $CR_3$ | $CR_3$ | $CR_3$ | $CR_3$ | $CR_3$ |
| C=O | H | a bond | $CH_2$ or bond | $CR_3$ | $CR_3$ | $CR_3$ | $CR_3$ | $CR_3$ |
| C=O | methyl | $CH_2$ | $CH_2$ or bond | $CR_3$ | $CR_3$ | $CR_3$ | $CR_3$ | $CR_3$ |
| C=O | methyl | O | $CH_2$ or bond | $CR_3$ | $CR_3$ | $CR_3$ | $CR_3$ | $CR_3$ |
| C=O | methyl | $NR_2$ | $CH_2$ or bond | $CR_3$ | $CR_3$ | $CR_3$ | $CR_3$ | $CR_3$ |
| C=O | methyl | S | $CH_2$ or bond | $CR_3$ | $CR_3$ | $CR_3$ | $CR_3$ | $CR_3$ |
| C=O | methyl | a bond | $CH_2$ or bond | $CR_3$ | $CR_3$ | $CR_3$ | $CR_3$ | $CR_3$ |
| C=O | D | $CH_2$ | $CH_2$ or bond | $CR_3$ | $CR_3$ | $CR_3$ | $CR_3$ | $CR_3$ |
| C=O | D | O | $CH_2$ or bond | $CR_3$ | $CR_3$ | $CR_3$ | $CR_3$ | $CR_3$ |
| C=O | D | $NR_2$ | $CH_2$ or bond | $CR_3$ | $CR_3$ | $CR_3$ | $CR_3$ | $CR_3$ |
| C=O | D | S | $CH_2$ or bond | $CR_3$ | $CR_3$ | $CR_3$ | $CR_3$ | $CR_3$ |
| C=O | D | a bond | $CH_2$ or bond | $CR_3$ | $CR_3$ | $CR_3$ | $CR_3$ | $CR_3$ |
| C=O | fluoro | $CH_2$ | $CH_2$ or bond | $CR_3$ | $CR_3$ | $CR_3$ | $CR_3$ | $CR_3$ |
| C=O | fluoro | O | $CH_2$ or bond | $CR_3$ | $CR_3$ | $CR_3$ | $CR_3$ | $CR_3$ |
| C=O | fluoro | $NR_2$ | $CH_2$ or bond | $CR_3$ | $CR_3$ | $CR_3$ | $CR_3$ | $CR_3$ |
| C=O | fluoro | S | $CH_2$ or bond | $CR_3$ | $CR_3$ | $CR_3$ | $CR_3$ | $CR_3$ |
| C=O | fluoro | a bond | $CH_2$ or bond | $CR_3$ | $CR_3$ | $CR_3$ | $CR_3$ | $CR_3$ |
| $CH_2$ | H | $CH_2$ | $CH_2$ or bond | $CR_3$ | $CR_3$ | $CR_3$ | $CR_3$ | $CR_3$ |
| $CH_2$ | H | O | $CH_2$ or bond | $CR_3$ | $CR_3$ | $CR_3$ | $CR_3$ | $CR_3$ |
| $CH_2$ | H | $NR_2$ | $CH_2$ or bond | $CR_3$ | $CR_3$ | $CR_3$ | $CR_3$ | $CR_3$ |
| $CH_2$ | H | S | $CH_2$ or bond | $CR_3$ | $CR_3$ | $CR_3$ | $CR_3$ | $CR_3$ |
| $CH_2$ | H | a bond | $CH_2$ or bond | $CR_3$ | $CR_3$ | $CR_3$ | $CR_3$ | $CR_3$ |
| $CH_2$ | methyl | $CH_2$ | $CH_2$ or bond | $CR_3$ | $CR_3$ | $CR_3$ | $CR_3$ | $CR_3$ |
| $CH_2$ | methyl | O | $CH_2$ or bond | $CR_3$ | $CR_3$ | $CR_3$ | $CR_3$ | $CR_3$ |
| $CH_2$ | methyl | $NR_2$ | $CH_2$ or bond | $CR_3$ | $CR_3$ | $CR_3$ | $CR_3$ | $CR_3$ |
| $CH_2$ | methyl | S | $CH_2$ or bond | $CR_3$ | $CR_3$ | $CR_3$ | $CR_3$ | $CR_3$ |
| $CH_2$ | methyl | a bond | $CH_2$ or bond | $CR_3$ | $CR_3$ | $CR_3$ | $CR_3$ | $CR_3$ |
| $CH_2$ | D | $CH_2$ | $CH_2$ or bond | $CR_3$ | $CR_3$ | $CR_3$ | $CR_3$ | $CR_3$ |
| $CH_2$ | D | O | $CH_2$ or bond | $CR_3$ | $CR_3$ | $CR_3$ | $CR_3$ | $CR_3$ |
| $CH_2$ | D | $NR_2$ | $CH_2$ or bond | $CR_3$ | $CR_3$ | $CR_3$ | $CR_3$ | $CR_3$ |
| $CH_2$ | D | S | $CH_2$ or bond | $CR_3$ | $CR_3$ | $CR_3$ | $CR_3$ | $CR_3$ |
| $CH_2$ | D | a bond | $CH_2$ or bond | $CR_3$ | $CR_3$ | $CR_3$ | $CR_3$ | $CR_3$ |
| $CH_2$ | fluoro | $CH_2$ | $CH_2$ or bond | $CR_3$ | $CR_3$ | $CR_3$ | $CR_3$ | $CR_3$ |
| $CH_2$ | fluoro | O | $CH_2$ or bond | $CR_3$ | $CR_3$ | $CR_3$ | $CR_3$ | $CR_3$ |
| $CH_2$ | fluoro | $NR_2$ | $CH_2$ or bond | $CR_3$ | $CR_3$ | $CR_3$ | $CR_3$ | $CR_3$ |
| $CH_2$ | fluoro | S | $CH_2$ or bond | $CR_3$ | $CR_3$ | $CR_3$ | $CR_3$ | $CR_3$ |
| $CH_2$ | fluoro | a bond | $CH_2$ or bond | $CR_3$ | $CR_3$ | $CR_3$ | $CR_3$ | $CR_3$ |
| C=O | H | $CH_2$ | $CH_2$ or bond | N | $CR_3$ | $CR_3$ | $CR_3$ | $CR_3$ |
| C=O | H | O | $CH_2$ or bond | N | $CR_3$ | $CR_3$ | $CR_3$ | $CR_3$ |
| C=O | H | $NR_2$ | $CH_2$ or bond | N | $CR_3$ | $CR_3$ | $CR_3$ | $CR_3$ |
| C=O | H | S | $CH_2$ or bond | N | $CR_3$ | $CR_3$ | $CR_3$ | $CR_3$ |
| C=O | H | a bond | $CH_2$ or bond | N | $CR_3$ | $CR_3$ | $CR_3$ | $CR_3$ |
| C=O | methyl | $CH_2$ | $CH_2$ or bond | N | $CR_3$ | $CR_3$ | $CR_3$ | $CR_3$ |
| C=O | methyl | O | $CH_2$ or bond | N | $CR_3$ | $CR_3$ | $CR_3$ | $CR_3$ |
| C=O | methyl | $NR_2$ | $CH_2$ or bond | N | $CR_3$ | $CR_3$ | $CR_3$ | $CR_3$ |
| C=O | methyl | S | $CH_2$ or bond | N | $CR_3$ | $CR_3$ | $CR_3$ | $CR_3$ |

TABLE B-continued

| X | X₁ | Q₁ | Q₂ | Y₁ | Y₂ | Y₃ | Y₄ | Y₅ |
|---|---|---|---|---|---|---|---|---|
| C=O | methyl | a bond | CH₂ or bond | N | CR₃ | CR₃ | CR₃ | CR₃ |
| C=O | D | CH₂ | CH₂ or bond | N | CR₃ | CR₃ | CR₃ | CR₃ |
| C=O | D | O | CH₂ or bond | N | CR₃ | CR₃ | CR₃ | CR₃ |
| C=O | D | NR₂ | CH₂ or bond | N | CR₃ | CR₃ | CR₃ | CR₃ |
| C=O | D | S | CH₂ or bond | N | CR₃ | CR₃ | CR₃ | CR₃ |
| C=O | D | a bond | CH₂ or bond | N | CR₃ | CR₃ | CR₃ | CR₃ |
| C=O | fluoro | CH₂ | CH₂ or bond | N | CR₃ | CR₃ | CR₃ | CR₃ |
| C=O | fluoro | O | CH₂ or bond | N | CR₃ | CR₃ | CR₃ | CR₃ |
| C=O | fluoro | NR₂ | CH₂ or bond | N | CR₃ | CR₃ | CR₃ | CR₃ |
| C=O | fluoro | S | CH₂ or bond | N | CR₃ | CR₃ | CR₃ | CR₃ |
| C=O | fluoro | a bond | CH₂ or bond | N | CR₃ | CR₃ | CR₃ | CR₃ |
| CH₂ | H | CH₂ | CH₂ or bond | N | CR₃ | CR₃ | CR₃ | CR₃ |
| CH₂ | H | O | CH₂ or bond | N | CR₃ | CR₃ | CR₃ | CR₃ |
| CH₂ | H | NR₂ | CH₂ or bond | N | CR₃ | CR₃ | CR₃ | CR₃ |
| CH₂ | H | S | CH₂ or bond | N | CR₃ | CR₃ | CR₃ | CR₃ |
| CH₂ | H | a bond | CH₂ or bond | N | CR₃ | CR₃ | CR₃ | CR₃ |
| CH₂ | methyl | CH₂ | CH₂ or bond | N | CR₃ | CR₃ | CR₃ | CR₃ |
| CH₂ | methyl | O | CH₂ or bond | N | CR₃ | CR₃ | CR₃ | CR₃ |
| CH₂ | methyl | NR₂ | CH₂ or bond | N | CR₃ | CR₃ | CR₃ | CR₃ |
| CH₂ | methyl | S | CH₂ or bond | N | CR₃ | CR₃ | CR₃ | CR₃ |
| CH₂ | methyl | a bond | CH₂ or bond | N | CR₃ | CR₃ | CR₃ | CR₃ |
| CH₂ | D | CH₂ | CH₂ or bond | N | CR₃ | CR₃ | CR₃ | CR₃ |
| CH₂ | D | O | CH₂ or bond | N | CR₃ | CR₃ | CR₃ | CR₃ |
| CH₂ | D | NR₂ | CH₂ or bond | N | CR₃ | CR₃ | CR₃ | CR₃ |
| CH₂ | D | S | CH₂ or bond | N | CR₃ | CR₃ | CR₃ | CR₃ |
| CH₂ | D | a bond | CH₂ or bond | N | CR₃ | CR₃ | CR₃ | CR₃ |
| CH₂ | fluoro | CH₂ | CH₂ or bond | N | CR₃ | CR₃ | CR₃ | CR₃ |
| CH₂ | fluoro | O | CH₂ or bond | N | CR₃ | CR₃ | CR₃ | CR₃ |
| CH₂ | fluoro | NR₂ | CH₂ or bond | N | CR₃ | CR₃ | CR₃ | CR₃ |
| CH₂ | fluoro | S | CH₂ or bond | N | CR₃ | CR₃ | CR₃ | CR₃ |
| CH₂ | fluoro | a bond | CH₂ or bond | N | CR₃ | CR₃ | CR₃ | CR₃ |
| C=O | H | CH₂ | CH₂ or bond | CR₃ | N | CR₃ | CR₃ | CR₃ |
| C=O | H | O | CH₂ or bond | CR₃ | N | CR₃ | CR₃ | CR₃ |
| C=O | H | NR₂ | CH₂ or bond | CR₃ | N | CR₃ | CR₃ | CR₃ |
| C=O | H | S | CH₂ or bond | CR₃ | N | CR₃ | CR₃ | CR₃ |
| C=O | H | a bond | CH₂ or bond | CR₃ | N | CR₃ | CR₃ | CR₃ |
| C=O | methyl | CH₂ | CH₂ or bond | CR₃ | N | CR₃ | CR₃ | CR₃ |
| C=O | methyl | O | CH₂ or bond | CR₃ | N | CR₃ | CR₃ | CR₃ |
| C=O | methyl | NR₂ | CH₂ or bond | CR₃ | N | CR₃ | CR₃ | CR₃ |
| C=O | methyl | S | CH₂ or bond | CR₃ | N | CR₃ | CR₃ | CR₃ |
| C=O | methyl | a bond | CH₂ or bond | CR₃ | N | CR₃ | CR₃ | CR₃ |
| C=O | D | CH₂ | CH₂ or bond | CR₃ | N | CR₃ | CR₃ | CR₃ |
| C=O | D | O | CH₂ or bond | CR₃ | N | CR₃ | CR₃ | CR₃ |
| C=O | D | NR₂ | CH₂ or bond | CR₃ | N | CR₃ | CR₃ | CR₃ |
| C=O | D | S | CH₂ or bond | CR₃ | N | CR₃ | CR₃ | CR₃ |
| C=O | D | a bond | CH₂ or bond | CR₃ | N | CR₃ | CR₃ | CR₃ |
| C=O | fluoro | CH₂ | CH₂ or bond | CR₃ | N | CR₃ | CR₃ | CR₃ |
| C=O | fluoro | O | CH₂ or bond | CR₃ | N | CR₃ | CR₃ | CR₃ |
| C=O | fluoro | NR₂ | CH₂ or bond | CR₃ | N | CR₃ | CR₃ | CR₃ |
| C=O | fluoro | S | CH₂ or bond | CR₃ | N | CR₃ | CR₃ | CR₃ |
| C=O | fluoro | a bond | CH₂ or bond | CR₃ | N | CR₃ | CR₃ | CR₃ |
| CH₂ | H | CH₂ | CH₂ or bond | CR₃ | N | CR₃ | CR₃ | CR₃ |
| CH₂ | H | O | CH₂ or bond | CR₃ | N | CR₃ | CR₃ | CR₃ |
| CH₂ | H | NR₂ | CH₂ or bond | CR₃ | N | CR₃ | CR₃ | CR₃ |
| CH₂ | H | S | CH₂ or bond | CR₃ | N | CR₃ | CR₃ | CR₃ |
| CH₂ | H | a bond | CH₂ or bond | CR₃ | N | CR₃ | CR₃ | CR₃ |
| CH₂ | methyl | CH₂ | CH₂ or bond | CR₃ | N | CR₃ | CR₃ | CR₃ |
| CH₂ | methyl | O | CH₂ or bond | CR₃ | N | CR₃ | CR₃ | CR₃ |
| CH₂ | methyl | NR₂ | CH₂ or bond | CR₃ | N | CR₃ | CR₃ | CR₃ |
| CH₂ | methyl | S | CH₂ or bond | CR₃ | N | CR₃ | CR₃ | CR₃ |
| CH₂ | methyl | a bond | CH₂ or bond | CR₃ | N | CR₃ | CR₃ | CR₃ |
| CH₂ | D | CH₂ | CH₂ or bond | CR₃ | N | CR₃ | CR₃ | CR₃ |
| CH₂ | D | O | CH₂ or bond | CR₃ | N | CR₃ | CR₃ | CR₃ |
| CH₂ | D | NR₂ | CH₂ or bond | CR₃ | N | CR₃ | CR₃ | CR₃ |
| CH₂ | D | S | CH₂ or bond | CR₃ | N | CR₃ | CR₃ | CR₃ |
| CH₂ | D | a bond | CH₂ or bond | CR₃ | N | CR₃ | CR₃ | CR₃ |
| CH₂ | fluoro | CH₂ | CH₂ or bond | CR₃ | N | CR₃ | CR₃ | CR₃ |
| CH₂ | fluoro | O | CH₂ or bond | CR₃ | N | CR₃ | CR₃ | CR₃ |
| CH₂ | fluoro | NR₂ | CH₂ or bond | CR₃ | N | CR₃ | CR₃ | CR₃ |
| CH₂ | fluoro | S | CH₂ or bond | CR₃ | N | CR₃ | CR₃ | CR₃ |
| CH₂ | fluoro | a bond | CH₂ or bond | CR₃ | N | CR₃ | CR₃ | CR₃ |
| C=O | H | CH₂ | CH₂ or bond | CR₃ | CR₃ | N | CR₃ | CR₃ |
| C=O | H | O | CH₂ or bond | CR₃ | CR₃ | N | CR₃ | CR₃ |
| C=O | H | NR₂ | CH₂ or bond | CR₃ | CR₃ | N | CR₃ | CR₃ |
| C=O | H | S | CH₂ or bond | CR₃ | CR₃ | N | CR₃ | CR₃ |
| C=O | H | a bond | CH₂ or bond | CR₃ | CR₃ | N | CR₃ | CR₃ |
| C=O | methyl | CH₂ | CH₂ or bond | CR₃ | CR₃ | N | CR₃ | CR₃ |
| C=O | methyl | O | CH₂ or bond | CR₃ | CR₃ | N | CR₃ | CR₃ |

TABLE B-continued

| X | X₁ | Q₁ | Q₂ | Y₁ | Y₂ | Y₃ | Y₄ | Y₅ |
|---|---|---|---|---|---|---|---|---|
| C=O | methyl | NR₂ | CH₂ or bond | CR₃ | CR₃ | N | CR₃ | CR₃ |
| C=O | methyl | S | CH₂ or bond | CR₃ | CR₃ | N | CR₃ | CR₃ |
| C=O | methyl | a bond | CH₂ or bond | CR₃ | CR₃ | N | CR₃ | CR₃ |
| C=O | D | CH₂ | CH₂ or bond | CR₃ | CR₃ | N | CR₃ | CR₃ |
| C=O | D | O | CH₂ or bond | CR₃ | CR₃ | N | CR₃ | CR₃ |
| C=O | D | NR₂ | CH₂ or bond | CR₃ | CR₃ | N | CR₃ | CR₃ |
| C=O | D | S | CH₂ or bond | CR₃ | CR₃ | N | CR₃ | CR₃ |
| C=O | D | a bond | CH₂ or bond | CR₃ | CR₃ | N | CR₃ | CR₃ |
| C=O | fluoro | CH₂ | CH₂ or bond | CR₃ | CR₃ | N | CR₃ | CR₃ |
| C=O | fluoro | O | CH₂ or bond | CR₃ | CR₃ | N | CR₃ | CR₃ |
| C=O | fluoro | NR₂ | CH₂ or bond | CR₃ | CR₃ | N | CR₃ | CR₃ |
| C=O | fluoro | S | CH₂ or bond | CR₃ | CR₃ | N | CR₃ | CR₃ |
| C=O | fluoro | a bond | CH₂ or bond | CR₃ | CR₃ | N | CR₃ | CR₃ |
| CH₂ | H | CH₂ | CH₂ or bond | CR₃ | CR₃ | N | CR₃ | CR₃ |
| CH₂ | H | O | CH₂ or bond | CR₃ | CR₃ | N | CR₃ | CR₃ |
| CH₂ | H | NR₂ | CH₂ or bond | CR₃ | CR₃ | N | CR₃ | CR₃ |
| CH₂ | H | S | CH₂ or bond | CR₃ | CR₃ | N | CR₃ | CR₃ |
| CH₂ | H | a bond | CH₂ or bond | CR₃ | CR₃ | N | CR₃ | CR₃ |
| CH₂ | methyl | CH₂ | CH₂ or bond | CR₃ | CR₃ | N | CR₃ | CR₃ |
| CH₂ | methyl | O | CH₂ or bond | CR₃ | CR₃ | N | CR₃ | CR₃ |
| CH₂ | methyl | NR₂ | CH₂ or bond | CR₃ | CR₃ | N | CR₃ | CR₃ |
| CH₂ | methyl | S | CH₂ or bond | CR₃ | CR₃ | N | CR₃ | CR₃ |
| CH₂ | methyl | a bond | CH₂ or bond | CR₃ | CR₃ | N | CR₃ | CR₃ |
| CH₂ | D | CH₂ | CH₂ or bond | CR₃ | CR₃ | N | CR₃ | CR₃ |
| CH₂ | D | O | CH₂ or bond | CR₃ | CR₃ | N | CR₃ | CR₃ |
| CH₂ | D | NR₂ | CH₂ or bond | CR₃ | CR₃ | N | CR₃ | CR₃ |
| CH₂ | D | S | CH₂ or bond | CR₃ | CR₃ | N | CR₃ | CR₃ |
| CH₂ | D | a bond | CH₂ or bond | CR₃ | CR₃ | N | CR₃ | CR₃ |
| CH₂ | fluoro | CH₂ | CH₂ or bond | CR₃ | CR₃ | N | CR₃ | CR₃ |
| CH₂ | fluoro | O | CH₂ or bond | CR₃ | CR₃ | N | CR₃ | CR₃ |
| CH₂ | fluoro | NR₂ | CH₂ or bond | CR₃ | CR₃ | N | CR₃ | CR₃ |
| CH₂ | fluoro | S | CH₂ or bond | CR₃ | CR₃ | N | CR₃ | CR₃ |
| CH₂ | fluoro | a bond | CH₂ or bond | CR₃ | CR₃ | N | CR₃ | CR₃ |
| C=O | H | CH₂ | CH₂ or bond | CR₃ | N | N | CR₃ | CR₃ |
| C=O | H | O | CH₂ or bond | CR₃ | N | N | CR₃ | CR₃ |
| C=O | H | NR₂ | CH₂ or bond | CR₃ | N | N | CR₃ | CR₃ |
| C=O | H | S | CH₂ or bond | CR₃ | N | N | CR₃ | CR₃ |
| C=O | H | a bond | CH₂ or bond | CR₃ | N | N | CR₃ | CR₃ |
| C=O | methyl | CH₂ | CH₂ or bond | CR₃ | N | N | CR₃ | CR₃ |
| C=O | methyl | O | CH₂ or bond | N | N | CR₃ | CR₃ | CR₃ |
| C=O | methyl | NR₂ | CH₂ or bond | N | N | CR₃ | CR₃ | CR₃ |
| C=O | methyl | S | CH₂ or bond | N | N | CR₃ | CR₃ | CR₃ |
| C=O | methyl | a bond | CH₂ or bond | N | N | CR₃ | CR₃ | CR₃ |
| C=O | D | CH₂ | CH₂ or bond | N | N | CR₃ | CR₃ | CR₃ |
| C=O | D | O | CH₂ or bond | N | N | CR₃ | CR₃ | CR₃ |
| C=O | D | NR₂ | CH₂ or bond | N | N | CR₃ | CR₃ | CR₃ |
| C=O | D | S | CH₂ or bond | N | N | CR₃ | CR₃ | CR₃ |
| C=O | D | a bond | CH₂ or bond | N | N | CR₃ | CR₃ | CR₃ |
| C=O | fluoro | CH₂ | CH₂ or bond | N | N | CR₃ | CR₃ | CR₃ |
| C=O | fluoro | O | CH₂ or bond | N | N | CR₃ | CR₃ | CR₃ |
| C=O | fluoro | NR₂ | CH₂ or bond | N | N | CR₃ | CR₃ | CR₃ |
| C=O | fluoro | S | CH₂ or bond | N | N | CR₃ | CR₃ | CR₃ |
| C=O | fluoro | a bond | CH₂ or bond | N | N | CR₃ | CR₃ | CR₃ |
| CH₂ | H | CH₂ | CH₂ or bond | N | N | CR₃ | CR₃ | CR₃ |
| CH₂ | H | O | CH₂ or bond | N | N | CR₃ | CR₃ | CR₃ |
| CH₂ | H | NR₂ | CH₂ or bond | N | N | CR₃ | CR₃ | CR₃ |
| CH₂ | H | S | CH₂ or bond | N | N | CR₃ | CR₃ | CR₃ |
| CH₂ | H | a bond | CH₂ or bond | N | N | CR₃ | CR₃ | CR₃ |
| CH₂ | methyl | CH₂ | CH₂ or bond | N | N | CR₃ | CR₃ | CR₃ |
| CH₂ | methyl | O | CH₂ or bond | N | N | CR₃ | CR₃ | CR₃ |
| CH₂ | methyl | NR₂ | CH₂ or bond | N | N | CR₃ | CR₃ | CR₃ |
| CH₂ | methyl | S | CH₂ or bond | N | N | CR₃ | CR₃ | CR₃ |
| CH₂ | methyl | a bond | CH₂ or bond | N | N | CR₃ | CR₃ | CR₃ |
| CH₂ | D | CH₂ | CH₂ or bond | N | N | CR₃ | CR₃ | CR₃ |
| CH₂ | D | O | CH₂ or bond | N | N | CR₃ | CR₃ | CR₃ |
| CH₂ | D | NR₂ | CH₂ or bond | N | N | CR₃ | CR₃ | CR₃ |
| CH₂ | D | S | CH₂ or bond | N | N | CR₃ | CR₃ | CR₃ |
| CH₂ | D | a bond | CH₂ or bond | N | N | CR₃ | CR₃ | CR₃ |
| CH₂ | fluoro | CH₂ | CH₂ or bond | N | N | CR₃ | CR₃ | CR₃ |
| CH₂ | fluoro | O | CH₂ or bond | N | N | CR₃ | CR₃ | CR₃ |
| CH₂ | fluoro | NR₂ | CH₂ or bond | N | N | CR₃ | CR₃ | CR₃ |
| CH₂ | fluoro | S | CH₂ or bond | N | N | CR₃ | CR₃ | CR₃ |
| CH₂ | fluoro | a bond | CH₂ or bond | N | N | CR₃ | CR₃ | CR₃ |
| C=O | H | CH₂ | CH₂ or bond | N | CR₃ | CR₃ | CR₃ | N |
| C=O | H | O | CH₂ or bond | N | CR₃ | CR₃ | CR₃ | N |
| C=O | H | NR₂ | CH₂ or bond | N | CR₃ | CR₃ | CR₃ | N |
| C=O | H | S | CH₂ or bond | N | CR₃ | CR₃ | CR₃ | N |
| C=O | H | a bond | CH₂ or bond | N | CR₃ | CR₃ | CR₃ | N |

TABLE B-continued

| X | X₁ | Q₁ | Q₂ | Y₁ | Y₂ | Y₃ | Y₄ | Y₅ |
|---|---|---|---|---|---|---|---|---|
| C=O | methyl | CH₂ | CH₂ or bond | N | CR₃ | CR₃ | CR₃ | N |
| C=O | methyl | O | CH₂ or bond | N | CR₃ | CR₃ | CR₃ | N |
| C=O | methyl | NR₂ | CH₂ or bond | N | CR₃ | CR₃ | CR₃ | N |
| C=O | methyl | S | CH₂ or bond | N | CR₃ | CR₃ | CR₃ | N |
| C=O | methyl | a bond | CH₂ or bond | N | CR₃ | CR₃ | CR₃ | N |
| C=O | D | CH₂ | CH₂ or bond | N | CR₃ | CR₃ | CR₃ | N |
| C=O | D | O | CH₂ or bond | N | CR₃ | CR₃ | CR₃ | N |
| C=O | D | NR₂ | CH₂ or bond | N | CR₃ | CR₃ | CR₃ | N |
| C=O | D | S | CH₂ or bond | N | CR₃ | CR₃ | CR₃ | N |
| C=O | D | a bond | CH₂ or bond | N | CR₃ | CR₃ | CR₃ | N |
| C=O | fluoro | CH₂ | CH₂ or bond | N | CR₃ | CR₃ | CR₃ | N |
| C=O | fluoro | O | CH₂ or bond | N | CR₃ | CR₃ | CR₃ | N |
| C=O | fluoro | NR₂ | CH₂ or bond | N | CR₃ | CR₃ | CR₃ | N |
| C=O | fluoro | S | CH₂ or bond | N | CR₃ | CR₃ | CR₃ | N |
| C=O | fluoro | a bond | CH₂ or bond | N | CR₃ | CR₃ | CR₃ | N |
| CH₂ | H | CH₂ | CH₂ or bond | N | CR₃ | CR₃ | CR₃ | N |
| CH₂ | H | O | CH₂ or bond | N | CR₃ | CR₃ | CR₃ | N |
| CH₂ | H | NR₂ | CH₂ or bond | N | CR₃ | CR₃ | CR₃ | N |
| CH₂ | H | S | CH₂ or bond | N | CR₃ | CR₃ | CR₃ | N |
| CH₂ | H | a bond | CH₂ or bond | N | CR₃ | CR₃ | CR₃ | N |
| CH₂ | methyl | CH₂ | CH₂ or bond | N | CR₃ | CR₃ | CR₃ | N |
| CH₂ | methyl | O | CH₂ or bond | N | CR₃ | CR₃ | CR₃ | N |
| CH₂ | methyl | NR₂ | CH₂ or bond | N | CR₃ | CR₃ | CR₃ | N |
| CH₂ | methyl | S | CH₂ or bond | N | CR₃ | CR₃ | CR₃ | N |
| CH₂ | methyl | a bond | CH₂ or bond | N | CR₃ | CR₃ | CR₃ | N |
| CH₂ | D | CH₂ | CH₂ or bond | N | CR₃ | CR₃ | CR₃ | N |
| CH₂ | D | O | CH₂ or bond | N | CR₃ | CR₃ | CR₃ | N |
| CH₂ | D | NR₂ | CH₂ or bond | N | CR₃ | CR₃ | CR₃ | N |
| CH₂ | D | S | CH₂ or bond | N | CR₃ | CR₃ | CR₃ | N |
| CH₂ | D | a bond | CH₂ or bond | N | CR₃ | CR₃ | CR₃ | N |
| CH₂ | fluoro | CH₂ | CH₂ or bond | N | CR₃ | CR₃ | CR₃ | N |
| CH₂ | fluoro | O | CH₂ or bond | N | CR₃ | CR₃ | CR₃ | N |
| CH₂ | fluoro | NR₂ | CH₂ or bond | N | CR₃ | CR₃ | CR₃ | N |
| CH₂ | fluoro | S | CH₂ or bond | N | CR₃ | CR₃ | CR₃ | N |
| CH₂ | fluoro | a bond | CH₂ or bond | N | CR₃ | CR₃ | CR₃ | N |
| C=O | H | CH₂ | CH₂ or bond | CR₃ | N | CR₃ | N | CR₃ |
| C=O | H | O | CH₂ or bond | CR₃ | N | CR₃ | N | CR₃ |
| C=O | H | NR₂ | CH₂ or bond | CR₃ | N | CR₃ | N | CR₃ |
| C=O | H | S | CH₂ or bond | CR₃ | N | CR₃ | N | CR₃ |
| C=O | H | a bond | CH₂ or bond | CR₃ | N | CR₃ | N | CR₃ |
| C=O | methyl | CH₂ | CH₂ or bond | CR₃ | N | CR₃ | N | CR₃ |
| C=O | methyl | O | CH₂ or bond | CR₃ | N | CR₃ | N | CR₃ |
| C=O | methyl | NR₂ | CH₂ or bond | CR₃ | N | CR₃ | N | CR₃ |
| C=O | methyl | S | CH₂ or bond | CR₃ | N | CR₃ | N | CR₃ |
| C=O | methyl | a bond | CH₂ or bond | CR₃ | N | CR₃ | N | CR₃ |
| C=O | D | CH₂ | CH₂ or bond | CR₃ | N | CR₃ | N | CR₃ |
| C=O | D | O | CH₂ or bond | CR₃ | N | CR₃ | N | CR₃ |
| C=O | D | NR₂ | CH₂ or bond | CR₃ | N | CR₃ | N | CR₃ |
| C=O | D | S | CH₂ or bond | CR₃ | N | CR₃ | N | CR₃ |
| C=O | D | a bond | CH₂ or bond | CR₃ | N | CR₃ | N | CR₃ |
| C=O | fluoro | CH₂ | CH₂ or bond | CR₃ | N | CR₃ | N | CR₃ |
| C=O | fluoro | O | CH₂ or bond | CR₃ | N | CR₃ | N | CR₃ |
| C=O | fluoro | NR₂ | CH₂ or bond | CR₃ | N | CR₃ | N | CR₃ |
| C=O | fluoro | S | CH₂ or bond | CR₃ | N | CR₃ | N | CR₃ |
| C=O | fluoro | a bond | CH₂ or bond | CR₃ | N | CR₃ | N | CR₃ |
| CH₂ | H | CH₂ | CH₂ or bond | CR₃ | N | CR₃ | N | CR₃ |
| CH₂ | H | O | CH₂ or bond | CR₃ | N | CR₃ | N | CR₃ |
| CH₂ | H | NR₂ | CH₂ or bond | CR₃ | N | CR₃ | N | CR₃ |
| CH₂ | H | S | CH₂ or bond | CR₃ | N | CR₃ | N | CR₃ |
| CH₂ | H | a bond | CH₂ or bond | CR₃ | N | CR₃ | N | CR₃ |
| CH₂ | methyl | CH₂ | CH₂ or bond | CR₃ | N | CR₃ | N | CR₃ |
| CH₂ | methyl | O | CH₂ or bond | CR₃ | N | CR₃ | N | CR₃ |
| CH₂ | methyl | NR₂ | CH₂ or bond | CR₃ | N | CR₃ | N | CR₃ |
| CH₂ | methyl | S | CH₂ or bond | CR₃ | N | CR₃ | N | CR₃ |
| CH₂ | methyl | a bond | CH₂ or bond | CR₃ | N | CR₃ | N | CR₃ |
| CH₂ | D | CH₂ | CH₂ or bond | CR₃ | N | CR₃ | N | CR₃ |
| CH₂ | D | O | CH₂ or bond | CR₃ | N | CR₃ | N | CR₃ |
| CH₂ | D | NR₂ | CH₂ or bond | CR₃ | N | CR₃ | N | CR₃ |
| CH₂ | D | S | CH₂ or bond | CR₃ | N | CR₃ | N | CR₃ |
| CH₂ | D | a bond | CH₂ or bond | CR₃ | N | CR₃ | N | CR₃ |
| CH₂ | fluoro | CH₂ | CH₂ or bond | CR₃ | N | CR₃ | N | CR₃ |
| CH₂ | fluoro | O | CH₂ or bond | CR₃ | N | CR₃ | N | CR₃ |
| CH₂ | fluoro | NR₂ | CH₂ or bond | CR₃ | N | CR₃ | N | CR₃ |
| CH₂ | fluoro | S | CH₂ or bond | CR₃ | N | CR₃ | N | CR₃ |
| CH₂ | fluoro | a bond | CH₂ or bond | CR₃ | N | CR₃ | N | CR₃ |
| C=O | H | CH₂ | CH₂ or bond | N | CR₃ | N | CR₃ | CR₃ |
| C=O | H | O | CH₂ or bond | N | CR₃ | N | CR₃ | CR₃ |
| C=O | H | NR₂ | CH₂ or bond | N | CR₃ | N | CR₃ | CR₃ |

TABLE B-continued

| X | $X_1$ | $Q_1$ | $Q_2$ | $Y_1$ | $Y_2$ | $Y_3$ | $Y_4$ | $Y_5$ |
|---|---|---|---|---|---|---|---|---|
| C=O | H | S | $CH_2$ or bond | N | $CR_3$ | N | $CR_3$ | $CR_3$ |
| C=O | H | a bond | $CH_2$ or bond | N | $CR_3$ | N | $CR_3$ | $CR_3$ |
| C=O | methyl | $CH_2$ | $CH_2$ or bond | N | $CR_3$ | N | $CR_3$ | $CR_3$ |
| C=O | methyl | O | $CH_2$ or bond | N | $CR_3$ | N | $CR_3$ | $CR_3$ |
| C=O | methyl | $NR_2$ | $CH_2$ or bond | N | $CR_3$ | N | $CR_3$ | $CR_3$ |
| C=O | methyl | S | $CH_2$ or bond | N | $CR_3$ | N | $CR_3$ | $CR_3$ |
| C=O | methyl | a bond | $CH_2$ or bond | N | $CR_3$ | N | $CR_3$ | $CR_3$ |
| C=O | D | $CH_2$ | $CH_2$ or bond | N | $CR_3$ | N | $CR_3$ | $CR_3$ |
| C=O | D | O | $CH_2$ or bond | N | $CR_3$ | N | $CR_3$ | $CR_3$ |
| C=O | D | $NR_2$ | $CH_2$ or bond | N | $CR_3$ | N | $CR_3$ | $CR_3$ |
| C=O | D | S | $CH_2$ or bond | N | $CR_3$ | N | $CR_3$ | $CR_3$ |
| C=O | D | a bond | $CH_2$ or bond | N | $CR_3$ | N | $CR_3$ | $CR_3$ |
| C=O | fluoro | $CH_2$ | $CH_2$ or bond | N | $CR_3$ | N | $CR_3$ | $CR_3$ |
| C=O | fluoro | O | $CH_2$ or bond | N | $CR_3$ | N | $CR_3$ | $CR_3$ |
| C=O | fluoro | $NR_2$ | $CH_2$ or bond | N | $CR_3$ | N | $CR_3$ | $CR_3$ |
| C=O | fluoro | S | $CH_2$ or bond | N | $CR_3$ | N | $CR_3$ | $CR_3$ |
| C=O | fluoro | a bond | $CH_2$ or bond | N | $CR_3$ | N | $CR_3$ | $CR_3$ |
| $CH_2$ | H | $CH_2$ | $CH_2$ or bond | N | $CR_3$ | N | $CR_3$ | $CR_3$ |
| $CH_2$ | H | O | $CH_2$ or bond | N | $CR_3$ | N | $CR_3$ | $CR_3$ |
| $CH_2$ | H | $NR_2$ | $CH_2$ or bond | N | $CR_3$ | N | $CR_3$ | $CR_3$ |
| $CH_2$ | H | S | $CH_2$ or bond | N | $CR_3$ | N | $CR_3$ | $CR_3$ |
| $CH_2$ | H | a bond | $CH_2$ or bond | N | $CR_3$ | N | $CR_3$ | $CR_3$ |
| $CH_2$ | methyl | $CH_2$ | $CH_2$ or bond | N | $CR_3$ | N | $CR_3$ | $CR_3$ |
| $CH_2$ | methyl | O | $CH_2$ or bond | N | $CR_3$ | N | $CR_3$ | $CR_3$ |
| $CH_2$ | methyl | $NR_2$ | $CH_2$ or bond | N | $CR_3$ | N | $CR_3$ | $CR_3$ |
| $CH_2$ | methyl | S | $CH_2$ or bond | N | $CR_3$ | N | $CR_3$ | $CR_3$ |
| $CH_2$ | methyl | a bond | $CH_2$ or bond | N | $CR_3$ | N | $CR_3$ | $CR_3$ |
| $CH_2$ | D | $CH_2$ | $CH_2$ or bond | N | $CR_3$ | N | $CR_3$ | $CR_3$ |
| $CH_2$ | D | O | $CH_2$ or bond | N | $CR_3$ | N | $CR_3$ | $CR_3$ |
| $CH_2$ | D | $NR_2$ | $CH_2$ or bond | N | $CR_3$ | N | $CR_3$ | $CR_3$ |
| $CH_2$ | D | S | $CH_2$ or bond | N | $CR_3$ | N | $CR_3$ | $CR_3$ |
| $CH_2$ | D | a bond | $CH_2$ or bond | N | $CR_3$ | N | $CR_3$ | $CR_3$ |
| $CH_2$ | fluoro | $CH_2$ | $CH_2$ or bond | N | $CR_3$ | N | $CR_3$ | $CR_3$ |
| $CH_2$ | fluoro | O | $CH_2$ or bond | N | $CR_3$ | N | $CR_3$ | $CR_3$ |
| $CH_2$ | fluoro | $NR_2$ | $CH_2$ or bond | N | $CR_3$ | N | $CR_3$ | $CR_3$ |
| $CH_2$ | fluoro | S | $CH_2$ or bond | N | $CR_3$ | N | $CR_3$ | $CR_3$ |
| $CH_2$ | fluoro | a bond | $CH_2$ or bond | N | $CR_3$ | N | $CR_3$ | $CR_3$ |
| C=O | H | $CH_2$ | $CH_2$ or bond | $CR_3$ | $CR_3$ | N | $CR_3$ | N |
| C=O | H | O | $CH_2$ or bond | $CR_3$ | $CR_3$ | N | $CR_3$ | N |
| C=O | H | $NR_2$ | $CH_2$ or bond | $CR_3$ | $CR_3$ | N | $CR_3$ | N |
| C=O | H | S | $CH_2$ or bond | $CR_3$ | $CR_3$ | N | $CR_3$ | N |
| C=O | H | a bond | $CH_2$ or bond | $CR_3$ | $CR_3$ | N | $CR_3$ | N |
| C=O | methyl | $CH_2$ | $CH_2$ or bond | $CR_3$ | $CR_3$ | N | $CR_3$ | N |
| C=O | methyl | O | $CH_2$ or bond | $CR_3$ | $CR_3$ | N | $CR_3$ | N |
| C=O | methyl | $NR_2$ | $CH_2$ or bond | $CR_3$ | $CR_3$ | N | $CR_3$ | N |
| C=O | methyl | S | $CH_2$ or bond | $CR_3$ | $CR_3$ | N | $CR_3$ | N |
| C=O | methyl | a bond | $CH_2$ or bond | $CR_3$ | $CR_3$ | N | $CR_3$ | N |
| C=O | D | $CH_2$ | $CH_2$ or bond | $CR_3$ | $CR_3$ | N | $CR_3$ | N |
| C=O | D | O | $CH_2$ or bond | $CR_3$ | $CR_3$ | N | $CR_3$ | N |
| C=O | D | $NR_2$ | $CH_2$ or bond | $CR_3$ | $CR_3$ | N | $CR_3$ | N |
| C=O | D | S | $CH_2$ or bond | $CR_3$ | $CR_3$ | N | $CR_3$ | N |
| C=O | D | a bond | $CH_2$ or bond | $CR_3$ | $CR_3$ | N | $CR_3$ | N |
| C=O | fluoro | $CH_2$ | $CH_2$ or bond | $CR_3$ | $CR_3$ | N | $CR_3$ | N |
| C=O | fluoro | O | $CH_2$ or bond | $CR_3$ | $CR_3$ | N | $CR_3$ | N |
| C=O | fluoro | $NR_2$ | $CH_2$ or bond | $CR_3$ | $CR_3$ | N | $CR_3$ | N |
| C=O | fluoro | S | $CH_2$ or bond | $CR_3$ | $CR_3$ | N | $CR_3$ | N |
| C=O | fluoro | a bond | $CH_2$ or bond | $CR_3$ | $CR_3$ | N | $CR_3$ | N |
| $CH_2$ | H | $CH_2$ | $CH_2$ or bond | $CR_3$ | $CR_3$ | N | $CR_3$ | N |
| $CH_2$ | H | O | $CH_2$ or bond | $CR_3$ | $CR_3$ | N | $CR_3$ | N |
| $CH_2$ | H | $NR_2$ | $CH_2$ or bond | $CR_3$ | $CR_3$ | N | $CR_3$ | N |
| $CH_2$ | H | S | $CH_2$ or bond | $CR_3$ | $CR_3$ | N | $CR_3$ | N |
| $CH_2$ | H | a bond | $CH_2$ or bond | $CR_3$ | $CR_3$ | N | $CR_3$ | N |
| $CH_2$ | methyl | $CH_2$ | $CH_2$ or bond | $CR_3$ | $CR_3$ | N | $CR_3$ | N |
| $CH_2$ | methyl | O | $CH_2$ or bond | $CR_3$ | $CR_3$ | N | $CR_3$ | N |
| $CH_2$ | methyl | $NR_2$ | $CH_2$ or bond | $CR_3$ | $CR_3$ | N | $CR_3$ | N |
| $CH_2$ | methyl | S | $CH_2$ or bond | $CR_3$ | $CR_3$ | N | $CR_3$ | N |
| $CH_2$ | methyl | a bond | $CH_2$ or bond | $CR_3$ | $CR_3$ | N | $CR_3$ | N |
| $CH_2$ | D | $CH_2$ | $CH_2$ or bond | $CR_3$ | $CR_3$ | N | $CR_3$ | N |
| $CH_2$ | D | O | $CH_2$ or bond | $CR_3$ | $CR_3$ | N | $CR_3$ | N |
| $CH_2$ | D | $NR_2$ | $CH_2$ or bond | $CR_3$ | $CR_3$ | N | $CR_3$ | N |
| $CH_2$ | D | S | $CH_2$ or bond | $CR_3$ | $CR_3$ | N | $CR_3$ | N |
| $CH_2$ | D | a bond | $CH_2$ or bond | $CR_3$ | $CR_3$ | N | $CR_3$ | N |
| $CH_2$ | fluoro | $CH_2$ | $CH_2$ or bond | $CR_3$ | $CR_3$ | N | $CR_3$ | N |
| $CH_2$ | fluoro | O | $CH_2$ or bond | $CR_3$ | $CR_3$ | N | $CR_3$ | N |
| $CH_2$ | fluoro | NR | $CH_2$ or bond | $CR_3$ | $CR_3$ | N | $CR_3$ | N |
| $CH_2$ | fluoro | S | $CH_2$ or bond | $CR_3$ | $CR_3$ | N | $CR_3$ | N |
| $CH_2$ | fluoro | a bond | $CH_2$ or bond | $CR_3$ | $CR_3$ | N | $CR_3$ | N |

In some embodiments of Table B, $R_2$ can be hydrogen. In some embodiments of Table B, $R_2$ can be a substituted or unsubstituted $C_1$-$C_6$ alkyl, for example, methyl, ethyl, n-propyl, isopropyl, n-butyl, isobutyl, sec-butyl, t-butyl, pentyl (straight-chained or branched), or hexyl (straight-chained or branched). In some embodiments of Table B, $R_2$ can be an unsubstituted $C_1$-$C_6$ alkyl, for example, methyl, ethyl, n-propyl, isopropyl, n-butyl, isobutyl, sec-butyl, t-butyl, pentyl (straight-chained or branched), or hexyl (straight-chained or branched). In some embodiments of Table B, $R_2$ can be acyl, for example, —(C=O)-methyl, —(C=O)-ethyl, —(C=O)-n-propyl, —(C=O)—isopropyl, —(C=O)-n-butyl, —(C=O)-isobutyl, —(C=O)-sec-butyl, —(C=O)-t-butyl, —(C=O)-pentyl (straight-chained or branched), or —(C=O)-hexyl (straight-chained or branched). In some embodiments of Table B, $R_2$ can be —(SO$_2$)—$C_1$-$C_6$ alkyl, for example, —(SO$_2$)-methyl, —(SO$_2$)-ethyl, —(SO$_2$)-n-propyl, —(SO$_2$)-isopropyl, —(SO$_2$)-n-butyl, —(SO$_2$)-isobutyl, —(SO$_2$)-sec-butyl, —(SO$_2$)-t-butyl, —(SO$_{02}$)-pentyl (straight-chained or branched), or —(SO$_2$)-hexyl (straight-chained or branched).

In some embodiments, a compound of Formula (I) is selected from:

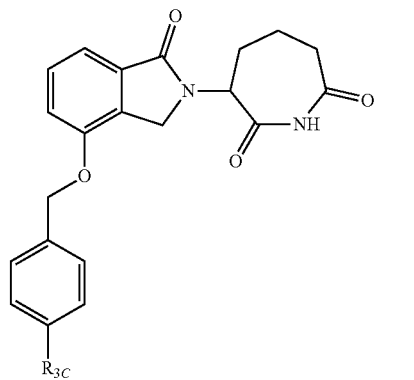

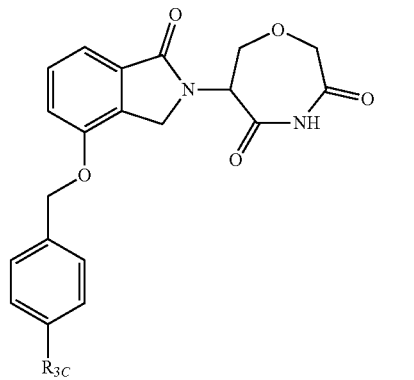

-continued

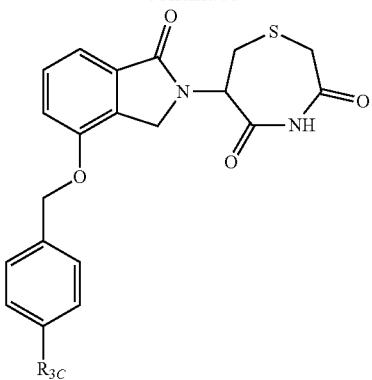

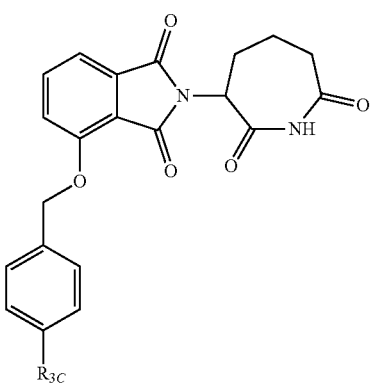

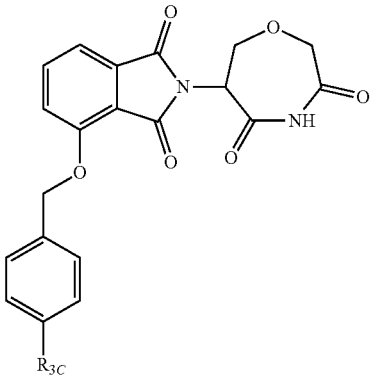

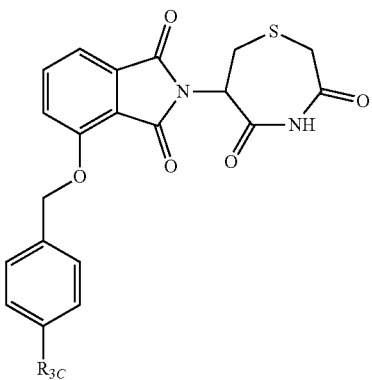

65
-continued
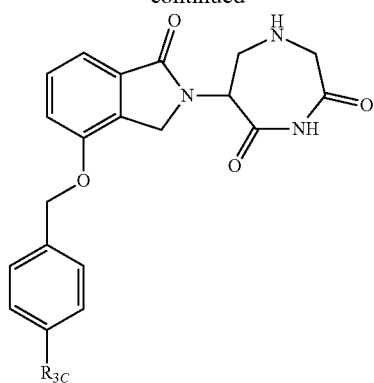
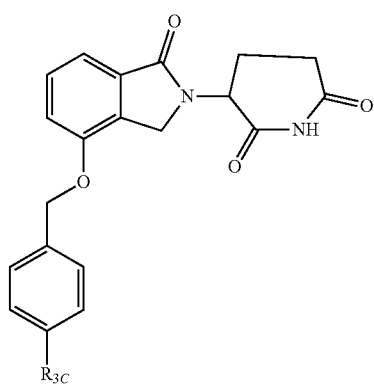
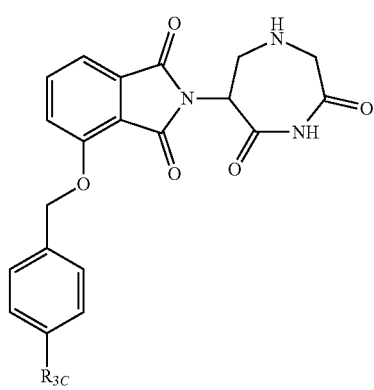
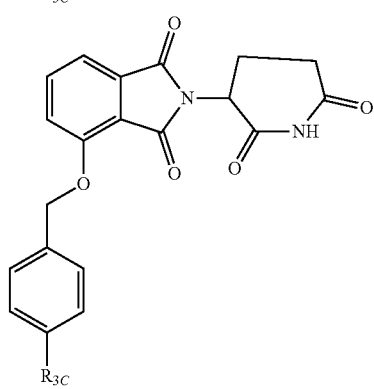
66
-continued
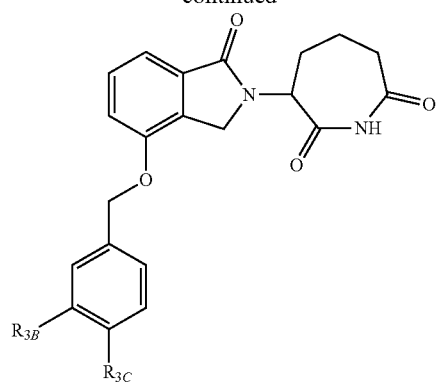
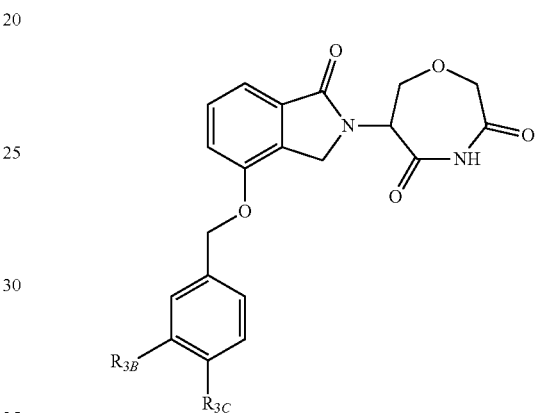
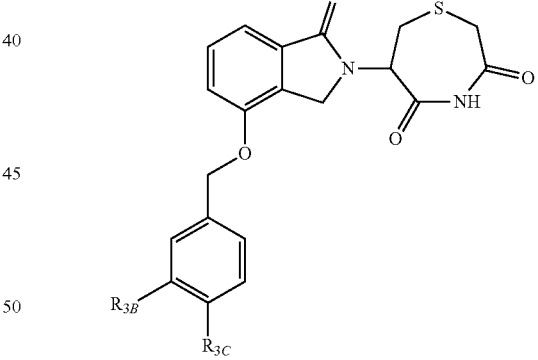
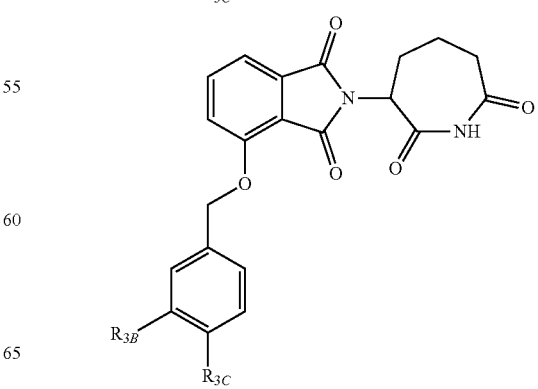

67
-continued
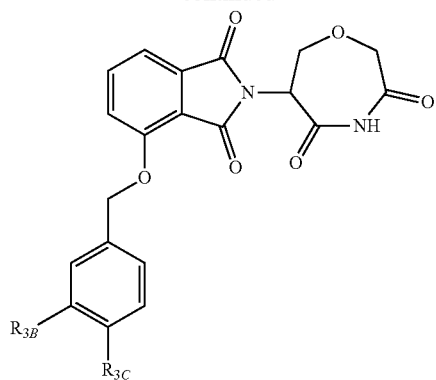
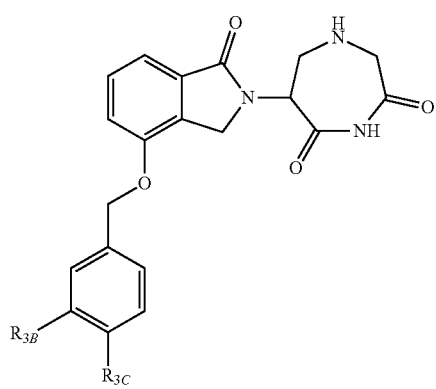
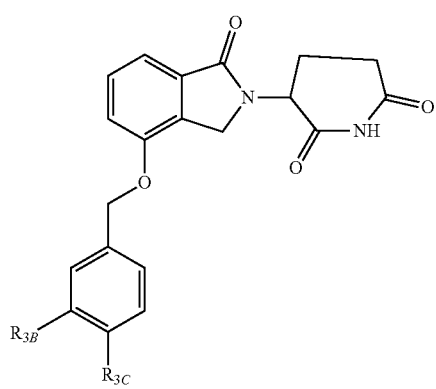
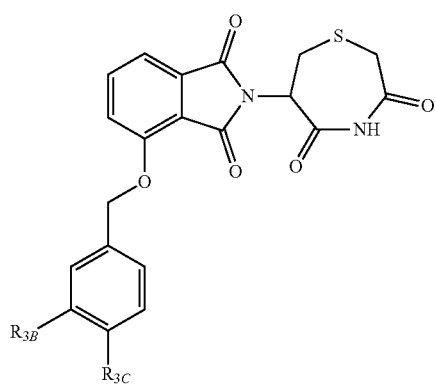
68
-continued
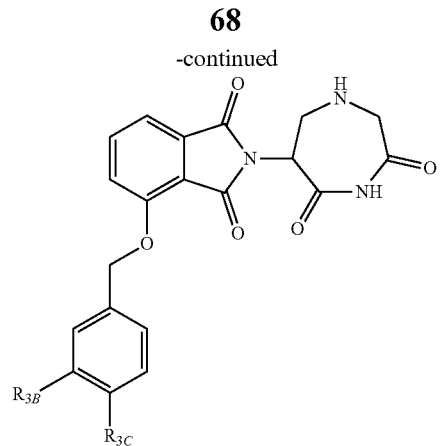
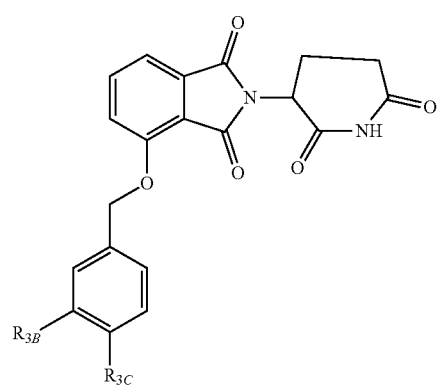
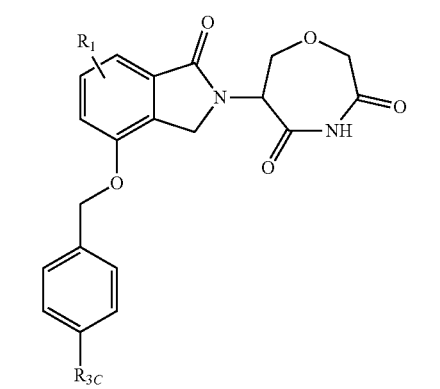
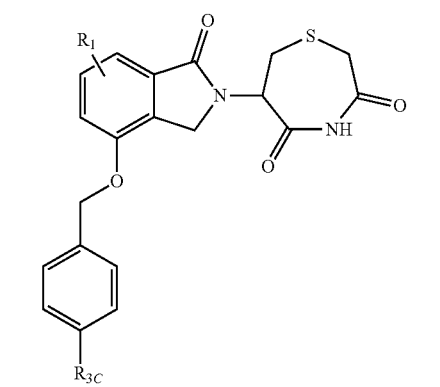

69
-continued
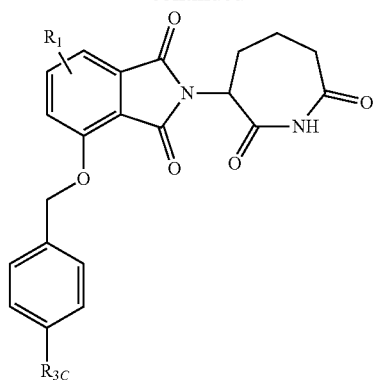
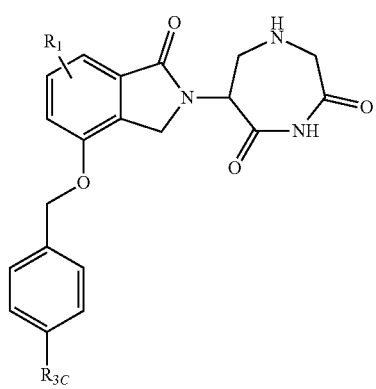
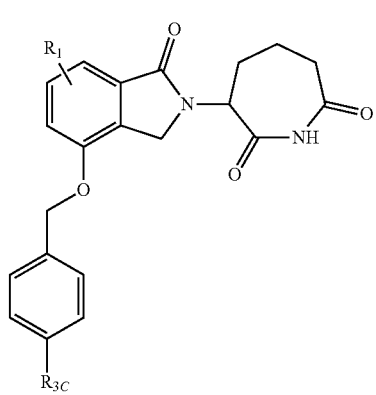
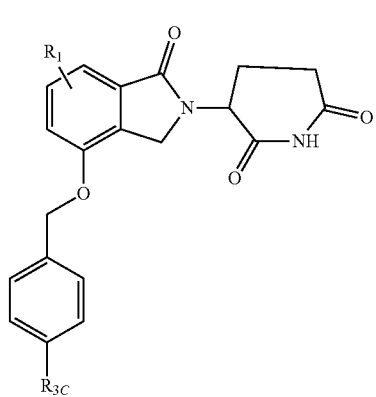
70
-continued
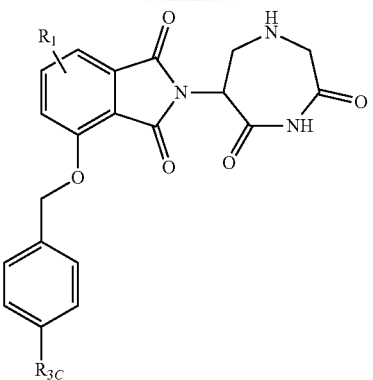
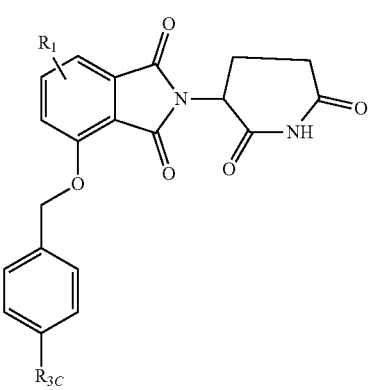
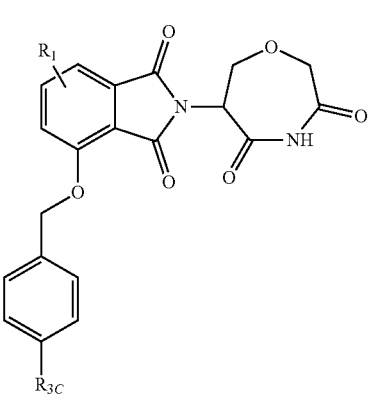
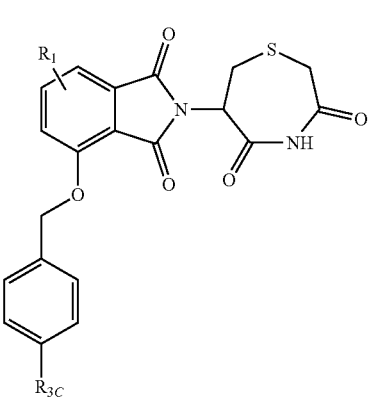

71
-continued
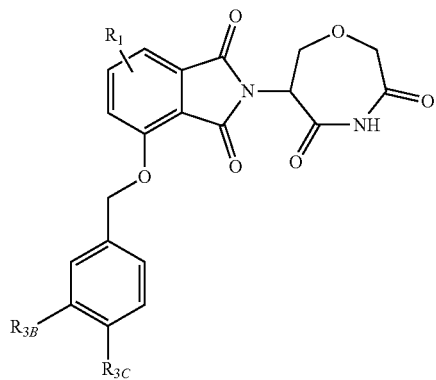
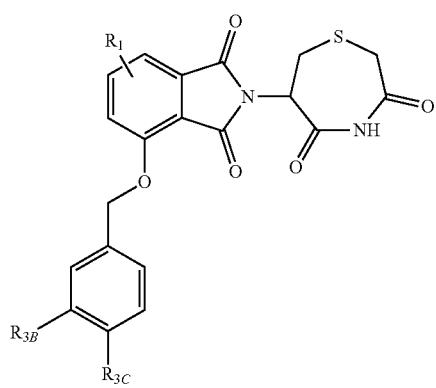
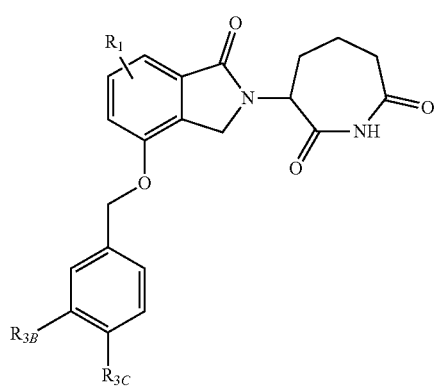
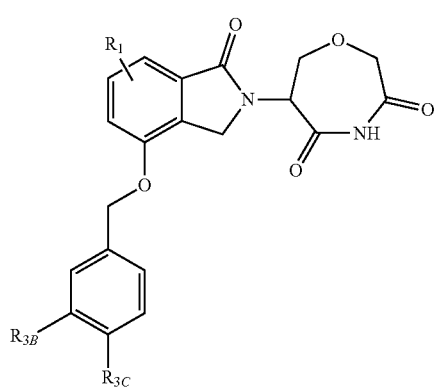
72
-continued
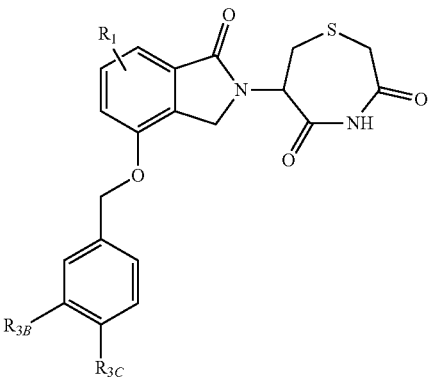
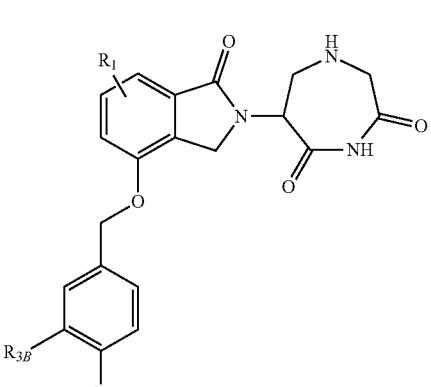
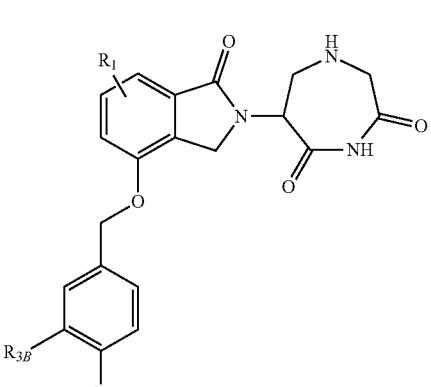
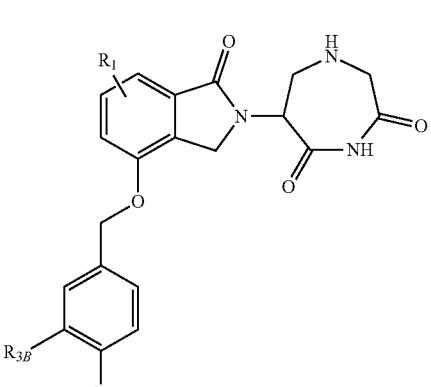

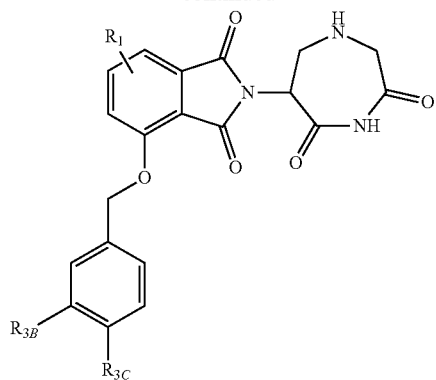
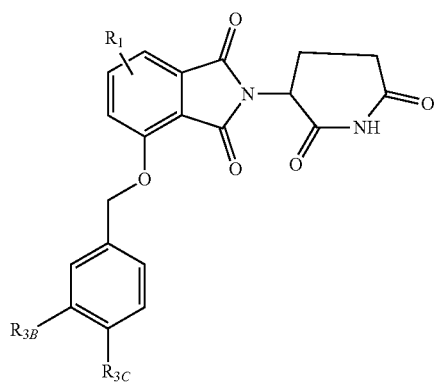
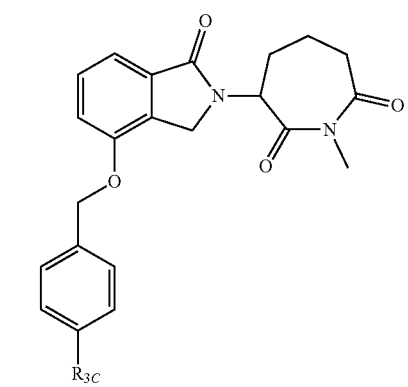
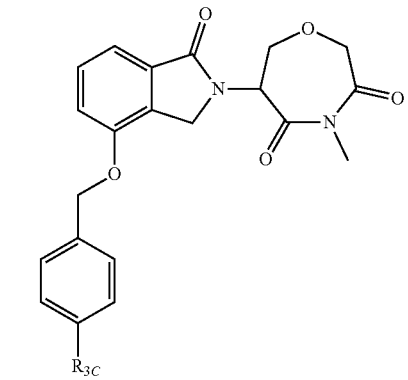
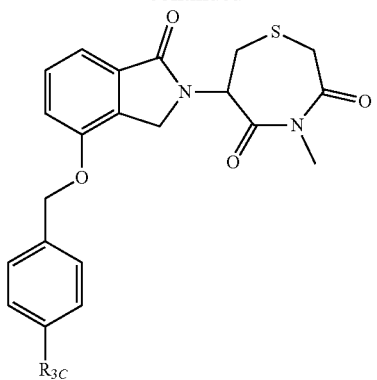

75
-continued
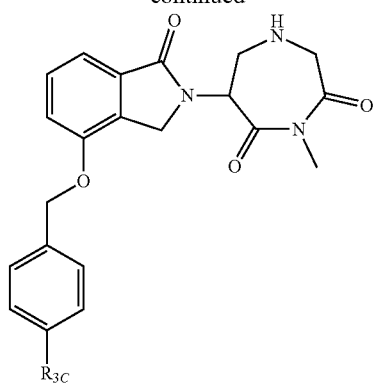
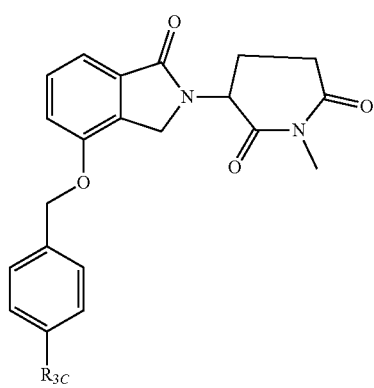
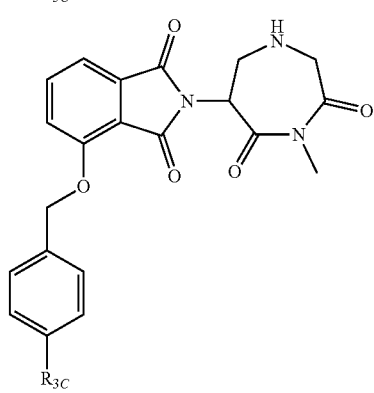
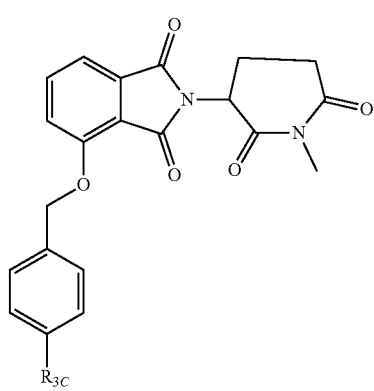
76
-continued
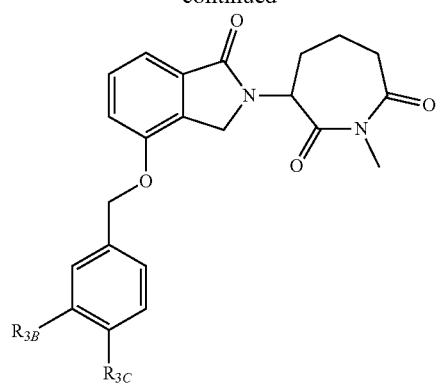
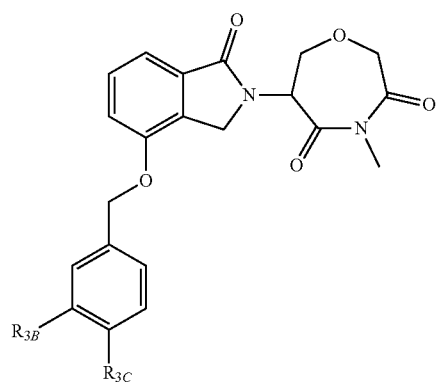
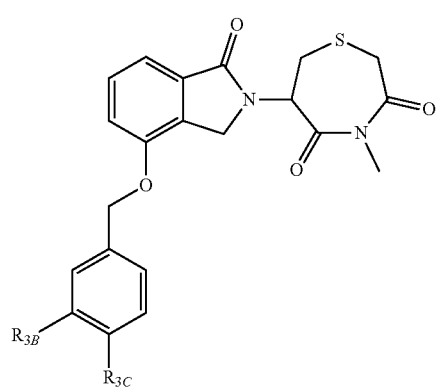
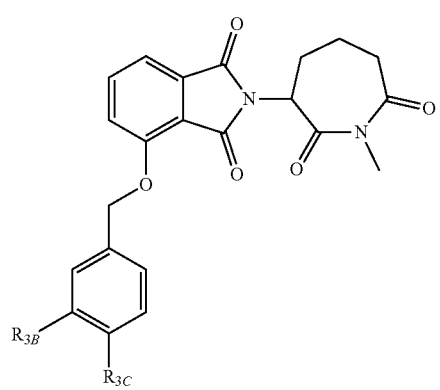

77
-continued
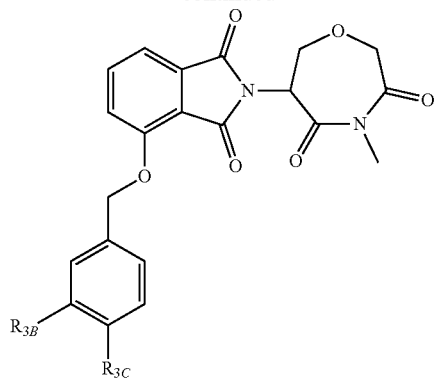
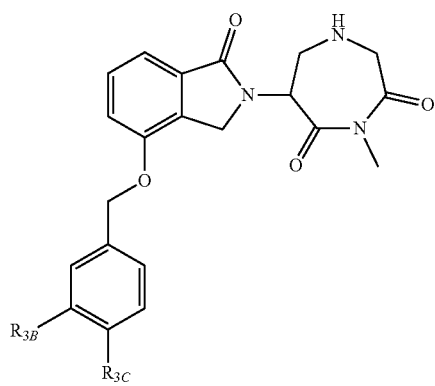
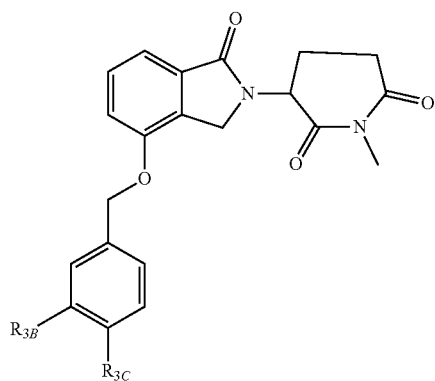
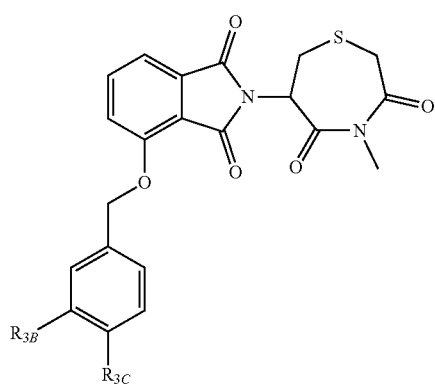
78
-continued
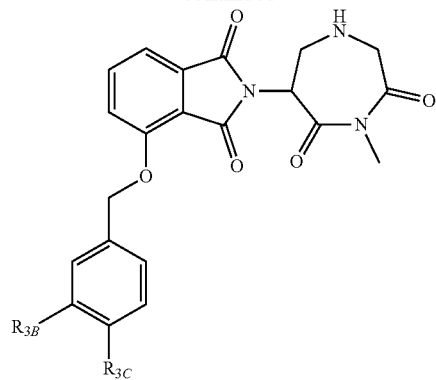
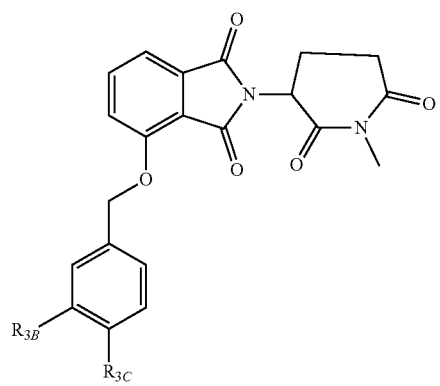
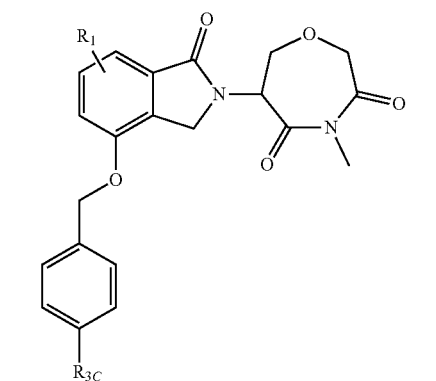
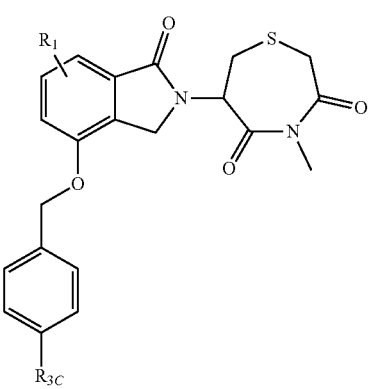

79
-continued
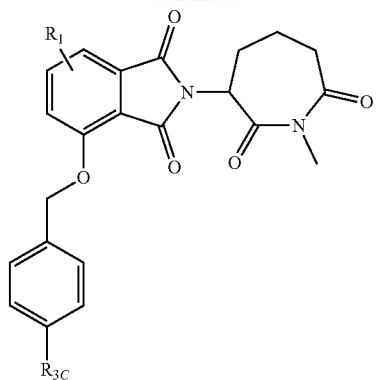
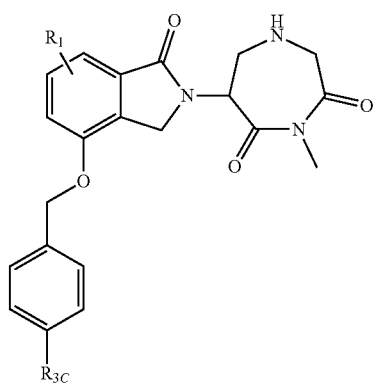
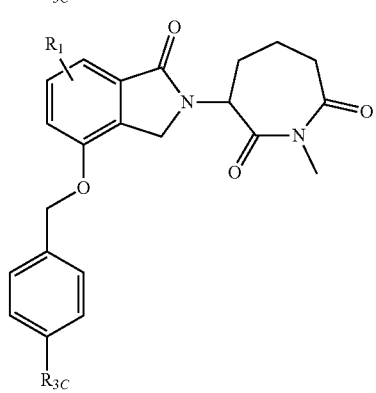
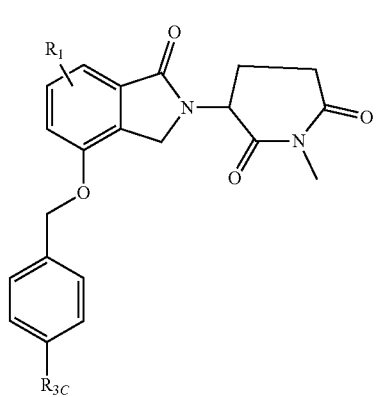
80
-continued
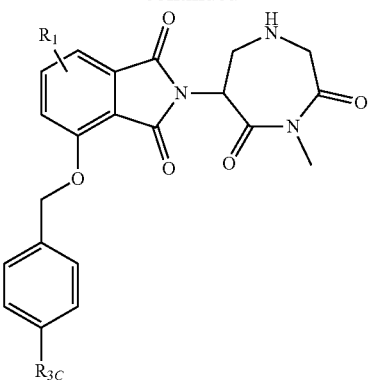
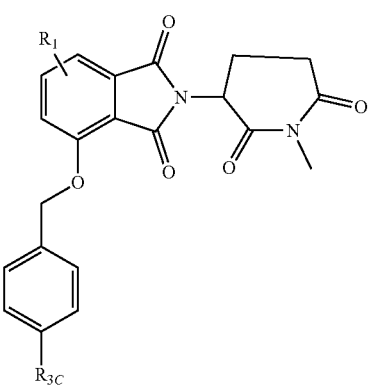
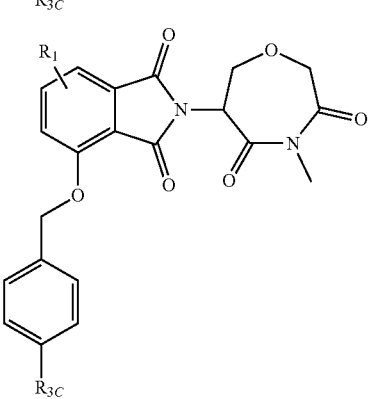
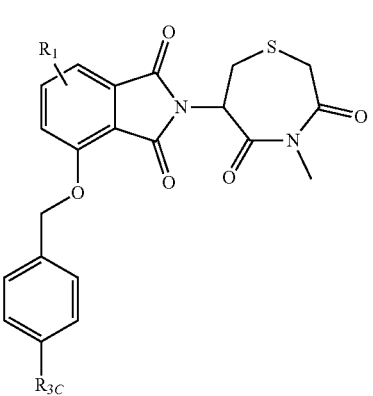

-continued

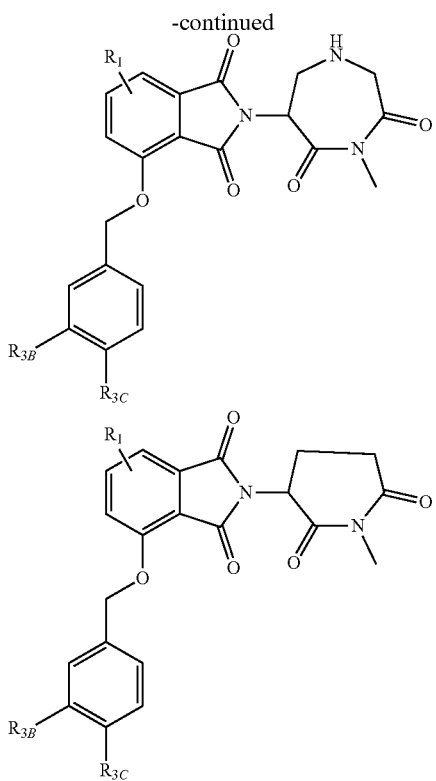

In some embodiments of this paragraph, $R_1$ can be fluoro. In some embodiments of this paragraph, $R_1$ can be chloro. In some embodiments of this paragraph, $R_1$ can be hydroxyl. In some embodiments of this paragraph, $R_1$ can be —$NH_2$. In some embodiments of this paragraph, $R_1$ can be —$CF_3$, —$CHF_2$, or —$CH_2F$. In some embodiments of this paragraph, $R_1$ can be an unsubstituted $C_1$-$C_6$ alkoxy, such as methoxy, ethoxy, n-propoxy, isopropoxy, n-butoxy, isobutoxy, sec-butoxy, t-butoxy, pentoxy (straight-chained or branched), or hexoxy (straight-chained or branched). In some embodiments of this paragraph, $R_1$ can be an unsubstituted $C_1$-$C_6$ alkyl, such as methyl, ethyl, n-propyl, isopropyl, n-butyl, isobutyl, sec-butyl, t-butyl, pentyl (straight-chained or branched), or hexyl (straight-chained or branched). In some embodiments of this paragraph, $R_1$ can be an unsubstituted $C_3$-$C_8$ cycloalkyl, such as cyclopropyl, cyclobutyl, cyclopentyl, cyclohexyl, cycloheptyl, and cyclooctyl. In some embodiments of this paragraph, $R_1$ can be an unsubstituted 3 to 10 membered heterocyclyl, for example, a monocyclic heterocyclyl, a bridged heterocyclyl, or a fused heterocyclyl, including groups such as pyrrolidine, piperidine, piperazine, and morpholine. In some embodiments of this paragraph, $R_{3B}$ can be hydroxyl. In some embodiments of this paragraph, $R_{3B}$ can be fluoro. In some embodiments of this paragraph, $R_{3B}$ can be chloro. In some embodiments of this paragraph, $R_{3B}$ can be a substituted or unsubstituted amino, for example, —$NH_2$, dimethylamino, diethylamino, isopropylethylamino, phenylamino, or benzylamino. In some embodiments of this paragraph, $R_{3B}$ can be —$CF_3$, —$CHF_2$, or —$CH_2F$. In some embodiments of this paragraph, $R_{3B}$ can be an unsubstituted $C_1$-$C_6$ alkoxy, such as methoxy, ethoxy, n-propoxy, isopropoxy, n-butoxy, isobutoxy, sec-butoxy, t-butoxy, pentoxy (straight-chained or branched), or hexoxy (straight-chained or branched). In some embodiments of this paragraph, $R_{3B}$ can be an unsubstituted $C_1$-$C_6$ alkyl, such as methyl, ethyl, n-propyl, isopropyl, n-butyl, isobutyl, sec-butyl, t-butyl, pentyl (straight-chained or branched), or hexyl (straight-chained or branched). In some embodiments of this paragraph, $R_{3B}$ can be an unsubstituted $C_3$-$C_8$ cycloalkyl, such as cyclopropyl, cyclobutyl, cyclopentyl, cyclohexyl, cycloheptyl, and cyclooctyl. In some embodiments of this paragraph, $R_{3C}$ can be a substituted or unsubstituted $C_3$-$C_8$ cycloalkyl, such as cyclopropyl, cyclobutyl, cyclopentyl, cyclohexyl, cycloheptyl, and cyclooctyl. In some embodiments of this paragraph, $R_{3C}$ can be an unsubstituted $C_3$-$C_8$ cycloalkyl, such as cyclopropyl, cyclobutyl, cyclopentyl, cyclohexyl, cycloheptyl, and cyclooctyl. In some embodiments of this paragraph, $R_{3C}$ can be a substituted or unsubstituted 3 to 10 membered heterocyclyl, for example, a monocyclic heterocyclyl, a bridged heterocyclyl, or a fused heterocyclyl, including groups such as pyrrolidine, piperidine, piperazine, and morpholine. In some embodiments of this paragraph, $R_{3C}$ can be an unsubstituted 3 to 10 membered heterocyclyl, for example, a monocyclic heterocyclyl, a bridged heterocyclyl, or a fused heterocyclyl, including groups such as pyrrolidine, piperidine, piperazine, and morpholine. In some embodiments of this paragraph, $R_{3C}$ can be a substituted or unsubstituted 5 to 10 membered heteroaryl, for example, a 5 or 6 membered heteroaryl containing at least one nitrogen, such as pyrrole, imidazole, oxazole, thiazole, pyridine, or pyrimidine. In some embodiments of this paragraph, $R_{3C}$ can be an unsubstituted 5 to 10 membered heteroaryl, for example, a 5 or 6 membered heteroaryl containing at least one nitrogen, such as pyrrole, imidazole, oxazole, thiazole, pyridine, or pyrimidine.

Compounds of Formula (I) can be provided in the form of pharmaceutically acceptable salts, solvates, or tautomers, thereof.

Some embodiments provide a pharmaceutical composition comprising a compound of Formula (I), or a pharmaceutically acceptable salt thereof; and a pharmaceutically acceptable excipient. In some embodiments, the pharmaceutical composition also contains at least one pharmaceutically acceptable inactive ingredient. The pharmaceutical composition can be formulated for intravenous injection, subcutaneous injection, oral administration, buccal administration, inhalation, nasal administration, topical administration, transdermal administration, ophthalmic administration, or otic administration. The pharmaceutical composition can be in the form of a tablet, a pill, a capsule, a liquid, an inhalant, a nasal spray solution, a suppository, a suspension, a gel, a colloid, a dispersion, a solution, an emulsion, an ointment, a lotion, an eye drop, or an ear drop.

In some embodiments, the pharmaceutical composition is formulated as a gel, salve, ointment, cream, emulsion, or paste for topical application to the skin.

Some embodiments provide a method of inhibiting the activity of a cytokine, comprising contacting a cell with an effective amount of a compound of Formula (I), or a pharmaceutically acceptable salt thereof. In some embodiments, the cytokine is selected from: IL-1β, IL-2, IL-6, and TNFα. In some embodiments, the cytokine is TNFα. In some embodiments, the cell is a cancer cell.

Some embodiments provide a method of inhibiting the activity of aiolos, comprising contacting a cell with an effective amount of a compound of Formula (I), or a pharmaceutically acceptable salt thereof.

Some embodiments provide a method of inhibiting the activity of ikaros, comprising contacting a cell with an effective amount of a compound of Formula (I), or a pharmaceutically acceptable salt thereof. In some embodiments, the cell is a cancer cell.

Some embodiments provide a method of inhibiting the activity of helios, comprising contacting a cell with an effective amount of a compound of Formula (I), or a pharmaceutically acceptable salt thereof. In some embodiments, the cell is a cancer cell.

Some embodiments provide a method of inhibiting the activity of CK-la, comprising contacting a cell with an effective amount of a compound of Formula (I), or a pharmaceutically acceptable salt thereof. In some embodiments, the cell is a cancer cell.

In some embodiments, the cell is a small cell lung cancer cell, a non-small cell lung cancer cell, a breast cancer cell, a prostate cancer cell, a head and neck cancer cell, a pancreatic cancer cell, a colon cancer cell, a rectal cancer cell, a teratoma cell, an ovarian cancer cell, an endometrial cancer cell, a brain cancer cell, a retinoblastoma cell, a leukemia cell, a skin cancer cell, a melanoma cell, a squamous cell carcinoma cell, a liposarcoma cell, a lymphoma cell, a multiple myeloma cell, a testicular cancer cell, a liver cancer cell, an esophageal cancer cell, a kidney carcinoma cell, an astrogliosis cell, a relapsed/refractory multiple myeloma cell, or a neuroblastoma cell.

In some embodiments, inhibiting the activity of a protein can include decreasing the activity of the protein by 20-50%, by 30-70%, by 40-90%, or any value in between. For example, inhibiting the activity of a protein can include decreasing the activity of the protein by 10%, 15%, 20%, 25%, 30%, 35%, 40% 45%, 50%, 55%, 60%, 65%, 70%, 75%, 80%, 85%, 90%, 95%, 99%, or any value in between.

Some embodiments provide a method of treating, ameliorating, or preventing a disease, disorder, or condition associated with a protein in a subject, the protein selected from a cytokine, aiolos, ikaros, helios, CK1α, and combinations of any of the foregoing; the method comprising administering a therapeutically effective amount of a compound of Formula (I), or a pharmaceutically acceptable salt thereof, or a pharmaceutical composition comprising a compound of Formula (I), or a pharmaceutically acceptable salt thereof, to the subject.

In some embodiments, the disease, disorder, or condition is a cancer selected from a hematological malignancy and a solid tumor In some embodiments, the disease, disorder, or condition is a cancer selected from small cell lung cancer, non-small cell lung cancer, breast cancer, prostate cancer, head and neck cancer, pancreatic cancer, colon cancer, rectal cancer, teratoma, ovarian cancer, endometrial cancer, brain cancer, retinoblastoma, leukemia, skin cancer, melanoma, squamous cell carcinoma, liposarcoma, lymphoma, multiple myeloma, testicular cancer, liver cancer, esophageal cancer, kidney carcinoma, astrogliosis, relapsed/refractory multiple myeloma, and neuroblastoma.

In some embodiments, the disease, disorder, or condition is selected from inflammation, fibromyalgia, rheumatoid arthritis, osteoarthritis, ankylosing spondylitis, psoriasis, psoriatic arthritis, inflammatory bowel diseases, Crohn's disease, ulcerative colitis, uveitis, inflammatory lung diseases, chronic obstructive pulmonary disease, and Alzheimer's disease. In some embodiments, the disease, disorder, or condition is selected from fibromyalgia, rheumatoid arthritis, osteoarthritis, ankylosing spondylitis, psoriasis, psoriatic arthritis, Crohn's disease, and ulcerative colitis.

In some embodiments, the protein is a cytokine. In some embodiments, the cytokine is selected from: IL-1β, IL-2, IL-6, and TNFα. In some embodiments, the subject is known to possess wild-type IL-1β, IL-2, IL-6, and TNFα. In some embodiments, the subject is known to overexpress one or more of IL-1β, IL-2, IL-6, and TNFα. In some embodiments, the subject is known to possess a mutant form of IL-1β, IL-2, IL-6, and/or TNFα.

In some embodiments, the cytokine is TNFα. In some embodiments, the subject is known to possess wild-type TNFα. In some embodiments, the subject is known to overexpress TNFα. In some embodiments, the subject is known to possess a mutant form of TNFα. In some embodiments, the protein is aiolos. In some embodiments, the subject is known to possess wild-type aiolos. In some embodiments, the subject is known to overexpress aiolos. In some embodiments, the subject is known to possess a mutant form of aiolos. In some embodiments, the protein is ikaros. In some embodiments, the subject is known to possess wild-type ikaros. In some embodiments, the subject is known to overexpress ikaros. In some embodiments, the subject is known to possess a mutant form of ikaros. In some embodiments, the protein is helios. In some embodiments, the subject is known to possess wild-type helios. In some embodiments, the subject is known to overexpress helios. In some embodiments, the subject is known to possess a mutant form of helios. In some embodiments, the protein is CK1α. In some embodiments, the subject is known to possess wild-type CK1α. In some embodiments, the subject is known to overexpress CK1α. In some embodiments, the subject is known to possess a mutant form of CK1α.

Other objects, features, and advantages of the compounds, methods, and compositions described herein will become apparent from the following detailed description. It should be understood, however, that the detailed description and the specific examples, while indicating specific embodiments, are given by way of illustration only, since various changes and modifications within the spirit and scope of the instant disclosure will become apparent to those skilled in the art from this detailed description Definitions Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise. As used in the specification and the appended claims, the singular forms "a," "an" and "the" include plural referents unless the context clearly dictates otherwise. Unless otherwise indicated, conventional methods of mass spectroscopy, NMR, HPLC, protein chemistry, biochemistry, recombinant DNA techniques and pharmacology are employed. The use of "or" or "and" means "and/or" unless stated otherwise. Furthermore, use of the term "including" as well as other forms, such as "include", "includes," and "included," is not limiting. As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least." When used in the context of a process, the term "comprising" means that the process includes at least the recited steps, but may include additional steps. When used in the context of a compound, composition, or device, the term "comprising" means that the compound, composition, or device includes at least the recited features or components, but may also include additional features or components.

The section headings used herein are for organizational purposes only and are not to be construed as limiting the subject matter described.

The terms "co-administration" and similar terms as used herein are broad terms, and are to be given their ordinary and customary meaning to a person of ordinary skill in the art (and are not to be limited to a special or customized meaning), and refer without limitation to administration of the selected therapeutic agents to a single patient, and are intended to include treatment regimens in which the agents are administered by the same or different route of administration or at the same or different time.

The terms "effective amount" and "therapeutically effective amount" are broad terms, and are to be given their ordinary and customary meaning to a person of ordinary skill in the art (and are not to be limited to a special or customized meaning), and refer without limitation to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study. Where a drug has been approved by the U.S. Food and Drug Administration (FDA) or a counterpart foreign medicines agency, a "therapeutically effective amount" optionally refers to the dosage approved by the FDA or its counterpart foreign agency for treatment of the identified disease or condition.

As used herein, any "R" group(s) such as, without limitation, $R_2$, $R_3$, $R_4$, $R_5$, $R_6$, $R_9$, and Rio represent substituents that can be attached to the indicated atom. An R group may be substituted or unsubstituted. If two "R" groups are described as being "taken together" the R groups and the atoms they are attached to can form a cycloalkyl, aryl, heteroaryl, or heterocycle. For example, without limitation, if $R^2$ and $R^3$, or $R^2$, $R^3$, or $R^4$, and the atom to which it is attached, are indicated to be "taken together" or "joined together" it means that they are covalently bonded to one another to form a ring:

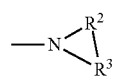

Whenever a group is described as being "substituted" or "optionally substituted" that group may be unsubstituted or substituted with one or more of the indicated substituents. Likewise, when a group is described as being "unsubstituted or substituted" if substituted, the substituent may be selected from one or more the indicated substituents. If no substituents are indicated, it is meant that the indicated or "substituted" group may be individually and independently substituted with one or more group(s) individually and independently selected from alkyl, alkenyl, alkynyl, cycloalkyl, aryl, heteroaryl, heterocyclyl, aralkyl, heteroaralkyl, (heterocyclyl)alkyl, hydroxy, protected hydroxyl, alkoxy, aryloxy, acyl, cyano, halogen, ester, nitro, silyl, haloalkyl, haloalkoxy, an unsubstituted amino, a substituted amino, and protected derivatives thereof.

As used herein, "$C_a$ to $C_b$" in which "a" and "b" are integers refer to the number of carbon atoms in an alkyl, alkenyl or alkynyl group, or the number of carbon atoms in the ring of a cycloalkyl, aryl, heteroaryl or heterocyclyl group. That is, the alkyl, alkenyl, alkynyl, ring of the cycloalkyl, ring of the aryl, ring of the heteroaryl or ring of the heterocyclyl can contain from "a" to "b", inclusive, carbon atoms. Thus, for example, a "$C_1$ to $C_4$ alkyl" group or a "$C_1$-$C_4$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—. Likewise, for example, a heterocyclyl group may contain from "a" to "b", inclusive, total atoms, such as a 3 to 10-membered heterocyclyl group, which includes 3 to ten total atoms (carbon and heteroatoms). If no "a" and "b" are designated with regard to an alkyl, alkenyl, alkynyl, cycloalkyl, aryl, heteroaryl or heterocyclyl group, the broadest range described in these definitions is to be assumed.

As used herein, "alkyl" refers to a straight or branched hydrocarbon chain that comprises a fully saturated (no double or triple bonds) hydrocarbon group. The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 6 carbon atoms. The alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, isopropyl, n-butyl, isobutyl, sec-butyl, and t-butyl. Typical alkyl groups include, but are in no way limited to, methyl, ethyl, propyl, isopropyl, butyl, isobutyl, tertiary butyl, pentyl, and hexyls. The alkyl group may be substituted or unsubstituted.

As used herein, "alkenyl" refers to an alkyl group, as defined herein, that contains in the straight or branched hydrocarbon chain one or more double bonds. An alkenyl group may be unsubstituted or substituted.

As used herein, "alkynyl" refers to an alkyl group as defined herein, that contains in the straight or branched hydrocarbon chain one or more triple bonds. An alkynyl group may be unsubstituted or substituted.

As used herein, "alkylene" refers to a straight-chained or branched alkyl group forming bonds to connect molecular fragments via their terminal carbon atoms. Examples include but are not limited to methylene (—$CH_2$—), ethylene (—$CH_2CH_2$—), propylene (—$CH_2CH_2CH_2$—), and butylene (—$CH_2CH_2CH_2CH_2$—). An alkylene group can be substituted by replacing one or more hydrogen of the alkylene group with a substituent(s) listed under the definition of "substituted."

As used herein, "cycloalkyl" refers to a completely saturated (no double or triple bonds) mono- or multi-cyclic hydrocarbon ring system. When composed of two or more rings, the rings may be joined together in a fused fashion. Cycloalkyl groups can contain 3 to 10 atoms in the ring(s) or 3 to 8 atoms in the ring(s). Typical cycloalkyl groups include, but are in no way limited to, cyclopropyl, cyclobutyl, cyclopentyl, cyclohexyl, cycloheptyl, and cyclooctyl. A cycloalkyl group may be unsubstituted or substituted.

As used herein, "cycloalkyl" refers to all carbon ring systems. Such systems can be unsaturated, can include some unsaturation, or can contain some aromatic portion, or be all aromatic. Cycloalkyl group can contain from 3 to 30 carbon atoms. A cycloalkyl group may be unsubstituted or substituted.

As used herein, "cycloalkylalkyl" refers to an -(alkylene)-R radical where R is cycloalkyl as defined above. Examples include, but are not limited to, cyclopropylmethyl and cyclohexylmethyl. A cycloalkylalkyl group may also be referred to as, for example, a ($C_1$-$C_6$ alkyl)-cycloalkyl group. A cycloalkylalkyl group may be unsubstituted or substituted.

As used herein, "aryl" refers to a carbocyclic (all carbon) monocyclic or multicyclic aromatic ring system (including, e.g., fused, bridged, or spiro ring systems where two carbocyclic rings share a chemical bond, e.g., one or more aryl rings with one or more aryl or non-aryl rings) that has a fully delocalized pi-electron system throughout at least one of the rings. The number of carbon atoms in an aryl group can vary. For example, the aryl group can be a $C_6$-$C_{14}$ aryl group, a $C_6$-$C_{10}$ aryl group, or a $C_6$ aryl group. Examples of aryl groups include, but are not limited to, benzene, naphthalene, and azulene. An aryl group may be substituted or unsubstituted.

As used herein, "aralkyl" refers to an -(alkylene)-R radical where R is aryl as defined above. Examples include, but are not limited to, benzyl and phenethyl. An aralkyl group may also be referred to as, for example, a ($C_1$-$C_6$ alkyl)-aryl group. An aralkyl group may be substituted or unsubstituted.

As used herein, "heteroaryl" refers to a monocyclic or multicyclic aromatic ring system (a ring system having a least one ring with a fully delocalized pi-electron system) that contain(s) one or more heteroatoms, that is, an element other than carbon, including but not limited to, nitrogen, oxygen, and sulfur, and at least one aromatic ring. The number of atoms in the ring(s) of a heteroaryl group can vary. For example, the heteroaryl group can contain 4 to 14 atoms in the ring(s), 5 to 10 atoms in the ring(s) or 5 to 6 atoms in the ring(s). Furthermore, the term "heteroaryl" includes fused ring systems where two rings, such as at least one aryl ring and at least one heteroaryl ring, or at least two heteroaryl rings, share at least one chemical bond. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline, and triazine. A heteroaryl group may be substituted or unsubstituted.

As used herein, "heteroaralkyl" refers to an -(alkylene)-R radical where R is heteroaryl as defined above. Examples include, but are not limited to, methylpyridyl and methylpyrimidyl. A heteroaralkyl group may also be referred to as, for example, a ($C_1$-$C_6$ alkyl)-heteroaryl group. A heteroaralkyl group may be substituted or unsubstituted.

As used herein, "heterocyclic" or "heterocyclyl" refers to three-, four-, five-, six-, seven-, eight-, nine-, ten-, up to 18-membered monocyclic, bicyclic, and tricyclic ring system wherein carbon atoms together with from 1 to 5 heteroatoms constitute said ring system. A heterocycle may optionally contain one or more unsaturated bonds situated in such a way, however, that a fully delocalized pi-electron system does not occur throughout all the rings. The heteroatoms are independently selected from oxygen, sulfur, and nitrogen. A heterocycle may further contain one or more carbonyl or thiocarbonyl functionalities, so as to make the definition include oxo-systems and thio-systems such as lactams, lactones, cyclic imides, cyclic thioimides, and cyclic carbamates. When composed of two or more rings, the rings may be joined together in a fused fashion. Additionally, any nitrogens in a heterocycle may be quaternized. Examples of such "heterocyclic" groups include but are not limited to, 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-oxide, piperidine, piperazine, pyrrolidine, pyrrolidone, pyrrolidione, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone, and their benzo-fused analogs (e.g., benzimidazolidinone, tetrahydroquinoline, 3,4-methylenedioxyphenyl). Heterocyclyl groups may be substituted or unsubstituted.

As used herein, "heterocyclylalkyl" refers to an -(alkylene)-R radical where R is heterocyclyl as defined above. Examples include, but are not limited to, methylpyrrolidinyl and methylpiperidinyl. A heterocyclylalkyl group may also be referred to as, for example, a ($C_1$-$C_6$ alkyl)-heterocyclyl group. A heterocyclylalkyl group may be substituted or unsubstituted.

As used herein, "alkoxy" refers to the formula —OR wherein R is an alkyl as defined above. A non-limiting list of alkoxys is methoxy, ethoxy, n-propoxy, n-butoxy, isobutoxy, sec-butoxy, and tert-butoxy. An alkoxy may be substituted or unsubstituted.

As used herein, "alkoxyalkyl" refers to an alkyl as defined above which is substituted with one or two alkoxy groups as defined above. Examples include, but are not limited to methoxyethyl, ethoxyethyl, and methoxypropyl. An alkoxyalkyl group may be substituted or unsubstituted.

As used herein, "acyl" refers to a hydrogen, alkyl, alkenyl, alkynyl, or aryl, as defined above, connected as substituents via a carbonyl group, as defined herein. Examples include formyl, acetyl, benzoyl, and acryl, with preferred acyl groups being $C_1$-$C_6$ alkyl carbonyl groups. An acyl may be substituted or unsubstituted.

As used herein, "hydroxyalkyl" refers to an alkyl group in which one or more of the hydrogen atoms are replaced by a hydroxy group. Exemplary hydroxyalkyl groups include but are not limited to, 2-hydroxyethyl, 3-hydroxypropyl, 2-hydroxypropyl, and 2,2-dihydroxyethyl. A hydroxyalkyl may be substituted or unsubstituted.

As used herein, "haloalkyl" refers to an alkyl group in which one or more of the hydrogen atoms are replaced by a halogen (e.g., mono-haloalkyl, di-haloalkyl, and tri-haloalkyl). Such groups include but are not limited to, chloromethyl, fluoromethyl, difluoromethyl, trifluoromethyl and 1-chloro-2-fluoromethyl, 2-fluoroisobutyl. A haloalkyl may be substituted or unsubstituted.

As used herein, "haloalkoxy" refers to an alkoxy group in which one or more of the hydrogen atoms are replaced by a halogen (e.g., mono-haloalkoxy, di-haloalkoxy and tri-haloalkoxy). Such groups include but are not limited to, chloromethoxy, fluoromethoxy, difluoromethoxy, trifluoromethoxy and 1-chloro-2-fluoromethoxy, 2-fluoroisobutoxy. A haloalkoxy may be substituted or unsubstituted.

As used herein, "aryloxy" refers to —OR, in which R is an aryl, as defined above, such as but not limited to phenyl. An aryloxy may be substituted or unsubstituted.

The term "ester" refers to a "—C(=O)OR" group in which R can be, for example, alkyl, alkenyl, alkynyl, aryl, heteroaryl, heterocyclyl, or cycloalkyl. An ester may be substituted or unsubstituted.

The term "unsubstituted amino" as used herein refers to a —NH$_2$ group.

The term "substituted amino" as used herein refers to a —NR$_a$R$_b$ group, wherein R$_a$ and R$_b$ are independently selected from hydrogen, alkyl, aryl, heteroaryl, cycloalkyl, heterocyclyl, aralkyl, heteroaralkyl, cycloalkylalkyl, and heterocyclylalkyl, as defined herein; and not more than one of wherein R$_a$ and R$_b$ can be hydrogen.

As used herein, the term "hydroxy" refers to a —OH group.

A "cyano" group refers to a "—CN" group.

A "carbonyl" group refers to a C=O group.

The term "halogen atom" or "halogen" as used herein, means any one of the radio-stable atoms of column 7 of the Periodic Table of the Elements, such as, fluorine, chlorine, bromine, and iodine.

In all of the definitions described herein, the terms used to define a new term are as previously defined herein.

Where the numbers of substituents is not specified (e.g., haloalkyl), there may be one or more substituents present. For example "haloalkyl" may include one or more of the same or different halogens. As another example, "C$_1$-C$_3$ alkoxyphenyl" may include one or more of the same or different alkoxy groups containing one, two, or three atoms.

As used herein, the abbreviations for any protective groups, amino acids and other compounds, are, unless indicated otherwise, in accord with their common usage, recognized abbreviations, or the IUPAC-IUB Commission on Biochemical Nomenclature (See, *Biochem.* 11:942-944 (1972)).

The terms "protecting group" and "protecting groups" as used herein refer to any atom or group of atoms that is added to a molecule in order to prevent existing groups in the molecule from undergoing unwanted chemical reactions. Examples of protecting group moieties are described in T. W. Greene and P. G. M. Wuts, *Protective Groups in Organic Synthesis*, 3. Ed. John Wiley & Sons, 1999, and in J. F. W. McOmie, *Protective Groups in Organic Chemistry* Plenum Press, 1973, both of which are hereby incorporated by reference for the limited purpose of disclosing suitable protecting groups. The protecting group moiety may be chosen in such a way, that they are stable to certain reaction conditions and readily removed at a convenient stage using methodology known from the art. A non-limiting list of protecting groups include benzyl; substituted benzyl; alkylcarbonyls (e.g., t-butoxycarbonyl (BOC), acetyl, or isobutyryl); arylalkylcarbonyls (e.g., benzyloxycarbonyl or benzoyl); substituted methyl ether (e.g., methoxymethyl ether); substituted ethyl ether; a substituted benzyl ether; tetrahydropyranyl ether; silyl ethers (e.g., trimethylsilyl, triethylsilyl, triisopropylsilyl, t-butyldimethylsilyl, or t-butyldiphenylsilyl); esters (e.g., benzoate ester); carbonates (e.g., methoxymethylcarbonate); sulfonates (e.g., tosylate or mesylate); acyclic ketal (e.g., dimethyl acetal); cyclic ketals (e.g., 1,3-dioxane or 1,3-dioxolanes); acyclic acetal; cyclic acetal; acyclic hemiacetal; cyclic hemiacetal; cyclic dithioketals (e.g., 1,3-dithiane or 1,3-dithiolane); and triarylmethyl groups (e.g., trityl; monomethoxytrityl (MMTr); 4,4'-dimethoxytrityl (DMTr); or 4,4',4"-trimethoxytrityl (TMTr)).

"Leaving group" as used herein refers to any atom or moiety that is capable of being displaced by another atom or moiety in a chemical reaction. More specifically, in some embodiments, "leaving group" refers to the atom or moiety that is displaced in a nucleophilic substitution reaction. In some embodiments, "leaving groups" are any atoms or moieties that are conjugate bases of strong acids. Examples of suitable leaving groups include, but are not limited to, tosylates and halogens. Non-limiting characteristics and examples of leaving groups can be found, for example in *Organic Chemistry*, 2d ed., Francis Carey (1992), pages 328-331; *Introduction to Organic Chemistry*, 2d ed., Andrew Streitwieser and Clayton Heathcock (1981), pages 169-171; and *Organic Chemistry*, 5$^{th}$ ed., John McMurry (2000), pages 398 and 408; all of which are incorporated herein by reference for the limited purpose of disclosing characteristics and examples of leaving groups.

The term "pharmaceutically acceptable salt" as used herein is a broad term, and is to be given its ordinary and customary meaning to a person of ordinary skill in the art (and is not to be limited to a special or customized meaning), and refers without limitation to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., HCl or HBr), H$_2$SO$_4$, HNO$_3$, and H$_3$PO$_4$. Pharmaceutical salts can also be obtained by reacting a compound with an organic acid such as aliphatic or aromatic carboxylic or sulfonic acids, for example formic acid, AcOH, propionic acid, glycolic acid, pyruvic acid, malonic acid, maleic acid, fumaric acid, trifluoroacetic acid, benzoic acid, cinnamic acid, mandelic acid, succinic acid, lactic acid, malic acid, tartaric acid, citric acid, ascorbic acid, nicotinic acid, methanesulfonic acid, ethanesulfonic acid, p-toluensulfonic acid, salicylic acid, stearic acid, muconic acid, butyric acid, phenylacetic acid, phenylbutyric acid, valproic acid, 1,2-ethanedisulfonic acid, 2-hydroxyethanesulfonic acid, benzenesulfonic acid, 2-naphthalenesulfonic acid, or naphthalenesulfonic acid. Pharmaceutical salts can also be obtained by reacting a compound with a base to form a salt such as an ammonium salt, an alkali metal salt, such as a Li, Na, or a K salt, an alkaline earth metal salt, such as a Ca, Mg, or Al salt, a salt of organic bases such as dicyclohexylamine, N-methyl-D-glucamine, tris(hydroxymethyl)methylamine, a C$_1$-C$_7$ alkylamine, cyclohexylamine, dicyclohexylamine, triethanolamine, ethylenediamine, ethanolamine, diethanolamine, triethanolamine, tromethamine, and salts with amino acids such as arginine and lysine; or a salt of an inorganic base, such as Al(OH)$_3$, C$_a$(OH)$_2$, KOH, Na$_2$CO$_3$, NaOH, or the like.

Some embodiments provide pharmaceutically acceptable salts of Formula (II). In some embodiments, the salt is selected from the group consisting of hydrochloride, sulfate, hemisulfate, acetate, fumarate, malate, and citrate.

The term "solvate" as used herein is a broad term, and is to be given its ordinary and customary meaning to a person of ordinary skill in the art (and is not to be limited to a special or customized meaning), and refers without limitation to mean that the solvent is complexed with a compound in a reproducible molar ratio, including, but not limited to, 0.5:1, 1:1, or 2:1. Thus, the term "pharmaceutically acceptable solvate," refers to a solvate wherein the solvent is one that does not cause significant irritation to an organism to which it is administered and does not abrogate the biological activity of the compound.

Some embodiments provide solvates of Formula (I). In some embodiments, the solvent in the solvate is selected from water, ethanol, and acetone, or combinations thereof.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, or may be stereoisomeric mixtures, and include all diastereomeric, and enantiomeric forms. In addition it is understood that, in any compound described herein having one or more double bond(s) generating geometrical isomers that can be defined as E or Z, each double bond may independently be E or Z a mixture thereof. Stereoisomers are obtained, if desired, by methods such as, stereoselective synthesis and/or the separation of stereoisomers by chiral chromatographic columns. Likewise, it is understood that, in any compound described, all tautomeric forms are also intended to be included.

Wherever a substituent is depicted as a di-radical (i.e., has two points of attachment to the rest of the molecule), it is to be understood that the substituent can be attached in any directional configuration unless otherwise indicated. Thus, for example, a substituent depicted as -AE- or

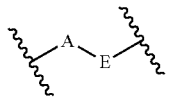

includes the substituent being oriented such that the A is attached at the leftmost attachment point of the molecule as well as the case in which A is attached at the rightmost attachment point of the molecule.

It is to be understood that where compounds disclosed herein have unfilled valencies, then the valencies are to be filled with hydrogens and/or deuteriums.

It is understood that the compounds described herein can be labeled isotopically or by another other means, including, but not limited to, the use of chromophores or fluorescent moieties, bioluminescent labels, or chemiluminescent labels. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium), hydrogen-2 (deuterium), and hydrogen-3 (tritium). Thus, reference herein to a compound encompasses all potential isotopic forms unless the context clearly dictates otherwise.

It is understood that the methods and formulations described herein include the use of salts, solvates, hydrates, and conformers of compounds of preferred embodiments, as well as metabolites and active metabolites of these compounds having the same type of activity. A conformer is a structure that is a conformational isomer. Conformational isomerism is the phenomenon of molecules with the same structural formula but different conformations (conformers) of atoms about a rotating bond. In specific embodiments, the compounds described herein exist in solvated forms with pharmaceutically acceptable solvents such as water, ethanol, or the like. In other embodiments, the compounds described herein exist in unsolvated form. Solvates contain either stoichiometric or non-stoichiometric amounts of a solvent, and may be formed during the process of crystallization with pharmaceutically acceptable solvents such as water, ethanol, or the like. Hydrates are formed when the solvent is water, or alcoholates are formed when the solvent is alcohol. In addition, the compounds provided herein can exist in unsolvated as well as solvated forms. In general, the solvated forms are considered equivalent to the unsolvated forms for the purposes of the compounds and methods provided herein. Compounds of Formula (I) can also be provided as, for example, amorphous forms, milled forms and nanoparticulate forms.

Likewise, it is understood that the compounds described herein, such as compounds of preferred embodiments, include the compound in any of the forms described herein (e.g., pharmaceutically acceptable salts, crystalline forms, amorphous form, solvated forms, enantiomeric forms, tautomeric forms, and the like).

Dosing Regimes

In some embodiments, about 1 mg to about 5 grams of a compound of Formula (I) is administered each day. In some embodiments, about 2 mg to about 2 grams of a compound of Formula (I) is administered each day. In some embodiments, the amount of a compound of Formula (I) administered each day is, or is about, 5 mg to 1 gram; 10 mg to 800 mg; 20 mg to 600 mg; 30 mg to 400 mg; 40 mg to 200 mg; 50 mg to 100 mg; or any amount in between.

In some embodiments, about 1 mg to about 5 grams of a compound of Formula (I) is administered each week. In some embodiments, about 2 mg to about 2 grams of a compound of Formula (I) is administered each week. In some embodiments, the amount of a compound of Formula (I) administered each week is, or is about, 5 mg to 1 gram; 10 mg to 800 mg; 20 mg to 600 mg; 30 mg to 400 mg; 40 mg to 200 mg; 50 mg to 100 mg; or any amount in between.

In some embodiments, about 1 mg to about 5 grams of a compound of Formula (I) is administered each cycle of treatment. In some embodiments, about 2 mg to about 2 grams of a compound of Formula (I) is administered each cycle of treatment. In some embodiments, the amount of a compound of Formula (I) administered each cycle of treatment is, or is about, 5 mg to 1 gram; 10 mg to 800 mg; 20 mg to 600 mg; 30 mg to 400 mg; 40 mg to 200 mg; 50 mg to 100 mg; or any amount in between.

In some embodiments, a compound of Formula (I) is administered at least once per day; twice per day; three times per day; or four times per day. In some embodiments, a compound of Formula (I) is administered at least once per week; twice per week; three times per week; or four times per week. In some embodiments, each cycle of treatment lasts 1 day; 2 days; 3 days; 4 days; 5 days; 6 days; 7 days; 8 days; 9 days; 10 days; 11 days; 12 days; 13 days; 14 days, or any time in between. In some embodiments, each cycle of treatment has at least 1 day; 2 days; 3 days; 4 days; 5 days; 6 days; 7 days; 8 days; 9 days; 10 days; 11 days; 12 days; 13 days; or 14 days, between administrations of a compound of Formula (I).

In some embodiments, a compound of Formula (I) is provided intravenously over about 10 min; about 20 min; about 30 min; about 1 hour; about 1.5 hrs; about 2 hrs; about 2.5 hrs; about 3 hrs; about 3.5 hrs; about 4 hrs, or any time in between.

EXAMPLES

Additional embodiments are disclosed in further detail in the following examples, which are not in any way intended to limit the scope of the claims.

Characterization of the compounds disclosed herein was performed with Bruker AV-500 and DRX-500 NMR spectrometers and a Perkin Elmer PE-SCIEX API-150 mass spectrometer.

In the synthetic procedures described herein, "workup and purification" refers to combining organic layers after an aqueous phase extraction, washing with brine, drying over $Na_2SO_4$, filtering, concentrating, and purified by silica gel chromatography with the indicated solvent system. The workup and purification may also include an optional washing step with 10% aq. $Na_2S_2O_3$/sat. aq. $NaHCO_3$ (1:1) prior to the wash with brine.

Example 1

Compound 1: (S)-3-(4-((4-(morpholinomethyl)benzyl)oxy)-1-oxoisoindolin-2-yl)azepane-2,7-dione

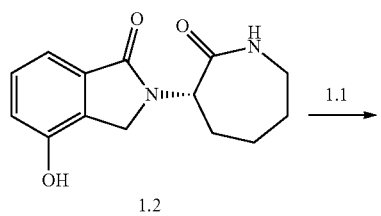

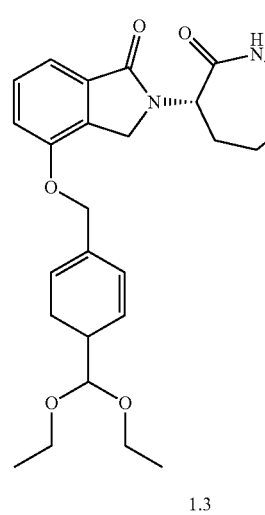

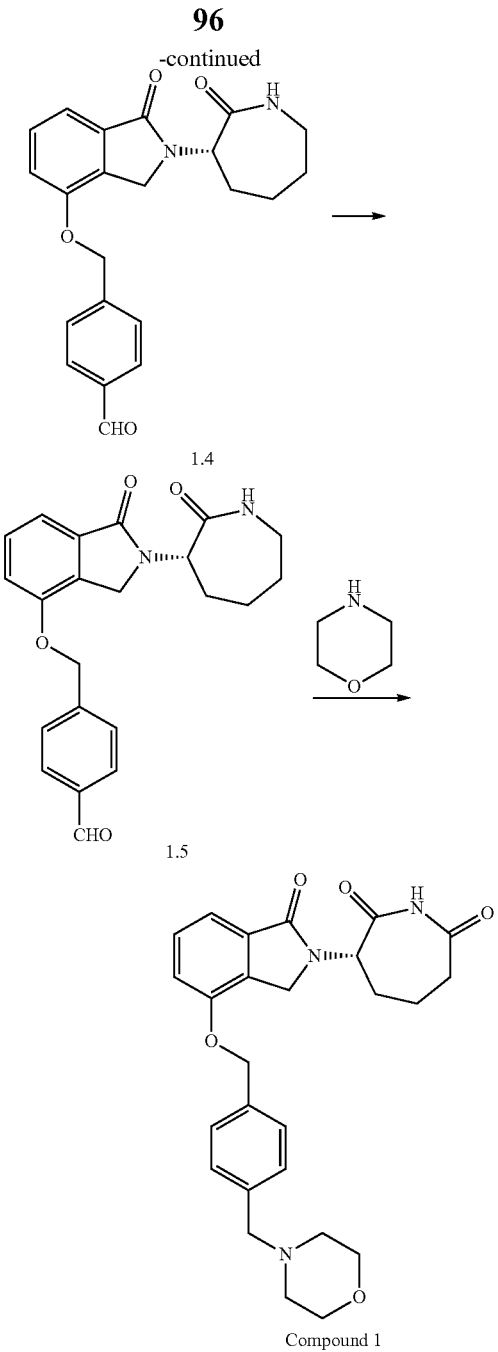

Compound 1

To a solution of 4-(diethoxymethyl)benzaldehyde (2.43 g, 11.67 mmol) in MeOH (40 mL) at 0° C. was added $NaBH_4$ (886.7 mg, 23.34 mmol). The suspension was stirred at RT for 3 h. The solvent was then removed, and the residue was diluted with water and extracted with DCM. The combined organic layers were dried over $Na_2SO_4$, filtered, concentrated, and the residue purified by silica gel chromatography with EtOAc in pet. ether (10% to 23%) to give (4-(diethoxymethyl)phenyl)methanol 1.1 (2.21 g, 90% yield) as a colorless oil. MS (ESI) m/z 165.1 [M–42]$^+$.

To a solution of compound 1.2 (323 mg, 1.24 mmol) in THF (20 mL) at 0° C. was added 1.1 (326.5 mg, 1.55 mmol) followed by $PPh_3$ (650.4 mg, 2.48 mmol). A solution of DEAD (431.9 mg, 2.48 mmol) in THF (1 mL) was added dropwise and the suspension was stirred at RT for 16 h. The solvent was removed, and the residue was purified by silica gel chromatography using EtOAc in pet. ether (40% to 100%) to give compound 1.3 (373 mg, 66.7% yield) as a white solid. MS (ESI) m/z 407.1 [M−45]+.

To a solution of compound 1.3 (473 mg, 1.05 mmol) in THF (10 mL) at RT was added 4 M HCl (1.31 mL), and the reaction was stirred at RT for 30 min. The solvent was removed, and the residue was dried under vacuum to give compound 1.4 (397 mg, 100% yield) as a white solid. MS (ESI) m/z 379.1 [M+1]+.

To a solution of compound 1.4 (396.9 mg, 1.05 mmol) in fluorobenzene/DMSO (30 mL/5 mL, 1 drop water in DMSO) was added Dess-Martin reagent (1.12 g, 2.63 mmol). The suspension was heated at 80° C. for 18 h. Additional Dess-Martin reagent (550 mg) was added and the mixture was heated at 80° C. for 5 h. The mixture was cooled to RT and filtered. The filtrate was added to sat. aq. Na$_2$S$_2$O$_3$. The suspension was stirred at 0° C. for 5 min then extracted with DCM. Workup and purification by silica gel chromatography using EtOAc in pet. ether (40-100%) provided compound 1.5 (184 mg, 45% yield) as a white solid. MS (ESI) m/z 393.1 [M+1]+.

To a solution of compound 1.5 (76 mg, 0.194 mmol) in DCM (10 mL) was added morpholine (25.3 mg, 0.291 mmol) followed by NaBH(OAc)$_3$ (82.3 mg, 0.384 mmol). The mixture was stirred at RT for 48 h, concentrated, purified by prep-TLC using EtOAc then further purified by prep-HPLC (5 M C$_{18}$ column, 0.1% TFA in H$_2$O, 0.1% TFA in ACN, 5%-95% 0.1% TFA in ACN) to afford Compound 1 (30.7 mg, 21.7% yield) as a white solid. $^1$H NMR (DMSO-d$_6$, 400 MHz) δ: 10.70 (s, 1H), 7.49-7.45 (m, 3H), 7.35-7.31 (m, 4H), 5.24-5.21 (m, 3H), 4.47 (s, 2H), 3.57 (s, 4H), 3.47 (s, 2H), 3.08 (t, J=11.2 Hz, 1H), 2.59-2.54 (m, 1H), 2.35 (s, 5H), 2.12-1.97 (m, 2H), 1.86-1.74 (m, 1H). MS (ESI) m/z 464.1 [M+H]+.

Example 2

Compound 2: (S)-3-(4-((4-((2,3-dihydro-4H-benzo [b][1,4]oxazin-4-yl)methyl)benzyl)oxy)-1-oxoisoindolin-2-yl)azepane-2,7-dione

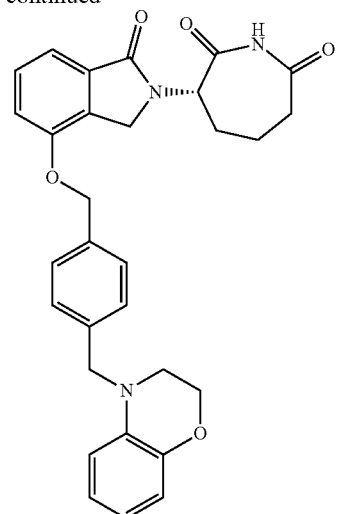

Compound 2

To a solution of compound 1.5 (90 mg, 0.229 mmol) in AcOH (4 mL) at RT was added 3,4-dihydro-2H-benzo[b] [1,4]oxazine (46.5 mg, 0.344 mmol) followed by NaBH (OAc)$_3$ (145.6 mg, 0.687 mmol). The mixture was stirred at RT for 3 h, the solvent removed, and the residue purified by prep-TLC using EtOAc in pet. ether (1:2) then further purified by prep-HPLC as previously described to afford Compound 2 (45.0 mg, 39% yield) as a white solid. $^1$H NMR (DMSO-d$_6$, 400 MHz) δ: 10.69 (s, 1H), 7.49-7.45 (m, 3H), 7.35-7.31 (m, 4H), 6.70-6.63 (m, 3H), 6.51 (t, J=7.2 Hz, 1H), 5.23-5.19 (m, 3H), 4.47 (d, J=8.8 Hz, 4H), 4.21 (t, J=3.6 Hz, 2H), 3.39-3.35 (m, 2H), 3.06 (t, J=13.2 Hz, 1H), 2.57 (d, J=18.0 Hz, 1H), 2.36-2.29 (m, 1H), 2.09-1.99 (m, 2H), 1.85-1.74 (m, 1H). MS (ESI) m/z 512.2 [M+H]+.

Example 3

Compound 3: ((S)-3-(4-((3-chloro-4-(morpholinomethyl)benzyl)oxy)-1-oxoisoindolin-2-yl)azepane-2,7-dione

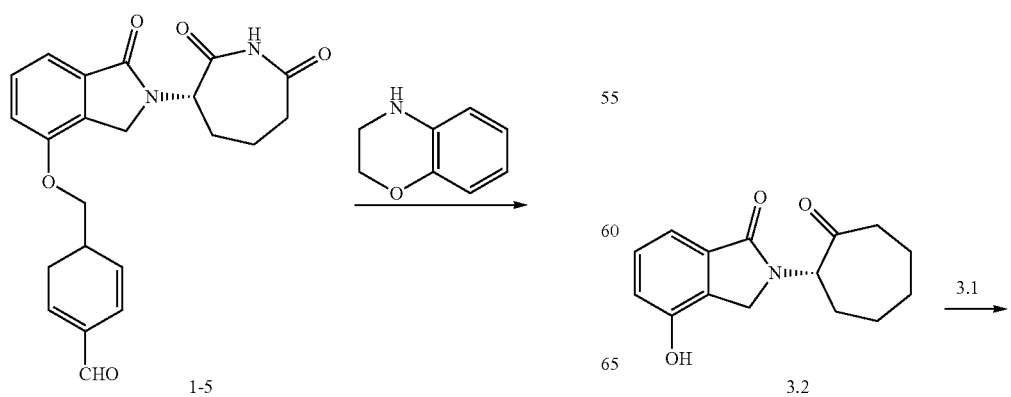

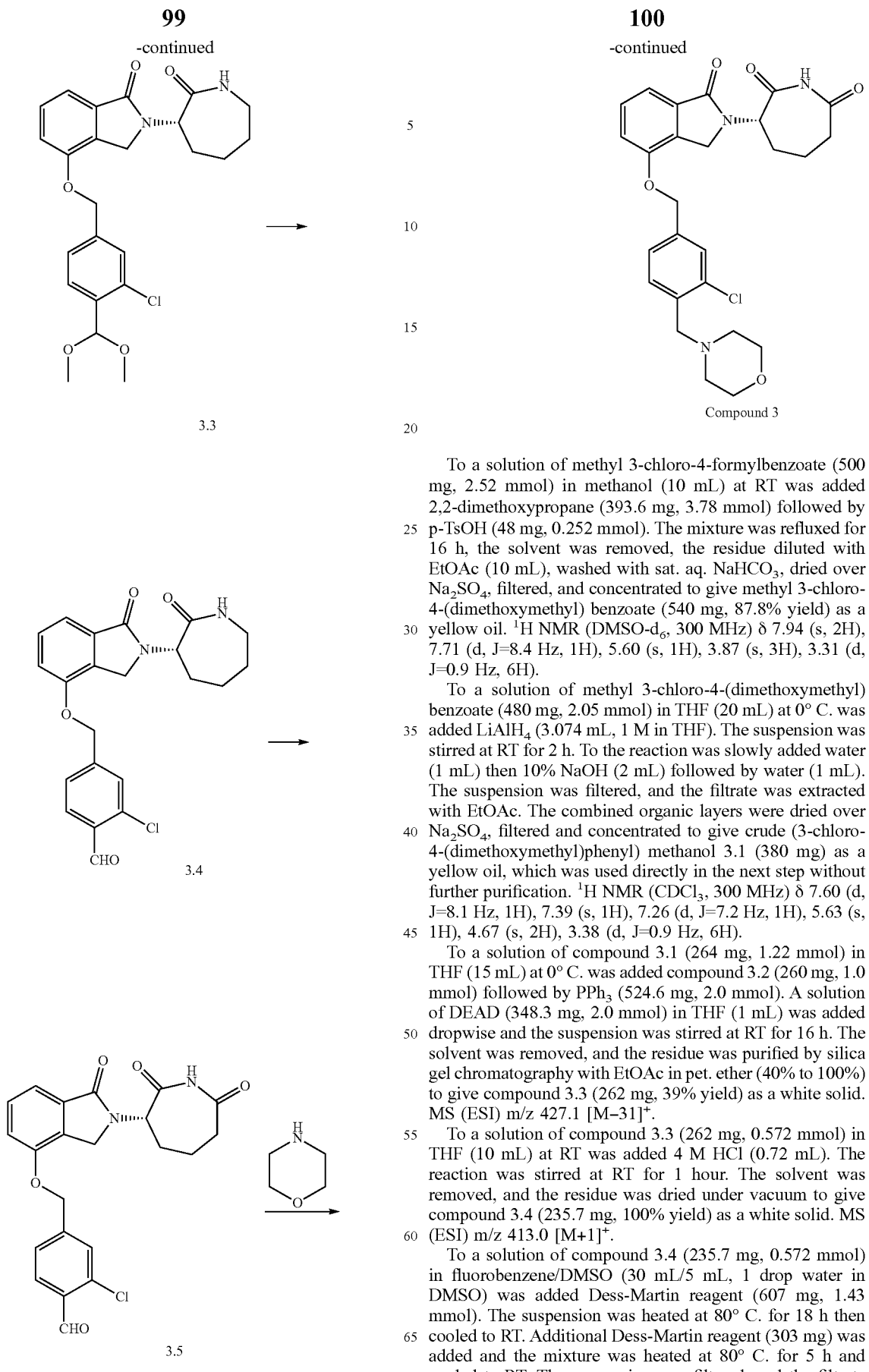

To a solution of methyl 3-chloro-4-formylbenzoate (500 mg, 2.52 mmol) in methanol (10 mL) at RT was added 2,2-dimethoxypropane (393.6 mg, 3.78 mmol) followed by p-TsOH (48 mg, 0.252 mmol). The mixture was refluxed for 16 h, the solvent was removed, the residue diluted with EtOAc (10 mL), washed with sat. aq. NaHCO$_3$, dried over Na$_2$SO$_4$, filtered, and concentrated to give methyl 3-chloro-4-(dimethoxymethyl) benzoate (540 mg, 87.8% yield) as a yellow oil. $^1$H NMR (DMSO-d$_6$, 300 MHz) δ 7.94 (s, 2H), 7.71 (d, J=8.4 Hz, 1H), 5.60 (s, 1H), 3.87 (s, 3H), 3.31 (d, J=0.9 Hz, 6H).

To a solution of methyl 3-chloro-4-(dimethoxymethyl) benzoate (480 mg, 2.05 mmol) in THF (20 mL) at 0° C. was added LiAlH$_4$ (3.074 mL, 1 M in THF). The suspension was stirred at RT for 2 h. To the reaction was slowly added water (1 mL) then 10% NaOH (2 mL) followed by water (1 mL). The suspension was filtered, and the filtrate was extracted with EtOAc. The combined organic layers were dried over Na$_2$SO$_4$, filtered and concentrated to give crude (3-chloro-4-(dimethoxymethyl)phenyl) methanol 3.1 (380 mg) as a yellow oil, which was used directly in the next step without further purification. $^1$H NMR (CDCl$_3$, 300 MHz) δ 7.60 (d, J=8.1 Hz, 1H), 7.39 (s, 1H), 7.26 (d, J=7.2 Hz, 1H), 5.63 (s, 1H), 4.67 (s, 2H), 3.38 (d, J=0.9 Hz, 6H).

To a solution of compound 3.1 (264 mg, 1.22 mmol) in THF (15 mL) at 0° C. was added compound 3.2 (260 mg, 1.0 mmol) followed by PPh$_3$ (524.6 mg, 2.0 mmol). A solution of DEAD (348.3 mg, 2.0 mmol) in THF (1 mL) was added dropwise and the suspension was stirred at RT for 16 h. The solvent was removed, and the residue was purified by silica gel chromatography with EtOAc in pet. ether (40% to 100%) to give compound 3.3 (262 mg, 39% yield) as a white solid. MS (ESI) m/z 427.1 [M−31]$^+$.

To a solution of compound 3.3 (262 mg, 0.572 mmol) in THF (10 mL) at RT was added 4 M HCl (0.72 mL). The reaction was stirred at RT for 1 hour. The solvent was removed, and the residue was dried under vacuum to give compound 3.4 (235.7 mg, 100% yield) as a white solid. MS (ESI) m/z 413.0 [M+1]$^+$.

To a solution of compound 3.4 (235.7 mg, 0.572 mmol) in fluorobenzene/DMSO (30 mL/5 mL, 1 drop water in DMSO) was added Dess-Martin reagent (607 mg, 1.43 mmol). The suspension was heated at 80° C. for 18 h then cooled to RT. Additional Dess-Martin reagent (303 mg) was added and the mixture was heated at 80° C. for 5 h and cooled to RT. The suspension was filtered, and the filtrate was added to sat. aq. Na$_2$S$_2$O$_3$ (30 mL). The suspension was stirred at 0° C. for 5 min then extracted with DCM. Workup and purification by silica gel chromatography using EtOAc in pet. ether (20% to 80%) provided compound 3.5 (72 mg, 30% yield) as a white solid. MS (ESI) m/z 427.0 [M+1]$^+$.

To a solution of compound 3.5 (54 mg, 0.127 mmol) in DCM (5 mL) at RT was added morpholine (22.1 mg, 0.254 mmol) followed by NaBH(OAc)$_3$ (80.8 mg, 0.38 mmol). The mixture was stirred at RT for 24 h. The solvent was removed, and the residue was purified by prep-TLC using EtOAc/petroleum ether (2:1) then by prep-HPLC, as previously described, to afford Compound 3 (19.9 mg, 32% yield) as a white solid. $^1$H NMR (DMSO-d$_6$, 400 MHz) δ: 10.70 (s, 1H), 7.57 (s, 1H), 7.53-7.45 (m, 3H), 7.33 (t, J=6.8 Hz, 2H), 5.27 (s, 2H), 5.20 (d, J=5.2 Hz, 1H), 4.49 (s, 2H), 3.59-3.56 (m, 6H), 3.11-3.03 (m, 1H), 2.58 (d, J=17.2 Hz, 1H), 2.42 (s, 4H), 2.38-2.33 (m, 1H), 2.14-1.99 (m, 2H), 1.86-1.76 (m, 1H). MS (ESI) m/z 498.1 [M+H]$^+$.

Example 4

Compound 4: (S)-3-(4-{[p-(4-Piperidyl)phenyl]methoxy}-2-isoindolinoyl)-2,7-azepanedione

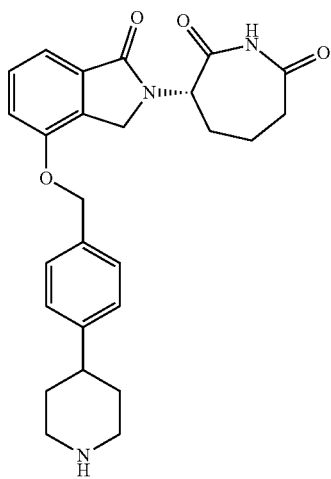 [SMILES: O=C1CCC[C@H](N2Cc3c(OCc4ccc(C5CCNCC5)cc4)cccc3C2=O)C(=O)N1]

To a solution of ethyl 4-iodobenzoate (750 mg, 2.72 mmol), tert-butyl 4-(4,4,5,5-tetramethyl-1,3,2-dioxaborolan-2-yl)-5,6-dihydropyridine-1(2H)-carboxylate (923 mg, 2.99 mmol) in DMF (50 mL) at RT were added [1,1'-bis(diphenylphosphino)ferrocene] dichloropalladium(II) (400 mg) and K$_2$CO$_3$ (1.12 g, 8.16 mmol). The suspension was stirred at 85° C. for 16 hrs. The mixture was filtered through a pad of Celite. The filtrate was diluted with water and extracted with EtOAc. Workup and purification with petroleum ether/EtOAc (8:1) provided 4-tert-butyl 4'-ethyl 1,2,3,6-tetrahydro-[1,1'-biphenyl]-4,4'-dicarboxylate (720 mg, 80% yield) as a white solid.

To a solution of 4-tert-butyl 4'-ethyl 1,2,3,6-tetrahydro-[1,1'-biphenyl]-4,4'-dicarboxylate (720 mg, 2.18 mmol) in EtOH (20 mL) was added palladium on activated carbon (80 mg) at RT. The mixture was stirred at RT for 3 hrs. The mixture was filtered through a pad of Celite and the filtrate was concentrated to obtain the crude product, which was purified by silica gel chromatography eluting with petroleum ether/EtOAc (7:1) to give ethyl 4-(4-(tert-butoxycarbonyl)cyclohexyl)benzoate (680 mg, 93% yield) as a colorless oil.

To a solution of ethyl 4-(4-(tert-butoxycarbonyl)cyclohexyl)benzoate (680 mg, 2.04 mmol) in THF (15 mL) at 0° C. was added LAH (1.0 M in THF, 1.63 mL, 4.08 mmol) dropwise. The mixture was stirred at RT for 2 hrs. The reaction was quenched with Na$_2$SO$_4$ decahydrate (5.0 g). After stirring at RT for 1 hour, the mixture was filtered, concentrated, and purified by silica gel chromatography eluting with MeOH in DCM (3%) to give tert-butyl 4-(4-(hydroxymethyl)phenyl)piperidine-1-carboxylate (410 mg, 69% yield) as a white solid.

To a solution of tert-butyl 4-(4-(hydroxymethyl)phenyl)piperidine-1-carboxylate (186 mg, 0.64 mmol), (S)-4-hydroxy-2-(2-oxoazepan-3-yl)isoindolin-1-one (200 mg, 0.51 mmol), triphenylphosphine (524 mg, 1.024 mmol) in THF (10 mL) at 0° C. was added DEAD (178 mg, 1.024 mmol) dropwise. The mixture was stirred at 0° C. for 16 hrs then concentrated to give the crude product which was purified by prep-HPLC (5 μM C$_{18}$ column, 0.1% TFA in H$_2$O, 0.1% TFA in ACN, 5%-95% 0.1% TFA in ACN) to afford (S)-tert-butyl 4-(4-(((1-oxo-2-(2-oxoazepan-3-yl)isoindolin-4-yl)oxy)methyl)phenyl)piperidine-1-carboxylate (200 mg, 56% yield) as a white solid. MS (ESI) m/z 478.1 [M+H-$^t$Bu]$^+$.

To a solution of (S)-tert-butyl 4-(4-(((1-oxo-2-(2-oxoazepan-3-yl)isoindolin-4-yl)oxy)methyl)phenyl)piperidine-1-carboxylate (200 mg, 0.375 mmol) in fluorobenzene/DMSO (10 mL/1 mL, 1 drops water in DMSO) at RT was added Dess-Martin reagent (397 mg, 0.94 mmol). The mixture was heated to 80° C. for 18 hrs. The mixture was then cooled to 0° C. and quenched with sat. aqueous sodium thiosulfate solution (25 mL). After stirring at 0° C. for 15 min, the mixture was extracted with DCM. Workup and purification with EtOAc/pet. ether (20% to 80%) provided (S)-tert-butyl 4-(4-(((2-(2,7-dioxoazepan-3-yl)-1-oxoisoindolin-4-yl)oxy)methyl) phenyl)piperidine-1-carboxylate (32 mg, 15% yield) as a white solid.

To a solution of (S)-tert-butyl 4-(4-(((2-(2,7-dioxoazepan-3-yl)-1-oxoisoindolin-4-yl) oxy)methyl)phenyl)piperidine-1-carboxylate (110 mg, 0.2 mmol) in DCM (4 mL) was added TFA (1 mL). The mixture was stirred at RT for 2 hrs then a sat. NaHCO$_3$ solution was added to reach pH=7, and the mixture was extracted with DCM. The combined organic phases were dried over anhydrous Na$_2$SO$_4$, filtered, and concentrated to give the crude product which was purified by prep-HPLC as previously described to afford Compound 4 (2.5 mg, 6.2% yield) as a white solid. $^1$H NMR (DMSO-d$_6$, 400 MHz) δ: 10.71 (s, 1H), 8.64 (s, 1H), 8.40 (s, 1H), 7.49 (m, 3H), 7.31 (m, 4H), 5.23 (m, 3H), 3.12 (s, 2H), 2.85 (m, 2H), 2.55 (m, 3H), 2.32 (m, 1H), 2.12 (m, 4H), 2.07 (m, 3H). MS (ESI) m/z 448.0 [M+H]$^+$.

Example 5

Compound 5: (S)-3-(4-{[p-(Aminomethyl)phenyl]methoxy}-2-isoindolinoyl)-2,7-azepanedione trifluoroacetic acid

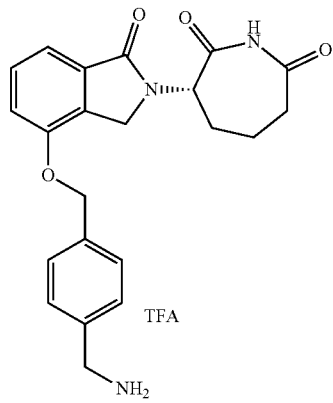 [SMILES: NCc1ccc(COc2cccc3c2CN([C@H]2CCCC(=O)NC2=O)C3=O)cc1]

To a solution of tert-butyl (3-(4-((4-((3-(N-(tert-butyl)sulfamoyl)phenyl)amino)-5-methylpyrimidin-2-yl)amino)phenoxy)propyl)carbamate (120 mg, 0.205 mmol) in DCM (8 mL) at RT was added TFA (2 mL). The mixture was stirred for 2 hrs. The solvent was evaporated to give 3-((2-((4-(3-aminopropoxy)phenyl)amino)-5-methylpyrimidin-4-yl)amino)-N-(tert-butyl)benzenesulfonamide (102 mg, crude) which was used directly in the next step without further purification. MS (ESI) m/z 485.1 [M+H]$^+$.

To a solution of (S)-4-hydroxy-2-(2-oxoazepan-3-yl)isoindolin-1-one (700 mg, 2.69 mmol), tert-butyl 4-(hydroxymethyl)benzylcarbamate (804 mg, 3.37 mmol), and triphenylphosphine (1.41 g, 5.38 mmol) in THF (10 mL) at RT was added a solution of DEAD (938.7 mg, 5.38 mmol) in THF (1 mL). The mixture was stirred at RT for 16 hrs. The solvent was evaporated, and the residue was purified by silica gel chromatography eluting with MeOH in DCM (from 0% to 7%) to give (S)-tert-butyl 4-(((1-oxo-2-(2-oxoazepan-3-yl)isoindolin-4-yl)oxy)methyl)benzyl carbamate (674 mg, 52% yield) as a white solid. MS (ESI) m/z 480.2 [M+H]$^+$.

To a solution of (S)-tert-butyl 4-(((1-oxo-2-(2-oxoazepan-3-yl)isoindolin-4-yl) oxy)methyl)benzylcarbamate (674 mg, 1.41 mmol) in fluorobenzene/DMSO (30 mL/5 mL, 1 drops H$_2$O in DMSO) at RT was added Dess-Martin reagent (1.49 g, 3.52 mmol). The mixture was stirred at 80° C. for 16 hrs. The mixture was cooled to RT and filtered. The filtrate was added to a cooled sat. aqueous sodium thiosulfate solution (30 mL) and stirred at 0° C. for 5 min then extracted with DCM. Workup and purification with EtOAc/petroleum ether from 40% to 100% provided (S)-tert-butyl 4-(((2-(2,7-dioxoazepan-3-yl)-1-oxoisoindolin-4-yl) oxy)methyl)benzylcarbamate (320 mg, 46% yield) as a white solid. MS (ESI) m/z 494.2[M+H]$^+$.

To a solution of (S)-tert-butyl 4-(((2-(2,7-dioxoazepan-3-yl)-1-oxoisoindolin-4-yl) oxy)methyl)benzylcarbamate (22 mg, 0.0446 mmol) in DCM (2 mL) was added TFA (0.5 mL) at RT. The mixture was stirred at RT for 2 hrs. The solvent was evaporated to give the desired product which was lyophilized to afford Compound 5 (17.6 mg, 78% yield) as a white solid. MS (ESI) m/z 394.1 [M+1]$^+$. $^1$H NMR (400 MHz, DMSO-d$_6$) δ 10.71 (s, 1H), 8.18 (s, 1H), 7.55 (d, J=7.6 Hz, 2H), 7.48-7.45 (m, 3H), 7.33-7.30 (m, 2H), 5.30 (s, 2H), 5.23 (dd, J=4.8, 12.4 Hz, 1H), 4.48 (s, 2H), 4.05 (d, J=5.2 Hz, 2H), 3.11-3.05 (m, 1H), 2.60-2.53 (m, 1H), 2.34-2.31 (m, 1H), 2.11-1.99 (m, 2H), 1.85-1.80 (m, 1H).

Example 6

Compound 6: (S)-3-(4-{[p-({2-[3-(p-{5-Methyl-4-[m-(tert-butylaminosulfonyl) phenylamino]-2-pyrimidinylamino}phenoxy)propylamino]acetylamino}methyl)phenyl]methoxy}-2-isoindolinoyl)-2,7-azepanedione

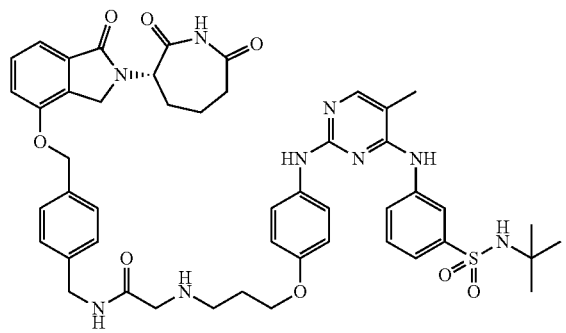 [SMILES: Cc1cnc(Nc2ccc(OCCCNCC(=O)NCc3ccc(COc4cccc5c4CN([C@H]4CCCC(=O)NC4=O)C5=O)cc3)cc2)nc1Nc1cccc(S(=O)(=O)NC(C)(C)C)c1]

To a solution of (S)-3-(4-((4-(aminomethyl)benzyl)oxy)-1-oxoisoindolin-2-yl)azepane-2,7-dione (112 mg, 0.284 mmol) in DCM (5 mL) at RT was added TEA (24.2 mg, 0.175 mmol) followed by 2-bromoacetyl chloride (45 mg, 0.284 mmol). The mixture was stirred for 1 hour. The solvent was evaporated, and the residue was purified by silica gel chromatography eluting with EtOAc/petroleum ether from 20% to 100% to give (S)-2-bromo-N-(4-(((2-(2,7-dioxoazepan-3-yl)-1-oxoisoindolin-4-yl)oxy)methyl)benzyl)acetamide (89 mg, 61% yield) as a white solid. MS (ESI) m/z 514.1 [M+H]$^+$.

To a solution of (S)-2-bromo-N-(4-(((2-(2,7-dioxoazepan-3-yl)-1-oxoisoindolin-4-yl) oxy)methyl)benzyl)acetamide (45 mg, 0.0877 mmol) in DMF (5 mL) at RT was added K$_2$CO$_3$ (24.2 mg, 0.175 mmol) followed by 3-((2-((4-(3-aminopropoxy)phenyl)amino)-5-methylpyrimidin-4-yl)amino)-N-(tert-butyl)benzenesulfonamide (45 mg, 0.0877 mmol). The mixture was heated at 50° C. for 2 hrs. The solvent was evaporated, and the residue was purified by prep-HPLC as previously described to afford Compound 6 (12.6 mg, 16% yield) as a white solid. MS (ESI) m/z 917.7 [M+H]+. $^1$H NMR (400 MHz, DMSO-d$_6$) δ 10.71 (s, 1H), 8.77 (s, 1H), 8.53 (s, 1H), 8.12 (d, J=8.0 Hz, 2H), 7.89 (s, 1H), 7.55-7.41 (m, 9H), 7.31-7.27 (m, 4H), 6.77 (d, J=8.8 Hz, 2H), 5.23-5.18 (m, 3H), 4.44 (s, 2H), 4.31 (d, J=5.6 Hz, 2H), 3.96 (t, J=6.4 Hz, 2H), 3.09-3.01 (m, 2H), 2.74-2.67 (m, 2H), 2.58-2.53 (m, 2H), 2.32-2.26 (m, 1H), 2.11 (s, 3H), 2.04-1.97 (m, 3H), 1.87-1.84 (m, 3H), 1.12 (s, 9H).

Example 7

Compound 7: (S)-3-(6-Fluoro-4-{[p-(morpholinomethyl)phenyl]methoxy}-2-isoindolinoyl)-2,7-azepanedione

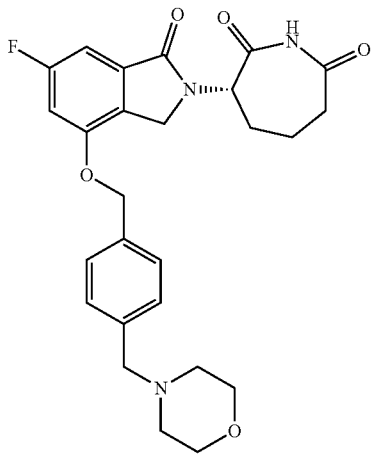 [SMILES: O=C1CCC[C@H](N2Cc3c(OCc4ccc(CN5CCOCC5)cc4)cc(F)cc3C2=O)C(=O)N1]

To a cooled (−15° C.) solution of 5-fluoro-2-methylbenzoic acid (1.0 g, 6.5 mmol) in sulfuric acid (8 mL) at RT was added nitric acid (0.44 mL) dropwise. The mixture was stirred for 1 hour then warmed to 0° C. stirred for 1 hour. The mixture was poured slowly into ice water and extracted with EtOAc. The combined organic layers were washed with brine, dried over anhydrous Na$_2$SO$_4$, filtered, and concentrated to give 5-fluoro-2-methyl-3-nitrobenzoic acid (830 mg, crude) which was used in the next step without further purification.

To a solution of 5-fluoro-2-methyl-3-nitrobenzoic acid (830 mg crude) in MeOH (8 mL) at 0° C. was added thionyl chloride (1 mL) dropwise. The mixture was then heated to reflux for 3 hrs. The solvent was evaporated to give the crude product which was purified by silica gel chromatography using petroleum ether/EtOAc (100:1 to 50:1) to afford methyl 5-fluoro-2-methyl-3-nitrobenzoate (530 mg, 59% yield) as a yellow solid.

To a solution of methyl 5-fluoro-2-methyl-3-nitrobenzoate (530 mg, 2.66 mmol) in MeOH (6 mL) at RT was added Pd/C (400 mg). The suspension was stirred at RT for 3 hrs under H$_2$. The suspension was filtered through a pad of Celite and the filtrate was concentrated to give methyl 3-amino-5-fluoro-2-methylbenzoate (420 mg, crude) which was used in the next step without further purification.

To methyl 3-amino-5-fluoro-2-methylbenzoate (420 mg, 2.28 mmol) in water at 0° C. was dropwise added sulfuric acid (5 mL) followed sodium nitrate (165 mg, 2.39 mmol, in 2.5 mL water). After stirring at 0° C. for 2.5 hrs, the mixture was dropwise added into sulfuric acid (50% in water) at 100° C. for 20 min then the mixture was cooled to RT and extracted with EtOAc. The combined organic layers were washed with brine, dried over anhydrous Na$_2$SO$_4$, filtered, and concentrated to give methyl 5-fluoro-3-hydroxy-2-methylbenzoate which was used in the next step without further purification.

To a solution of methyl 5-fluoro-3-hydroxy-2-methylbenzoate (320 mg, 1.74 mmol) in DMF (6 mL) 0° C. was added sodium hydride (60%, 84 mg, 2.1 mmol). The mixture was stirred at this temperature for 15 min then iodomethane was added. After stirring at 0° C. for 15 min, the mixture was warmed to RT and stirred for 1 hour. The reaction was quenched with water and extracted with tert-butyl methyl ether. The combined organic layers were washed with brine, dried over anhydrous Na$_2$SO$_4$, filtered, and concentrated to afford methyl 5-fluoro-3-methoxy-2-methylbenzoate (327 mg crude) which was used in the next step without further purification.

To a solution of methyl 5-fluoro-3-methoxy-2-methylbenzoate (5.4 g, 30.8 mmol) in carbon tetrachloride (40 mL) at RT was added NBS (8.2 g, 46.3 mmol) and 2,2'-azobis(2-methylpropionitrile) (2.0 mg, 12.3 mmol). The mixture was refluxed overnight, the solvent was evaporated, and the crude product was purified by silica gel chromatography (petroleum ether/EtOAc, 100:1 to 20:1) to afford methyl 2-(bromomethyl)-5-fluoro-3-methoxybenzoate (4.6 g, 59% yield) as a white solid.

To a solution of (S)-3-aminoazepan-2-one (56 mg, 0.43 mmol) and TEA (72 mg, 0.72 mmol in DMF (2 mL) was added a solution of methyl 2-(bromomethyl)-5-fluoro-3-methoxybenzoate (100 mg, 0.36 mmol) in DMF (2 mL). The mixture was stirred at 50° C. for 3 hrs, concentrated, and washed with EtOAc to afford (S)-6-fluoro-4-methoxy-2-(2-oxoazepan-3-yl)isoindolin-1-one (100 mg, 95% yield) as a white solid. MS (ESI) m/z 293.0 [M+H]$^+$.

To a solution of (S)-6-fluoro-4-methoxy-2-(2-oxoazepan-3-yl)isoindolin-1-one (100 mg, 0.34 mmol) in DCM (6 mL), boron tribromide (515 mg, 2.05 mmol in 2 mL DCM) was added at 0° C. After stirring at this temperature for 15 min, the mixture was warmed to RT and stirred for 3 hrs. The reaction was quenched by water at 0° C., concentrated, and purified by silica gel chromatography (DCM/MeOH, 100:1 to 20:1) to afford (S)-6-fluoro-4-hydroxy-2-(2-oxoazepan-3-yl)isoindolin-1-one (20 mg, 21% yield) as a white solid. MS (ESI) m/z 279.0 [M+H]$^+$.

To a solution of (S)-6-fluoro-4-hydroxy-2-(2-oxoazepan-3-yl)isoindolin-1-one (250 mg, 0.90 mmol) and (4-(diethoxymethyl)phenyl)MeOH (284 mg, 1.35 mmol), triphenylphosphine (472 mg, 1.8 mmol) in THF (2.5 mL), was added DEAD (373 mg, 1.80 mmol) at 0° C. The mixture was stirred for 15 min, warmed to RT and stirred for 1 hr, the solvent was evaporated and the crude product was purified by silica gel chromatography (DCM/MeOH, 100:1 to 50:1) to afford (S)-4-((4-(diethoxymethyl)benzyl)oxy)-6-fluoro-2-(2-oxoazepan-3-yl)isoindolin-1-one (310 mg, 73% yield) as a white solid.

To a solution of (S)-4-((4-(diethoxymethyl)benzyl)oxy)-6-fluoro-2-(2-oxoazepan-3-yl) isoindolin-1-one (120 mg, 0.303 mmol) in fluorobenzene/DMSO (24 mL/6 mL) was added Dess-Martin periodinane reagent (321.3 mg, 0.758 mmol). The mixture was stirred at 80° C. for 16 hrs. After cooling to RT, Dess-Martin reagent (160 mg) was added. The suspension was heated to 80° C. for another 16 hrs. After cooling to RT, the reaction was quenched with sat. aqueous sodium thiosulfate solution (15 mL) and stirred for 5 min. The resulting mixture was extracted with DCM. Workup and purification with EtOAc in petroleum ether from 10% to 69% to give (S)-4-(((2-(2,7-dioxoazepan-3-yl)-6-fluoro-1-oxoisoindolin-4-yl)oxy)methyl)benzaldehyde (45 mg, 36% yield) as a white solid. MS (ESI) m/z 411.1 [M+H]$^+$.

To a solution of (S)-4-(((2-(2,7-dioxoazepan-3-yl)-6-fluoro-1-oxoisoindolin-4-yl)oxy)methyl)benzaldehyde (30 mg, 0.076 mmol) in DCM (4 mL) at RT was added morpholine (13 mg, 0.152 mmol) followed by sodium triacetoxyborohydride (32 mg, 0.152 mmol). The mixture was stirred at RT for 16 hrs then the solvent was evaporated. The residue was purified by prep-TLC (EtOAc) to give the crude product which was purified by prep-HPLC as previously described to afford Compound 7 (5.5 mg, 15% yield) as a white solid. MS (ESI) m/z 481.8 [M+H]+. 1H NMR (400 MHz, DMSO-d6) δ 10.72 (s, 1H), 7.45 (d, J=7.2 Hz, 2H), 7.34 (d, J=7.6 Hz, 2H), 7.30 (d, J=8.1 Hz, 1H), 7.11 (d, J=7.2 Hz, 1H), 5.32-5.19 (m, 1H), 5.24 (s, 2H), 4.44 (s, 2H), 3.57 (s, 4H), 3.47 (s, 2H), 3.21-3.06 (m, 1H), 2.59-2.57 (m, 1H), 2.34 (s, 5H), 2.02-1.96 (m, 2H), 1.82-1.75 (m, 1H).

Example 8

Compound 8: (S)-3-{4-[(p-Morpholinocarbonlphenyl)methoxy]-2-isoindolinoyl}-2,7-azepanedione

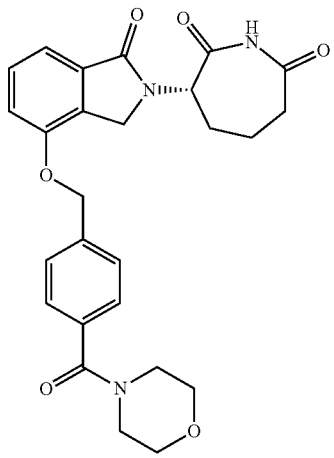 [SMILES: O=C1CCC[C@H](N2Cc3c(OCc4ccc(C(=O)N5CCOCC5)cc4)cccc3C2=O)C(=O)N1]

To a solution of 4-(hydroxymethyl)benzoic acid (500 mg, 3.28 mmol) in DMF (5 mL) was added morpholine (326 mg, 3.94 mmol), followed by HOBt (678.9 mg, 4.92 mmol), EDAC.HCl (944 mg, 4.92 mmol) and DIEA (846.2 mg, 6.56 mmol). The mixture was stirred at RT for 16 hrs. The reaction was diluted with water (5 mL) and extracted with DCM. Workup and purification with EtOAc/petroleum ether from 30% to 90% provided (4-(hydroxymethyl)phenyl)(morpholino)methanone (520 mg, 72% yield) as a colorless oil. MS (ESI) m/z 221.1 [M+H]+.

To a solution of (S)-4-hydroxy-2-(2-oxoazepan-3-yl)isoindolin-1-one (100 mg, 0.385 mmol), (4-(hydroxymethyl)phenyl)(morpholino)methanone (85 mg, 1.55 mmol) and triphenylphosphine (201 mg, 0.77 mmol) in THF (3 mL) at 0° C. was added a solution of DEAD (134 mg, 0.77 mmol) in THF (1 mL) dropwise. The mixture was stirred at RT for 16 hrs. The solvent was evaporated, and the residue was purified by prep-TLC (EtOAc) to give (S)-4-((4-(morpholine-4-carbonyl)benzyl)oxy)-2-(2-oxoazepan-3-yl)isoindolin-1-one (135 mg, 76% yield) as a white solid. MS (ESI) m/z=333.1 [M+1]+.

To a solution of (S)-4-((4-(morpholine-4-carbonyl)benzyl)oxy)-2-(2-oxoazepan-3-yl)isoindolin-1-one (135 mg, 0.292 mmol) in fluorobenzene/DMSO (12 mL/2 mL, 1 drop H2O in DMSO) was added Dess-Martin periodinane (309.6 mg, 0.73 mmol). The suspension was stirred at 80° C. overnight, cooled to RT, filtered, and the filtrate was added to sat. aqueous sodium thiosulfate solution (10 mL). After stirring at 0° C. for 5 min, the mixture was extracted with DCM. The combined organic layers were washed with 10% sodium thiosulfate/sat. NaHCO3 (1:1), and brine, dried over anhydrous Na2SO4, filtered, and concentrated to give the crude product which was purified by prep-TLC (EtOAc) to afford Compound 8 (52.5 mg, 38% yield) as a white solid. MS (ESI) m/z 333.1 [M+H]+. 1H NMR (400 MHz, DMSO-d6) δ 10.68 (s, 1H), 7.57 (d, J=8.0 Hz, 2H), 7.51-7.44 (m, 3H), 7.33 (d, J=8.0 Hz, 2H), 5.31 (s, 2H), 5.23 (dd, J=5.2, 12.4 Hz, 1H), 4.49 (s, 2H), 3.60 (s, 6H), 3.11-3.03 (m, 1H), 2.60-2.54 (m, 1H), 2.38-2.29 (m, 1H), 2.12-1.98 (m, 2H), 1.86-1.76 (m, 1H).

Example 9

Compound 9: (S)-3-(4-{[m-(Aminomethyl)phenyl]methoxy}-2-isoindolinoyl)-2,7-azepanedione trifluoroacetic acid

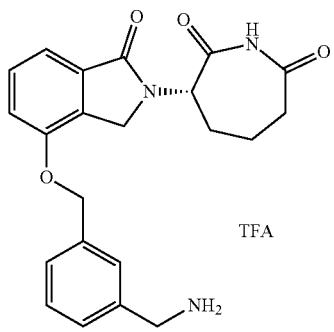 [SMILES: NCc1cccc(COc2cccc3c2CN([C@H]2CCCC(=O)NC2=O)C3=O)c1]

To a solution of (S)-4-hydroxy-2-(2-oxoazepan-3-yl)isoindolin-1-one (150 mg, 0.577 mmol), 3-(hydroxymethyl)benzonitrile (154 mg, 1.15 mmol) and triphenylphosphine (378 mg, 1.44 mmol) in THF (3.5 mL) at RT was added DEAD (251 mg, 1.44 mmol). The mixture was stirred for 30 min. The solvent was evaporated, and the residue was purified by prep-TLC (DCM/MeOH, 100:1 to 30:1) to give (S)-3-(((1-oxo-2-(2-oxoazepan-3-yl)isoindolin-4-yl)oxy)methyl)benzonitrile (235 mg, 81% yield) as a white solid. MS (ESI) m/z 376.2 [M+H]+.

To a solution of (S)-3-(((1-oxo-2-(2-oxoazepan-3-yl)isoindolin-4-yl) oxy)methyl) benzonitrile (200 mg, 0.48 mmol) in fluorobenzene/DMSO (15 mL/2 mL) at RT was added Dess-Martin periodinane (508 mg, 1.2 mmol). The mixture was heated to 80° C. overnight cooled to RT, and 20 mL of sat. sodium thiosulfate solution was added, and the mixture was extracted with DCM. Workup provided the crude product which was washed with tert-butyl methyl ether to afford (S)-3-(((2-(2,7-dioxoazepan-3-yl)-1-oxoisoindolin-4-yl)oxy)methyl) benzonitrile (120 mg, 58% yield) as a white solid. MS (ESI) m/z 390.1 [M+H]+.

To a solution of (S)-3-(((2-(2,7-dioxoazepan-3-yl)-1-oxoisoindolin-4-yl)oxy)methyl)benzonitrile (130 mg, 0.334 mmol) in THF (8 mL) at RT was added di-tert-butyl dicarbonate (146 mg, 0.668 mmol) and Raney Ni (60 mg). After degassing and purging with H2, the mixture was stirred at RT overnight. The suspension was filtered through a Celite pad. The filtrate was concentrated and purified by prep-TLC (EtOAc) to give (S)-tert-butyl 3-(((2-(2,7-dioxoazepan-3-yl)-1-oxoisoindolin-4-yl)oxy)methyl) benzylcarbamate as a white solid (150 mg, 59%).

To a solution of (S)-tert-butyl 3-(((2-(2,7-dioxoazepan-3-yl)-1-oxoisoindolin-4-yl)oxy) methyl) benzylcarbamate (75 mg, 0.152 mmol) in DCM (2 mL) at RT was added TFA (1 mL). The mixture was stirred at RT for 30 min. The solvent was evaporated, and the residue was lyophilized to give Compound 9 (40 mg, 66% yield) as a white solid. MS (ESI) m/z 394.2 [M+H]$^+$. $^1$H NMR (400 MHz, DMSO-d$_6$) δ 10.73 (s, 1H), 8.18 (s, 3H), 7.58-7.43 (m, 5H), 7.34 (d, J=7.2 Hz, 2H), 5.28-5.23 (m, 3H), 4.80 (m, 2H), 4.10-4.07 (m, 2H), 3.08-3.06 (m, 1H), 2.60-2.55 (m, 1H), 2.32-2.29 (m, 1H), 2.12-1.99 (m, 2H), 1.80-1.77 (m, 1H).

Example 10

Compound 10: (S)-3-(4-{[m-(Morpholinomethyl)phenyl]methoxy}-2-isoindolinoyl)-2,7-azepanedione

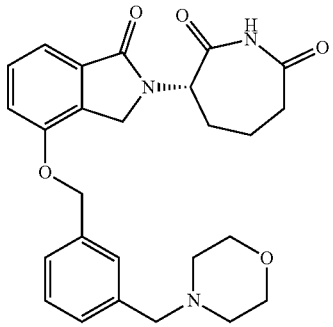 [SMILES: O=C1CCC[C@H](N2Cc3c(OCc4cccc(CN5CCOCC5)c4)cccc3C2=O)C(=O)N1]

To a solution of (S)-4-hydroxy-2-(2-oxoazepan-3-yl)isoindolin-1-one (160 mg, 0.615 mmol), 1,3-phenylenedimethanol (170 mg, 1.23 mmol) and triphenylphosphine (402 mg, 1.538 mmol) in THF (8 mL), was added DEAD (268 mg, 1.53 mmol) at RT. The mixture was stirred at RT for 30 min. The solvent was evaporated, and the residue was purified by prep-TLC (DCM/MeOH, 100:1 to 30:1) to give (S)-4-((3-(hydroxymethyl)benzyl)oxy)-2-(2-oxoazepan-3-yl)isoindolin-1-one (156 mg, 59% yield) as a white solid. MS (ESI) m/z 381.2 [M+H]$^+$.

To a solution of (S)-4-((3-(hydroxymethyl)benzyl)oxy)-2-(2-oxoazepan-3-yl) isoindolin-1-one (138 mg, 0.363 mmol) in fluorobenzene/DMSO (4 mL/1 mL) at RT was added Dess-Martin periodinane (462 mg, 1.09 mmol). After stirring at 80° C. overnight, the mixture was cooled to RT, and 20 mL of sat. sodium thiosulfate solution was added followed, and the mixture was extracted with DCM. Workup provided the crude product which was washed with tert-butyl methyl ether to afford (S)-3-(((2-(2,7-dioxoazepan-3-yl)-1-oxoisoindolin-4-yl)oxy)methyl)benzaldehyde (85 mg, 60% yield) as a white solid. MS (ESI) m/z 391.2 [M+H]$^+$.

To a solution of (S)-3-(((2-(2,7-dioxoazepan-3-yl)-1-oxoisoindolin-4-yl)oxy)methyl) benzaldehyde (80 mg, 0.204 mmol) and morpholine (36 mg, 0.408 mmol) in DCM (4 mL) at RT was added NaBH(OAc)$_3$ (87 mg, 0.408 mmol). The mixture was stirred overnight. The solvent was evaporated, and the residue was purified by prep-TLC using DCM/MeOH (10:1) to give Compound 10 (30.5 mg, 32% yield) as a white solid. MS (ESI) m/z 464.2[M+H]$^+$. $^1$H NMR (400 MHz, DMSO-d$_6$) δ 10.73 (s, 1H), 7.49-7.27 (m, 7H), 5.27-5.22 (m, 3H), 4.47 (s, 2H), 3.56 (s, 4H), 3.48 (s, 2H), 3.12-3.05 (m, 1H), 2.58 (d, J=16.8 Hz, 1H), 2.34 (s, 5H), 2.12-2.06 (m, 1H), 2.04-1.99 (m, 1H), 1.82-1.78 (m, 1H).

Example 11

Compound 11: (S)-3-(4-{[p-(Morpholinomethyl)phenyl]methoxy}-3-oxo-2H-isoindol-2-oyl)-2,7-azepanedione

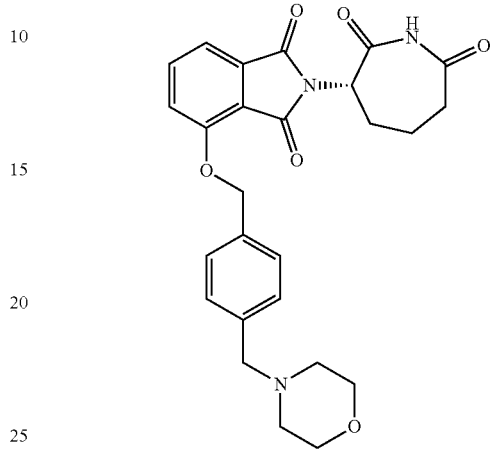

To a solution of 3-methoxyphthalic acid (3.0 g, 15.306 mmol) in THF (24 mL) at RT was added acetic anhydride (10 mL). The mixture was stirred at 80° C. for 3 hrs. The solvent was evaporated to give 4-methoxyisobenzofuran-1,3-dione (2.72 g, quant. yield) as a white solid. MS (ESI) m/z=178.9 [M+H]$^+$.

To a solution of (S)-3-aminoazepan-2-one (1.96 g, 15.28 mmol) in AcOH/ACN (28 mL/20 mL) at RT was added 4-methoxyisobenzofuran-1,3-dione (2.71 g, 15.28 mmol). The mixture was stirred at 85° C. overnight then cooled to RT. Sodium acetate (3.13 g, 38.20 mmol) was added followed by AcOH (12 mL). The mixture was stirred at 85° C. overnight. The solvent was evaporated then the residue was diluted with water (30 mL) and stirred at RT for 30 min. The resulting suspension was filtered and the filter cake was washed with EtOAc to give (S)-4-methoxy-2-(2-oxoazepan-3-yl)isoindoline-1,3-dione (2.154 g, 49% yield) as a white solid. MS (ESI) m/z=289.1 [M+H]$^+$.

To a solution of (S)-4-methoxy-2-(2-oxoazepan-3-yl)isoindoline-1,3-dione (2.1 g, 7.292 mmol) in DCM (40 mL) at 0° C. was added tribromoborane (3.4 mL) in DCM (10 mL) dropwise. After stirring at RT for 3 hrs, the mixture was diluted with ice-water and extracted with DCM. The combined organic layers were washed with brine, dried over anhydrous Na$_2$SO$_4$, filtered, and concentrated to give the crude product which was washed with EtOAc to afford (S)-4-hydroxy-2-(2-oxoazepan-3-yl)isoindoline-1,3-dione (1 g, 50% yield) as a light yellow solid. MS (ESI) m/z=275.0 [M+H]$^+$.

To a solution of (S)-4-hydroxy-2-(2-oxoazepan-3-yl)isoindoline-1,3-dione (300 mg, 1.095 mmol), 1,4-phenylenedimethanol (272 mg, 1.971 mmol) and triphenylphosphine (574 mg, 2.190 mmol) in THF (5 mL) at 0° C. was added DEAD (381 mg, 2.19 mmol). The mixture was stirred at RT overnight. The solvent was evaporated and the crude product was purified by silica gel chromatography using EtOAc/petroleum ether from 20% to 96% to give (S)-4-((4-(hydroxymethyl) benzyl)oxy)-2-(2-oxoazepan-3-yl)isoindoline-1,3-dione (168 mg, 39% yield) as a white solid. MS (ESI) m/z=395.1 [M+H]$^+$.

To a solution of (S)-4-((4-(hydroxymethyl)benzyl)oxy)-2-(2-oxoazepan-3-yl)isoindoline-1,3-dione (140 mg, 0.355 mmol) in 1,2-dichloroethane/DMSO (12 mL/2 mL) at RT was added Dess-Martin reagent (753 mg, 1.775 mmol). The mixture was stirred at 80° C. overnight. The mixture was cooled to RT and filtered, and the filtrate was quenched with sat. sodium thiosulfate solution (15 mL). After stirring for 10 min, the mixture was extracted with DCM. Workup and purification with EtOAc/petroleum ether from 20% to 96% to afford (S)-4-(((2-(2,7-dioxoazepan-3-yl)-1,3-dioxoisoindolin-4-yl)oxy)methyl)benzaldehyde (95 mg, 54% yield) as a yellow solid.

To a solution of (S)-4-(((2-(2,7-dioxoazepan-3-yl)-1,3-dioxoisoindolin-4-yl)oxy)methyl)benzaldehyde (75 mg, 0.1847 mmol) in DCM (3 mL) at RT was added morpholine (32 mg, 0.3694 mmol) and sodium triacetoxyborohydride (78 mg, 0.3694 mmol) and the mixture stirred overnight. The solvent was evaporated and the crude product was purified by prep-TLC using DCM/MeOH (10:1) to give Compound 11 (42 mg, 48% yield) as a white solid. MS (ESI) m/z=477.8 [M+H]$^+$. $^1$H NMR (DMSO-d$_6$, 400 MHz) δ: 10.84 (s, 1H), 7.82-7.35 (m, 7H), 5.35 (s, 2H), 5.19-5.15 (m, 1H), 3.60-3.50 (m, 4H), 3.50-3.40 (m, 2H), 3.14-3.07 (m, 1H), 2.70-2.60 (m, 1H), 2.35 (s, 4H), 2.19-1.87 (m, 4H).

Example 12

Compound 12: (S)-3-(4-{[p-(Morpholinomethyl)phenyl]methoxy}-2-isoindolinoyl)-2,5-pyrrolidinedione

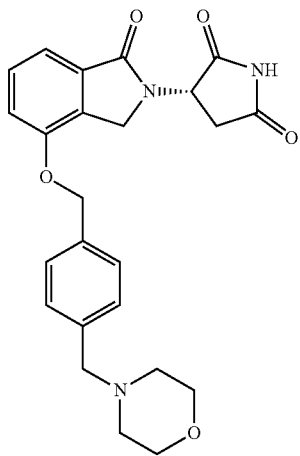 [SMILES: O=C1C[C@H](N2Cc3c(OCc4ccc(CN5CCOCC5)cc4)cccc3C2=O)C(=O)N1]

To a stirred solution of (S)-4-amino-2-((tert-butoxycarbonyl)amino)-4-oxobutanoic acid (2.0 g, 8.6 mmol) in THF (10 mL) and MeOH (10 mL) at 0° C. was added (trimethylsilyl)diazomethane solution (2 M in hexane, 6.5 mL) dropwise. The mixture was stirred at 0° C. for 1 hour then concentrated to give (S)-methyl 4-amino-2-((tert-butoxycarbonyl)amino)-4-oxobutanoate (crude) as a colorless oil.

To a stirred solution of (S)-methyl 4-amino-2-((tert-butoxycarbonyl)amino)-4-oxobutanoate (8.6 mmol) in DCM (6 mL) at RT was added TFA (3 mL). After stirring overnight, the mixture was concentrated to give (S)-methyl 2,4-diamino-4-oxobutanoate, which was used directly for the next step.

To a solution of (S)-methyl 2,4-diamino-4-oxobutanoate (8.6 mmol) and methyl 2-(bromomethyl)-3-methoxybenzoate (2.2 g, 8.6 mmol) in DMF (20 mL) was added TEA (3.6 mL). After stirring at 50° C. for 5 hrs, the mixture was diluted with water and extracted with EtOAc. Workup and purification with EtOAc/pet. ether (20% to 80%) provided (S)-methyl 4-amino-2-(4-methoxy-1-oxoisoindolin-2-yl)-4-oxobutanoate (1.2 g, 48% yield) as a yellow solid. MS (ESI) m/z=293.0 [M+H]$^+$.

To a solution of (S)-methyl 4-amino-2-(4-methoxy-1-oxoisoindolin-2-yl)-4-oxobutanoate (1.2 g, 4.1 mmol) in DCM (12 mL) at 0° C. was added boron tribromide (2.3 mL) dropwise. The mixture was stirred at RT for 2 hrs and quenched by water and MeOH. The solvent was evaporated, and the residue was purified by silica gel chromatography (DCM/MeOH, 20:1) to give (S)-4-amino-2-(4-hydroxy-1-oxoisoindolin-2-yl)-4-oxobutanoic acid (3 g, crude) as a yellow solid. MS (ESI) m/z=265.0 [M+H]$^+$.

To a solution of (S)-4-amino-2-(4-hydroxy-1-oxoisoindolin-2-yl)-4-oxobutanoic acid (3 g crude) in THF (15 mL) and MeOH (15 mL) was added (trimethylsilyl)diazomethane solution (2 M in hexane, 6.8 mL) at 0° C. dropwise. The mixture was stirred at 0° C. for 1.5 hrs and concentrated. The residue was purified by silica gel chromatography (DCM/MeOH, 10:1) to give (S)-methyl 4-amino-2-(4-hydroxy-1-oxoisoindolin-2-yl)-4-oxobutanoate (470 mg, 43% yield) as a white solid. MS (ESI) m/z=279.0 [M+H]$^+$.

To a solution of (S)-methyl 4-amino-2-(4-hydroxy-1-oxoisoindolin-2-yl)-4-oxobutanoate (300 mg, 1.08 mmol), (4-(morpholinomethyl)phenyl)methanol (335 mg, 1.62 mmol) and triphenylphosphine (567 mg, 2.16 mmol in THF, 8 mL) at 0° C. was added DEAD (376 mg, 2.16 mmol) and the mixture was stirred at RT overnight. The solvent was evaporated, and the residue was purified by prep-TLC (DCM/MeOH, 10:1) to give (S)-methyl-4-amino-2-(4-((4-(morpholinomethyl)benzyl)oxy)-1-oxoisoindolin-2-yl)-4-oxobutanoate (150 mg, 30% yield) as a white solid. MS (ESI) m/z=468.1 [M+H]$^+$.

To a solution of (S)-methyl-4-amino-2-(4-((4-(morpholinomethyl)benzyl)oxy)-1-oxoisoindolin-2-yl)-4-oxobutanoate (100 mg, 0.21 mmol) in THF (6 mL) at RT was added lithium hydroxide (11 mg, 0.42 mmol). The mixture was stirred for 3 hrs then diluted with water and adjusted pH to 3 with 1 N HCl. Workup and purification with by prep-TLC (DCM/MeOH, 10:1) to afford Compound 12 (13 mg, 14% yield) as a yellow solid. MS (ESI) m/z=453.9 [M+H]$^+$. $^1$H NMR (400 MHz, DMSO-d$_6$) δ 11.49 (brs, 1H), 7.51-7.44 (m, 3H), 7.34-7.30 (m, 4H), 5.27 (t, J=8.0 Hz, 1H), 5.23 (s, 2H), 4.61 (d, J=17.2 Hz, 1H), 4.27 (d, J=17.2 Hz, 1H), 3.57 (t, J=4.0 Hz, 4H), 3.46 (s, 2H), 2.94 (d, J=7.6 Hz, 2H), 2.34 (s, 4H).

Example 13

Compound 13: (S)-3-(4-{[p-({3-[3-(p-{5-Methyl-4-[m-(tert-butylaminosulfonyl)phenylamino]-2-pyrimidinylamino}phenoxy)propyl]ureido}methyl)phenyl]methoxy}-2-isoindolinoyl)-2,7-azepanedione

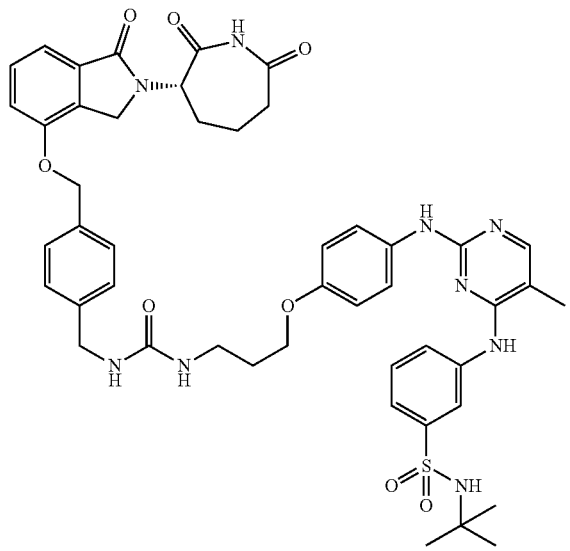 [SMILES: Cc1cnc(Nc2ccc(OCCCNC(=O)NCc3ccc(COc4cccc5c4CN([C@H]4CCCC(=O)NC4=O)C5=O)cc3)cc2)nc1Nc1cccc(S(=O)(=O)NC(C)(C)C)c1]

To a solution of tert-butyl (3-(4-((4-((3-(N-(tert-butyl)sulfamoyl)phenyl)amino)-5-methylpyrimidin-2-yl)amino)phenoxy)propyl)carbamate (100 mg, 0.171 mmol) in dry DCM (8 mL) at 0° C. was added TFA (2 mL). The reaction was stirred at RT for 16 hrs. The solvent was evaporated, and the residue was dried to give the amine TFA salt (100 mg, crude). The amine TFA salt was dissolved in THF (5 mL) and TEA (34.5 mg, 0.342 mmol) was added at RT followed by 4-nitrobenzyl chloroformate (34.2 mg, 0.171 mmol). The mixture was stirred for 1 hour. The solvent was evaporated to give 4-nitrophenyl (3-(4-((4-((3-(N-(tert-butyl)sulfamoyl)phenyl)amino)-5-methylpyrimidin-2-yl)amino)phenoxy)propyl) carbamate (30 mg, crude) which was used directly for the next step. MS (ESI) m/z 650.2[M+H]$^+$.

To a solution of (S)-tert-butyl 4-(((2-(2,7-dioxoazepan-3-yl)-1-oxoisoindolin-4-yl) oxy)methyl)benzylcarbamate (23 mg, 0.046 mmol) in DCM (4 mL) at RT was added TFA (1 mL). The solvent was evaporated, and the residue was dried to give the amine TFA salt (30 mg, crude) as a yellow gum. The amine TFA salt was dissolved in THF (5 mL) and TEA (10 mg, 0.092 mmol) was added at RT followed by a suspension of 4-nitrophenyl (3-(4-((4-((3-(N-(tert-butyl)sulfamoyl)phenyl)amino)-5-methylpyrimidin-2-yl)amino)phenoxy)propyl)carbamate (30 mg, 0.046 mmol) in THF (1 mL). The reaction was stirred at 60° C. for 3 hrs. The solvent was evaporated, and the residue was purified by silica gel chromatography eluting with MeOH/DCM from 0% to 9% to give Compound 13 (22.3 mg, 53% yield) as a white solid. MS (ESI) m/z 903.7[M+H]$^+$. $^1$H NMR (400 MHz, DMSO-d$_6$) δ 10.72 (s, 1H), 8.82 (s, 1H), 8.57 (s, 1H), 8.15-8.12 (m, 2H), 7.89 (s, 1H), 7.59 (s, 1H), 7.54-7.41 (m, 7H), 7.31-7.25 (m, 4H), 6.79 (d, J=8.8 Hz, 2H), 6.37 (t, J=6.0 Hz, 1H), 6.06 (t, J=5.2 Hz, 1H), 5.23-5.19 (m, 3H), 4.45 (s, 2H), 4.21 (d, J=6.4 Hz, 2H), 3.91 (t, J=5.6 Hz, 2H), 3.19-3.15 (m, 2H), 3.09-3.02 (m, 1H), 2.58-2.54 (m, 1H), 2.35-2.31 (m, 1H), 2.11 (s, 3H), 2.04-1.97 (m, 1H), 1.82-1.78 (m, 3H), 1.12 (s, 9H).

Example 14

Compound 14: (S)-3-(4-{[p-(Morpholinomethyl)phenoxy]methyl}-2-isoindolinoyl)-2,7-azepanedione

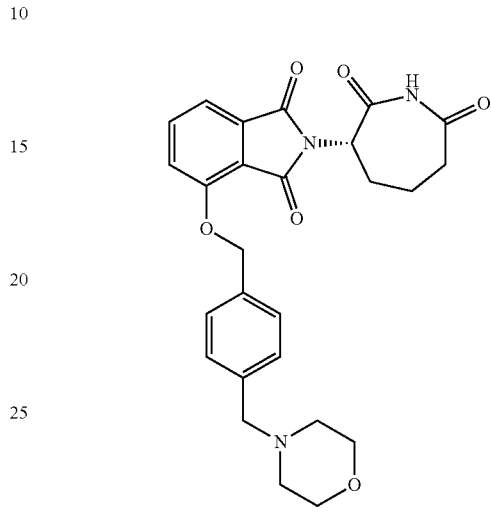

To a solution of (S)-1-oxo-2-(2-oxoazepan-3-yl)isoindoline-4-carbaldehyde (910 mg, 3.35 mmol) in THF (25 mL) at RT was added sodium borohydride (254 mg, 6.70 mmol). The mixture was stirred for 2 hrs. The reaction was concentrated to give the crude product which was purified by silica gel chromatography eluting with MeOH/DCM (1:10) to give (S)-4-(hydroxymethyl)-2-(2-oxoazepan-3-yl) isoindolin-1-one (539 mg, 59% yield) as a white solid. MS (ESI) m/z=275.1[M+H]$^+$.

To a solution of (S)-4-(hydroxymethyl)-2-(2-oxoazepan-3-yl) isoindolin-1-one (539 mg, 1.97 mmol), 4-hydroxybenzaldehyde (288 mg, 2.36 mmol) and triphenylphosphine (1.03 g, 3.93 mmol) in THF (30 mL) at 0° C. was added DEAD (685 mg, 3.93 mmol). The mixture was stirred for 15 min then warmed to RT and stirred overnight. The solvent was evaporated to give the crude product, which was purified by silica gel chromatography eluting with MeOH/DCM from 0% to 5% to afford (S)-4-((1-oxo-2-(2-oxoazepan-3-yl)isoindolin-4-yl)methoxy)benzaldehyde (520 mg, 70% yield) as a white solid. MS (ESI) m/z 379.1 [M+H]$^+$.

To a solution of (S)-4-((1-oxo-2-(2-oxoazepan-3-yl)isoindolin-4-yl) methoxy) benzaldehyde (520 mg, 1.38 mmol) in fluorobenzene/DMSO (24 mL/4 mL, 1 drop water in DMSO) was added Dess-Martin reagent (1.46 g, 3.44 mmol). The suspension was heated at 80° C. for 18 hrs. The suspension was cooled to RT then added to sat. aqueous sodium thiosulfate solution (20 mL) at 0° C. and stirred for 5 min then extracted with DCM. Workup and purification with EtOAc/petroleum ether from 20% to 96% to give (S)-4-((2-(2,7-dioxoazepan-3-yl)-1-oxoisoindolin-4-yl) methoxy)benzaldehyde (174.2 mg, 32% yield) a white solid. MS (ESI) m/z 393.1 [M+H]$^+$.

To a solution of (S)-4-((2-(2,7-dioxoazepan-3-yl)-1-oxoisoindolin-4-yl) methoxy) benzaldehyde (100 mg, 0.255 mmol) in THF (5 mL) at RT was added morpholine (88 mg, 1.02 mmol), followed by sodium cyanoborohydride (64 mg, 1.02 mmol). The mixture was stirred for 2 hrs. The solvent was evaporated, and the residue was purified by prep-HPLC as previously described to give Compound 14 (22.1 mg, 19% yield) as a white solid. MS (ESI) m/z=498.1 [M+H]+. 1H NMR (DMSO-d6, 400 MHz) δ: 10.76 (s, 1H), 7.73-7.71 (m, 2H), 7.55 (t, J=7.6 Hz, 1H), 7.23 (d, J=8.4 Hz, 2H), 7.01 (d, J=8.4 Hz, 2H), 5.25 (s, 2H), 4.63 (s, 2H), 3.55 (s, 4H), 3.36 (s, 2H), 3.13-3.06 (m, 1H), 2.59-2.55 (m, 1H), 2.32 (s, 4H), 2.17-1.97 (m, 3H), 1.86-1.76 (m, 1H).

Example 15

Compound 15: (S)-3-(5-{[p-(Morpholinomethyl)phenyl]methoxy}-2-isoindolinoyl)-2,7-azepanedione

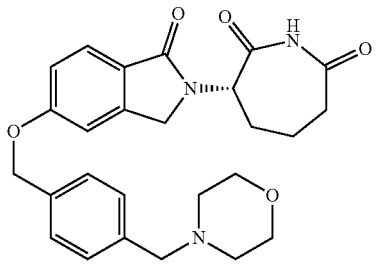 [SMILES: O=C1CCC[C@H](N2Cc3cc(OCc4ccc(CN5CCOCC5)cc4)ccc3C2=O)C(=O)N1]

To a solution of methyl 4-methoxy-2-methylbenzoate (10 g, 55.56 mmol) in carbon tetrachloride (150 mL) at RT was added NBS (10 g, 55.57 mmol) and 2,2'-azobis(2-methylpropionitrile) (4.0 mg, 9.43 mmol). The mixture was stirred at reflux 6 hrs. The solvent was evaporated to give the crude product which was purified by silica gel chromatography (EtOAc/petroleum ether, 1:20 to 1:5) to give methyl 2-(bromomethyl)-4-methoxybenzoate (13.6 g, 94% yield) as a white solid.

To a solution of (S)-3-aminoazepan-2-one (1.6 g, 12.4 mmol) in DMF (16 mL) at RT was added TEA (2.9 mL, 20.6 mmol) and methyl 2-(bromomethyl)-4-methoxybenzoate (2.7 g, 10.3 mmol) in 4 mL DMF. The mixture was stirred at 85° C. overnight. The solvent was evaporated and the crude product was purified by silica gel chromatography (DCM/MeOH, 50:1) to give (S)-5-methoxy-2-(2-oxoazepan-3-yl)isoindolin-1-one (1.39 g, 49% yield) as a white solid. MS (ESI) m/z 275.0 [M+H]+.

To a solution of (S)-5-methoxy-2-(2-oxoazepan-3-yl)isoindolin-1-one (1.0 g, 3.65 mmol) in DCM (12 mL) at 0° C. was added boron tribromide (2.0 mL, 21.89 mmol, in 4 mL DCM) dropwise. The mixture was stirred at this temperature for 30 min then warmed to RT for 2 hrs and quenched by water and MeOH. The solvent was evaporated, and the residue was purified by silica gel chromatography (DCM/MeOH, 20:1) to give (S)-5-hydroxy-2-(2-oxoazepan-3-yl)isoindolin-1-one (1.7 g crude) as a white solid. MS (ESI) m/z 261.0 [M+H]+.

To a solution of (S)-5-hydroxy-2-(2-oxoazepan-3-yl)isoindolin-1-one (500 mg, 1.92 mmol), 1,4-phenylenedimethanol (1.0 g, 7.68 mmol) and triphenylphosphine (2.0 g, 7.68 mmol) in THF (2 mL) at RT was added DEAD (1.3 mg, 7.68 mmol) at RT. The mixture was stirred for 2 hrs. The solvent was evaporated, and the residue was purified by silica gel chromatography (DCM/MeOH, 50:1 to 20:1) to give (S)-5-((4-(hydroxymethyl)benzyl)oxy)-2-(2-oxoazepan-3-yl)isoindolin-1-one (90 mg, 12% yield) as a white solid. MS (ESI) m/z 381.1 [M+H]+.

To a solution of (S)-5-((4-(hydroxymethyl)benzyl)oxy)-2-(2-oxoazepan-3-yl)isoindolin-1-one (60 mg, 0.157 mmol) in fluorobenzene/DMSO (6.0 mL/1.5 mL) at RT was added Dess-Martin periodinane (268 mg, 0.631 mmol). After stirring at 80° C. overnight, the mixture was cooled to RT then 20 mL of sat. sodium thiosulfate solution was added, and the mixture was stirred at RT for 5 min. Workup and purification with by prep-TLC using hexanes/EtOAc (1:1) provided (S)-4-(((2-(2,7-dioxoazepan-3-yl)-1-oxoisoindolin-5-yl)oxy)methyl)benzaldehyde (15 mg, 16% yield) as a white solid. MS (ESI) m/z 393.0 [M+H]+.

To a solution of (S)-4-(((2-(2,7-dioxoazepan-3-yl)-1-oxoisoindolin-5-yl)oxy) methyl)benzaldehyde (15 mg, 0.038 mmol) and morpholine (7 mg, 0.076 mmol) in DCM at RT was added sodium triacetoxyborohydride (16 mg, 0.076 mmol). The mixture was stirred for 28 hrs. The solvent was evaporated, and the crude product was purified by prep-TLC using DCM/MeOH (10:1) to give Compound 15 (6.5 mg, 38% yield) as a white solid. MS (ESI) m/z 464.2 [M+H]+. 1H NMR (400 MHz, DMSO-d6) δ 10.71 (s, 1H), 7.64 (d, J=8.4 Hz, 1H), 7.43 (d, J=8.0 Hz, 2H), 7.34 (d, J=8.0 Hz, 2H), 7.27 (s, 1H), 7.13 (d, J=8.8 Hz, 1H), 5.23-5.19 (m, 3H), 4.48-4.47 (m, 2H), 3.58-3.56 (m, 4H), 3.47 (s, 2H), 3.08-3.06 (m, 1H), 2.60-2.51 (m, 1H), 2.35 (s, 4H), 2.27-2.24 (m, 1H), 2.10-2.00 (m, 2H), 1.80-1.77 (m, 1H).

Example 16

Compound 16: (S)-6-(4-{[p-(Morpholinomethyl)phenyl]methoxy}-2-isoindolinoyl)-1,4-oxazepane-3,5-dione

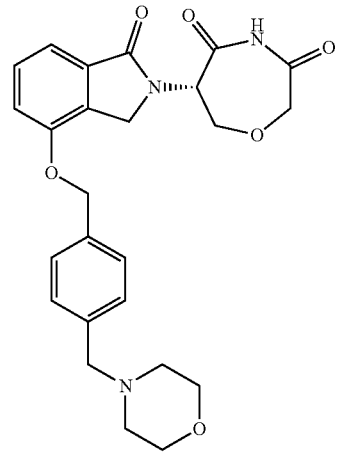 [SMILES: O=C1COC[C@H](N2Cc3c(OCc4ccc(CN5CCOCC5)cc4)cccc3C2=O)C(=O)N1]

To a solution of 3-hydroxy-2-methylbenzoic acid (20 g, 0.13 mmol) in MeOH (240 mL) at 0° C. was added thionyl chloride dropwise, then the mixture was stirred at reflux for 3 hrs. The solvent was evaporated, and the residue was purified by silica gel chromatography (petroleum ether/EtOAc, 20:1 to 5:1) to give methyl 3-hydroxy-2-methylbenzoate (18.7 g, 86% yield) as a yellow solid.

To a solution of methyl 3-hydroxy-2-methylbenzoate (18.7 g, 0.11 mol) and imidazole (19.0 g, 0.25 mol) in DMF (28 mL) at RT was added tert-butyldimethylsilyl chloride (20.4 g, 0.12 mol). After stirring at 60° C. for 3 hrs, the mixture was cooled to RT and extracted with tert-butyl methyl ether. The combined organic layers were dried over anhydrous Na2SO4, filtered, and concentrated to give methyl 3-((tert-butyldimethylsilyl)oxy)-2-methylbenzoate (32 g crude) as a yellow solid which was used in the next step without further purification.

To a solution of 3-((tert-butyldimethylsilyl)oxy)-2-methylbenzoate (5.0 g, 17.8 mmol) in carbon tetrachloride (30 mL) at RT was added NBS (4.7 g, 26.8 mmol) and 2,2'-azobis(2-methylpropionitrile) (1.1 g, 7.1 mmol). The suspension was stirred at reflux for 5 hrs. The solvent was evaporated, and the residue was purified by silica gel chromatography (petroleum ether/EtOAc, 100:1 to 50:1) to give methyl 2-(bromomethyl)-3-((tert-butyldimethylsilyl) oxy) benzoate (5.8 g, 90% yield) as a yellow oil.

To a solution of methyl 2-(bromomethyl)-3-((tert-butyldimethylsilyl)oxy) benzoate (490 mg, 1.4 mmol) in DMF (6 mL) at RT was added TEA (0.4 mL, 2.8 mmol) and (S)-6-amino-1,4-oxazepan-5-one (200 mg, 1.5 mmol, in 2 mL of DMF). The mixture was stirred at RT for 4 hrs, then heated to 80° C. overnight. The mixture was concentrated, and the residue was diluted with THF (10 mL). TBAF (200 mg, 0.76 mmol) was added, and the mixture was stirred at reflux for 2 hrs. The solvent was evaporated and the residue purified by silica gel chromatography (DCM/MeOH, 50:1 to 20:1) to give (S)-6-(4-hydroxy-1-oxoisoindolin-2-yl)-1,4-oxazepan-5-one (183 mg, 50% yield) as a white solid. MS (ESI) m/z 263.0 [M+H]⁺.

To a solution of (S)-6-(4-hydroxy-1-oxoisoindolin-2-yl)-1,4-oxazepan-5-one (230 mg, 0.87 mmol), 1,4-phenylenedimethanol (182 mg, 1.31 mmol) and triphenylphosphine (568 mg, 2.17 mmol) in THF (2.5 mL) at RT was added DEAD (377 mg, 2.17 mmol). The mixture was stirred at RT for 3 hrs. The solvent was evaporated and the crude product was purified by silica gel chromatography (DCM/MeOH, 100:1 to 20:1) to give (S)-6-(4-((4-(hydroxymethyl)benzyl)oxy)-1-oxoisoindolin-2-yl)-1,4-oxazepan-5-one (110 mg, 33% yield) as a white solid. MS (ESI) m/z 383.1 [M+H]⁺.

To a solution of (S)-6-(4-((4-(hydroxymethyl)benzyl) oxy)-1-oxoisoindolin-2-yl)-1,4-oxazepan-5-one (110 mg, 0.288 mmol) in ACN/DMSO (8 mL/2 mL) at RT was added Dess-Martin periodinane (732 mg, 1.72 mmol). The mixture was stirred at 80° C. for 4 hrs, then cooled to RT, and 20 mL of a sat. sodium thiosulfate solution was added followed by stirring for 5 min. The mixture was extracted with DCM. Workup and purification with DCM then DCM/EtOAc, 5:1 to 1:1 to give (S)-4-(((2-(3,5-dioxo-1,4-oxazepan-6-yl)-1-oxoisoindolin-4-yl) oxy)methyl)benzaldehyde (58 mg, 51% yield) as a white solid. MS (ESI) m/z 395.0 [M+H]⁺.

To a solution of (S)-4-(((2-(3,5-dioxo-1,4-oxazepan-6-yl)-1-oxoisoindolin-4-yl)oxy)methyl)benzaldehyde (58 mg, 0.147 mmol) and morpholine (26 mg, 0.294 mmol) in DCM (1.5 mL) at RT was added sodium triacetoxyborohydride (64 mg, 0.294 mmol). The mixture was stirred at RT for 4 hrs then concentrated. The crude product was purified by prep-TLC using DCM/MeOH (10:1) to give Compound 16 (19 mg, 20% yield) as a white solid. MS (ESI) m/z 465.9 [M+H]⁺. ¹H NMR (400 MHz, DMSO-d₆) δ 11.11 (s, 1H), 7.48-7.44 (m, 3H), 7.35-7.32 (m, 4H), 5.67-5.66 (m, 1H), 5.24 (s, 2H), 4.71 (d, J=17.2 Hz, 1H), 4.55 (d, J=10.4 Hz, 2H), 4.40-4.35 (m, 2H), 4.06-4.05 (m, 1H), 3.57-3.55 (m, 4H), 3.47 (s, 2H), 2.35 (s, 4H).

Example 17

Compound 17: 3-(4-{[p-({2-[3-(p-{5-Methyl-4-[m-(tert-butylaminosulfonyl)phenylamino]-2-pyrimidinylamino}phenoxy)propylamino]acetylamino}methyl)phenyl]methoxy}-2-isoindolinoyl)-2,6-piperidinedione

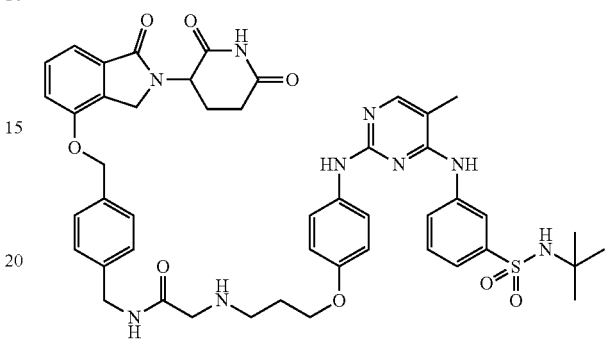

To a solution of 3-hydroxy-2-methylbenzoic acid (20 g, 0.13 mol) in MeOH (240 mL) at 0° C. was added thionyl chloride (30 mL, 0.41 mol) dropwise. The mixture was stirred at reflux for 3 hrs. The solvent was evaporated, and the residue was purified by silica gel chromatography using petroleum ether/EtOAc (20:1 to 5:1) to give methyl 3-hydroxy-2-methylbenzoate (18.7 g, 86% yield) as a yellow solid.

To a solution of methyl 3-hydroxy-2-methylbenzoate (18.7 g, 0.11 mol) and imidazole (19.0 g, 0.25 mol) in DMF (28 mL) at RT, tert-butyldimethylsilyl chloride (20.4 g, 0.12 mol) was added. After stirring at 60° C. for 3 hrs, the mixture was cooled to RT and extracted with tert-butyl methyl ether. The combined organic layers were dried over anhydrous Na₂SO₄, filtered, and concentrated to give methyl 3-((tert-butyldimethylsilyl)oxy)-2-methylbenzoate (32 g crude) as a yellow solid which was used in the next step without further purification.

To a solution of methyl 3-((tert-butyldimethylsilyl)oxy)-2-methylbenzoate (3.0 g, 10.7 mmol) in carbon tetrachloride (22 mL) at RT was added NBS (2.9 g, 16.0 mmol) and 2,2'-azobis(2-methylpropionitrile) (701 mg, 4.3 mmol). The mixture was stirred at 80° C. for 5 hrs. The solvent was evaporated to give the crude product which was purified by silica gel chromatography (petroleum ether/EtOAc, 30:1) to give methyl 2-(bromomethyl)-3-((tert-butyldimethylsilyl) oxy)benzoate (3.7 g 97%) as a yellow oil.

To a solution of methyl 2-(bromomethyl)-3-((tert-butyldimethylsilyl) oxy)benzoate (1.0 g, 2.77 mmol) and TEA (0.8 mL, 5.54 mmol) in DMF (6 mL) at RT was added tert-butyl 2,5-diamino-5-oxopentanoate (670 mg, 3.32 mmol) in DMF (4 mL). The mixture was stirred for 2 hrs then heated to 80° C. and stirred overnight. The solvent was evaporated to give the crude product which was purified by silica gel chromatography (DCM/MeOH, 100:1 to 50:1) to afford tert-butyl 5-amino-4-(4-hydroxy-1-oxoisoindolin-2-yl)-5-oxopentanoate (820 mg, 88% yield) as a white solid. MS (ESI) m/z 279.0 [M+H−56]⁺.

To a solution of tert-butyl 5-amino-4-(4-hydroxy-1-oxoisoindolin-2-yl)-5-oxopentanoate (450 mg, 1.34 mmol), 4-(hydroxymethyl)benzonitrile (360 mg, 2.69 mmol) and triphenylphosphine (1.4 g, 5.36 mmol) in THF (2 mL) at RT was added DEAD (932 mg, 5.36 mmol) dropwise. The mixture was stirred at RT for 4 h. The solvent was evaporated and the crude product was purified by silica gel chromatography (DCM/MeOH, 100:1 to 20:1) to give tert-butyl 5-amino-4-(4-((4-cyanobenzyl)oxy)-1-oxoisoindolin-2-yl)-5-oxopentanoate (290 mg, 39% yield) as a white solid. MS (ESI) m/z 394.0 [M+H−56]+.

To a solution of tert-butyl 5-amino-4-(4-((4-cyanobenzyl)oxy)-1-oxoisoindolin-2-yl)-5-oxopentanoate (200 mg, 0.45 mmol) in DCM (6 mL) at RT was added TFA (1.5 mL). The mixture was stirred at RT for 5 hrs then concentrated to give 5-amino-4-(4-((4-cyanobenzyl)oxy)-1-oxoisoindolin-2-yl)-5-oxopentanoic acid TFA salt (250 mg crude) as a white solid, which was used for the next step without further purification. MS (ESI) m/z 394.0 [M+H]+.

To a solution of 5-amino-4-(4-((4-cyanobenzyl)oxy)-1-oxoisoindolin-2-yl)-5-oxopentanoic acid TFA salt (250 mg, 0.45 mmol) in ACN (8 mL) at RT was added CDI (291 mg, 1.80 mmol). The mixture was stirred at 95° C. for 6 hrs. The solvent was evaporated to give the crude product which was purified by silica gel chromatography (DCM/MeOH, 100:1 to 50:1) to give 4-(((2-(2,6-dioxopiperidin-3-yl)-1-oxoisoindolin-4-yl)oxy) methyl)benzonitrile (130 mg 77%) as a white solid. MS (ESI) m/z 376.0 [M+H]+.

To a solution of 4-(((2-(2,6-dioxopiperidin-3-yl)-1-oxoisoindolin-4-yl)oxy) methyl)benzonitrile (130 mg, 0.346 mmol) and di-tert-butyl dicarbonate (0.16 mL, 0.693 mmol) in DCM (4 mL) and THF (4 mL) at RT was added Raney-Ni (80 mg). The mixture was stirred at RT for 16 hrs under H2 then MeOH (4 mL) was added, and the mixture was heated to 80° C. for 5 hrs. After cooling to RT, the suspension was filtrated through a Celite pad and the filtrate was concentrated to give the crude product, which was purified by silica gel chromatography using DCM/MeOH (50:1 to 20:1) to afford tert-butyl 4-(((2-(2,6-dioxopiperidin-3-yl)-1-oxoisoindolin-4-yl)oxy)methyl)benzylcarbamate (100 mg, 60% yield) as a white solid. MS (ESI) m/z 380.0 [M+H−100]+.

To a solution of tert-butyl 4-(((2-(2,6-dioxopiperidin-3-yl)-1-oxoisoindolin-4-yl)oxy)methyl)benzylcarbamate (100 mg, 0.208 mmol) in DCM (4 mL) at RT was added TFA (2 mL). The mixture was stirred at RT overnight. The solvent was evaporated to give 3-(4-((4-(aminomethyl)benzyl)oxy)-1-oxoisoindolin-2-yl)piperidine-2,6-dione TFA salt (80 mg crude) as a white solid, which was used for the next step without further purification. MS (ESI) m/z 380.0 [M+H]+.

To a solution of tert-butyl 2-((3-(4-((4-((3-(N-(tert-butyl)sulfamoyl) phenyl)amino)-5-methylpyrimidin-2-yl)amino)phenoxy)propyl)amino) acetate (70 mg, 0.117 mmol) in DCM (4 mL) at RT was added TFA (1.5 mL) and the mixture was stirred at RT overnight. The solvent was evaporated, and the residue was dissolved in DMF (4 mL) then 3-(4-((4-(aminomethyl)benzyl)oxy)-1-oxoisoindolin-2-yl)piperidine-2,6-dione (80 mg, 0.162 mmol), DIEA (63 mg, 0.486 mmol), HOBt (33 mg, 0.243 mmol) and EDAC.HCl (47 mg, 0.243 mmol) were added. The mixture was stirred at RT for 18 hrs. The solvent was evaporated and the crude product was purified by prep-HPLC as previously described to give Compound 17 (11.3 mg, 10% yield) as a white solid. MS (ESI) m/z 904.3 [M+H]+. 1H NMR (400 MHz, DMSO-d6) δ 10.98 (s, 1H), 8.79 (s, 1H), 8.54 (s, 1H), 8.32 (t, J=6.0 Hz, 1H), 8.15 (s, 2H), 7.89 (s, 1H), 7.58-7.40 (m, 9H), 7.32-7.26 (m, 4H), 6.78 (d, J=8.8 Hz, 2H), 5.19 (s, 2H), 5.12-5.07 (m, 1H), 4.41-4.21 (m, 4H), 3.96 (t, J=6.4 Hz, 2H), 3.16 (s, 2H), 2.93-2.86 (m, 1H), 2.65-2.62 (m, 2H), 2.59-2.51 (m, 1H), 2.46-2.41 (m, 1H), 2.11 (s, 3H), 2.09-1.95 (m, 1H), 1.90-1.80 (m, 2H), 1.12 (s, 9H).

Example 18

Compound 18: (S)-3-(6-Fluoro-4-{[p-({3-[3-(p-{5-methyl-4-[m-(tert-butylaminosulfonyl)phenylamino]-2-pyrimidinylamino}phenoxy) propyl] ureido}methyl) phenyl]methoxy}-2-isoindolinoyl)-2,6-piperidinedione

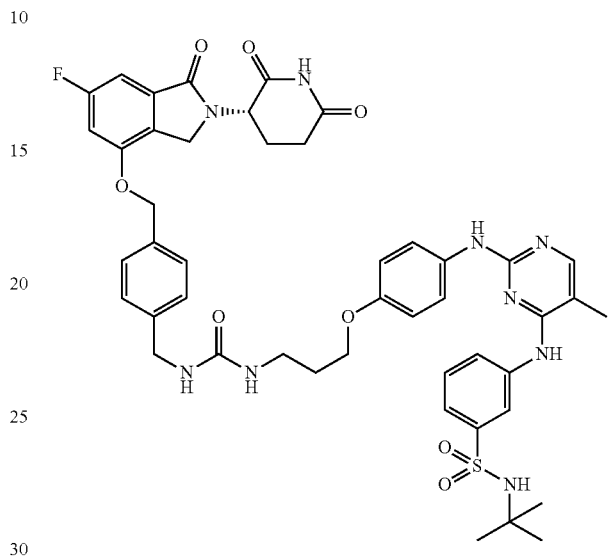

To a solution of methyl 5-fluoro-3-hydroxy-2-methylbenzoate (3.2 g, 17.4 mmol) and imidazole (2.9 g, 43.5 mmol) in DMF (6 mL) at RT was added tert-butyldimethylsilyl chloride (3.1 g, 20.8 mmol). The mixture was stirred at 60° C. for 1 hr, cooled to RT and extracted with tert-butyl methyl ether, dried over anhydrous Na2SO4, concentrated to give methyl 3-((tert-butyldimethylsilyl)oxy)-5-fluoro-2-methylbenzoate (5.2 g crude) as a yellow oil, which was used for the next step without further purification.

To a solution of methyl 3-((tert-butyldimethylsilyl)oxy)-5-fluoro-2-methylbenzoate (3.2 g, 10.7 mmol) in carbon tetrachloride (30 mL) at RT was added NBS (2.9 g, 16.1 mmol) and 2,2'-azobis(2-methylpropionitrile) (700 mg, 4.3 mmol). The mixture was stirred at 80° C. for 6 h. The solvent was evaporated to give the crude product which was purified by silica gel chromatography (petroleum ether/EtOAc, 10:1) to give methyl 2-(bromomethyl)-3-((tert-butyldimethylsilyl)oxy)-5-fluorobenzoate (4.0 g, quant. yield) as a yellow oil.

To a solution of methyl 2-(bromomethyl)-3-((tert-butyldimethylsilyl)oxy)-5-fluorobenzoate (1.0 g, 2.66 mmol) and TEA (0.7 mL, 5.32 mmol) in DMF (6 mL) at RT was added (S)-tert-butyl 4,5-diamino-5-oxopentanoate (696 mg, 2.92 mmol) in 4 mL DMF. The mixture was stirred for 2 h then heated to 80° C. overnight. The solvent was evaporated to give the crude product which was purified by silica gel chromatography (DCM/MeOH, 50:1 to 20:1) to give (S)-tert-butyl 5-amino-4-(6-fluoro-4-hydroxy-1-oxoisoindolin-2-yl)-5-oxopentanoate (1.0 g crude) as a white solid. MS (ESI) m/z 297.0 [M+H−56]+.

To a solution of (S)-tert-butyl 5-amino-4-(6-fluoro-4-hydroxy-1-oxoisoindolin-2-yl)-5-oxopentanoate (500 mg, 1.42 mmol), 4-(hydroxymethyl)benzonitrile (283 mg, 2.13 mmol) and triphenylphosphine (930 mg, 3.55 mmol) in THF (4 mL) at RT was added DEAD (617 mg, 3.55 mmol). The mixture was stirred at RT for 2 hrs. The solvent was evaporated, and the residue was purified by silica gel chromatography (DCM/MeOH, 100:1 to 50:1) to give (S)-tert-butyl 5-amino-4-(4-((4-cyanobenzyl)oxy)-6-fluoro-1-oxoisoindolin-2-yl)-5-oxopentanoate (350 mg, 52% yield) as a yellow solid. MS (ESI) m/z 412.0 [M+H−56]⁺.

To a solution of (S)-tert-butyl 5-amino-4-(4-((4-cyanobenzyl)oxy)-6-fluoro-1-oxoisoindolin-2-yl)-5-oxopentanoate (350 mg, 0.75 mmol) in DCM (4 mL) at RT was added TFA (4 mL). The mixture was stirred at RT overnight. The solvent was evaporated to give (S)-5-amino-4-(4-((4-cyanobenzyl)oxy)-6-fluoro-1-oxoisoindolin-2-yl)-5-oxopentanoic acid (400 mg crude) as a yellow solid, which was used for the next step without further purification. MS (ESI) m/z 412.0 [M+H]⁺.

To a solution of (S)-5-amino-4-(4-((4-cyanobenzyl)oxy)-6-fluoro-1-oxoisoindolin-2-yl)-5-oxopentanoic acid (400 mg, 0.75 mmol) in ACN (10 mL) at RT was added CDI (485 mg, 2.99 mmol). The mixture was stirred at 95° C. for 3.5 hrs. The solvent was evaporated to give the crude product, which was purified by silica gel chromatography (DCM/MeOH, 100:1 to 50:1) to give (S)-4-(((2-(2,6-dioxopiperidin-3-yl)-6-fluoro-1-oxoisoindolin-4-yl)oxy)methyl)benzonitrile (200 mg 68%) as a white solid. MS (ESI) m/z 394.0 [M+H]⁺.

To a solution of (S)-4-(((2-(2,6-dioxopiperidin-3-yl)-6-fluoro-1-oxoisoindolin-4-yl)oxy)methyl)benzonitrile (200 mg, 0.51 mmol) and di-tert-butyl dicarbonate (166 mg, 0.76 mmol) in THF (6 mL) at RT was added Raney-Ni (80 mg). The mixture was stirred under H₂ overnight. The suspension was filtered and the filtrate was concentrated and purified by silica gel chromatography (DCM/MeOH, 100:1 to 20:1) to give (S)-tert-butyl 4-(((2-(2,6-dioxopiperidin-3-yl)-6-fluoro-1-oxoisoindolin-4-yl)oxy)methyl)benzylcarbamate (90 mg, 35% yield) as a white solid. MS (ESI) m/z 398.0 [M+H−100]⁺.

To a solution of (S)-tert-butyl 4-(((2-(2,6-dioxopiperidin-3-yl)-6-fluoro-1-oxoisoindolin-4-yl)oxy)methyl)benzylcarbamate (70 mg, 0.146 mmol) in DCM (2 mL) at RT was added TFA (0.5 mL). The mixture was stirred at RT for 2 hrs. The solvent was evaporated to give (S)-3-(4-((4-(aminomethyl)benzyl)oxy)-6-fluoro-1-oxoisoindolin-2-yl)piperidine-2,6-dione (80 mg crude) as a white solid, which was used for the next step without further purification. MS (ESI) m/z 398.0 [M+H]⁺.

To a solution of (S)-3-(4-((4-(aminomethyl)benzyl)oxy)-6-fluoro-1-oxoisoindolin-2-yl)piperidine-2,6-dione (80 mg, 0.146 mmol) and TEA (45 mg, 0.438 mmol) in THF at RT was added 4-nitrophenyl (3-(4-((4-((3-(N-(tert-butyl)sulfamoyl)phenyl)amino)-5-methylpyrimidin-2-yl)amino)phenoxy)propyl)carbamate (90 mg, 0.138 mmol). After stirring for 15 min, TEA (103 mg, 1.022 mmol) was added, and the reaction was stirred for 2 hrs. The solvent was evaporated to give the crude product which was purified by prep-HPLC as previously described to afford Compound 18 (60.9 mg, 46% yield) as a white solid. MS (ESI) m/z 908.3 [M+H]⁺. ¹H NMR (400 MHz, DMSO-d₆) δ 10.96 (s, 1H), 8.76 (s, 1H), 8.52 (s, 1H), 8.14-8.12 (m, 2H), 7.88 (s, 1H), 7.55-7.40 (m, 7H), 7.26-7.24 (m, 3H), 7.11-7.08 (m, 1H), 6.79 (d, J=8.8 Hz, 2H), 6.36 (t, J=5.6 Hz, 1H), 6.04 (t, J=5.6 Hz, 1H), 5.20 (s, 2H), 5.11-5.06 (m, 1H), 4.36 (d, J=17.2 Hz, 1H), 4.23-4.19 (m, 3H), 3.91 (t, J=6.0 Hz, 2H), 3.19-3.14 (m, 2H), 2.89-2.82 (m, 1H), 2.58-2.50 (m, 1H), 2.45-2.40 (m, 1H), 2.11 (s, 3H), 1.99-1.89 (m, 1H), 1.82-1.79 (m, 2H), 1.12 (s, 9H).

Example 19

Compound 19: 2-[(S)-2,7-Dioxo-3-azepanyl]-4-{[p-(morpholinomethyl)phenyl]methoxy}-1-oxo-5-isoindolinecarbonitrile

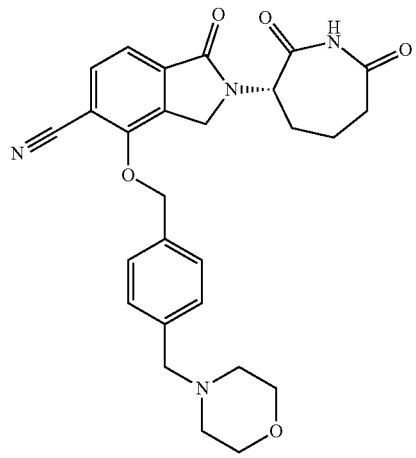 [SMILES: N#Cc1ccc2c(c1OCc1ccc(CN3CCOCC3)cc1)CN([C@H]1CCCC(=O)NC1=O)C2=O]

To a solution of 3-hydroxy-2-methylbenzoic acid (100.0 g, 660 mmol) in dry MeOH (700 mL) at 0° C. was added thionyl chloride (156.0 g, 1316 mmol). The reaction was heated to 70° C. for 3 hrs. The reaction was cooled to RT and the solvent was evaporated. The residue was diluted with water and extracted with EtOAc. Workup and purification with EtOAc in petroleum ether from 0% to 8% to give methyl 3-hydroxy-2-methylbenzoate (102 g, 93% yield) as a white solid.

NBS (53.6 g, 301.2 mmol) was added to a solution of methyl 3-hydroxy-2-methylbenzoate (50.0 g, 301.2 mmol) in DCM (800 mL) at −78° C. The mixture was stirred at −78° C. for 1 hour then concentrated. The crude product was purified by silica gel chromatography eluting with EtOAc in petroleum ether (from 0% to 8%) to give methyl 4-bromo-3-hydroxy-2-methylbenzoate (15.0 g, 21% yield) as a colorless solid.

To a solution of methyl 4-bromo-3-hydroxy-2-methylbenzoate (10.0 g, 40.82 mmol) in DMF (50 mL) was added zinc cyanide (480 mg, 40.82 mmol) and tetrakis(triphenylphosphine)palladium (240 mg, 2.04 mmol). The mixture was heated to 100° C. for 5 hrs. The reaction was cooled to RT and the solvent was evaporated. The residue was diluted with water and extracted with EtOAc. Workup and purification with EtOAc in petroleum ether (from 0% to 15%) to give methyl 4-cyano-3-hydroxy-2-methylbenzoate (2.1 g, 27% yield) as a white solid.

To a solution of methyl 4-cyano-3-hydroxy-2-methylbenzoate (2.1 g, 11.0 mmol) and imidazole (1.5 g, 22.0 mmol) in DMF (6 mL) at RT was added tert-butyldimethylsilyl chloride (1.98 g, 13.2 mmol). After stirring at 60° C. for 1 hour, the solution was cooled to RT and extracted with tert-butyl methyl ether, dried over anhydrous Na₂SO₄, filtered, concentrated to give methyl 3-((tert-butyldimethylsilyl)oxy)-4-cyano-2-methylbenzoate (3.2 g crude) as a yellow oil, which was used for the next step without further purification.

To a solution of methyl 3-((tert-butyldimethylsilyl)oxy)-4-cyano-2-methylbenzoate (3.2 g, 10.5 mmol) in carbon tetrachloride (50 mL) at RT was added NBS (2.43 g, 13.64 mmol) and 2,2'-azobis(2-methylpropionitrile) (690 mg, 4.2 mmol). The suspension was stirred at 80° C. for 5 hrs. The solvent was evaporated to give the crude product which was purified by silica gel chromatography (petroleum ether/EtOAc, 10:1) to give methyl 2-(bromomethyl)-3-((tert-butyldimethylsilyl)oxy)-4-cyanobenzoate (3.5 g 87%) as a colorless oil.

To a solution of methyl 2-(bromomethyl)-3-((tert-butyldimethylsilyl)oxy)-4-cyanobenzoate (2.65 g, 6.92 mmol) and TEA (1.39 g, 113.8 mmol) in DMF (20 mL) at RT was added (S)-3-aminoazepan-2-one (1.06 g, 8.3 mmol). The mixture was stirred for 2 hrs then heated to 50° C. overnight. After cooling to RT, tetrabutylammonium fluoride (2.61 g, 8.3 mmol) was added. The mixture was heated to 50° C. for 1 hour. The solvent was evaporated to give the crude product which was purified by silica gel chromatography (DCM/MeOH, 50:1 to 20:1) to afford (S)-4-hydroxy-1-oxo-2-(2-oxoazepan-3-yl)isoindoline-5-carbonitrile (1.3 g, crude) as a yellow solid.

To a solution of (S)-4-hydroxy-1-oxo-2-(2-oxoazepan-3-yl)isoindoline-5-carbonitrile (1.0 g, 3.5 mmol), 4-(bromomethyl)benzaldehyde (900 mg, 4.6 mmol) in DMF (515 mL) was added $K_2CO_3$ 970 mg, 7.1 mmol). The mixture was heated to 50° C. for 2 h. The solvent was evaporated to give the crude product, which was purified by silica gel chromatography (DCM/MeOH, 50:1 to 20:1) to afford (S)-4-((4-formylbenzyl)oxy)-1-oxo-2-(2-oxoazepan-3-yl) isoindoline-5-carbonitrile (600 mg, 42% yield) as a yellow solid. MS (ESI) m/z 404.2 [M+H]$^+$.

To a solution of (S)-4-((4-formylbenzyl)oxy)-1-oxo-2-(2-oxoazepan-3-yl) isoindoline-5-carbonitrile (980 mg, 2.44 mmol) in ACN/DMSO (12 mL/2 mL) at RT was added Dess-Martin periodinane (2.6 g, 6.1 mmol). The mixture was stirred at 80° C. overnight. The mixture was cooled to RT and 100 mL of a sat. sodium thiosulfate solution was added followed by stirring for 5 min. The mixture was extracted with DCM. Workup and purification with DCM/ACN, 5:1 to 3:1 provided (S)-2-(2,7-dioxoazepan-3-yl)-4-((4-formylbenzyl)oxy)-1-oxoisoindoline-5-carbonitrile (600 mg, 59% yield) as a white solid. MS (ESI) m/z 418.0 [M+H]$^+$.

To a solution of (S)-2-(2,7-dioxoazepan-3-yl)-4-((4-formylbenzyl)oxy)-1-oxoisoindoline-5-carbonitrile (700 mg, 1.68 mmol) and morpholine (292 mg, 3.36 mmol) in DCM (15 mL) at RT was added sodium triacetoxyborohydride (850 mg, 4.2 mmol). The mixture was stirred for 3 hrs then concentrated. The residue was purified by silica gel chromatography (DCM/ACN, 3:1 to 1:1) to afford Compound 19 (800 mg, 57% yield) as a white solid. MS (ESI) m/z 489.2 [M+H]$^+$.

$^1$H NMR (400 MHz, DMSO-d$_6$) δ 10.79 (s, 1H), 7.91 (d, J=7.6 Hz, 1H), 7.54-7.46 (m, 3H), 7.36 (d, J=8.4 Hz, 2H), 5.47 (s, 2H), 5.29-5.25 (m, 1H), 4.86 (t, J=2.4 Hz, 2H), 3.58-3.56 (m, 4H), 3.47 (s, 2H), 3.14-3.06 (m, 1H), 2.58 (d, J=16.4 Hz, 1H), 2.40-2.34 (m, 5H), 2.13-2.00 (m, 2H), 1.83-1.81 (m, 1H).

Example 20

Compound 20: (S)-3-(4-{[p-({3-[3-(p-{5-Methyl-4-[m-(tert-butylaminosulfonyl) phenylamino]-2-pyrimidinylamino}phenoxy)propyl]ureido}methyl) phenyl]methoxy}-2-isoindolinoyl)-2,6-piperidinedione

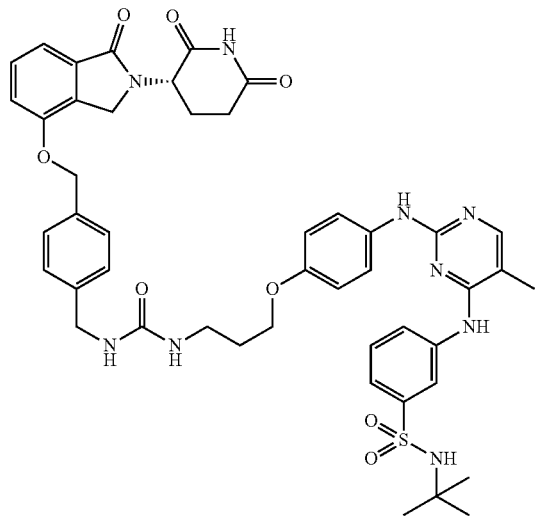 [SMILES: Cc1cnc(Nc2ccc(OCCCNC(=O)NCc3ccc(COc4cccc5c4CN([C@H]4CCC(=O)NC4=O)C5=O)cc3)cc2)nc1Nc1cccc(S(=O)(=O)NC(C)(C)C)c1]

To a solution of (S)-tert-butyl 4-(((2-(2,6-dioxopiperidin-3-yl)-1-oxoisoindolin-4-yl) oxy)methyl)benzylcarbamate (100 mg, 0.2 mmol) in DCM (4 mL) at RT was added TFA (1 mL). The mixture was stirred for 1 hour then the solvent was evaporated to give (S)-3-(4-((4-(aminomethyl)benzyl)oxy)-1-oxoisoindolin-2-yl)piperidine-2,6-dione TFA salt which was used for the next step without further purification. MS (ESI) m/z=380.0 [M+H]$^+$.

To a solution of (S)-3-(4-((4-(aminomethyl)benzyl)oxy)-1-oxoisoindolin-2-yl) piperidine-2,6-dione TFA salt (0.2 mmol) in DCM (4 mL) at RT was added TEA (41 mg, 0.4 mmol) and 4-nitrophenyl carbonochloridate (50 mg, 0.24 mmol). After stirring for 2 hrs, the mixture was concentrated to afford (S)-4-nitrophenyl 4-(((2-(2,6-dioxopiperidin-3-yl)-1-oxoisoindolin-4-yl)oxy)methyl)benzylcarbamate, which was used for the next step.

To a solution of tert-butyl (3-(4-((4-((3-(N-(tert-butyl)sulfamoyl)phenyl) amino)-5-methylpyrimidin-2-yl)amino)phenoxy)propyl)carbamate (120 mg, 0.2 mmol) in DCM (2 mL) was added TFA (1 mL). The mixture was stirred at RT for 1 hr then the solvent was evaporated to give 3-((2-((4-(3-aminopropoxy)phenyl)amino)-5-methylpyrimidin-4-yl)amino)-N-(tert-butyl)benzenesulfonamide, which was used for the next step. MS (ESI) m/z=485.1 [M+H]$^+$.

To a solution of phenyl (S)-4-nitrophenyl 4-(((2-(2,6-dioxopiperidin-3-yl)-1-oxoisoindolin-4-yl)oxy)methyl)benzylcarbamate (0.2 mmol) in THF (4 mL) was added TEA (0.2 mL) followed by a solution of 3-((2-((4-(3-aminopropoxy)phenyl)amino)-5-methylpyrimidin-4-yl)amino)-N-(tert-butyl)benzenesulfonamide (0.2 mmol) in DCM (4 mL) and the mixture was stirred at RT overnight. The solvent was evaporated and the residue was purified by silica gel chromatography (DCM/MeOH, 10:1) and prep-HPLC as previously described to afford Compound 20 (11.5 mg, 6.5% yield) as a white solid. MS (ESI) m/z=890.3 [M+H]$^+$. $^1$H NMR (400 MHz, DMSO-d$_6$) δ 10.94 (s, 1H), 8.76 (s, 1H), 8.52 (s, 1H), 8.11-8.14 (m, 2H), 7.89 (s, 1H), 7.39-7.78 (m, 8H), 7.24-7.31 (m, 4H), 6.79 (d, J=8.8 Hz, 2H), 6.35 (t, J=6.0 Hz, 1H), 6.03 (t, J=5.6 Hz, 1H), 5.19 (s, 2H), 5.09 (dd, J=4.8, 13.2 Hz, 1H), 4.19-4.41 (m, 4H), 3.91 (t, J=6.0 Hz, 2H), 3.16 (q, J=6.4 Hz, 2H), 2.85-2.94 (m, 1H), 2.53-2.58 (m, 1H), 2.42-2.49 (m, 1H), 2.11 (s, 3H), 1.95-1.99 (m, 1H), 1.77-1.84 (m, 2H), 1.12 (s, 9H).

Example 21

Compound 21: (S)-3-(6-Fluoro-4-{[p-({2-[3-(p-{5-methyl-4-[m-(tert-butylsulfonylamino) phenylamino]-2-pyrimidinylamino}phenoxy)propylamino]acetylamino}methyl)phenyl]methoxy}-2-isoindolinoyl)-2,7-azepanedione

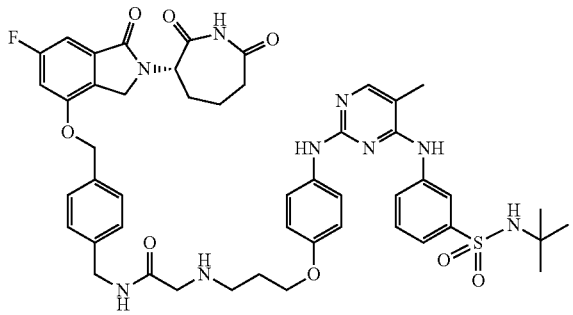 [SMILES: Cc1cnc(Nc2ccc(OCCCNCC(=O)NCc3ccc(COc4cc(F)cc5c4CN([C@H]4CCCC(=O)NC4=O)C5=O)cc3)cc2)nc1Nc1cccc(S(=O)(=O)NC(C)(C)C)c1]

To a solution of (S)-3-aminoazepan-2-one (2.0 g, 15.9 mmol) and TEA (2.8 mL, 19.9 mmol) in DMF (30 mL) at RT was added methyl 2-(bromomethyl)-3-((tert-butyldimethylsilyl)oxy)-5-fluorobenzoate (5.0 g, 13.3 mmol) in 10 mL DMF. The mixture was stirred for 2 hrs, heated to 50° C. overnight, and cooled to RT. TBAF (2.4 g, 9.31 mmol) was added and the mixture was heated to 70° C. for 1 hr. The solvent was evaporated and the residue was purified by silica gel chromatography (DCM/MeOH, 100:1 to 30:1) to give (S)-6-fluoro-4-hydroxy-2-(2-oxoazepan-3-yl) isoindolin-1-one (3.1 g, 83% yield) as a yellow solid. MS (ESI) m/z 279.0 [M+H]+.

To a solution of (S)-6-fluoro-4-hydroxy-2-(2-oxoazepan-3-yl) isoindolin-1-one (320 mg, 1.15 mmol), tert-butyl 4-(hydroxymethyl)benzylcarbamate (409 mg, 1.72 mmol) and triphenylphosphine (602 mg, 2.30 mmol) in THF (2 mL) at RT was added DEAD (400 mg, 2.30 mmol) and the mixture was stirred for 30 min. The solvent was evaporated and the residue was purified by silica gel chromatography (DCM/MeOH, 100:1 to 30:1) to give (S)-tert-butyl 4-(((6-fluoro-1-oxo-2-(2-oxoazepan-3-yl)isoindolin-4-yl)oxy) methyl) benzylcarbamate (430 mg, 75% yield) as a yellow solid. MS (ESI) m/z 398.1 [M+H−100]+.

To a solution of (S)-tert-butyl 4-(((6-fluoro-1-oxo-2-(2-oxoazepan-3-yl) isoindolin-4-yl)oxy)methyl)benzylcarbamate (200 mg, 0.40 mmol) in ACN/DMSO (4 mL/1 mL) at RT was added Dess-Martin periodinane (426 mg, 1.00 mmol). The mixture was stirred at 80° C. overnight. After cooling to RT, 20 mL of sat. sodium thiosulfate solution was added, and the mixture was extracted with DCM. Workup provided the crude product which was washed with tert-butyl methyl ether to afford (S)-tert-butyl 4-(((2-(2,7-dioxoazepan-3-yl)-6-fluoro-1-oxoisoindolin-4-yl)oxy)methyl)benzylcarbamate (100 mg, 50% yield) as a white solid. MS (ESI) m/z 412.0 [M+H−100]+.

To a solution of (S)-tert-butyl 4-(((2-(2,7-dioxoazepan-3-yl)-6-fluoro-1-oxoisoindolin-4-yl)oxy)methyl)benzylcarbamate (61 mg, 0.117 mmol) in DCM (4 mL) at RT was added TFA (1 mL). The reaction was stirred at RT for 1 hour. The solvent was evaporated to give the amine TFA salt as a yellow gum.

The amine TFA salt was dissolved in DMA (1 mL) and 2-((3-(4-((4-((3-(N-(tert-butyl) sulfamoyl)phenyl)amino)-5-methylpyrimidin-2-yl)amino)phenoxy)propyl) amino)acetic acid (76 mg, 0.141 mmol) was added, followed by HOBt (23.7 mg, 0.176 mmol), EDAC.HCl (34.1 mg, 0.176 mmol) and DIEA (30.0 mg, 0.234 mmol). The reaction was stirred at RT for 10 hrs. The solvent was evaporated, and the residue was purified by prep-HPLC as previously described to afford Compound 21 (10.8 mg, 10.2% yield) as a white solid. MS (ESI) m/z 936.4[M+H]+. 1H NMR (400 MHz, DMSO-d6) δ 10.69 (s, 1H), 8.75 (s, 1H), 8.51 (s, 1H), 8.29 (t, J=6.0 Hz, 1H), 8.14-8.11 (m, 2H), 7.88 (s, 1H), 7.54-7.23 (m, 10H), 7.09-7.07 (m, 1H), 6.77 (d, J=4.8 Hz, 2H), 5.20-5.17 (m, 3H), 4.40 (s, 2H), 4.30 (d, J=6.0 Hz, 2H), 3.96 (t, J=2.4 Hz, 2H), 3.15 (s, 2H), 3.09-3.00 (m, 1H), 2.67-2.54 (m, 3H), 2.32-2.25 (m, 3H), 2.11 (s, 3H), 2.05-1.96 (m, 2H), 1.84-1.71 (m, 3H), 1.12 (s, 9H).

Example 23

Compound 22: (S)-3-[5-(Aminomethyl)-4-{[p-(morpholinomethyl)phenyl]methoxy}-2-isoindolinoyl]-2,7-azepanedione ditrifluoroacetic acid

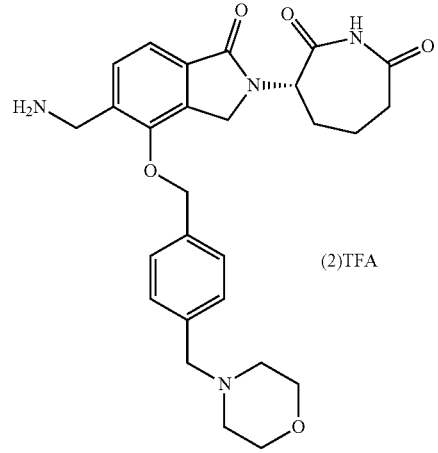 [SMILES: NCc1ccc2c(c1OCc1ccc(CN3CCOCC3)cc1)CN([C@H]1CCCC(=O)NC1=O)C2=O]

To a solution of (S)-2-(2,7-dioxoazepan-3-yl)-4-((4-(morpholinomethyl) benzyl)oxy)-1-oxoisoindoline-5-carbonitrile (700 mg, 1.43 mmol) and di-tert-butyl dicarbonate (625 mg, 2.87 mmol) in DMF (10 mL)/THF (15 mL) at RT was added Raney-Ni (500 mg). The mixture was stirred at RT for 48 hrs under H2. The suspension was filtered through a Celite pad and concentrated to give the crude product which was purified by silica gel chromatography (DCM/CAN, 3:1 to 1:1) to afford (S)-tert-butyl((2-(2,7-dioxoazepan-3-yl)-4-((4-(morpholinomethyl)benzyl)oxy)-1-oxoisoindolin-5-yl) methyl)carbamate (800 mg, 85% yield) as a white solid. MS (ESI) m/z 593.1 [M+H]+.

To a solution of (S)-tert-butyl ((2-(2,7-dioxoazepan-3-yl)-4-((4-(morpholinomethyl) benzyl)oxy)-1-oxoisoindolin-5-yl)methyl)carbamate (70 mg, 0.118 mmol) in DCM (3 mL) at RT was added TFA (1.0 mL). The mixture was stirred for 1 hour. The solvent was evaporated to afford Compound 22 (70 mg, 83% yield) as a white solid. MS (ESI) m/z 493.2 [M+H]+. 1H NMR (400 MHz, DMSO-d6) δ 10.75 (s, 1H), 10.56 (s, 1H), 8.29 (s, 3H), 7.64-7.52 (m, 6H), 5.36 (s, 2H), 5.28-5.24 (m, 1H), 4.85-4.73 (m, 2H), 4.39 (s, 2H), 4.14 (s, 2H), 3.97 (s, 2H), 3.65 (s, 2H), 3.24-3.01 (m, 4H), 2.61-2.57 (m, 2H), 2.37-2.32 (m, 1H), 2.15-2.03 (m, 2H), 1.87-1.78 (m, 1H).

Example 24

Compound 23: (S)-3-[5-({3-[3-(p-{5-Methyl-4-[m-(tert-butylaminosulfonyl)phenylamino]-2-pyrimidinylamino}phenoxy)propyl]ureido}methyl)-4-{[p-(morpholinomethyl)phenyl]methoxy}-2-isoindolinoyl]-2,6-piperidinedione To a solution of (S)-5-amino-4-(5-cyano-4-((4-(morpholinomethyl)benzyl) oxy)-1-oxoisoindolin-2-yl)-5-oxopentanoic acid (200 mg, 0.41 mmol) in ACN (10 mL) at RT was added CDI (200 mg, 1.22 mmol). The mixture was heated to 50° C. for 2 hrs. The solvent was evaporated, and the residue was purified by silica gel chromatography (DCM/MeOH, 50:1 to 10:1) to give (S)-2-(2,6-dioxopiperidin-3-yl)-4-((4-(morpholinomethyl)benzyl)oxy)-1-oxoisoindoline-5-carbonitrile (100 mg, 52% yield) as a white solid. MS (ESI) m/z 475.2 [M+H]+. 1H NMR (400 MHz, DMSO-d6) δ 11.05 (s, 1H), 7.92 (d, J=7.6 Hz, 1H), 7.54 (d, J=8 Hz, 1H), 7.47 (d, J=8 Hz, 2H), 7.36 (d, J=8 Hz, 2H), 5.45 (s, 2H), 5.18-5.14 (m, 1H), 4.85-4.66 (m, 2H), 3.58-3.56 (m, 4H), 3.47 (s, 2H), 2.96-2.89 (m, 1H), 2.65-2.60 (m, 1H), 2.47-2.44 (m, 1H), 2.36-2.33 (m, 4H), 2.05-1.99 (m, 1H).

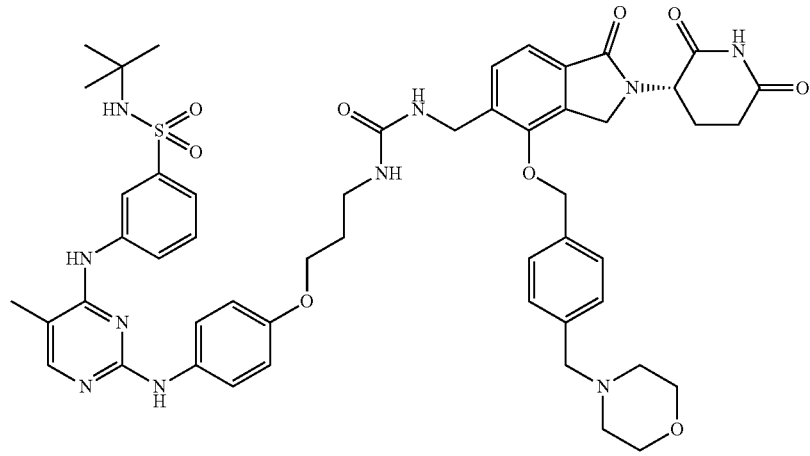 [SMILES: Cc1cnc(Nc2ccc(OCCCNC(=O)NCc3ccc4c(c3OCc3ccc(CN5CCOCC5)cc3)CN([C@H]3CCC(=O)NC3=O)C4=O)cc2)nc1Nc1cccc(S(=O)(=O)NC(C)(C)C)c1]

To a solution of methyl 2-(bromomethyl)-3-((tert-butyldimethylsilyl)oxy)-4-cyanobenzoate (3.5 g, 9.096 mmol) and TEA (1.84 g, 18.2 mmol) in DMF (15 mL) at RT was added (S)-tert-butyl 4,5-diamino-5-oxopentanoate (2.6 g, 10.91 mmol). The mixture was stirred for 2 hrs then heated to 50° C. overnight. After cooling to RT, tetrabutylammonium fluoride (4.3 g, 13.6 mmol) added. The mixture was heated to 50° C. for 1 hr. The solvent was evaporated to give the crude product which was purified by silica gel chromatography (DCM/MeOH, 50:1 to 20:1) to give (S)-tert-butyl 5-amino-4-(5-cyano-4-hydroxy-1-oxoisoindolin-2-yl)-5-oxopentanoate (1.1 g, yield; 34% yield) as a yellow solid.

To a solution of (S)-tert-butyl 5-amino-4-(5-cyano-4-hydroxy-1-oxoisoindolin-2-yl)-5-oxopentanoate (200 mg, 0.56 mmol), 4-(4-(chloromethyl)benzyl)morpholine (188 mg, 0.835 mmol) in DMF (5 mL) was added K2CO3 (156 mg, 1.13 mmol) and the mixture was heated to 50° C. for 2 hrs. The solvent was evaporated and the residue was purified by silica gel chromatography (DCM/MeOH, 50:1 to 20:1) to afford (S)-tert-butyl 5-amino-4-(5-cyano-4-((4-(morpholinomethyl)benzyl)oxy)-1-oxoisoindolin-2-yl)-5-oxopentanoate (240 mg, 80% yield) as a yellow solid.

To a solution of (S)-tert-butyl 5-amino-4-(5-cyano-4-((4-(morpholinomethyl)benzyl) oxy)-1-oxoisoindolin-2-yl)-5-oxopentanoate (240 mg, 0.44 mmol) in DCM (5 mL) at RT was added TFA (2 mL). The mixture was stirred overnight and concentrated to afford (S)-5-amino-4-(5-cyano-4-((4-(morpholinomethyl)benzyl)oxy)-1-oxoisoindolin-2-yl)-5-oxopentanoic acid (200 mg, crude) as a yellow oil, which was used for the next step without further purification.

To a solution of (S)-2-(2,6-dioxopiperidin-3-yl)-4-((4-(morpholinomethyl) benzyl)oxy)-1-oxoisoindoline-5-carbonitrile (600 mg, 1.265 mmol) and di-tert-butyl dicarbonate (550 mg, 2.53 mmol) in DMF (5 mL) and MeOH (10 mL) at RT was added Raney-Ni (300 mg). The mixture was stirred at RT for 16 hrs under H2. The suspension was filtered through a Celite pad and concentrated to give the crude product which was purified by silica gel chromatography (DCM/MeOH, 50:1 to 20:1) to afford (S)-tert-butyl ((2-(2,6-dioxopiperidin-3-yl)-4-((4-(morpholinomethyl) benzyl)oxy)-1-oxoisoindolin-5-yl)methyl) carbamate (400 mg, 55% yield) as a white solid. MS (ESI) m/z 579.1 [M+H]+.

To a solution of (S)-tert-butyl ((2-(2,6-dioxopiperidin-3-yl)-4-((4-(morpholinomethyl) benzyl)oxy)-1-oxoisoindolin-5-yl)methyl)carbamate (250 mg, 0.435 mmol) in DCM (4 mL) at RT was added TFA (1.0 mL). The mixture was stirred at RT for 1 hour. The solvent was evaporated to give (S)-3-(5-(aminomethyl)-4-((4-(morpholinomethyl) benzyl)oxy)-1-oxoisoindolin-2-yl)piperidine-2,6-dione (250 mg, 81% yield) as a white solid. MS (ESI) m/z 479.2 [M+H]+. 1H NMR (400 MHz, DMSO-d6) δ 11.02 (s, 1H), 10.37 (s, 1H), 8.25 (s, 3H), 7.61-7.59 (m, 3H), 7.55-7.53 (m, 3H), 5.32 (s, 2H), 5.17-5.12 (m, 1H), 4.78-4.55 (m, 2H), 4.36 (s, 2H), 4.14 (d, J=4.4 Hz, 2H), 3.91 (s, 2H), 3.71-3.60 (m, 2H), 3.26-3.09 (m, 4H), 2.96-2.91 (m, 1H), 2.66-2.61 (m, 1H), 2.46-2.42 (m, 1H), 2.04-1.99 (m, 1H).

To a solution of (S)-3-(5-(aminomethyl)-4-((4-(morpholinomethyl)benzyl) oxy)-1-oxoisoindolin-2-yl)piperidine-2,6-dione (150 mg, 0.21 mmol) in formic acid (5 mL) at RT was added formaldehyde (1 mL, 40%). The mixture was heated to 100° C. for 1 hour. The solvent was evaporated, and the residue was purified by prep-HPLC as previously described to give (S)-3-(5-((dimethylamino)methyl)-4-((4-(morpholinomethyl)benzyl)oxy)-1-oxoisoindolin-2-yl)piperidine-2,6-dione (80 mg, 79% yield) as a white solid. MS (ESI) m/z 507.2 [M+H]$^+$. $^1$H NMR (400 MHz, DMSO-d$_6$) δ 11.05 (s, 1H), 10.91 (s, 1H), 10.01 (s, 1H), 7.68-7.54 (m, 6H), 5.37 (s, 2H), 5.17-5.06 (m, 2H), 4.85-4.78 (m, 1H), 4.65-4.61 (m, 1H), 4.38 (s, 4H), 3.96 (s, 2H), 3.67 (s, 2H), 3.24-2.92 (m, 4H), 2.83-2.61 (m, 7H), 2.50-2.42 (m, 1H), 2.07-2.01 (m, 1H).

To a solution of (S)-3-(5-(aminomethyl)-4-((4-(morpholinomethyl)benzyl) oxy)-1-oxoisoindolin-2-yl)piperidine-2,6-dione (80 mg, 0.112 mmol) in THF (5 mL) was added TEA (113 mg, 1.12 mmol). The mixture was stirred at RT for 10 min then 4-nitrophenyl (3-(4-((4-((3-(N-(tert-butyl) sulfamoyl)phenyl)amino)-5-methylpyrimidin-2-yl) amino) phenoxy)propyl)carbamate (80 mg, 0.124 mmol) was added, followed by TEA (90 mg, 0.9 mmol). After stirring at RT for 1 h, the mixture was concentrated and the residue was purified by prep-HPLC as previously described to afford Compound 23 (40 mg, 36% yield) as a white solid. MS (ESI) m/z 989.4 [M+H]$^+$. $^1$H NMR (400 MHz, DMSO-d$_6$) δ 11.01 (s, 1H), 8.79 (s, 1H), 8.54 (s, 1H), 8.13 (s, 2H), 7.90 (s, 1H), 7.57-7.33 (m, 11H), 6.79 (d, J=8 Hz, 2H), 6.36-6.33 (m, 1H), 6.16-6.13 (m, 1H), 5.16-5.09 (m, 3H), 4.65-4.54 (m, 2H), 4.33 (d, J=4 Hz, 2H), 3.93-3.90 (m, 2H), 3.56 (s, 4H), 3.46 (s, 2H), 3.18-3.15 (m, 2H), 2.97-2.88 (m, 1H), 2.62-2.58 (m, 1H), 2.34 (s, 4H), 2.12 (s, 3H), 2.01-1.92 (m, 1H), 1.89 (s, 1H), 1.82-1.79 (m, 2H), 1.12 (s, 9H).

Example 25

Compound 24: (S)-3-(4-{[p-({2-[3-(p-{5-Methyl-4-[m-(tert-butylaminosulfonyl) phenylamino]-2-pyrimidinylamino}phenoxy)propylamino]acetylamino}methyl)phenyl]methoxy}-2-isoindolinoyl)-2,6-piperidinedione

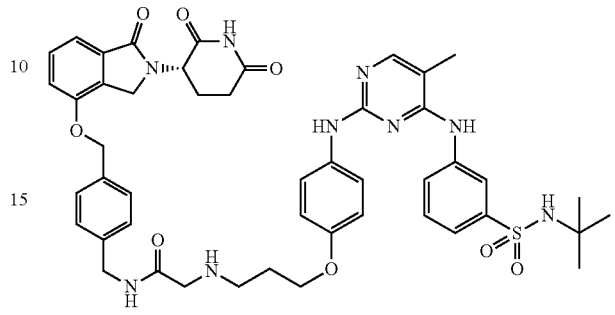

To a solution of 2-((3-(4-((4-((3-(N-(tert-butyl)sulfamoyl)phenyl)amino)-5-methylpyrimidin-2-yl)amino)phenoxy)propyl)amino)acetic acid (54 mg, 0.1 mmol) and (S)-3-(4-((4-(aminomethyl)benzyl)oxy)-1-oxoisoindolin-2-yl)piperidine-2,6-dione (0.1 mmol) in DMF (2 mL) at RT was added DIEA (26 mg, 0.2 mmol), HOBt (20 mg, 0.15 mmol) and EDAC.HCl (29 mg, 0.15 mmol) and the mixture was stirred overnight. The solvent was evaporated, and the residue was purified by prep-TLC (DCM/MeOH, 10:1) to afford Compound 24 (6.0 mg, 6.7% yield) as a white solid. MS (ESI) m/z=904.3 [M+H]$^+$. $^1$H NMR (400 MHz, DMSO-d$_6$) δ 10.95 (s, 1H), 8.76 (s, 1H), 8.52 (s, 1H), 8.48 (s, 1H), 8.11-8.14 (m, 2H), 7.89 (s, 1H), 7.40-7.54 (m, 8H), 7.27-7.31 (m, 4H), 6.78 (d, J=9.2 Hz, 2H), 5.20 (s, 2H), 5.09 (dd, J=5.2, 13.2 Hz, 1H), 4.21-4.41 (m, 4H), 3.96 (t, J=6.0 Hz, 2H), 2.85-2.94 (m, 1H), 2.76 (t, J=6.0 Hz, 2H), 2.53-2.58 (m, 1H), 2.40-2.45 (m, 2H), 2.11 (s, 3H), 1.95-1.98 (m, 2H), 1.87-1.90 (m, 2H), 1.12 (s, 9H).

Example 26

Compound 25: (S)-3-(6-Fluoro-4-{[p-({2-[3-(p-{5-methyl-4-[m-(tert-butylaminosulfonyl) phenylamino]-2-pyrimidinylamino}phenoxy)propylamino]acetylamino}methyl)phenyl]methoxy}-2-isoindolinoyl)-2,6-piperidinedione

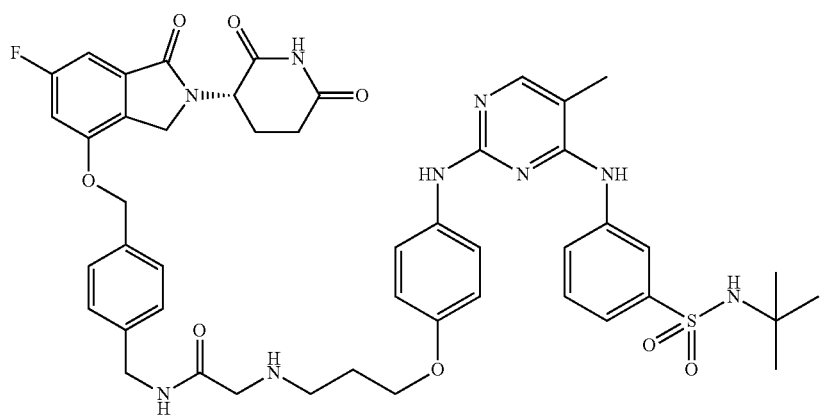 [SMILES: Cc1cnc(Nc2ccc(OCCCNCC(=O)NCc3ccc(COc4cc(F)cc5c4CN([C@H]4CCC(=O)NC4=O)C5=O)cc3)cc2)nc1Nc1cccc(S(=O)(=O)NC(C)(C)C)c1]

To a solution of methyl 5-fluoro-3-hydroxy-2-methylbenzoate (3.2 g, 17.4 mmol) and inidazole (2.9 g, 43.5 mmol) in DMF (6 mL) at RT was added tert-butyldimethylsilyl chloride (3.1 g, 20.8 mmol). The mixture was stirred at 60° C. for 1 hour then cooled to RT and extracted with tert-butyl methyl ether. The combined organic layers were dried over anhydrous $Na_2SO_4$, filtered, and concentrated to give methyl 3-((tert-butyldimethylsilyl)oxy)-5-fluoro-2-methylbenzoate (5.2 g crude) as a yellow oil which was used for the next step without further purification.

To a solution of methyl 3-((tert-butyldimethylsilyl)oxy)-5-fluoro-2-methylbenzoate (3.2 g, 10.7 mmol) in carbon tetrachloride (30 mL) at RT was added NBS (2.9 g, 16.1 mmol) and 2,2'-azobis(2-methylpropionitrile) (700 mg, 4.3 mmol). The mixture was stirred at 80° C. for 6 hrs. The solvent was evaporated to give the crude product which was purified by silica gel chromatography (petroleum ether/EtOAc, 10:1) to afford methyl 2-(bromomethyl)-3-((tert-butyldimethylsilyl)oxy)-5-fluorobenzoate (4.0 g, quant. yield) as a yellow oil.

To a solution of methyl 2-(bromomethyl)-3-((tert-butyldimethylsilyl)oxy)-5-fluorobenzoate (1.0 g, 2.66 mmol) and TEA (0.7 mL, 5.32 mmol) in DMF (6 mL) at RT was added tert-butyl 4,5-diamino-5-oxopentanoate (696 mg, 2.92 mmol) in 4 mL DMF. The mixture was stirred for 2 hrs, then heated to 80° C. overnight. The solvent was evaporated to give the crude product which was purified by silica gel chromatography (DCM/MeOH, 50:1 to 20:1) to afford tert-butyl 5-amino-4-(6-fluoro-4-hydroxy-1-oxoisoindolin-2-yl)-5-oxopentanoate (1.0 g crude) as a white solid. MS (ESI) m/z 297.0 $[M+H-56]^+$.

To a solution of tert-butyl 5-amino-4-(6-fluoro-4-hydroxy-1-oxoisoindolin-2-yl)-5-oxopentanoate (500 mg, 1.42 mmol), 4-(hydroxymethyl)benzonitrile (283 mg, 2.13 mmol) and triphenylphosphine (930 mg, 3.55 mmol) in THF (4 mL) at RT was added DEAD (617 mg, 3.55 mmol). The mixture was stirred at RT for 2 hrs. The solvent was evaporated, and the residue was purified by silica gel chromatography (DCM/MeOH, 100:1 to 50:1) to give tert-butyl 5-amino-4-(4-((4-cyanobenzyl)oxy)-6-fluoro-1-oxoisoindolin-2-yl)-5-oxopentanoate (350 mg, 52% yield) as a yellow solid. MS (ESI) m/z 412.0 $[M+H-56]^+$.

To a solution of tert-butyl 5-amino-4-(4-((4-cyanobenzyl)oxy)-6-fluoro-1-oxoisoindolin-2-yl)-5-oxopentanoate (350 mg, 0.75 mmol) in DCM (4 mL) at RT was added TFA (4 mL). The mixture was stirred at RT overnight. The solvent was evaporated to give 5-amino-4-(4-((4-cyanobenzyl)oxy)-6-fluoro-1-oxoisoindolin-2-yl)-5-oxopentanoic acid (400 mg, crude) as a yellow solid which was used for the next step without further purification. MS (ESI) m/z 412.0 $[M+H]^+$.

To a solution of 5-amino-4-(4-((4-cyanobenzyl)oxy)-6-fluoro-1-oxoisoindolin-2-yl)-5-oxopentanoic acid (400 mg, 0.75 mmol) in ACN (10 mL) at RT was added CDI (485 mg, 2.99 mmol). The mixture was stirred at 95° C. for 3.5 hrs. The solvent was evaporated to give the crude product which was purified by silica gel chromatography (DCM/MeOH, 100:1 to 50:1) to afford 4-(((2-(2,6-dioxopiperidin-3-yl)-6-fluoro-1-oxoisoindolin-4-yl)oxy)methyl)benzonitrile (200 mg, 68%) as a white solid. MS (ESI) m/z 394.0 $[M+H]^+$.

To a solution of 4-(((2-(2,6-dioxopiperidin-3-yl)-6-fluoro-1-oxoisoindolin-4-yl) oxy)methyl)benzonitrile (200 mg, 0.51 mmol) and di-tert-butyl dicarbonate (166 mg, 0.76 mmol) in THF (6 mL) at RT was added Raney-Ni (80 mg). The mixture was stirred at RT under $H_2$ overnight. The suspension was filtered through a Celite pad and the filtrate was concentrated to give the crude product which was purified by silica gel chromatography (DCM/MeOH, 100:1 to 20:1) to afford tert-butyl 4-(((2-(2,6-dioxopiperidin-3-yl)-6-fluoro-1-oxoisoindolin-4-yl)oxy)methyl)benzylcarbamate (90 mg, 35% yield) as a white solid. MS (ESI) m/z 398.0 $[M+H-100]^+$.

To a solution of tert-butyl 4-(((2-(2,6-dioxopiperidin-3-yl)-6-fluoro-1-oxoisoindolin-4-yl)oxy) methyl)benzylcarbamate (80 mg, 0.161 mmol) in DCM (4 mL) at RT was added TFA (1 mL). The reaction was stirred for 1 hour. The solvent was evaporated, and the residue was dried to give the amine TFA salt as a yellow gum.

The amine TFA salt was dissolved in DMA (1 mL) and 2-((3-(4-((4-((3-(N-(tert-butyl) sulfamoyl)phenyl)amino)-5-methylpyrimidin-2-yl)amino)phenoxy)propyl) amino)acetic acid (109 mg, 0.161 mmol) was added, followed by HOBt (32.6 mg, 0.242 mmol), EDAC.HCl (46.5 mg, 0.242 mmol) and DIEA (41.5 mg, 0.322 mmol) and the mixture was stirred at RT for 10 hrs. The solvent was evaporated, and the residue was purified by prep-HPLC as previously described to afford Compound 25 (23.9 mg, 16% yield) as a white solid. MS (ESI) m/z 922.3$[M+H]^+$. $^1$H NMR (400 MHz, DMSO-$d_6$) δ 10.96 (s, 1H), 8.75 (s, 1H), 8.52 (s, 1H), 8.29 (t, J=6.4 Hz, 1H), 8.14-8.11 (m, 2H), 7.88 (s, 1H), 7.55-7.23 (m, 10H), 7.10-7.08 (m, 1H), 6.77 (d, J=5.2 Hz, 2H), 5.19 (s, 2H), 5.08 (dd, J=8.4, 13.6 Hz, 1H), 4.37-4.18 (m, 4H), 3.95 (t, J=6.4 Hz, 1H), 3.16 (s, 2H), 2.93-2.83 (m, 1H), 2.66-2.57 (m, 3H), 2.11 (s, 3H), 2.02-1.93 (m, 1H), 1.86-1.79 (m, 3H), 1.12 (s, 9H).

Example 27

Compound 26: (S)-3-(4-{2-[p-(Morpholinomethyl)phenyl]ethoxy}-2-isoindolinoyl)-2,7-azepanedione

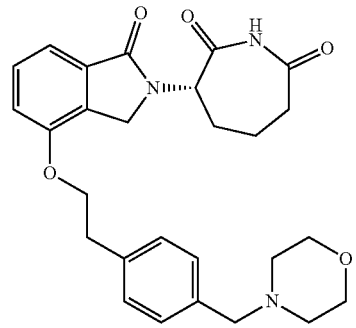 [SMILES: O=C1CCC[C@H](N2Cc3c(OCCc4ccc(CN5CCOCC5)cc4)cccc3C2=O)C(=O)N1]

To a solution of methyl 4-(2-methoxy-2-oxoethyl)benzoate (5 g, 0.24 mol) in THF (25 mL) at 0° C. was added lithium aluminium hydride (IM solution in THF, 36 mL) dropwise. The mixture was stirred at 0° C. for 2 hrs then the reaction was quenched by $Na_2SO_4$ decahydrate, diluted with EtOAc and filtered. The filtrate was washed with brine, dried over anhydrous $Na_2SO_4$, filtered, and concentrated to give 2-(4-(hydroxymethyl)phenyl)ethanol (3 g, crude) as a yellow oil. $^1$H NMR (400 MHz, DMSO-$d_6$) δ 7.13-7.23 (m, 4H), 5.08 (t, J=5.6 Hz, 1H), 4.61 (t, J=5.2, 8.4 Hz, 1H), 4.44 (d, J=7.0 Hz, 2H), 3.54-3.59 (m, 2H), 2.69 (t, J=7.2 Hz, 2H).

To a stirred solution of 2-(4-(hydroxymethyl)phenyl)ethanol (3 g, crude, 19.7 mmol) in chloroform (30 mL) was added manganese dioxide (6.9 g, 79 mmol). The mixture was stirred at 70° C. overnight then filtered and concentrated. The residue was purified by silica gel chromatography (petroleum/EtOAc, 5:1) to give 4-(2-hydroxyethyl)benzaldehyde (1.3 g, 38% over 2 steps) as a yellow oil. $^1$H NMR (300 MHz, CDCl₃) δ 9.90 (s, 1H), 7.76 (d, J=8.0 Hz, 2H), 7.34 (d, J=8.0 Hz, 2H), 3.84 (t, J=6.4 Hz, 2H), 2.88 (t, J=6.4 Hz, 2H).

To a stirred solution of 4-(2-hydroxyethyl)benzaldehyde (1.3 g, 8.67 mmol) in DCM (20 mL) was added tosyl chloride (2.5 g, 13 mmol) and TEA (4.8 mL). The mixture was stirred at RT overnight then evaporated and purified by silica gel chromatography (petroleum/EtOAc, 5:1) to give 4-formylphenethyl 4-methylbenzenesulfonate (2 g, 77% yield) as a white solid.

To a stirred solution of (S)-4-hydroxy-2-(2-oxoazepan-3-yl)isoindolin-1-one (250 mg, 0.96 mmol) and 4-formylphenethyl 4-methylbenzenesulfonate (392 mg, 1.15 mmol) in ACN (5 mL) at RT was added K₂CO₃ (400 mg, 2.88 mmol). After stirring at 80° C. overnight, the mixture was concentrated, and the residue was purified by silica gel chromatography (DCM/MeOH, 50:1) to give (S)-4-(2-((1-oxo-2-(2-oxoazepan-3-yl)isoindolin-4-yl)oxy)ethyl)benzaldehyde (100 mg, 27% yield) as a colorless oil. MS (ESI) m/z=393.1 [M+H]⁺.

To a solution of (S)-4-(2-((1-oxo-2-(2-oxoazepan-3-yl)isoindolin-4-yl)oxy)ethyl)benzaldehyde (100 mg, 0.25 mmol) in 1,2-dichloroethane (6 mL) and DMSO (1 mL) at RT was added Dess-Martin reagent (530 mg, 1.25 mol). The mixture was stirred at 80° C. overnight then cooled to RT and filtered. The filtrate was quenched with sat. sodium thiosulfate solution and extracted with DCM. Workup and purification by prep-TLC (EtOAc) to give (S)-4-(2-((2-(2,7-dioxoazepan-3-yl)-1-oxoisoindolin-4-yl)oxy)ethyl)benzaldehyde (40 mg, 38% yield) as a white solid. MS (ESI) m/z=407.0 [M+H]⁺.

To a solution of (S)-4-(2-((2-(2,7-dioxoazepan-3-yl)-1-oxoisoindolin-4-yl)oxy)ethyl)benzaldehyde (40 mg, 0.1 mmol) and morpholine (26 mg, 0.3 mmol) in DCM (5 mL) at RT was added sodium triacetoxyborohydride (106 mg, 0.5 mmol). The mixture was stirred overnight then concentrated. The residue was purified by prep-HPLC as previously described to afford Compound 26 (18 mg, 38% yield) as a white solid. MS (ESI) m/z=478.1 [M+H]⁺. ¹H NMR (400 MHz, DMSO-d₆) δ 10.72 (s, 1H), 7.45 (t, J=8.0 Hz, 1H), 7.23-7.30 (m, 6H), 5.22 (dd, J=4.8, 12.4 Hz, 1H), 4.36 (s, 2H), 4.32 (t, J=6.8 Hz, 2H), 3.55 (t, J=4.4 Hz, 4H), 3.41 (s, 2H), 3.03-3.08 (m, 3H), 2.59-2.60 (m, 1H), 2.29-2.32 (m, 5H), 1.99-2.10 (m, 2H), 1.74-1.84 (m, 1H).

Example 28

Compound 27: (S)-3-[5-({3-[3-(p-{5-Methyl-4-[m-(tert-butylaminosulfonyl)phenylamino]-2-pyrimidinylamino}phenoxy)propyl]ureido}methyl)-4-{[p-(morpholinomethyl)phenyl]methoxy}-2-isoindolinoyl]-2,7-azepanedione

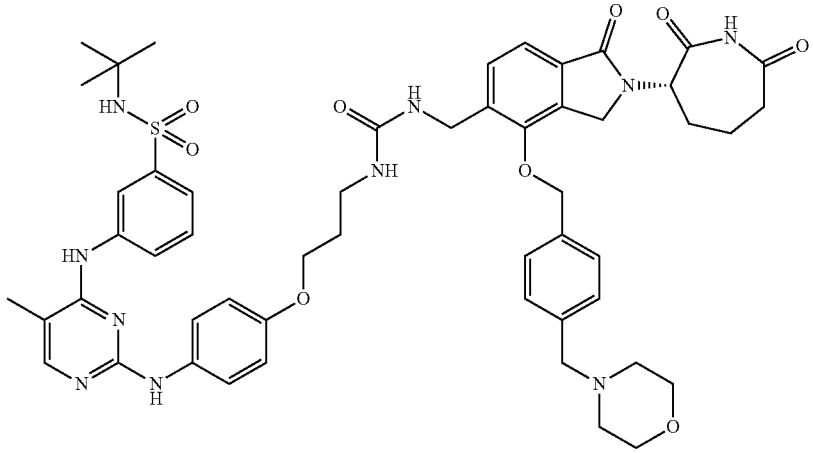 [SMILES: Cc1cnc(Nc2ccc(OCCCNC(=O)NCc3ccc4c(c3OCc3ccc(CN5CCOCC5)cc3)CN([C@H]3CCCC(=O)NC3=O)C4=O)cc2)nc1Nc1cccc(S(=O)(=O)NC(C)(C)C)c1]

To a solution of (S)-3-(5-(aminomethyl)-4-((4-(morpholinomethyl)benzyl) oxy)-1-oxoisoindolin-2-yl)azepane-2,7-dione (50 mg, 0.084 mmol) in THF (5 mL) at RT was added TEA (68 mg, 0.672 mmol) followed by a suspension of 4-nitrophenyl (3-(4-((4-((3-(N-(tert-butyl) sulfamoyl)phenyl)amino)-5-methylpyrimidin-2-yl)amino)phenoxy)propyl) carbamate (54 mg, 0.084 mmol) in THF (1 mL). The mixture was stirred for 3 hrs. The solvent was evaporated, and the residue was purified by silica gel chromatography eluting with DCM/MeOH from 0% to 10% to give the crude product (70 mg) as a white gum, which was further purified by prep-HPLC as previously described to afford Compound 27 (27.7 mg, 33% yield) as a white solid. MS (ESI) m/z 1003.4[M+H]⁺. ¹H NMR (400 MHz, DMSO-d₆) δ 10.70 (s, 1H), 8.76 (s, 1H), 8.53 (s, 1H), 8.13 (s, 1H), 7.90 (s, 1H), 7.59-7.38 (m, 9H), 7.34 (d, J=8.0 Hz, 2H), 6.79 (d, J=8.8 Hz, 2H), 6.34 (t, J=6.0 Hz, 1H), 6.13 (t, J=5.6 Hz, 1H), 5.23 (dd, J=4.8, 12.0 Hz, 1H), 5.18 (s, 2H), 4.65 (s, 2H), 4.33 (d, J=5.2 Hz, 2H), 3.92 (t, J=6.0 Hz, 2H), 3.58-3.55 (m, 4H), 3.47 (s, 2H), 3.20-3.15 (m, 2H), 3.12-3.04 (m, 1H), 2.60-2.56 (m, 1H), 2.35-2.31 (m, 5H), 2.12 (s, 3H), 2.08-1.99 (m, 1H), 1.86-1.78 (m, 4H), 1.12 (s, 9H).

PBMC Assays

Frozen primary blood mononuclear cells (PBMCs) were purchased from AllCells. Cells were quick thawed, washed once with RPMI-1640/10% FBS.

1% Penicillin/1% Streptomycin and plated in 96 well plates at 200,000 cells per well. Cells were pretreated with DMSO only, or Compound 1 for 1 hour and then induced with 100 ng/mL lipopolysaccharide (LPS) for 18-24 hrs. The supernatant was analyzed for IL-1 beta, IL-6, and TNFα, using Meso Scale assay according to manufacturer's protocol. The negative control wells were treated with DMSO.

For the IL-2 analysis, 96 well plates were precoated with 1 μg/mL anti-human CD3 antibody (OKT3, eBioscience Inc.). After washing with PBS, Compound 1 was added (50 μL/well) followed by PBMCs diluted at 3-4 million cells/mL (150 μL/well). Plates were incubated for 24 hr and the supernatants collected for Mesoscale IL-2 analysis.

Figure 2:
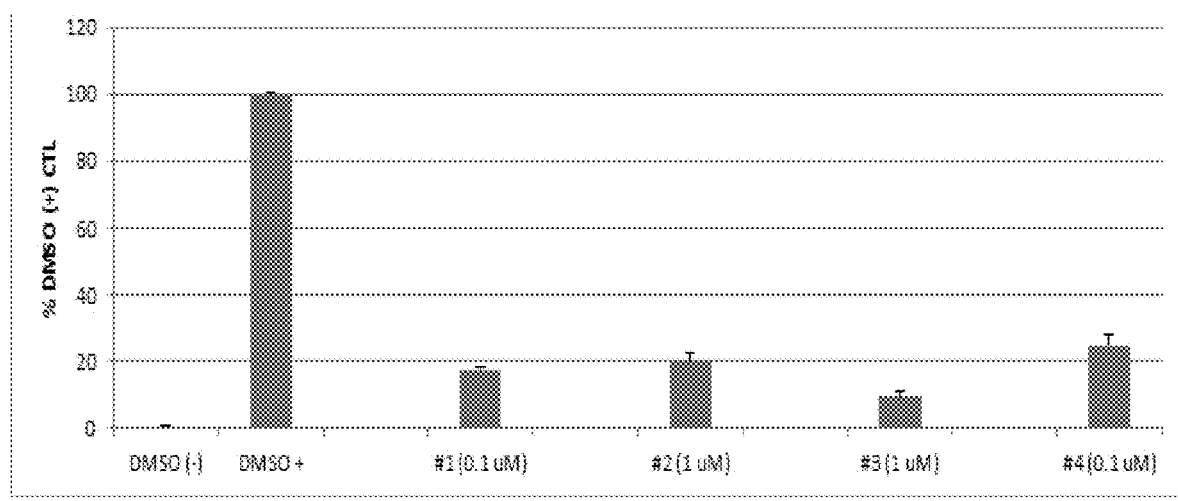
FIG. 2 represents the activity against IL-6 in peripheral blood mononuclear cells (PBMCs), plated in 96 well plates and pretreated with compound for 1 hour and then induced with 100 ng/mL LPS for 18-24 hrs. Cytokines were measured according to MesoScale protocol. Negative control wells were treated with DMSO. Compound activity was measured as a percentage of LPS-induced activity.
Figure 3:
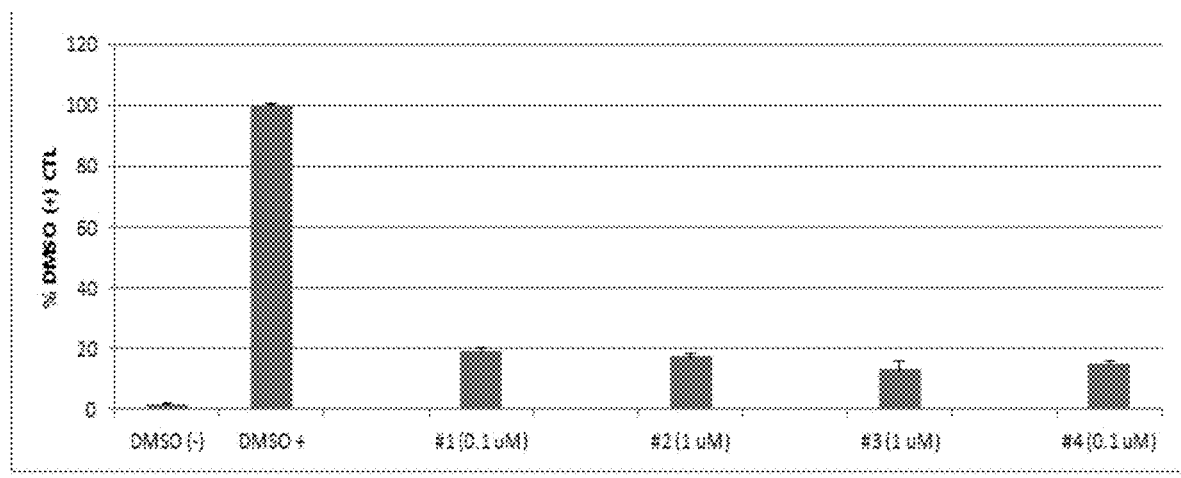
FIG. 3 represents the activity against TNFα in peripheral blood mononuclear cells (PBMCs), plated in 96 well plates and pretreated with compound for 1 hour and then induced with 100 ng/mL LPS for 18-24 hrs. Cytokines in the media were measured according to MesoScale protocol. The negative control wells were treated with DMSO. Compound activity is measured as a percentage of LPS-induced activity.
Figure 4:
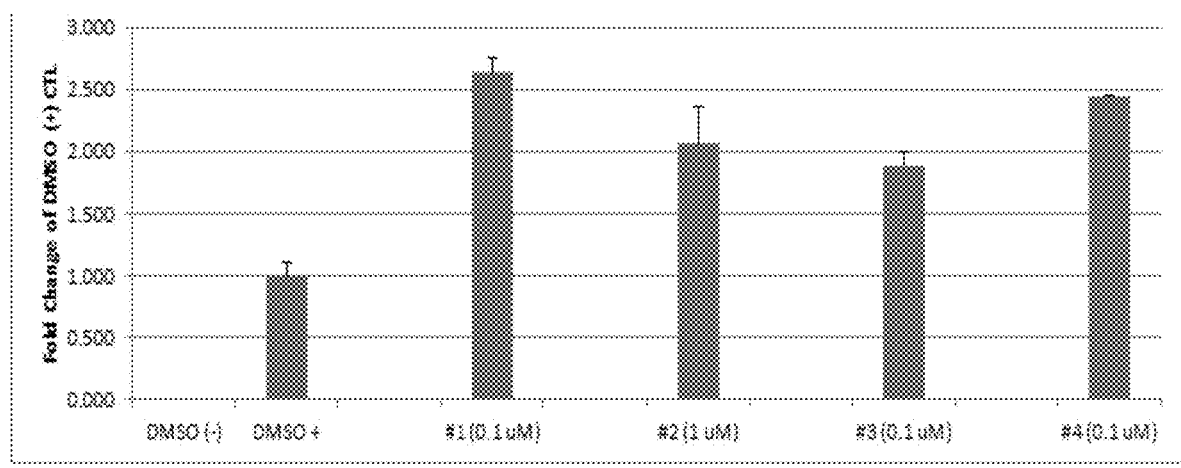
FIG. 4 represents Anti-CD3-induced IL-2 secretion in PBMCs. 1 μg/mL anti-CD3 (OKT-3) antibody in PBS coated onto 96-well plates overnight at 4° C. Approximately, 550,000 PBMCs were added to each well, followed by addition of DMSO only (control) or Compound 1. Induction was measured after 24 hrs as fold difference from the DMSO stimulated control.

Compound activity was measured as fold difference from the DMSO control. IL-1β activity is shown in FIG. 1; IL-6 activity is shown in FIG. 2; TNFα activity is shown in FIG. 3; and IL-2 activity is shown in FIG. 4. Additional data for compounds (shown as percent inhibition) at 10 μM is shown in Table 1; at 1 μM in Table 2; and at 0.1 μM in Table 3. Additional data for IL-activity (measured as fold-change in activity) is shown in Tables 4-6.

TABLE 1

| Compound No. | IL-1β % Inhibition | IL-6 % Inhibition | TNFα % Inhibition |
|---|---|---|---|
| 3 | 93 | 77 | 94 |
| 12 | 99.6 | 100 | 99 |
| 14 | 65 | 42 | 83 |
| 15 | 81 | 50 | 87 |
| 16 | 52 | 78 | 75 |
| 17 | 100 | 100 | 100 |
| 18 | 83 | 45 | 89 |
| 21 | 11 | 7 | 30 |
| 24 | 23 | 1 | 23 |
| 28 | 5 | 2 | 5 |

TABLE 2

| Compound No. | IL-1β % Inhibition | IL-6 % Inhibition | TNFα % Inhibition |
|---|---|---|---|
| 1 | 88 | 71 | 93 |
| 2 | 86 | 67 | 90 |
| 3 | 93 | 79 | 93 |
| 4 | 86 | 67 | 90 |
| 6 | 92 | 76 | 83 |
| 12 | 23 | 0 | 32 |
| 13 | 51 | 59 | 84 |
| 14 | 76 | 37 | 82 |
| 15 | 59 | 10 | 65 |
| 16 | 24 | 5 | 27 |
| 17 | 75 | 35 | 75 |
| 18 | 80 | 49 | 83 |
| 19 | 65 | 43 | 73 |
| 20 | 43 | 5 | 57 |
| 21 | 6 | 8 | 20 |
| 22 | 74 | 27 | 80 |
| 23 | 79 | 32 | 88 |
| 24 | 7 | 9 | 10 |
| 25 | 8 | 32 | 25 |
| 26 | 81 | 8 | 87 |
| 27 | 62 | 4 | 72 |
| 28 | 6 | 5 | 9 |
| 29 | 2 | 11 | 11 |

TABLE 3

| Compound No. | IL-1β % Inhibition | IL-6 % Inhibition | TNFα % Inhibition |
|---|---|---|---|
| 1 | 83 | 63 | 89 |
| 2 | 72 | 43 | 81 |
| 3 | 91 | 72 | 91 |
| 4 | 72 | 43 | 81 |
| 5 | 64 | 37 | 55 |
| 6 | 68 | 42 | 62 |
| 7 | 71 | 55 | 62 |
| 8 | 73 | 56 | 63 |
| 9 | 74 | 51 | 62 |
| 10 | 52 | 27 | 48 |
| 11 | 21 | 12 | 21 |
| 19 | 22 | 12 | 41 |
| 20 | 30 | 1 | 43 |
| 22 | 69 | 23 | 78 |
| 23 | 35 | 23 | 48 |
| 25 | 0 | 3 | 13 |
| 26 | 78 | 5 | 82 |
| 27 | 50 | 5 | 60 |
| 29 | 0 | 11 | 12 |

TABLE 4

IL-2 Compound 10 μM

| Compound No. | Fold Change |
|---|---|
| 12 | 0.7 |
| 13 | 0.1 |
| 14 | 2.3 |
| 15 | 2.1 |
| 16 | 0.2 |
| 17 | 0.1 |
| 18 | 3.3 |
| 21 | 1 |
| 24 | 1 |
| 28 | 1.9 |

TABLE 5

IL-2 Compound at 1 μM

| Compound No. | Fold Change |
|---|---|
| 1 | 0.8 |
| 2 | 2.3 |
| 3 | 0.7 |
| 4 | 2.3 |
| 5 | 2.1 |
| 6 | 2.5 |
| 7 | 1.1 |
| 8 | 2.3 |
| 9 | 1.6 |
| 10 | 2.1 |
| 11 | 1.9 |
| 12 | 1 |
| 13 | 0.3 |
| 14 | 2.2 |
| 15 | 1.9 |
| 16 | 0.7 |
| 17 | 1.5 |
| 18 | 3.2 |
| 19 | 2.4 |
| 20 | 1.4 |
| 21 | 0.9 |
| 22 | 2.4 |
| 23 | 1.3 |
| 24 | 1 |
| 25 | 1 |
| 26 | 2.7 |
| 27 | 1.5 |
| 28 | 1.5 |
| 29 | 0.9 |

TABLE 6

IL-2
Compound at 0.1 µM

| Compound No. | Fold Change |
|---|---|
| 1 | 2.1 |
| 2 | 1.3 |
| 3 | 2 |
| 4 | 1.3 |
| 5 | 1.2 |
| 6 | 1 |
| 7 | 1 |
| 8 | 1.8 |
| 9 | 1.6 |
| 10 | 1.9 |
| 11 | 1.2 |
| 19 | 1.5 |
| 20 | 0.9 |
| 22 | 2 |
| 23 | 0.9 |
| 25 | 0.9 |
| 26 | 2.6 |
| 27 | 1.3 |
| 29 | 0.9 |

Western Blot Analysis

Western Blot Protocol: Jurkat cells were grown in RPMI 1640 supplemented with streptomycin, penicillin and 10% fetal bovine serum.

Jurkat cells were cultured at approximately $10^6$ cells per mL, DMSO or the indicated compound at the indicated concentration was added to the cells and allowed to incubate for the indicated period. Whole cell extracts were prepared with RIPA Reagent according to manufacturer's protocol (Pierce). Briefly, ~$5\times10^6$ cells were washed once in PBS, the cell pellet was resuspended in RIPA solution and allowed to incubate for 10 min at room temperature. Cell debris was removed by centrifugation and the cleared whole cell lysate was transferred to a new tube for further analysis.

Figure 5A:
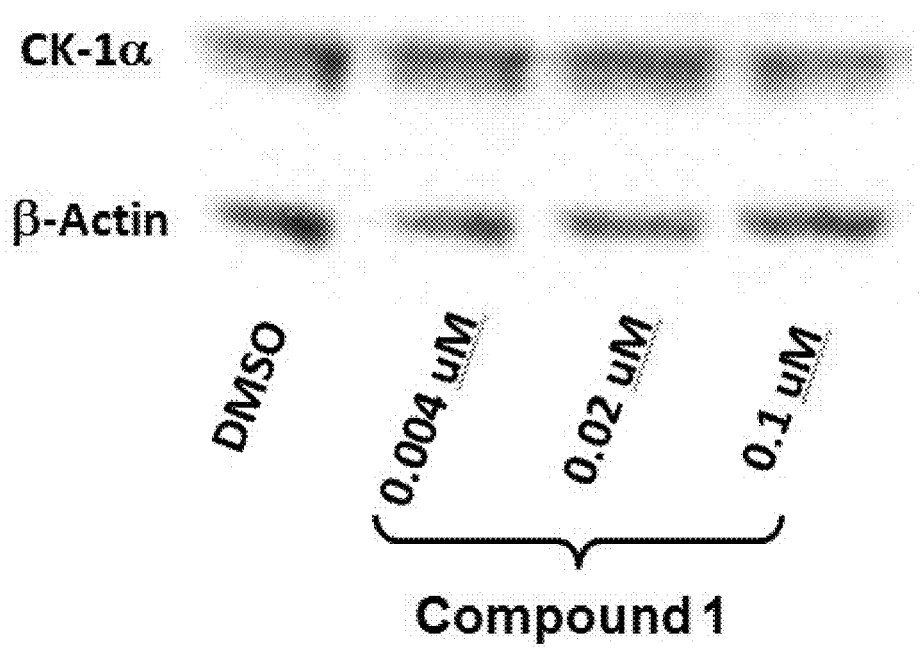
FIG. 5A represents a Western Blot from Jurkat cells treated with Control (DMSO only), or the indicated concentration of Compound 1. Cells were lysed using RIPA Buffer (Pierce) and a Western Blot was performed using anti-casein kinase 1 alpha, (CK1-α) and anti-β-actin antibodies.
Figure 5B:
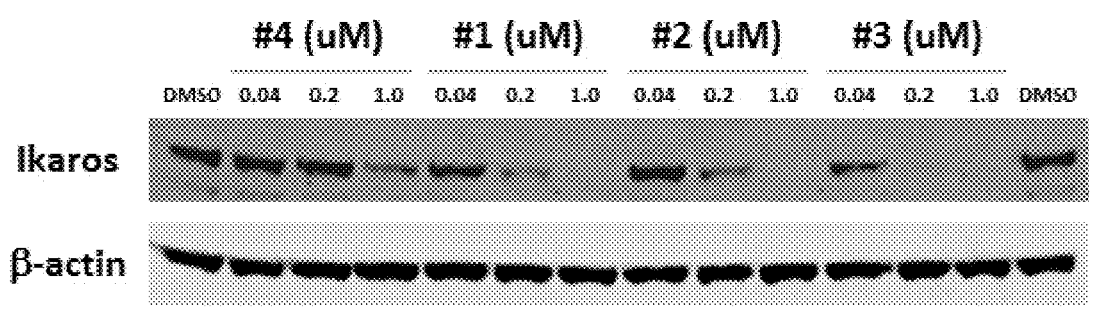
FIG. 5B represents a Western Blot from Jurkat cells treated with Control (DMSO only), or the indicated concentration of Compound 1, 2, 3, or 4. Cells were lysed using RIPA Buffer (Pierce) and a Western Blot was performed using anti-ikaros and anti-β-actin antibodies.

For Western blot analysis, whole cell extracts were separated on 4-12% SDS-polyacrylamide gels, transferred to nitrocellulose and probed with the indicated primary antibodies. Membranes were subsequently washed and probed with the appropriate horseradish peroxidase (HRP)-conjugated secondary antibody. The signal was detected using the WesternBright Sirius Reagent (Advansta). Results are shown in FIG. 5A and FIG. 5B.

The following antibodies were used in these studies: Beta-actin: Mouse anti-b-Actin was obtained from Cell Signaling (8H10D10). CK1α goat polyclonal antibody: Santa Cruz Biotechnology, sc-6477 (Santa Cruz, Calif.) Ikaros rabbit monoclonal antibody: Cell Signaling, #9034, D10E5 (Danver, Mass.) Donkey anti-goat IgG-HRP: Santa Cruz Biotechnology, sc-2056 (Santa Cruz, Calif.) Goat anti-rabbit IgG-HRP: Cell Signaling, #7074 (Danver, Mass.) Goat anti-mouse IgG-HRP: Sigma, A4416 (St. Louis, Mo.)

Cell Viability Assay

Molm-13 and MV-4-11 cells were cultivated in RPMI-1640 (10% FBS/1% pen-strep) and were plated in white walled 96-well plates at 20,000 cells/well.

Cells were treated with compound at the indicated concentration or DMSO (control) and the cultures were incubated for 3 days at 37° C. and 5% $CO_2$. Following the incubation period, 100 µL of CellTiterGlow (CTG) reagent (CellTiter-Glo® Luminescent Cell Viability Assay, Promega (Madison, Wis.)) was added to each well. Following a 10 min incubation with shaking, luminescence was measured using a Victor Wallac Luminometer.

Molm-13 cellular proliferation activity is shown in Tables 7-9. MV-4-11 cellular proliferation activity in shown in Tables 10 and 11.

TABLE 7

Molm-13 Proliferation
Compound at 10 µM

| Compound No. | % Inhibition |
|---|---|
| 1 | 37 |
| 2 | 30 |
| 3 | 29 |
| 5 | 40 |
| 6 | 91 |
| 8 | 16 |
| 9 | 34 |
| 10 | 38 |
| 18 | 99 |

TABLE 8

Molm-13 Proliferation
Compound at 1 µM

| Compound No. | % Inhibition |
|---|---|
| 1 | 15 |
| 2 | 5 |
| 3 | 1 |
| 13 | 29 |
| 14 | 35 |
| 20 | 99 |
| 22 | 56 |
| 23 | 30 |
| 26 | 66 |
| 27 | 37 |

TABLE 9

Molm-13 Proliferation
Compound at 0.1 µM

| Compound No. | % Inhibition |
|---|---|
| 1 | 30 |
| 20 | 93 |
| 22 | 31 |
| 26 | 21 |

TABLE 10

MV-4-11 Proliferation
Compound at 10 µM

| Compound No. | % Inhibition |
|---|---|
| 1 | 5 |
| 2 | 16 |
| 3 | 20 |
| 4 | 0 |
| 5 | 3 |
| 6 | 76 |
| 7 | 0 |
| 8 | 0 |
| 9 | 10 |
| 10 | 35 |
| 11 | 0 |
| 12 | 35 |

TABLE 10-continued

MV-4-11 Proliferation
Compound at 10 μM

| Compound No. | % Inhibition |
| --- | --- |
| 13 | 50 |
| 14 | 0 |
| 15 | 99 |
| 16 | 99 |
| 17 | 98 |
| 18 | 99 |
| 19 | 0 |
| 20 | 88 |
| 21 | 97 |
| 22 | 4 |
| 23 | 79 |
| 24 | 80 |
| 25 | 90 |
| 26 | 23 |
| 27 | 36 |

TABLE 11

MV-4-11 Proliferation
Compound at 1 μM

| Compound No. | % Inhibition |
| --- | --- |
| 1 | 2 |
| 2 | 6 |
| 3 | 0 |
| 4 | 0 |
| 5 | 1 |
| 6 | 0 |
| 7 | 0 |
| 8 | 0 |
| 9 | 2 |
| 10 | 1 |
| 11 | 0 |
| 12 | 0 |
| 13 | 0 |
| 14 | 0 |
| 15 | 38 |
| 16 | 0 |
| 17 | 31 |
| 18 | 99 |
| 19 | 0 |
| 20 | 77 |
| 21 | 0 |
| 22 | 2 |
| 23 | 8 |
| 24 | 44 |
| 25 | 54 |
| 26 | 2 |
| 27 | 10 |

While the disclosure has been illustrated and described in detail in the drawings and foregoing description, such illustration and description are to be considered illustrative or exemplary and not restrictive. The disclosure is not limited to the disclosed embodiments. Variations to the disclosed embodiments can be understood and effected by those skilled in the art in practicing the claimed disclosure, from a study of the drawings, the disclosure and the appended claims.

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated.

Where a range of values is provided, it is understood that the upper and lower limit, and each intervening value between the upper and lower limit of the range is encompassed within the embodiments.

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

What is claimed is:

1. A method of treating or ameliorating a disease, disorder, or condition associated with the malfunction of a protein in a subject, comprising administering a therapeutically effective amount of a compound of Formula (I) or a pharmaceutically acceptable salt thereof to the subject in need thereof, wherein the protein is aiolos, ikaros, helios, CK1α, IL-1β, IL-2, IL-6, or TNFα;

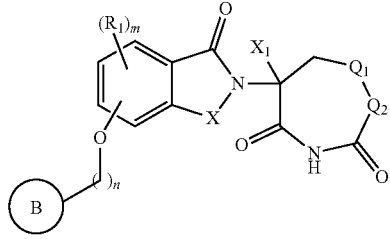

wherein:
$Q_1$ is $CH_2$ or a bond;
$Q_2$ is $CH_2$;
X is $CH_2$ or C=O;
$X_1$ is hydrogen, methyl, or fluoro;
ring B is

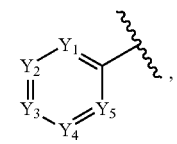

wherein $Y_1$ is N or $CR_{3A}$; $Y_2$ is N or $CR_{3B}$; $Y_3$ is N or $CR_{3C}$; $Y_4$ is N or $CR_{3D}$; and $Y_5$ is N or $CR_{3E}$; wherein at least one of $Y_1$, $Y_2$, $Y_3$, $Y_4$, and $Y_5$ is respectively $CR_{3A}$, $CR_{3B}$, $CR_{3C}$, $CR_{3D}$, or $CR_{3E}$; and wherein one or more of $R_{3A}$, $R_{3B}$, $R_{3C}$, $R_{3D}$, and $R_{3E}$ is not hydrogen;

each $R_1$ is independently deuterium, hydroxyl, halogen, nitro, substituted or unsubstituted amino, substituted or unsubstituted $C_1$-$C_6$ alkoxy, substituted or unsubstituted $C_1$-$C_6$ alkyl, substituted or unsubstituted $C_2$-$C_6$ alkenyl, substituted or unsubstituted $C_3$-$C_8$ cycloalkyl, substituted or unsubstituted 3 to 10 membered heterocyclyl, substituted or unsubstituted $C_6$-$C_{10}$ aryl, substituted or unsubstituted 5 to 10 membered heteroaryl, or L-Y;

each $R_{3A}$, $R_{3B}$, $R_{3C}$, $R_{3D}$, and $R_{3E}$ is independently hydrogen, deuterium, hydroxyl, halogen, nitro, substituted or unsubstituted amino, substituted or unsubstituted $C_1$-$C_6$ alkoxy, substituted or unsubstituted $C_1$-$C_6$ alkyl, substituted or unsubstituted $C_2$-$C_6$ alkenyl, substituted or unsubstituted $C_3$-$C_8$ cycloalkyl, substituted or unsubstituted 3 to 10 membered heterocyclyl, substituted or unsubstituted alkoxyalkyl, substituted or unsubstituted cycloalkylalkyl, substituted or unsubstituted heterocyclylalkyl, substituted or unsubstituted aralkyl, substituted or unsubstituted heteroaralkyl, or L-Y;

m is an integer of 0, 1, 2, or 3;
n is an integer of 1 or 2;
L is —$Z_1$—($R_4$)$_t$—$Z_2$—; —$Z_1$—($R_4$—O—$R_4$)$_t$—$Z_2$—; —$Z_1$—($R_4$—NH—$R_4$)$_t$—$Z_2$—; —$Z_1$—($R_4$—(NHCO)—$R_4$)$_t$—$Z_2$—; —$Z_1$—($R_4$—(NHC(O)NH)—$R_4$)$_t$—$Z_2$—; or —$Z_1$—($R_4$—(CONH)—$R_4$)$_t$—$Z_2$—;
each $Z_1$ and $Z_2$ is independently —NH—; —O—; —$CH_2$—; —NH(CO)—; —(CO)NH—; —$CH_2$NH—; —NHCH$_2$—; —(CO)NHCH$_2$—; —CH$_2$CH$_2$NH—; —CH$_2$NH(CO)—; or —NHCH$_2$CH$_2$—;
each $R_4$ is independently unsubstituted $C_1$-$C_6$ alkylene;
each t is independently an integer of 1, 2, 3, 4, 5, or 6; and
each Y is independently selected from the group consisting of

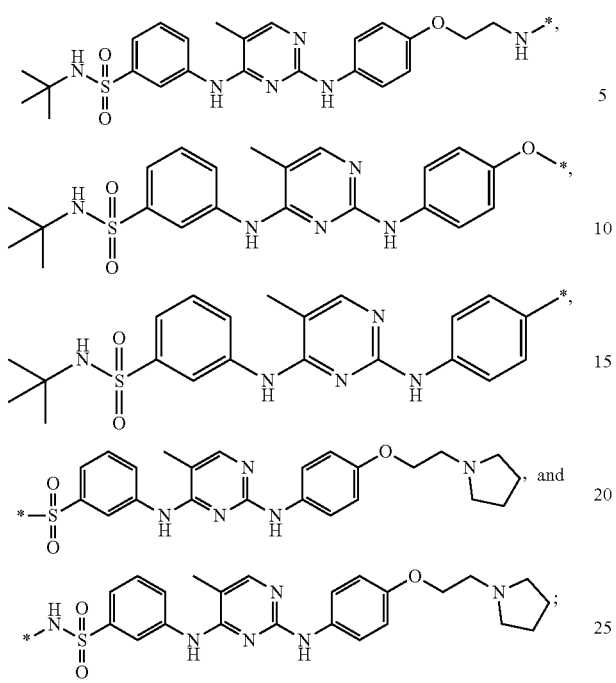

wherein * represents the point of attachment to the L group; and wherein, when $R_1$ is L-Y, then none of $R_{3A}$, $R_{3B}$, $R_{3C}$, $R_{3D}$, and $R_{3E}$ is L-Y; and when $Q_1$ is a bond and $X_1$ is hydrogen or methyl; then one of $R_1$, $R_{3A}$, $R_{3B}$, $R_{3C}$, $R_{3D}$, and $R_{3E}$ is L-Y.

2. The method of claim 1, wherein the disease, disorder, or condition is cancer.

3. The method of claim 1, wherein the cancer is selected from the group consisting of small cell lung cancer, non-small cell lung cancer, breast cancer, prostate cancer, head and neck cancer, pancreatic cancer, colon cancer, rectal cancer, teratoma, ovarian cancer, endometrial cancer, brain cancer, retinoblastoma, leukemia, skin cancer, melanoma, squamous cell carcinoma, liposarcoma, lymphoma, multiple myeloma, testicular cancer, liver cancer, esophageal cancer, kidney carcinoma, astrogliosis, relapsed/refractory multiple myeloma, and neuroblastoma.

4. The method of claim 1, wherein the disease, disorder, or condition is selected from the group consisting of inflammation, fibromyalgia, rheumatoid arthritis, osteoarthritis, ankylosing spondylitis, psoriasis, psoriatic arthritis, inflammatory bowel diseases, Crohn's disease, ulcerative colitis, uveitis, inflammatory lung diseases, chronic obstructive pulmonary disease, and Alzheimer's disease.

5. The method of claim 1, wherein m is an integer of 1 and $R_1$ is halogen, substituted or unsubstituted amino, substituted or unsubstituted $C_1$-$C_6$ alkoxy, substituted or unsubstituted $C_3$-$C_8$ cycloalkyl, or substituted or unsubstituted $C_1$-$C_6$ alkyl.

6. The method of claim 5, wherein $R_1$ is fluoro, chloro, —$NH_2$—, —$NH(CH_3)$, —$N(CH_3)_2$, —$CF_3$, —$OCH_3$, —$OCH_2CH_3$, —$OCH(CH_3)_2$, —$CH_3$, —$CH_2CH_3$, —$CH(CH_3)_2$, unsubstituted cyclopropyl, unsubstituted cyclobutyl, or unsubstituted cyclopentyl.

7. The method of claim 1, wherein ring B is:

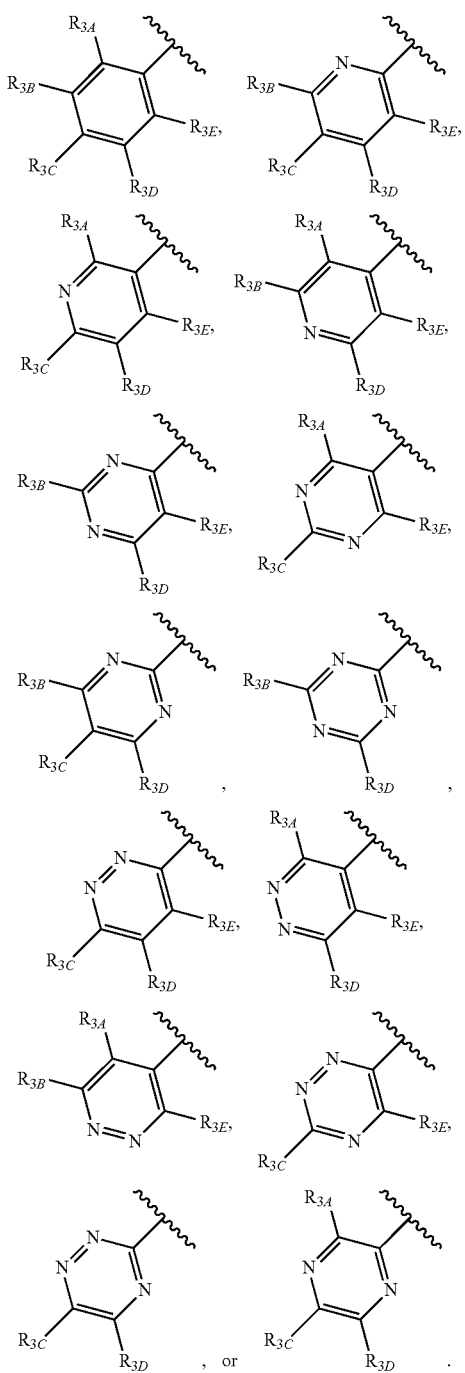

8. The method of claim 7, wherein each of $R_{3A}$, $R_{3B}$, $R_{3C}$, $R_{3D}$, and $R_{3E}$ is independently hydrogen, hydroxyl, halogen, nitro, unsubstituted amino, unsubstituted $C_1$-$C_6$ haloalkyl, unsubstituted $C_1$-$C_6$ alkoxy, unsubstituted $C_1$-$C_6$ alkyl, substituted or unsubstituted $C_3$-$C_8$ cycloalkyl, substituted or unsubstituted 3 to 10 membered heterocyclyl, substituted or unsubstituted alkoxyalkyl, substituted or unsubstituted cycloalkylalkyl, substituted or unsubstituted heterocyclylalkyl, substituted or unsubstituted aralkyl, or substituted or unsubstituted heteroaralkyl.

9. The method of claim 8, wherein ring B is

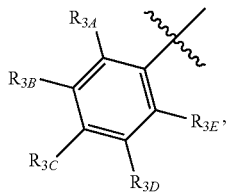

and one of $R_{3A}$, $R_{3B}$, $R_{3C}$, $R_{3D}$, and $R_{3E}$ is —CH$_2$NH$_2$,

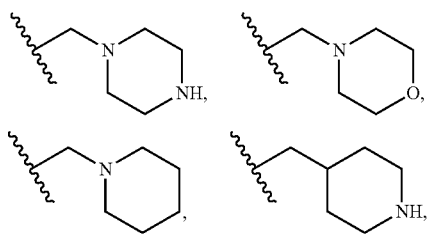

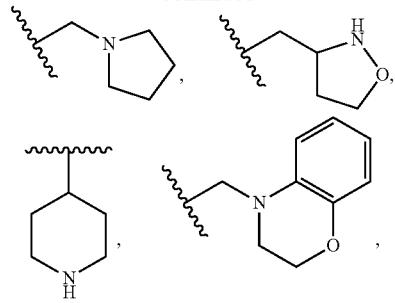

or L-Y, and the others of $R_{3A}$, $R_{3B}$, $R_{3C}$, $R_{3D}$, and $R_{3E}$ are each independently hydrogen or halogen.

10. The method of claim 9, wherein $R_{3C}$ is L-Y and L is —$Z_1$—(R$_4$—(NHCO)—R$_4$)$_t$—$Z_2$—; —$Z_1$—(R$_4$—(CONH)—R$_4$)$_t$—$Z_2$—; or —$Z_1$—(R$_4$—(NHC(O)NH)—R$_4$)$_t$—$Z_2$—.

11. The method of claim 10, wherein each $Z_1$ and $Z_2$ is independently —NH—; —O—; —CH$_2$—; —NH(CO)—; —(CO)NH—; —CH$_2$NH(CO)—; —CH$_2$NH—; —NHCH$_2$—, or —NHCH$_2$CH$_2$—.

12. The method of claim 9, wherein $R_{3C}$ is L-Y and wherein L-Y has a structure selected from the group consisting of:

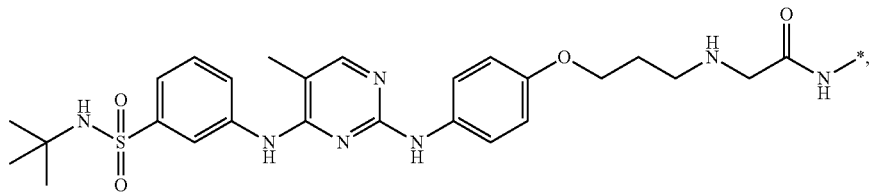

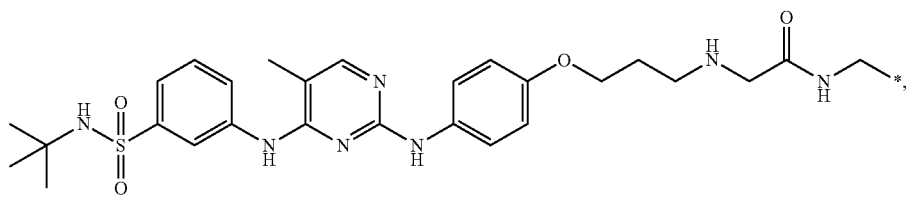

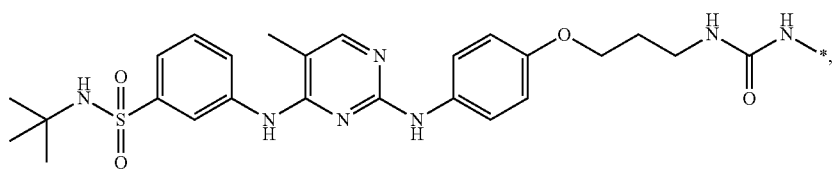

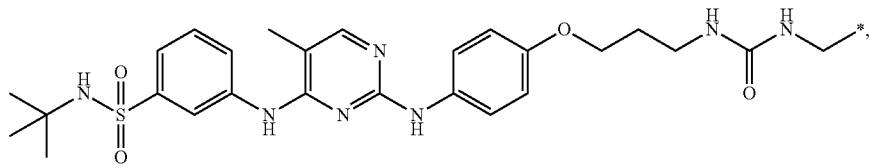

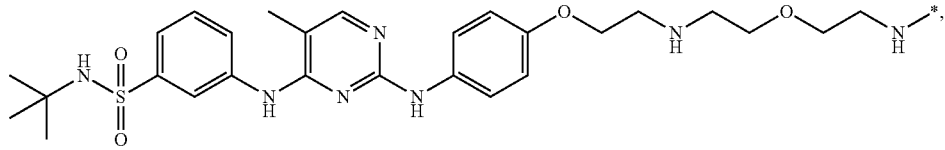

-continued
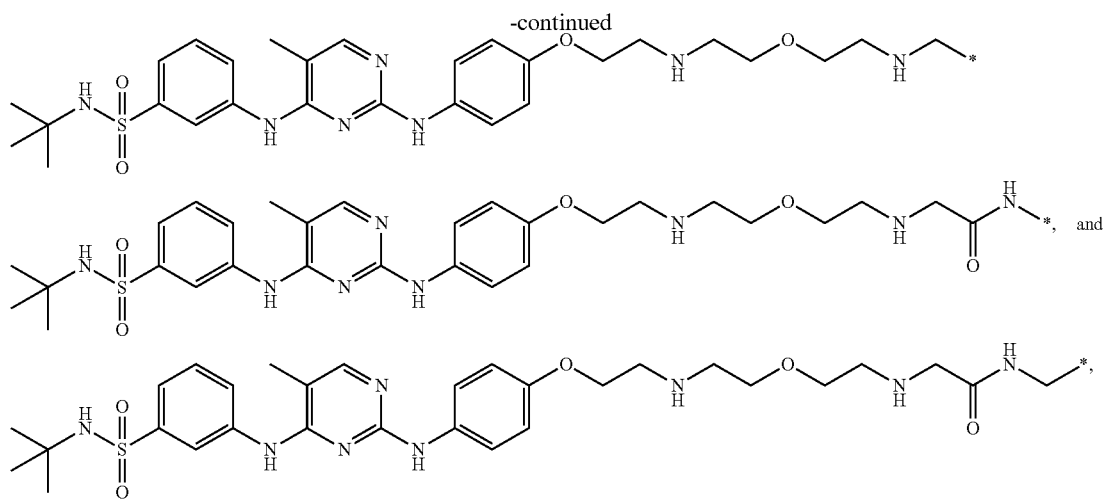
where "*" represents the point of connection of the L-Y moiety to ring B.
13. The method of claim 1, wherein the compound is selected from the group consisting of:
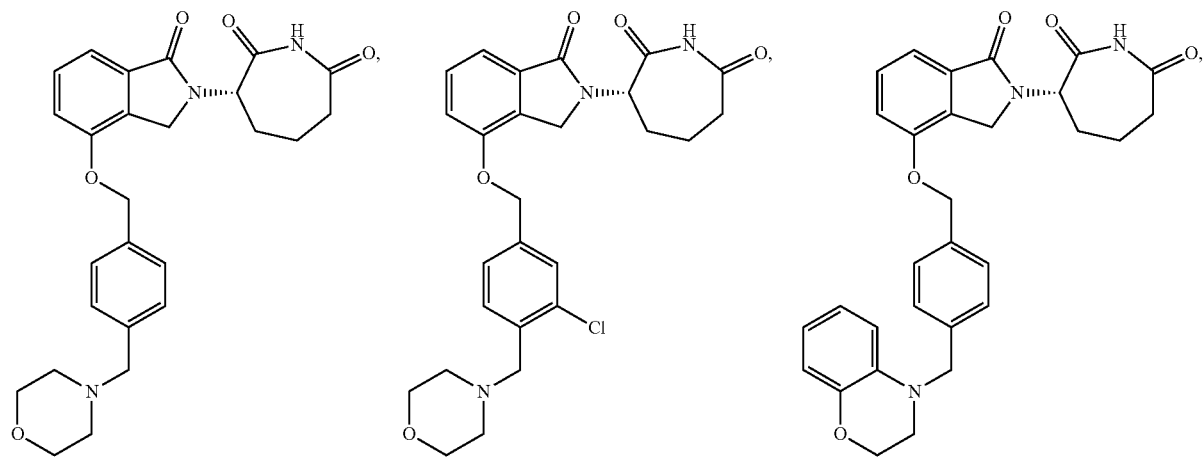
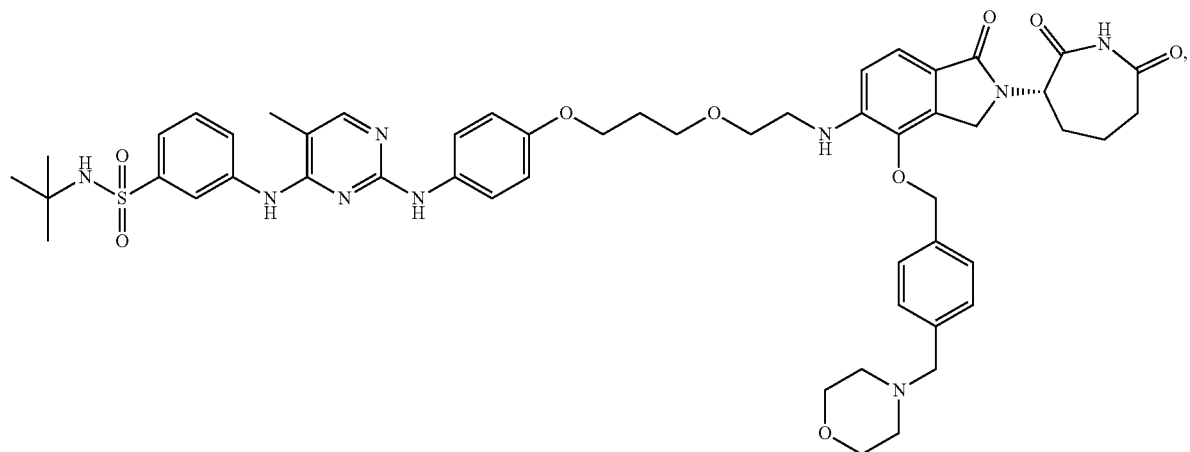

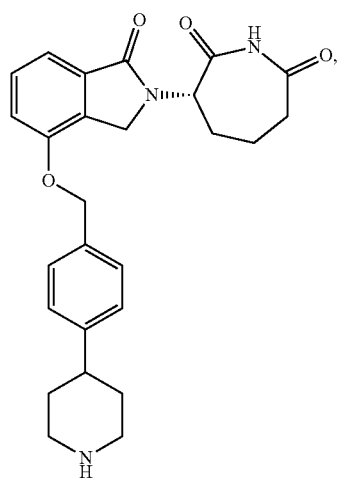
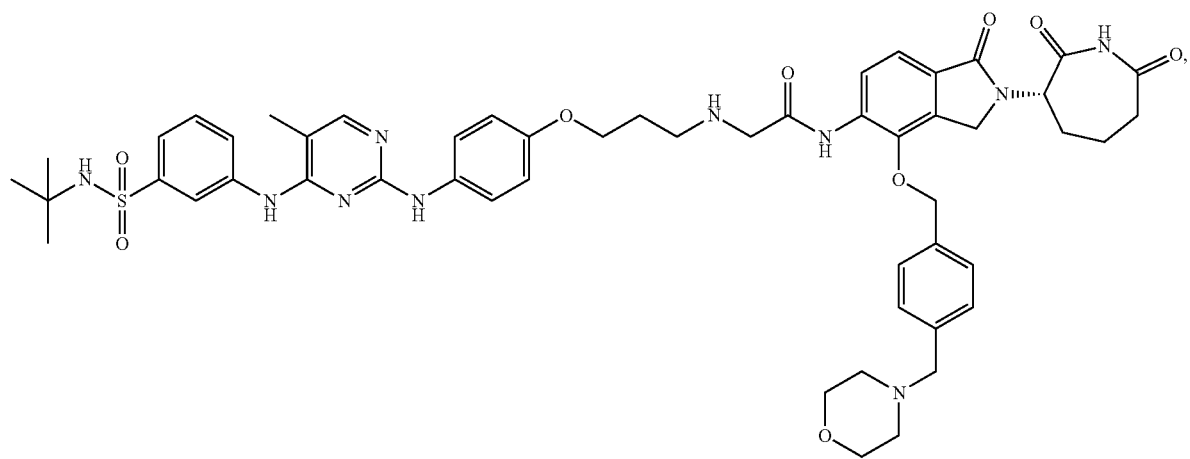
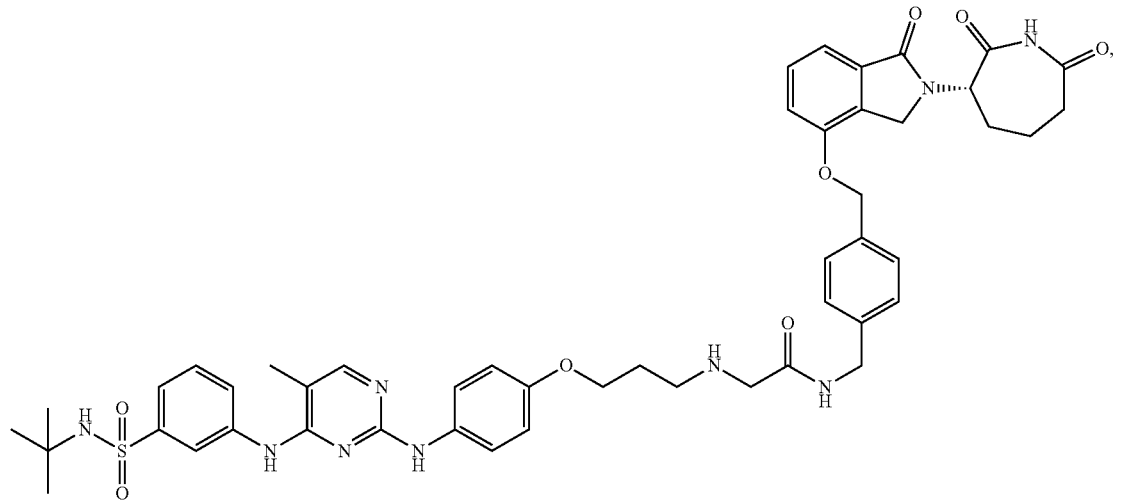

151 -continued 152
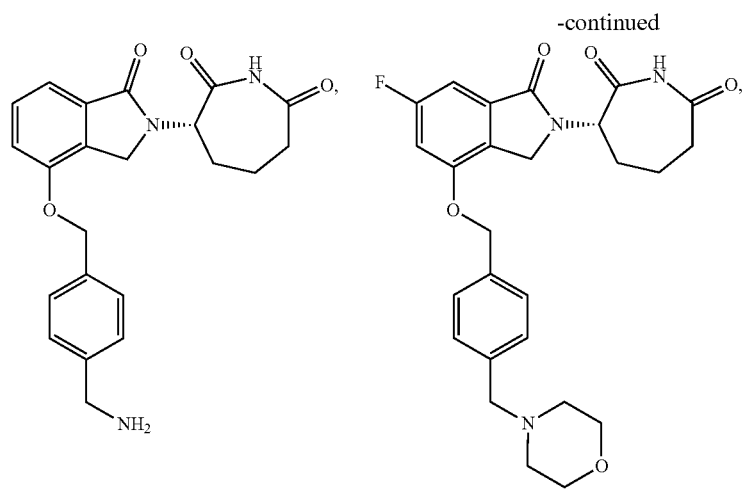
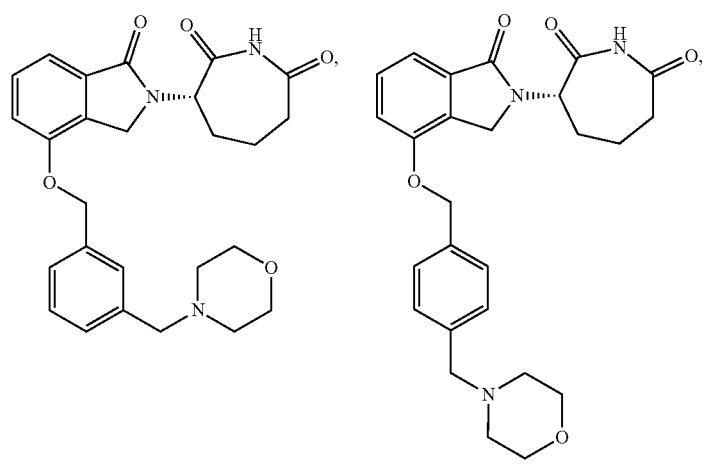
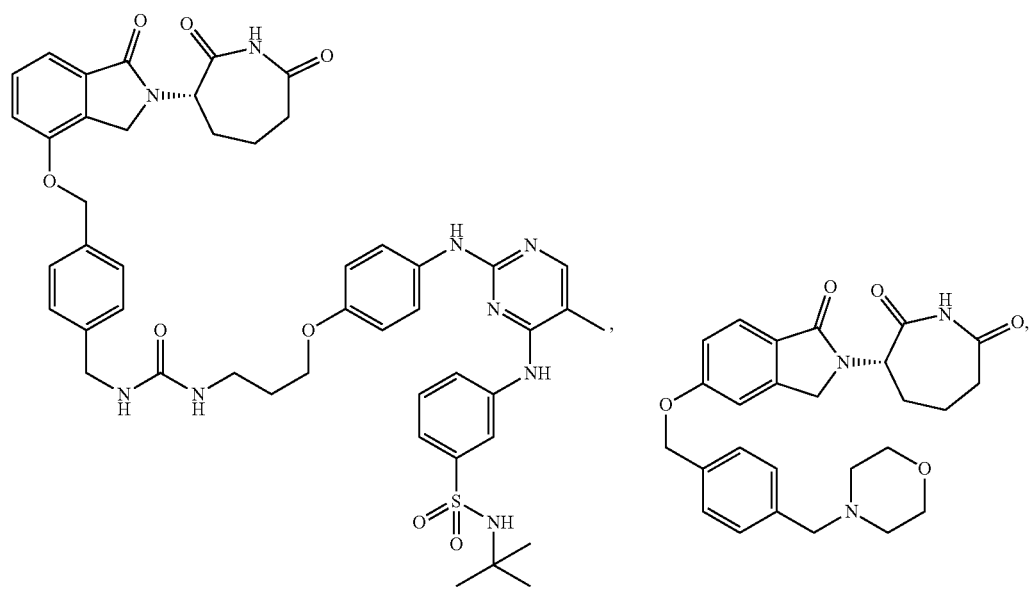

-continued
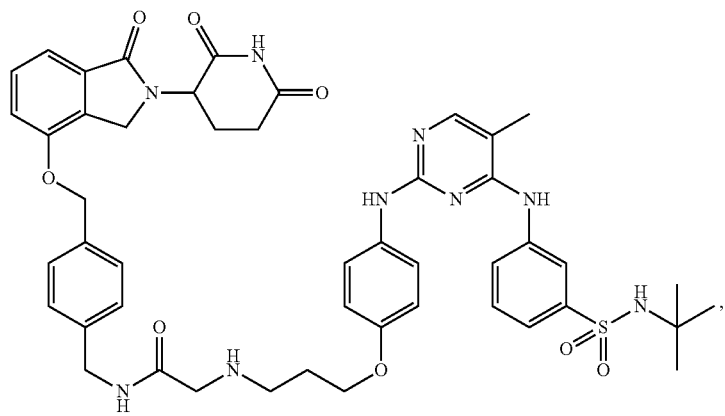
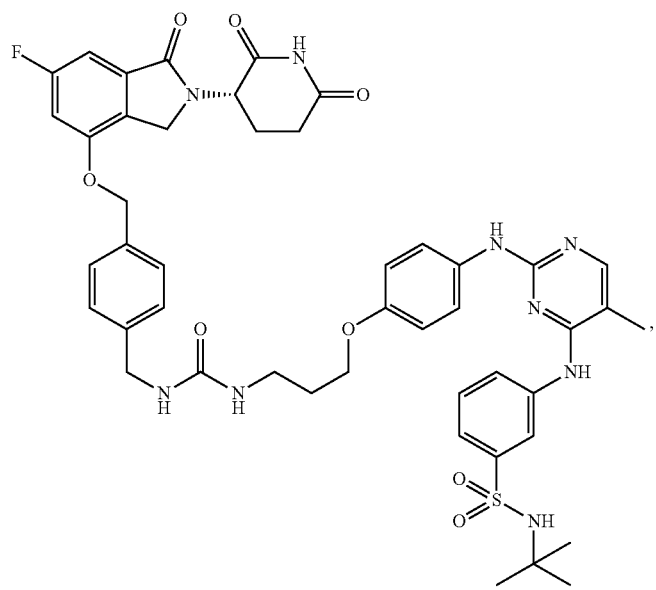
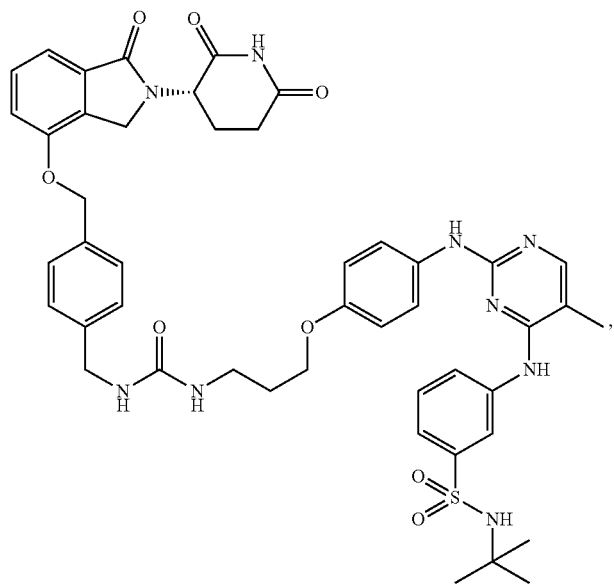

-continued
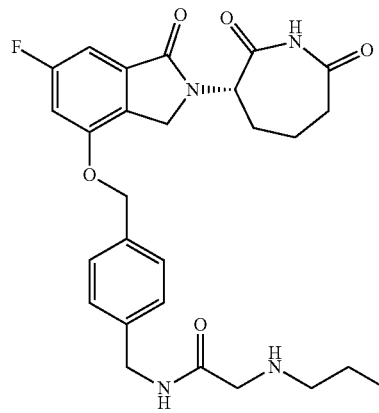
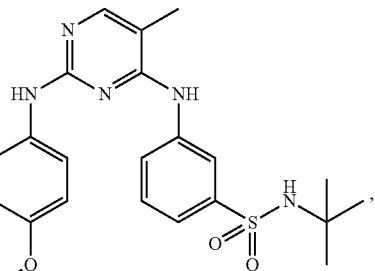
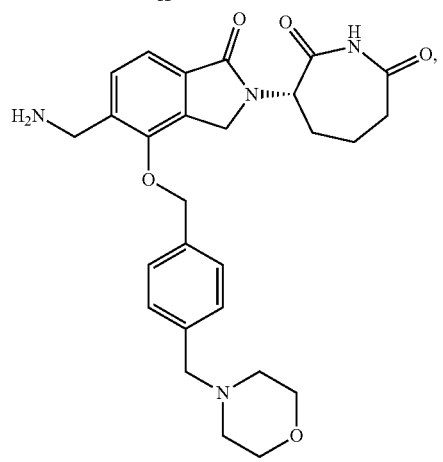
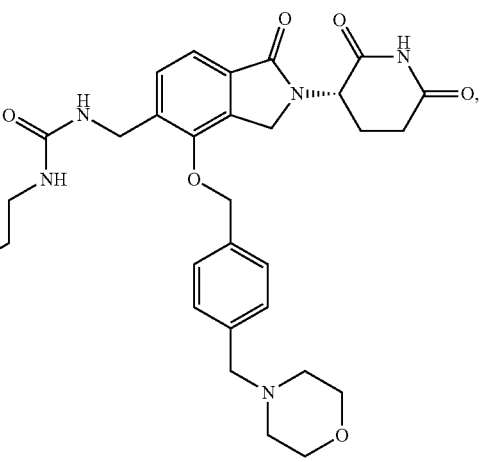
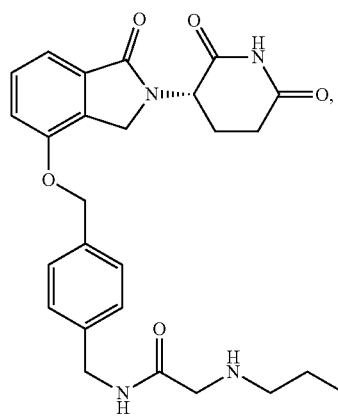
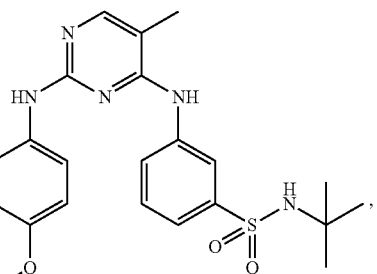

-continued

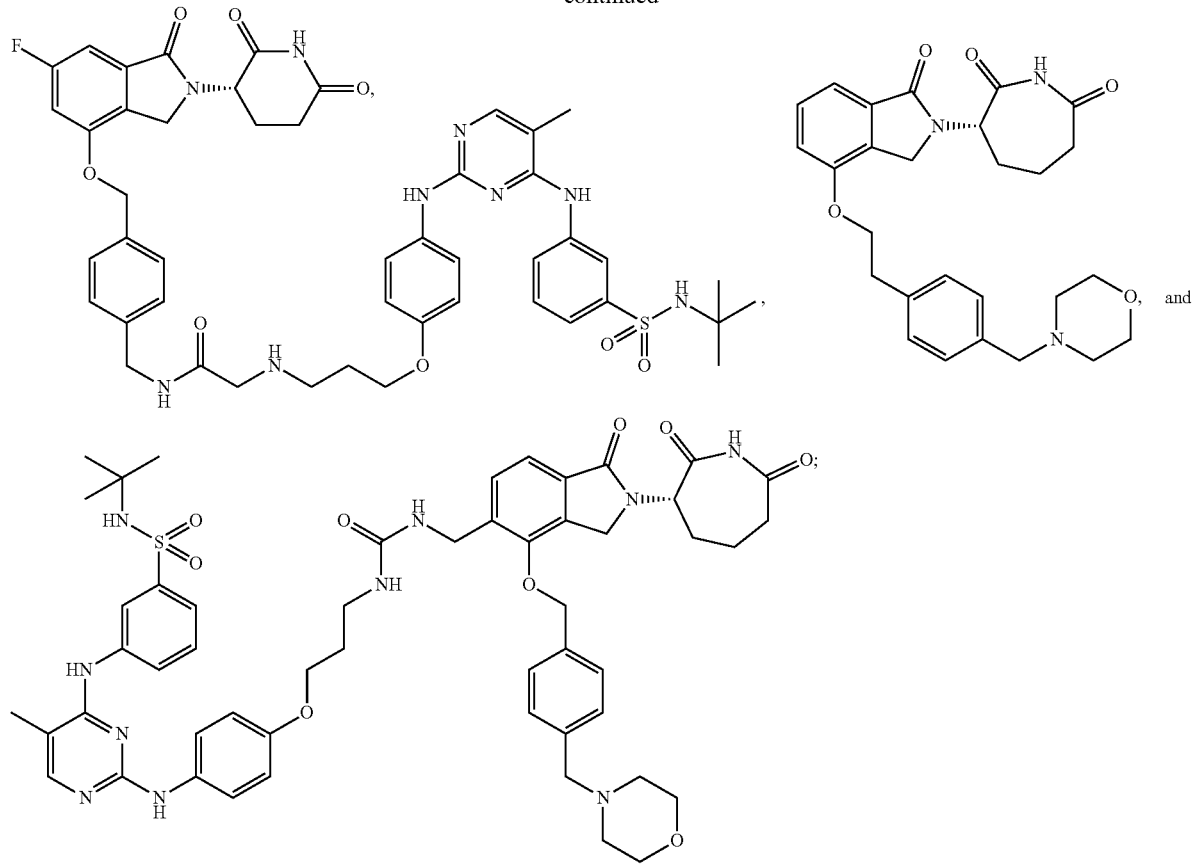

and pharmaceutically acceptable salts thereof.

14. A method of treating or ameliorating cancer in a subject, comprising administering a therapeutically effective amount of a compound of Formula (I) or a pharmaceutically acceptable salt thereof to the subject in need thereof, wherein the treatment of the cancer is beneficial from increased expression of IL-2 or down-regulation of aiolos, ikaros, helios, CK1α, IL-1β, IL-6, or TNFα;

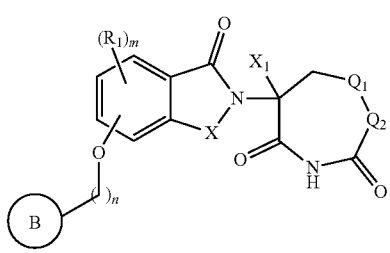

(I)

wherein:
$Q_1$ is $CH_2$ or a bond;
$Q_2$ is $CH_2$;
X is $CH_2$ or C=O;
$X_1$ is hydrogen, methyl, or fluoro;
ring B is

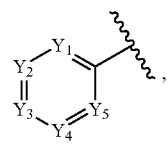

wherein $Y_1$ is N or $CR_{3A}$; $Y_2$ is N or $CR_{3B}$; $Y_3$ is N or $CR_{3C}$; $Y_4$ is N or $CR_{3D}$; and $Y_5$ is N or $CR_{3E}$; wherein at least one of $Y_1$, $Y_2$, $Y_3$, $Y_4$, and $Y_5$ is respectively $CR_{3A}$, $CR_{3B}$, $CR_{3C}$, $CR_{3D}$, or $CR_{3E}$; and wherein one or more of $R_{3A}$, $R_{3B}$, $R_{3C}$, $R_{3D}$, and $R_{3E}$ is not hydrogen;

each $R_1$ is independently deuterium, hydroxyl, halogen, nitro, substituted or unsubstituted amino, substituted or unsubstituted $C_1$-$C_6$ alkoxy, substituted or unsubstituted $C_1$-$C_6$ alkyl, substituted or unsubstituted $C_2$-$C_6$ alkenyl, substituted or unsubstituted $C_3$-$C_8$ cycloalkyl, substituted or unsubstituted 3 to 10 membered heterocyclyl, substituted or unsubstituted $C_6$-$C_{10}$ aryl, substituted or unsubstituted 5 to 10 membered heteroaryl, or L-Y;

each $R_{3A}$, $R_{3B}$, $R_{3C}$, $R_{3D}$, and $R_{3E}$ is independently hydrogen, deuterium, hydroxyl, halogen, nitro, substituted or unsubstituted amino, substituted or unsubstituted $C_1$-$C_6$ alkoxy, substituted or unsubstituted $C_1$-$C_6$ alkyl, substituted or unsubstituted $C_2$-$C_6$ alkenyl, substituted or unsubstituted $C_3$-$C_8$ cycloalkyl, substituted or unsubstituted 3 to 10 membered heterocyclyl, substituted or unsubstituted alkoxyalkyl, substituted or unsubstituted cycloalkylalkyl, substituted or unsubstituted heterocyclylalkyl, substituted or unsubstituted aralkyl, substituted or unsubstituted heteroaralkyl, or L-Y;

m is an integer of 0, 1, 2, or 3;
n is an integer of 1 or 2;
L is —$Z_1$—($R_4$)$_t$—$Z_2$—; —$Z_1$—($R_4$—O—$R_4$)$_t$—$Z_2$—; —$Z_1$—($R_4$—NH—$R_4$)$_t$—$Z_2$—; —$Z_1$—($R_4$—(NHCO)—$R_4$)$_t$—$Z_2$—; —$Z_1$—($R_4$—(NHC(O)NH)—$R_4$)$_t$—$Z_2$—; or —$Z_1$—($R_4$—(CONH)—$R_4$)$_t$—$Z_2$—;
each $Z_1$ and $Z_2$ is independently —NH—; —O—; —CH—; —NH(CO)—; —(CO)NH—; —$CH_2$NH—; —NH$CH_2$—; —(CO)NH$CH_2$—; —$CH_2CH_2$NH—; —$CH_2$NH(CO)—; or —NH$CH_2CH_2$—;
each $R_4$ is independently unsubstituted $C_1$-$C_6$ alkylene;
each t is independently an integer of 1, 2, 3, 4, 5, or 6; and
each Y is independently selected from the group consisting of

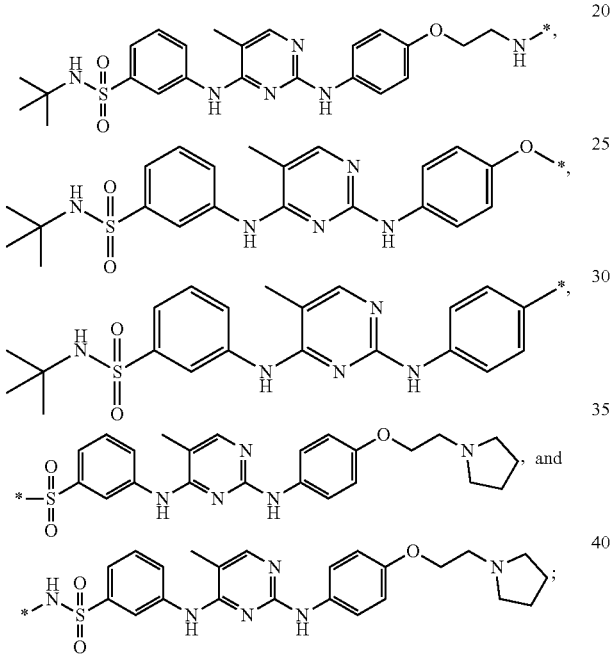

wherein * represents the point of attachment to the L group; and
wherein, when $R_1$ is L-Y, then none of $R_{3A}$, $R_{3B}$, $R_{3C}$, $R_{3D}$, and $R_{3E}$ is L-Y; and when $Q_1$ is a bond and $X_1$ is hydrogen or methyl; then one of $R_1$, $R_{3A}$, $R_{3B}$, $R_{3C}$, $R_{3D}$, and $R_{3E}$ is L-Y.

15. The method of claim 14, wherein the cancer is selected from the group consisting of small cell lung cancer, non-small cell lung cancer, breast cancer, prostate cancer, head and neck cancer, pancreatic cancer, colon cancer, rectal cancer, teratoma, ovarian cancer, endometrial cancer, brain cancer, retinoblastoma, leukemia, skin cancer, melanoma, squamous cell carcinoma, liposarcoma, lymphoma, multiple myeloma, testicular cancer, liver cancer, esophageal cancer, kidney carcinoma, astrogliosis, relapsed/refractory multiple myeloma, and neuroblastoma.

16. The method of claim 15, wherein the cancer is leukemia, melanoma, lymphoma, multiple myeloma, or relapsed/refractory multiple myeloma.

17. The method of claim 14, wherein m is an integer of 1 and $R_1$ is halogen, substituted or unsubstituted amino, substituted or unsubstituted $C_1$-$C_6$ alkoxy, substituted or unsubstituted $C_3$-$C_8$ cycloalkyl, or substituted or unsubstituted $C_1$-$C_6$ alkyl.

18. The method of claim 17, wherein $R_1$ is fluoro, chloro, —$NH_2$, —NH($CH_3$), —N($CH_3$)$_2$, —$CF_3$, —$OCH_3$, —$OCH_2CH_3$, —OCH($CH_3$)$_2$, —$CH_3$, —$CH_2CH_3$, —CH($CH_3$)$_2$, unsubstituted cyclopropyl, unsubstituted cyclobutyl, or unsubstituted cyclopentyl.

19. The method of claim 14, wherein ring B is:

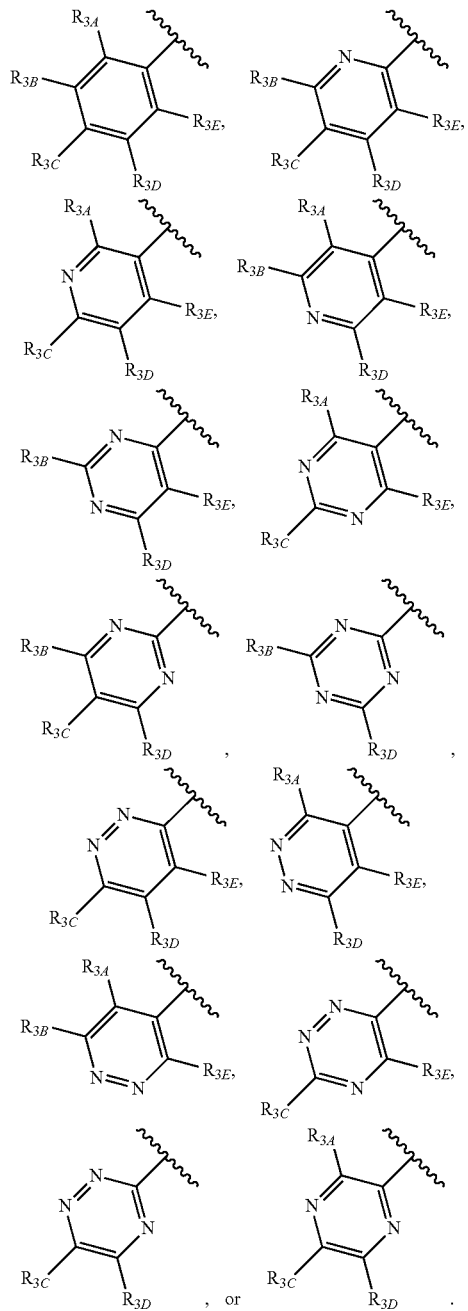

20. The method of claim 19, wherein each of $R_{3A}$, $R_{3B}$, $R_{3C}$, $R_{3D}$, and $R_{3E}$ is independently hydrogen, hydroxyl, halogen, nitro, unsubstituted amino, unsubstituted $C_1$-$C_6$ haloalkyl, unsubstituted $C_1$-$C_6$ alkoxy, unsubstituted $C_1$-$C_6$ alkyl, substituted or unsubstituted $C_3$-$C_8$ cycloalkyl, substituted or unsubstituted 3 to 10 membered heterocyclyl, substituted or unsubstituted alkoxyalkyl, substituted or unsubstituted cycloalkylalkyl, substituted or unsubstituted heterocyclylalkyl, substituted or unsubstituted aralkyl, or substituted or unsubstituted heteroaralkyl.

21. The method of claim 20, wherein ring B is

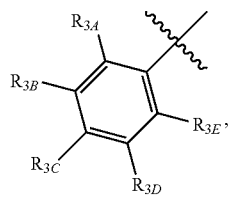

and one of $R_{3A}$, $R_{3B}$, $R_{3C}$, $R_{3D}$, and $R_{3E}$ is —CH$_2$NH$_2$,

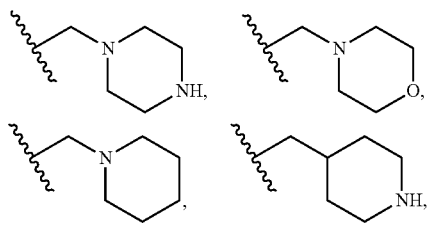

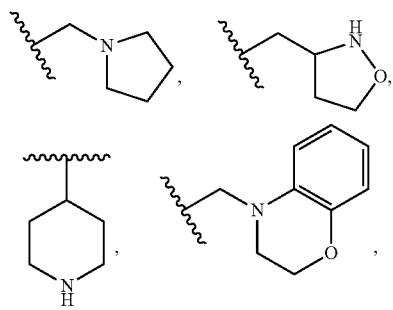

or L-Y, and the others of $R_{3A}$, $R_{3B}$, $R_{3C}$, $R_{3D}$, and $R_{3E}$ are each independently hydrogen or halogen.

22. The method of claim 21, wherein $R_{3C}$ is L-Y and L is —Z$_1$—(R$_4$—(NHCO)—R$_4$)$_t$—Z$_2$—;    —Z$_1$—(R$_4$—(CONH)—R$_4$)$_t$—Z$_2$—;  or  —Z$_1$—(R$_4$—(NHC(O)NH)—R$_4$)$_t$—Z$_2$—.

23. The method of claim 22, wherein each $Z_1$ and $Z_2$ is independently —NH—; —O—; —CH$_2$—; —NH(CO)—; —(CO)NH—; —CH$_2$NH(CO)—; —CH$_2$NH—; —NHCH$_2$—, or —NHCH$_2$CH$_2$—.

24. The method of claim 9, wherein $R_{3C}$ is L-Y and wherein L-Y has a structure selected from the group consisting of:

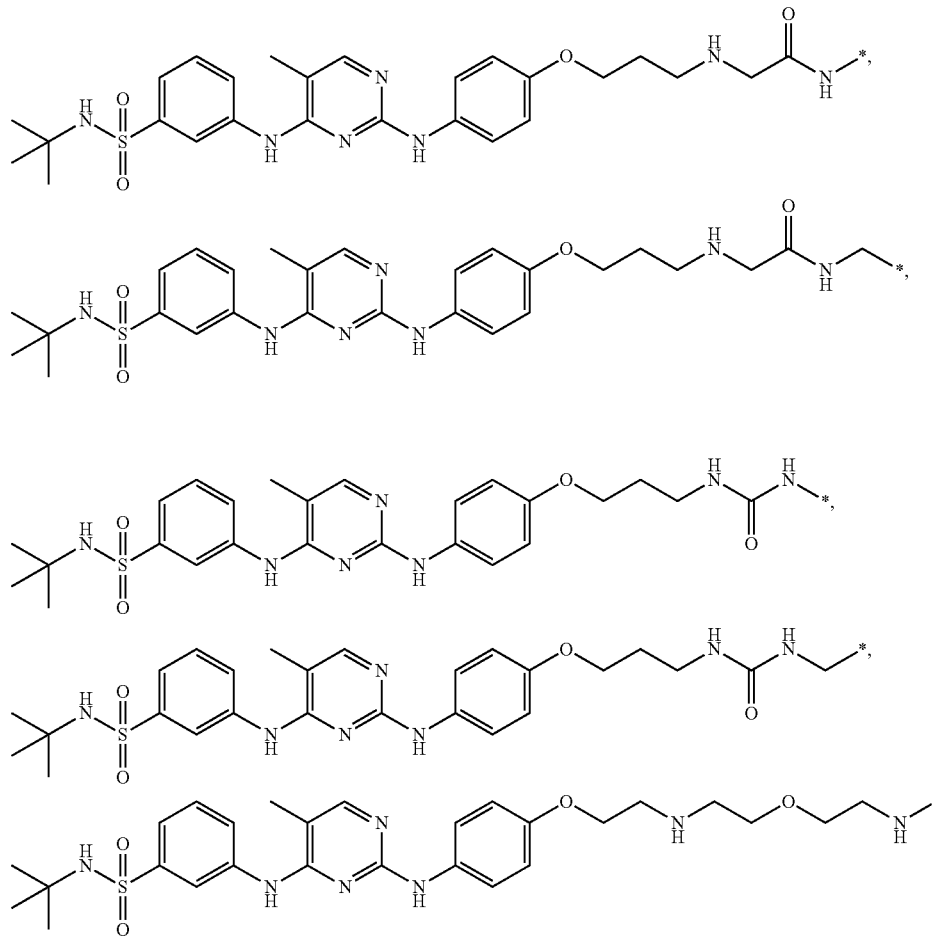

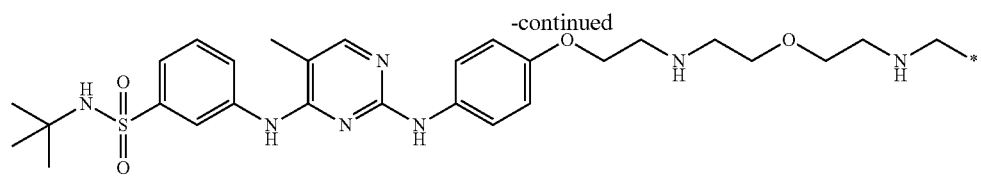
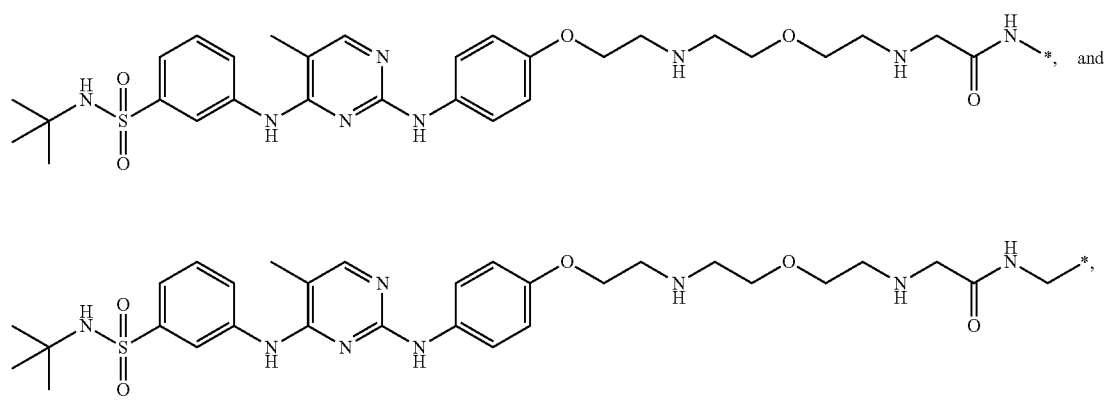
where "*" represents the point of connection of the L-Y moiety to ring B.
25. The method of claim 14, wherein the compound is selected from the group consisting of:
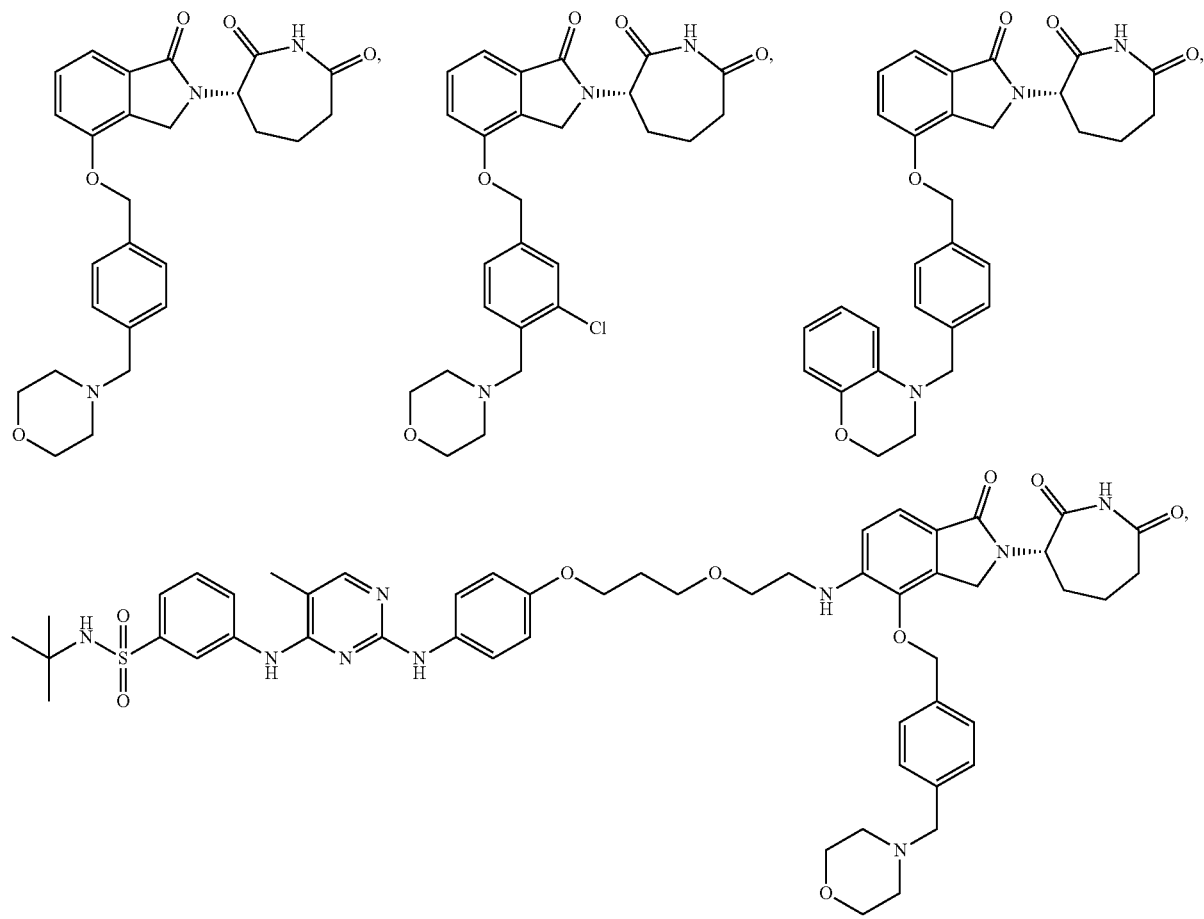

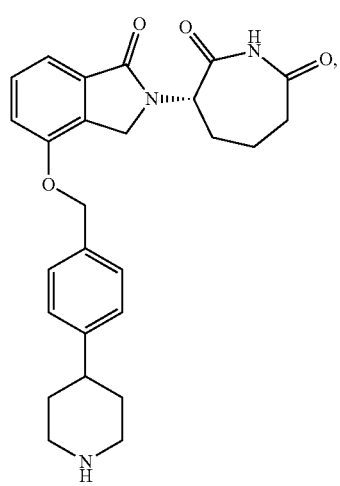
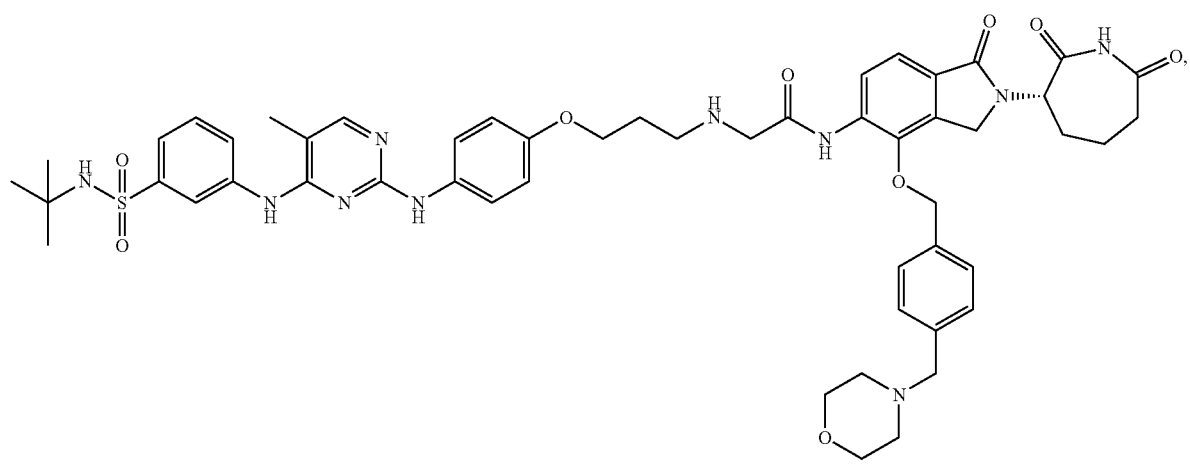
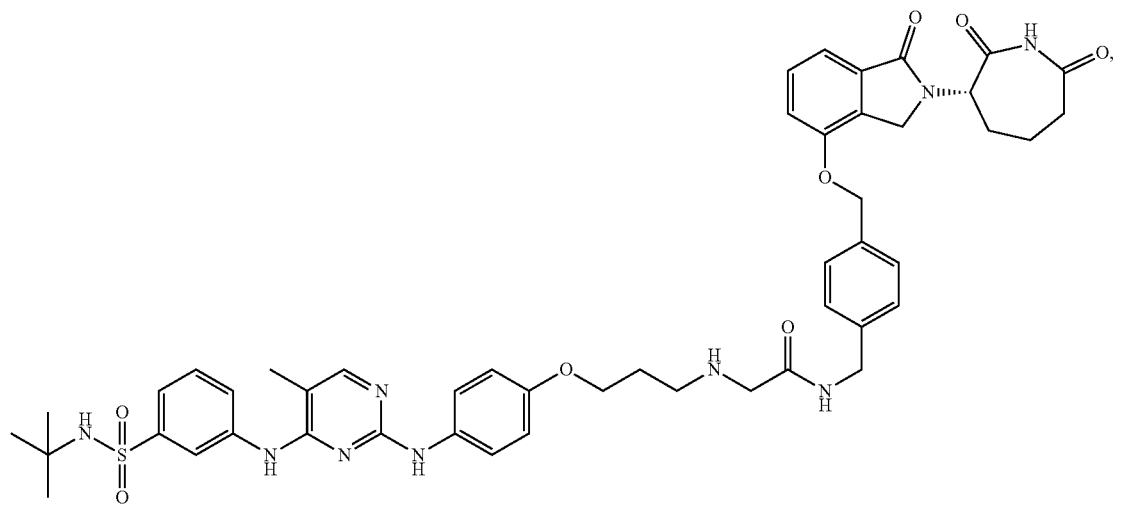

167 168
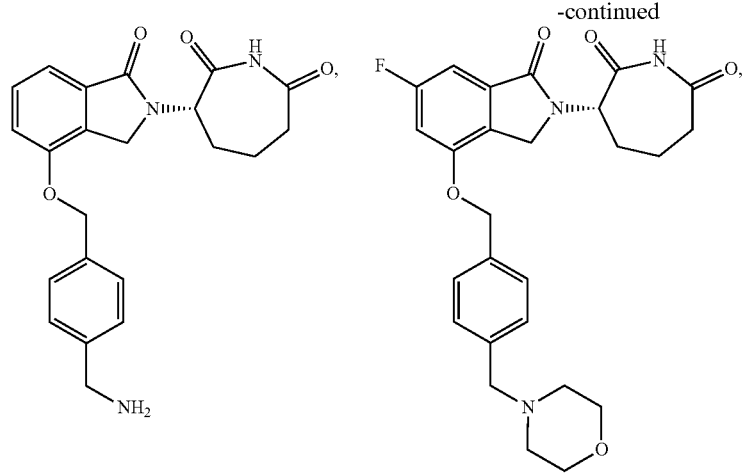
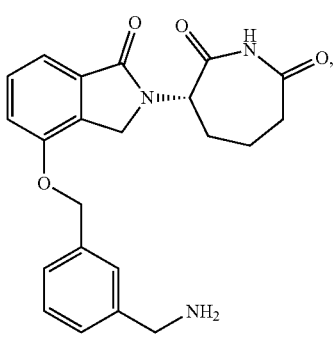
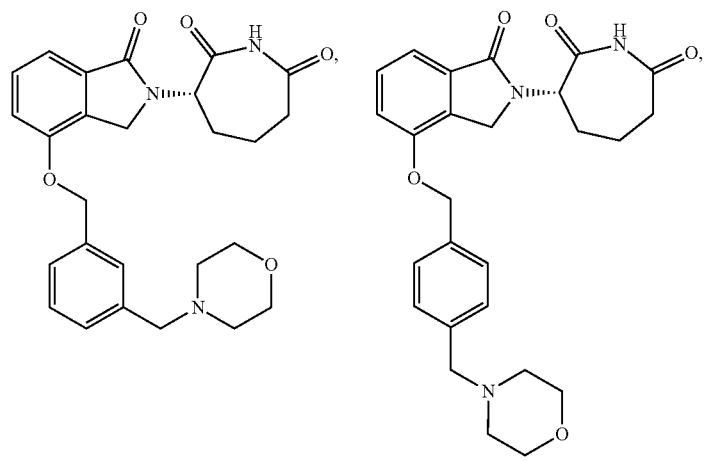
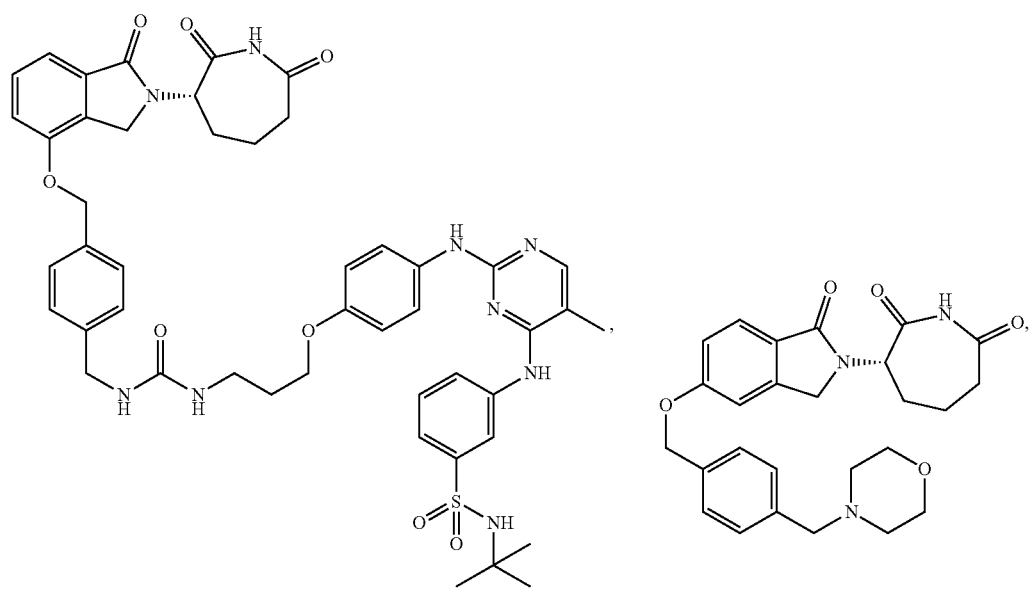

-continued
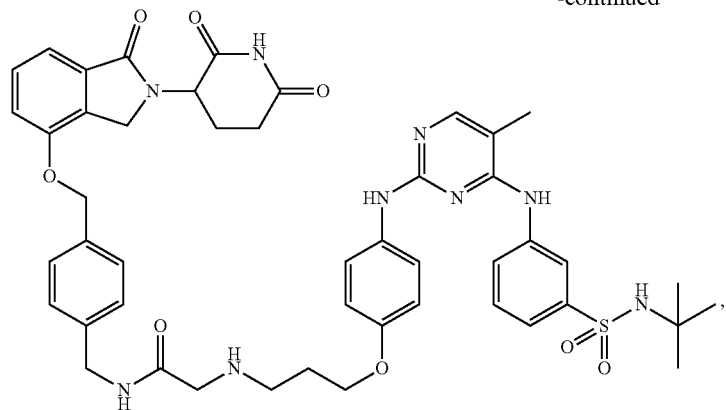
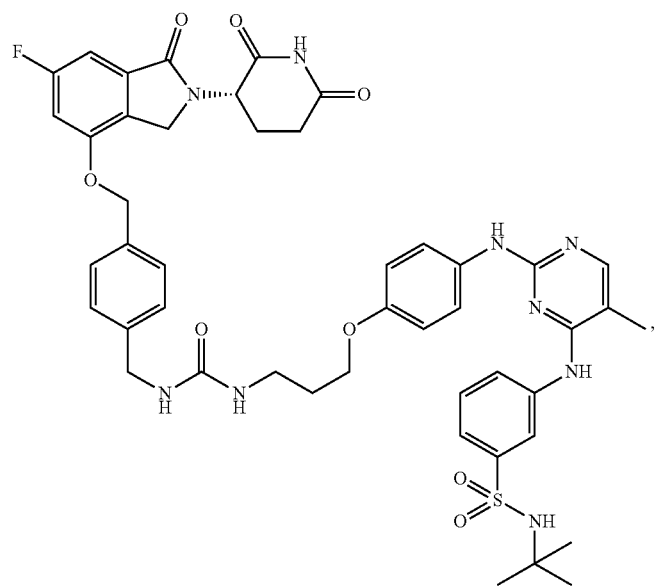
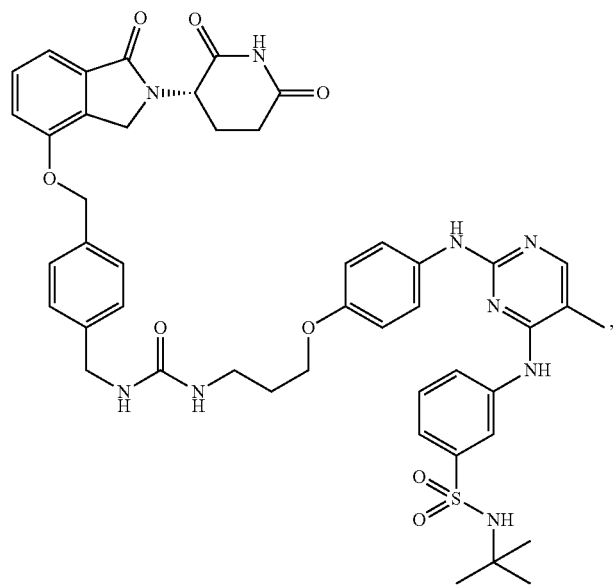

-continued
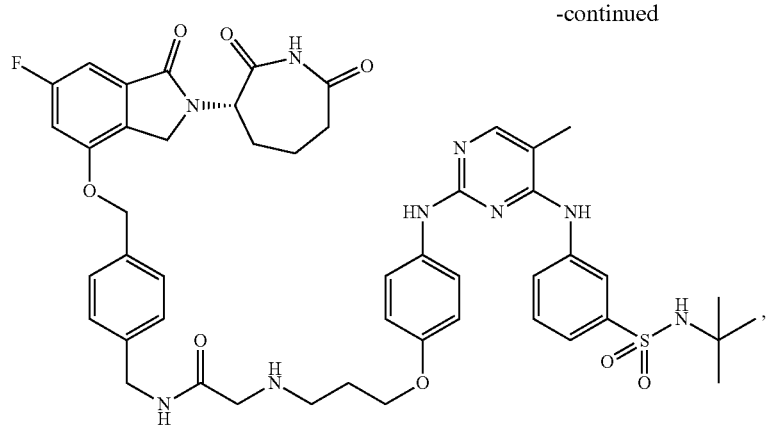
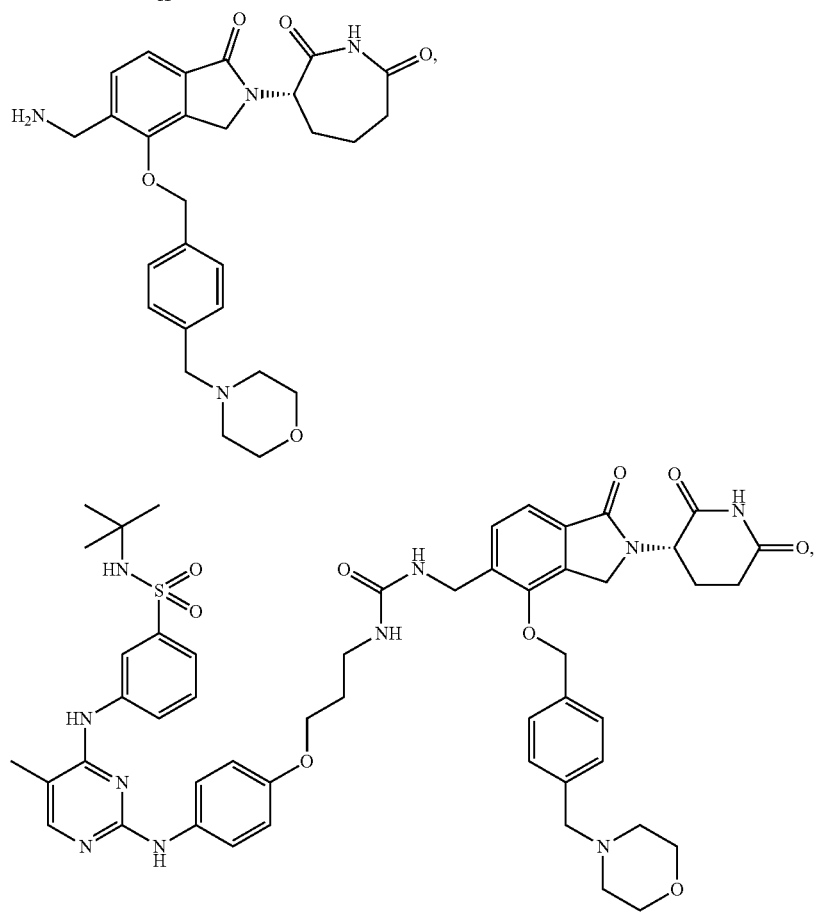
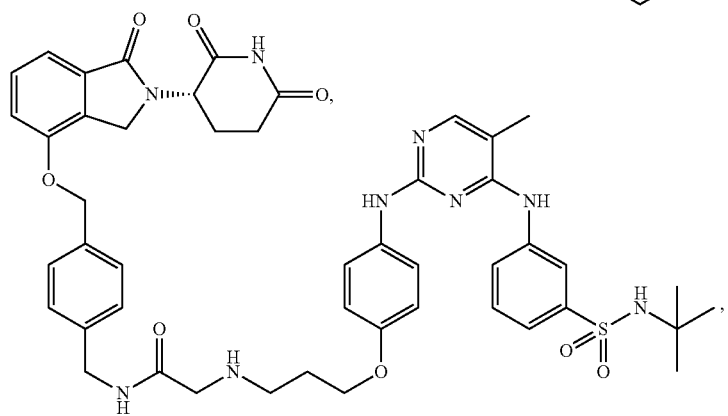

-continued

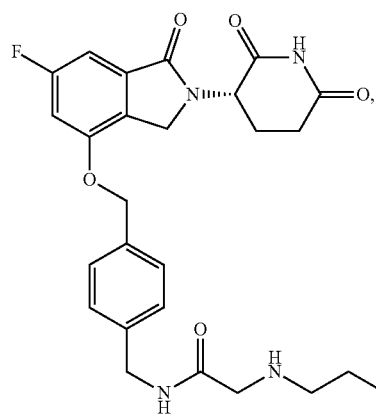

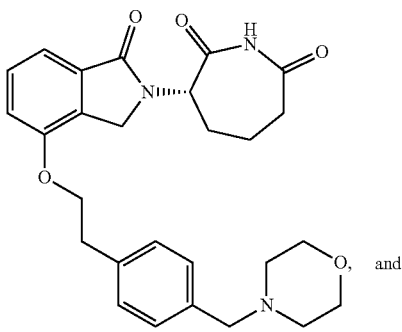

and

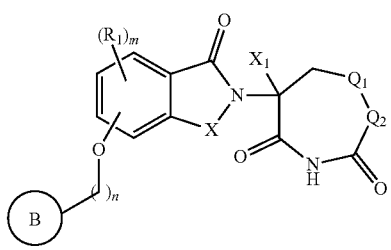

and pharmaceutically acceptable salts thereof.

26. A method of inhibiting the activity of a protein, comprising contacting a cell with an effective amount of a compound of Formula (I) or a pharmaceutically acceptable salt thereof, wherein the protein is IL-1β, IL-2, IL-6, TNFα, aiolos, ikaros, helios, or CK-1α;

(I)

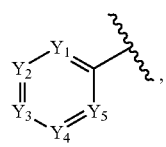

wherein:
$Q_1$ is $CH_2$ or a bond;
$Q_2$ is $CH_2$;
X is $CH_2$ or C=O;
$X_1$ is hydrogen, methyl, or fluoro;
ring B is wherein $Y_1$ is N or $CR_{3A}$; $Y_2$ is N or $CR_{3B}$; $Y_3$ is N or $CR_{3C}$; $Y_4$ is N or $CR_{3D}$; and $Y_5$ is N or $CR_{3E}$; wherein at least one of $Y_1$, $Y_2$, $Y_3$, $Y_4$, and $Y_5$ is respectively $CR_{3A}$, $CR_{3B}$, $CR_{3C}$, $CR_{3D}$, or $CR_{3E}$; and wherein one or more of $R_{3A}$, $R_{3B}$, $R_{3C}$, $R_{3D}$, and $R_{3E}$ is not hydrogen;

each $R_1$ is independently deuterium, hydroxyl, halogen, nitro, substituted or unsubstituted amino, substituted or unsubstituted $C_1$-$C_6$ alkoxy, substituted or unsubstituted $C_1$-$C_6$ alkyl, substituted or unsubstituted $C_2$-$C_6$ alkenyl, substituted or unsubstituted $C_3$-$C_8$ cycloalkyl, substituted or unsubstituted 3 to 10 membered heterocyclyl, substituted or unsubstituted $C_6$-$C_{10}$ aryl, substituted or unsubstituted 5 to 10 membered heteroaryl, or L-Y;

each $R_{3A}$, $R_{3B}$, $R_{3C}$, $R_{3D}$, and $R_{3E}$ is independently hydrogen, deuterium, hydroxyl, halogen, nitro, substituted or unsubstituted amino, substituted or unsubstituted $C_1$-$C_6$ alkoxy, substituted or unsubstituted $C_1$-$C_6$ alkyl, substituted or unsubstituted $C_2$-$C_6$ alkenyl, substituted or unsubstituted $C_3$-$C_8$ cycloalkyl, substituted or unsubstituted 3 to 10 membered heterocyclyl, substituted or unsubstituted alkoxyalkyl, substituted or unsubstituted cycloalkylalkyl, substituted or unsubstituted heterocyclylalkyl, substituted or unsubstituted aralkyl, substituted or unsubstituted heteroaralkyl, or L-Y;

m is an integer of 0, 1, 2, or 3;

n is an integer of 1 or 2;

L is $-Z_1-(R_4)_t-Z_2-$; $-Z_1-(R_4-O-R_4)_t-Z_2-$; $-Z_1-(R_4-NH-R_4)_t-Z_2-$; $-Z_1-(R_4-(NHCO)-R_4)_t-Z_2-$; $-Z_1-(R_4-(NHC(O)NH)-R_4)_t-Z_2-$; or $-Z_1-(R_4-(CONH)-R_4)_t-Z_2-$;

each $Z_1$ and $Z_2$ is independently $-NH-$; $-O-$; $-CH-$; $-NH(CO)-$; $-(CO)NH-$; $-CH_2NH-$; $-NHCH_2-$; $-(CO)NHCH_2-$; $-CH_2CH_2NH-$; $-CH_2NH(CO)-$; or $-NHCH_2CH_2-$;

each $R_4$ is independently unsubstituted $C_1$-$C_6$ alkylene;

each t is independently an integer of 1, 2, 3, 4, 5, or 6; and each Y is independently selected from the group consisting of

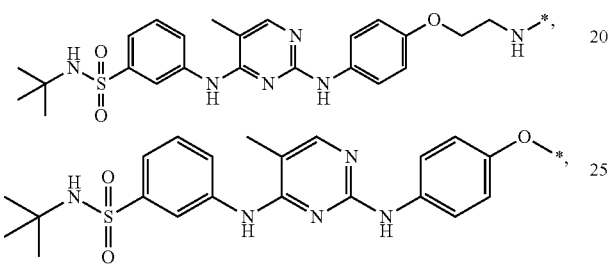

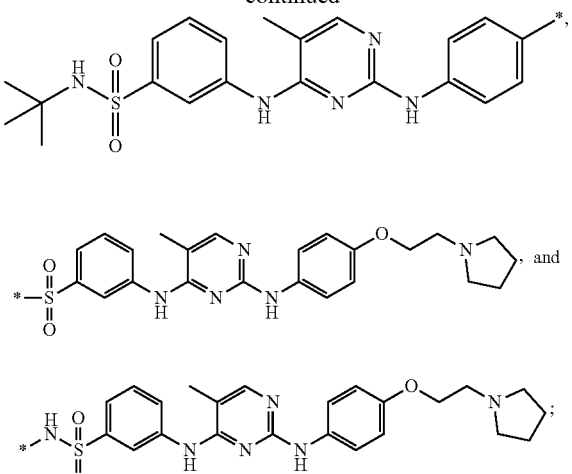

wherein * represents the point of attachment to the L group; and wherein, when $R_1$ is L-Y, then none of $R_{3A}$, $R_{3B}$, $R_{3C}$, $R_{3D}$, and $R_{3E}$ is L-Y; and when $Q_1$ is a bond and $X_1$ is hydrogen or methyl; then one of $R_1$, $R_{3A}$, $R_{3B}$, $R_{3C}$, $R_{3D}$, and $R_{3E}$ is L-Y.

* * * * *